(12) United States Patent
Dong et al.

(10) Patent No.: US 7,459,554 B2
(45) Date of Patent: Dec. 2, 2008

(54) IMIDAZOPYRAZINE TYROSINE KINASE INHIBITORS

(75) Inventors: Han-Qing Dong, Syosset, NY (US); Kenneth Foreman, Syosset, NY (US); Mark Joseph Mulvihill, East Northport, NY (US); Anthony Innocenzo Nigro, Westwood, NJ (US); Arno G. Steinig, East Northport, NY (US); Douglas Werner, Holtsville, NY (US); Robin Wilkes, Oxfordshire (GB)

(73) Assignee: OSI Pharmaceuticals, Inc., Melville, NY (US)

( * ) Notice: Subject to any disclaimer, the term of this patent is extended or adjusted under 35 U.S.C. 154(b) by 365 days.

(21) Appl. No.: 10/965,182

(22) Filed: Oct. 14, 2004

(65) Prior Publication Data

US 2006/0084654 A1 Apr. 20, 2006
US 2008/0227788 A9 Sep. 18, 2008

Related U.S. Application Data

(60) Provisional application No. 60/511,712, filed on Oct. 15, 2003.

(51) Int. Cl.
*C07D 413/00* (2006.01)
*C07D 471/00* (2006.01)
*C07D 487/00* (2006.01)
*C07D 491/00* (2006.01)
*C07D 495/00* (2006.01)
*C07D 497/00* (2006.01)
*C07D 415/00* (2006.01)

(52) U.S. Cl. .................. 544/120; 544/350; 540/599
(58) Field of Classification Search .................. 544/120, 544/350; 540/599
See application file for complete search history.

(56) References Cited

U.S. PATENT DOCUMENTS

| | | | |
|---|---|---|---|
| 5,217,999 A | 6/1993 | Levitzki | |
| 5,302,606 A | 4/1994 | Spada | |
| 5,397,787 A | 3/1995 | Buzzetti | |
| 5,556,874 A | 9/1996 | Dobrusin | |
| 6,194,439 B1 | 2/2001 | Dow | |
| 6,265,411 B1 | 7/2001 | Thomas | |
| 6,337,338 B1 | 1/2002 | Kozlowski | |
| 6,362,336 B1 | 3/2002 | Lohmann | |
| 6,486,179 B2 | 11/2002 | Jirousek | |
| 6,939,874 B2 | 9/2005 | Harmange | |
| 7,087,602 B2 | 8/2006 | Thomas | |
| 7,115,617 B2 | 10/2006 | Buchanan | |
| 7,202,243 B2 | 4/2007 | Hendrix | |
| 7,244,733 B2 | 7/2007 | Hunt | |
| 7,271,262 B2 | 9/2007 | La Greca | |
| 7,326,699 B2 | 2/2008 | Capraro | |
| 7,332,497 B2 | 2/2008 | Hirst | |
| 7,345,038 B2 | 3/2008 | Bright | |
| 2004/0014774 A1 | 1/2004 | Myers | |
| 2004/0220189 A1 | 11/2004 | Sun | |
| 2005/0054638 A1 | 3/2005 | Barlaam | |
| 2005/0215564 A1 | 9/2005 | Stiles | |
| 2006/0069084 A1 | 3/2006 | Burns | |
| 2006/0154982 A1 | 7/2006 | Larsson | |
| 2006/0166992 A1 | 7/2006 | Hendrix | |
| 2006/0235031 A1 * | 10/2006 | Arnold et al. | ............ 514/263.2 |
| 2007/0238734 A1 | 10/2007 | Nemecek | |

FOREIGN PATENT DOCUMENTS

WO WO 97/28161 8/1997
WO WO 01/72751 10/2001

OTHER PUBLICATIONS

Albert, A. et al. (1970) Journal of the Chemical Society, vol. 11, pp. 1540-1547.
Albert, A. et al. (1969) Chem. Biol.Pterdines.Proc.Int.Symp., 4th, 4:1-5.
Baserga R. (1999) Exp.Cell.Res, vol. 253, pp. 1-6.
Hartz R A et al (2002) Bioorganic & Medicinal Chemistry Letters, vol. 12,pp. 291-294.
Parrizas et al (1997) Endocrinology, vol. 138, pp. 1427-1433.
(1998) Expert Opinion Ther. Pat., vol. 8, pp. 475-478, (Thomas et al).
International Search Report in PCT/US2004/034219, May 6, 2005.
International Preliminary Report on Patentability in PCT/US2004/034219, May 6, 2005.
Written Opinion of the International Search Authority in PCT/US2004/034219, May 6, 2005.
Machine English Translation of JP 07133280, (1995) Akio et al.
Abstract of JP 07133280, Akio et al (1995).

* cited by examiner

*Primary Examiner*—Zachary C Tucker

(57) ABSTRACT

Compounds of the formula

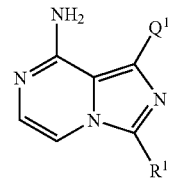

and pharmaceutically acceptable salts thereof, wherein $Q^1$ and $R^1$ are defined herein, inhibit the IGF-1R enzyme and are useful for the treatment and/or prevention of various diseases and conditions that respond to treatment by inhibition of tyrosine kinases.

68 Claims, No Drawings

IMIDAZOPYRAZINE TYROSINE KINASE INHIBITORS

This application claims the priority benefit of U.S. Appl. No. 60/511,712, filed Oct. 15, 2003, entitled "Imidazopyrazine Tyrosine Kinase Inhibitors."

BACKGROUND OF THE INVENTION

The present invention is directed to novel imidazopyrazines, their salts, and compositions comprising them. In particular, the present invention is directed to imidazopyrazines as novel tyrosine kinase inhibitors that inhibit tyrosine kinase enzymes in animals, including humans, for the treatment and/or prevention of various diseases and conditions such as cancer.

Phosphoryl transferases are a large family of enzymes that transfer phosphorous-containing groups from one substrate to another. Kinases are a class of enzymes that function in the catalysis of phosphoryl transfer. The phosphorylation is usually a transfer reaction of a phosphate group from ATP to the protein substrate. Almost all kinases contain a similar 250-300 amino acid catalytic domain. Protein kinases, with at least 400 identified, constitute the largest subfamily of structurally related phosphoryl transferases and are responsible for the control of a wide variety of signal transduction processes within the cell. The protein kinases may be categorized into families by the substrates they phosphorylate (e.g., protein-tyrosine, protein-serine/threonine, etc.). Protein kinase sequence motifs have been identified that generally correspond to each of these kinase families. Lipid kinases (e.g. PI3K) constitute a separate group of kinases with structural similarity to protein kinases.

The "kinase domain" appears in a number of polypeptides which serve a variety of functions. Such polypeptides include, for example, transmembrane receptors, intracellular receptor associated polypeptides, cytoplasmic located polypeptides, nuclear located polypeptides and subcellular located polypeptides. The activity of protein kinases can be regulated by a variety of mechanisms and any individual protein might be regulated by more than one mechanism. Such mechanisms include, for example, autophosphorylation, transphosphorylation by other kinases, protein-protein interactions, protein-lipid interactions, protein-polynucleotide interactions, ligand binding, and post-translational modification.

Phosphorylation of target proteins occurs in response to a variety of extracellular signals (hormones, neurotransmitters, growth and differentiation factors, etc.), cell cycle events, environmental or nutritional stresses, etc. Protein and lipid kinases regulate many different cell processes by adding phosphate groups to targets such as proteins or lipids. Such cell processes include, for example, proliferation, growth, differentiation, metabolism, cell cycle events, apoptosis, motility, transcription, translation and other signaling processes. Kinase catalyzed phosphorylation acts as molecular on/off switches to modulate or regulate the biological function of the target protein. Thus, protein and lipid kinases can function in signaling pathways to activate or inactivate, or modulate the activity (either directly or indirectly) of the targets. These targets may include, for example, metabolic enzymes, regulatory proteins, receptors, cytoskeletal proteins, ion channels or pumps, or transcription factors.

A partial list of protein kinases includes abl, AKT, bcr-abl, Blk, Brk, Btk, c-kit, c-met, c-src, CDK1, CDK2, CDK3, CDK4, CDKS, CDK6, CDK7, CDK8, CDK9, CDK10, cRaf1, CSFir, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ron, tie, tie2, TRK, Yes, and Zap70. Thus, protein kinases represent a large family of proteins which play a central role in the regulation of a wide variety of cellular processes, maintaining control over cellular function. Uncontrolled signaling due to defective control of protein phosphorylation has been implicated in a number of diseases and disease conditions, including, for example, inflammation, cancer, allergy/asthma, disease and conditions of the immune system, disease and conditions of the central nervous system (CNS), cardiovascular disease, dermatology, and angiogenesis.

Initial interest in protein kinases as pharmacological targets was stimulated by findings that many viral oncogenes encode structurally modified cellular protein kinases with constitutive enzyme activity. One early example was the Rous sarcoma virus (RSV) or avian sarcoma virus (ASV), which caused highly malignant tumors of the same type or sarcomas within infected chickens. Subsequently, deregulated protein kinase activity, resulting from a variety of mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore become an important therapeutic target.

Protein tyrosine kinases (PTKs) are enzymes that catalyse the phosphorylation of specific tyrosine residues in cellular proteins. Such post-translational modification of the substrate proteins, often enzymes themselves, acts as a molecular switch regulating cell proliferation, activation or differentiation (for review, see Schlessinger and Ullrich, 1992, *Neuron* 9:383-391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular). The Receptor Tyrosine Kinases (RTKs) comprise a large family of transmembrane receptors with at least nineteen distinct RTK subfamilies having diverse biological activities. The RTK family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, RTK mediated signal transduction is initiated by extracellular interaction with a specific growth factor (ligand), typically followed by receptor dimerization, stimulation of the intrinsic protein tyrosine kinase activity and receptor transphosphorylation. Binding sites are thereby created for intracellular signal transduction molecules and lead to the formation of complexes with a spectrum of cytoplasmic signaling molecules that facilitate the appropriate cellular response such as cell division, differentiation, metabolic effects, and changes in the extracellular microenvironment (see Schlessinger and Ullrich, 1992, *Neuron* 9:1-20).

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413-423; Songyang et al., 1994, *Mol. Cell. Biol.* 14:2777-2785; Songyang et al., 1993, *Cell* 72:767-778; and Koch et al., 1991, *Science* 252:668-678; Shoelson, *Curr Opin. Chem. Biol.* (1997), 1(2), 227-234; Cowburn, *Curr Opin. Struct. Biol.* (1997), 7(6), 835-838). Several intracellular substrate proteins that associate with RTKs have been identified. They may be divided into two principal groups: (1) substrates which have a catalytic domain; and (2) substrates which lack such a domain but serve as adapters and associate with catalytically active molecules (Songyang et al., 1993, *Cell* 72:767-778). The specificity of the interactions between receptors or proteins and SH2 or PTB domains of their substrates is determined by the amino acid residues immediately surrounding the phosphorylated tyrosine residue. For example, differences in the binding affinities between SID domains and the amino acid sequences surrounding the phosphotyrosine residues on particular receptors correlate with the observed differences in their substrate phosphorylation profiles (Songyang et al., 1993, *Cell* 72:767-778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, Tie-2 and c-Met, and growth factors that bind thereto, have been suggested to play a role in angiogenesis, although some may promote angiogenesis indirectly (Mustonen and Alitalo, *J. Cell Biol.* 129:895-898, 1995). One such receptor tyrosine kinase, known as "fetal liver kinase 1" (FLK-1), is a member of the type III subclass of RTKs. Human FLK-1 is also known as "kinase insert domain-containing receptor" (KDR) (Terean et al., *Oncogene* 6:1677-83, 1991). It is also called "vascular endothelial cell growth factor receptor 2" (VEGFR-2) since it binds vascular endothelial cell growth factor (VEGF) with high affinity. The murine version of FLK-1/VEGFR-2 has also been called NYK. (Oelrichs et al, *Oncogene* 8(1):11-15, 1993). Numerous studies (such as those reported in Millauer et al., supra), suggest that VEGF and FLK-1/KDR/VEGFR-2 are a ligand-receptor pair that play an important role in the proliferation of vascular endothelial cells (vasculogenesis), and the formation and sprouting of blood vessels (angiogenesis). Accordingly, VEGF plays a role in the stimulation of both normal and pathological angiogenesis (Jakeman et al., *Endocrinology* 133:848-859, 1993; Kolch et al., *Breast Cancer Research and Treatment* 36: 139-155, 1995; Ferrara et al., *Endocrine Reviews* 18(1); 4-25, 1997; Ferrara et al., Regulation of Angiogenesis (ed. L D. Goldberg and E. M. Rosen), 209-232, 1997). In addition, VEGF has been implicated in the control and enhancement of vascular permeability (Connolly, et al., 1. *Biol. Chem.* 264: 20017-20024, 1989; Brown et al., *Regulation of Angiogenesis* (ed. L D. Goldberg and E. M. Rosen), 233-269, 1997).

Another type III subclass RTK related to FLK-1/KDR (DeVries et al. *Science* 255:989-991, 1992; Shibuya et al., *Oncogene* 5:519-524, 1990) is "fms-like tyrosine kinase-I" (Flt-1), also called "vascular endothelial cell growth factor receptor 1" (VEGFR-1). Members of the FLK-1/KDR/VEGFR-2 and Flt-1/VEGPR-1 subfamilies are expressed primarily on endothelial cells. These subclass members are specifically stimulated by members of the VEGF family of ligands (Klagsbum and D'Amore, *Cytokine & Growth Factor Reviews* 7: 259270, 1996). VEGF binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is no related to cell growth (Mustonen and Alitalo, supra).

Placenta growth factor (PlGF) has an amino acid sequence that exhibits significant homology to the VEGF sequence (Park et al., 1. *Biol. Chem.* 269:25646-54, 1994; Maglione et al. *Oncogene* 8:925-31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al., 1. *Biol. Chem.* 273 (35): 22272-22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is thought to play a role in the regulation of extracellular matrix degradation, cell adhesion, and migration through modulation of the expression and activity of urokinase type plasminogen activator and plasminogen activator inhibitor 1 (Pepper et al., *Proc. Natl. Acad. Sci. U.S.A.* (1998), 95(20):11709-11714).

VEGF-C can also bind KDR/VEGFR-2 and stimulate proliferation and migration of endothelial cells in vitro and angiogenesis in in vivo models (Lymboussaki et. al., *Am. J Pathol.* (1998), 153(2):395-403; Witzenbichler et al., *Am. J. Pathol.* (1998), 153(2), 381-394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14), 8413-8418).

Structurally similar to VEGF-C, VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548-553 and references therein). VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

Tie-2 (TEK) is a member of a recently discovered family of endothelial cell specific RTKs involved in critical angiogenic processes such as vessel branching, sprouting, remodeling, maturation and stability. Tie-2 is the first mammalian RTK for which both agonist ligands (e.g., Angiopoietin1 ("Ang1"), which stimulates receptor autophosphorylation and signal transduction), and antagonist ligands (e.g., Angiopoietin2 ("Ang2")), have been identified. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. Recently, significant upregulation of Tie-2 expression has been found within the vascular synovial pannus of arthritic joints of humans, consistent with a role in the inappropriate neovascularization, suggesting that Tie-2 plays a role in the progression of rheumatoid arthritis. Point mutations producing constitutively activated forms of Tie-2 have been identified in association with human venous malformation disorders. Tie-2 inhibitors are, thereful, useful in treating such disorders, and in other situations of inappropriate neovascularization.

Non-receptor tyrosine kinases represent a collection of cellular enzymes which lack extracellular and transmembrane sequences (see, Bohlen, 1993, *Oncogene* 8:2025-2031). Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses.

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2 (cdk1)/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, the hallmark of cancer, is dependent upon elevated cdk activities in these cells. The loss of control of cdk regulation is a frequent event in hyperproliferative diseases and cancer (Pines, *Current Opinion in Cell Biology*, 4:144-148 (1992); Lees, *Current Opinion in Cell Biology*, 7:773-780 (1995); Hunter and Pines, *Cell*, 79:573-582 (1994)). The inhibition of elevated cdk activities in cancer cells by cdc2/cyclin B kinase inhibitors could suppress proliferation and may restore the normal control of cell cycle progression.

Malignant cells are associated with the loss of control over one or more cell cycle elements. These elements range from cell surface receptors to the regulators of transcription and translation, including the insulin-like growth factors, insulin growth factor-I (IGF-1) and insulin growth factor-2 (IGF-2). [M. J. Ellis, "The Insulin-Like Growth Factor Network and Breast Cancer", Breast Cancer, Molecular Genetics, Pathogenesis and Therapeutics, Humana Press 1999]. The insulin growth factor system consists of families of ligands, insulin growth factor binding proteins, and receptors.

A major physiological role of the IGF-1 system is the promotion of normal growth and regeneration, and overexpressed IGF-1R can initiate mitogenesis and promote ligand-dependent neoplastic transformation. Furthermore, IGF-1R plays an important role in the establishment and maintenance of the malignant phenotype.

IGF-1R exists as a heterodimer, with several disulfide bridges. The tyrosine kinase catalytic site and the ATP binding site are located on the cytoplasmic portion of the beta subunit. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines.

Apoptosis is a ubiquitous physiological process used to eliminate damaged or unwanted cells in multicellular organisms. Disregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, regulators of apoptosis have become an important therapeutic target. It is now established that a major mode of tumor survival is escape from apoptosis. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

Inappropriately high protein kinase activity has been implicated in many diseases resulting from abnormal cellular function. This might arise either directly or indirectly, by failure of the proper control mechanisms for the kinase, related to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect.

The type 1 insulin-like growth factor receptor (IGF-1R) is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth.

Several clinical reports underline the important role of the IGF-1 pathway in human tumor development: 1) IGF-1R overexpression is frequently found in various tumors (breast, colon, lung, sarcoma.) and is often associated with an aggressive phenotype. 2) High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.*, 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses. Therefore, much research is ongoing for inhibitors of kinases involved in mediating or maintaining disease states to treat such diseases. Examples of such kinase research include, for example: (1) inhibition of c-Src (Brickell, *Critical Reviews in Oncogenesis*, 3:401-406 (1992); Courtneidge, *Seminars in Cancer Biology*, 5:236-246 (1994), raf (Powis, *Pharmacology & Therapeutics*, 62:57-95 (1994)) and the cyclin-dependent kinases (CDKs) 1, 2 and 4 in cancer (Pines, *Current Opinion in Cell Biology*, 4:144-148 (1992); Lees, *Current Opinion in Cell Biology*, 7:773-780 (1995); Hunter and Pines, *Cell*, 79:573-582 (1994)), (2) inhibition of CDK2 or PDGF-R kinase in restenosis (Buchdunger et al., *Proceedings of the National Academy of Science USA*, 92:2258-2262 (1995)), (3) inhibition of CDK5 and GSK3 kinases in Alzheimers (Hosoi et al., *Journal of Biochemistry (Tokyo)*, 117:741-749 (1995); Aplin et al., *Journal of Neurochemistry*, 67:699-707 (1996), (4) inhibition of c-Src kinase in osteoporosis (Tanaka et al., *Nature*, 383:528-531 (1996), (5) inhibition of GSK-3 kinase in type-2 diabetes (Borthwick et al., *Biochemical & Biophysical Research Communications*, 210:738-745 (1995), (6) inhibition of the p38 kinase in inflammation (Badger et al., *The Journal of Pharmacology and Experimental Therapeutics*, 279:1453-1461 (1996)), (7) inhibition of VEGF-R 1-3 and TIE-1 and 2 kinases in diseases which involve angiogenesis (Shawver et al., *Drug Discovery Today*, 2:50-63 (1997)), (8) inhibition of UL97 kinase in viral infections (He et al., *Journal of Virology*, 71:405-411 (1997)), (9) inhibition of CSF-1R kinase in bone and hematopoetic diseases (Myers et. al., *Bioorganic & Medicinal Chemistry Letters*, 7:421-424 (1997), and (10) inhibition of Lck kinase in autoimmune diseases and transplant rejection (Myers et. al., *Bioorganic & Medicinal Chemistry Letters*, 7:417-420 (1997)).

Inhibitors of certain kinases may be useful in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199-3202 (1996); Kohn et al., *Journal of Cellular Biochemistry*, 54:44-452 (1994). Inhibition of CDK 2 or 4 will prevent progression into the cycle in normal cells and limit the toxicity of cytotoxics which act in S-phase, G2 or mitosis.

Furthermore, CDK2/cyclin E activity has also been shown to regulate NF-kB. Inhibition of CDK2 activity stimulates NF-kB-dependent gene expression, an event mediated through interactions with the p300 co-activator (Perkins et al., *Science*, 275:523-527 (1997)). NF-kB regulates genes involved in inflammatory responses (such as hematopoetic growth factors, chemokines and leukocyte adhesion molecules) (Baeuerle and Henkel, *Annual Review of Immunology*, 12:141-179 (1994)) and maybe involved in the suppression of apoptotic signals within the cell (Beg and Baltimore, *Science*, 274:782-784 (1996); Wang et al., *Science*, 274:784-787 (1996); Van Antwerp et al., *Science*, 274:787-789 (1996). Thus, inhibition of CDK2 may suppress apoptosis induced by cytotoxic drugs via a mechanism which involves NF-kB and be useful where regulation of NF-kB plays a role in etiology of disease.

A further example of the usefulness of kinase inhibition is fungal infections: Aspergillosis is a common infection in immune-compromised patients (Armstrong, *Clinical Infectious Diseases*, 16: 1-7 (1993)). Inhibition of the Aspergillus kinases Cdc2/CDC28 or Nim A (Osmani et al., *EMBO Journal*, 10:2669-2679 (1991); Osmani et al., *Cell*, 67:283-291 (1991)) may cause arrest or death in the fungi, effectively treating these infections.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

In view of the importance of PTKs to the control, regulation, and modulation of cell proliferation and the diseases and disorders associated with abnormal cell proliferation, many attempts have been made to identify receptor and non-receptor tyrosine kinase inhibitors using a variety of approaches, including the use of mutant ligands (U.S. Pat. No. 4,966,849), soluble receptors and antibodies (International Patent Publication No. WO 94/10202; Kendall & Thomas, 1994, *Proc. Natl. Acad. Sci* 90:10705-09; Kim et al., 1993, *Nature* 362: 841-844), RNA ligands (Jellinek, et al., *Biochemistry* 33:1045056; Takano, et al., 1993, *Mol. Bio. Cell* 4:358A; Kinsella, et al. 1992, *Exp. Cell Res.* 199:56-62; Wright, et al., 1992, 1. *Cellular Phys.* 152:448-57) and tyrosine kinase inhibitors (International Patent Publication Nos. WO 94/03427; WO 92/21660; WO 91/15495; WO 94/14808; U.S. Pat. No. 5,330,992; Mariani, et al., 1994, *Froc. Am. Assoc. Cancer Res.* 35:2268).

More recently, attempts have been made to identify small molecules which act as tyrosine kinase inhibitors. Bis-, mono-cyclic, bicyclic or heterocyclic aryl compounds (International Patent Publication No. WO 92/20642) and vinylene-azaindole derivatives (International Patent Publication No. WO 94/14808) have been described generally as tyrosine kinase inhibitors. Styryl compounds (U.S. Pat. No. 5,217, 999), styryl-substituted pyridyl compounds (U.S. Pat. No.

5,302,606), certain quinazoline derivatives (EP Application No. 0566266 A1; *Expert Opin. Ther. Pat.* (1998), 8(4): 475-478), selenoindoles and selenides (International Patent Publication No. WO 94/03427), tricyclic polyhydroxylic compounds (International Patent Publication No. WO 92/21660) and benzylphosphonic acid compounds (International Patent Publication No. WO 91/15495) have been described as compounds for use as tyrosine kinase inhibitors for use in the treatment of cancer. Anilinocinnolines (PCT WO97/34876) and quinazoline derivative compounds (International Patent Publication No. WO 97/22596; International Patent Publication No. WO97/42187) have been described as inhibitors of angiogenesis and vascular permeability. Bis(indolylmaleimide) compounds have been described as inhibiting particular PKC serine/threonine kinase isoforms whose signal transducing function is associated with altered vascular permeability in VEGF-related diseases (International Patent Publication Nos. WO 97/40830 and WO 97/40831).

IGF-1R performs important roles in cell division, development, and metabolism, and in its activated state, plays a role in oncogenesis and suppression of apoptosis. IGF-1R is known to be overexpressed in a number of cancer cell lines (IGF-1R overexpression is linked to acromegaly and to cancer of the prostate). By contrast, down-regulation of IGF-1R expression has been shown to result in the inhibition of tumorigenesis and an increased apoptosis of tumor cells.

International Patent Publication Nos. WO 03/018021 and WO 03/018022 describe pyrimidines for treating IGF-1R related disorders, International Patent Publication Nos. WO 02/102804 and WO 02/102805 describe cyclolignans and cyclolignans as IGF-1R inhibitors, International Patent Publication No. WO 02/092599 describes pyrrolopyrimidines for the treatment of a disease which responds to an inhibition of the IGF-1R tyrosine kinase, International Patent Publication No. WO 01/72751 describes pyrrolopyrimidines as tyrosine kinase inhibitors. International Patent Publication No. WO 00/71129 describes pyrrolotriazine inhibitors of kinases. International Patent Publication No. WO 97/28161 describes pyrrolo[2,3-d]pyrimidines and their use as tyrosine kinase inhibitors.

Parrizas, et al. describes tyrphostins with in vitro and in vivo IGF-1R inhibitory activity (Endocrinology, 138:1427-1433 (1997)), and International Patent Publication No. WO 00/35455 describes heteroaryl-aryl ureas as IGF-1R inhibitors. International Patent Publication No. WO 03/048133 describes pyrimidine derivatives as modulators of IGF-1R. International Patent Publication No. WO 03/024967 describes chemical compounds with inhibitory effects towards kinase proteins. International Patent Publication No. WO 03/068265 describes methods and compositions for treating hyperproliferative conditions. International Patent Publication No. WO 00/17203 describes pyrrolopyrimidines as protein kinase inhibitors. Japanese Patent Publication No. JP 07/133,280 describes a cephem compound, its production and antimicrobial composition. A. Albert et al., *Journal of the Chemical Society*, 11: 1540-1547 (1970) describes pteridine studies and pteridines unsubstituted in the 4-position, a synthesis from pyrazines via 3,4-dyhdropteridines. A. Albert et al., *Chem. Biol. Pteridines Proc. Int. Symp.*, 4th, 4: 1-5 (1969) describes a synthesis of pteridines (unsubstituted in the 4-position) from pyrazines, via 3-4-dihydropteridines.

SUMMARY OF THE INVENTION

The present invention relates to compounds of Formula I:

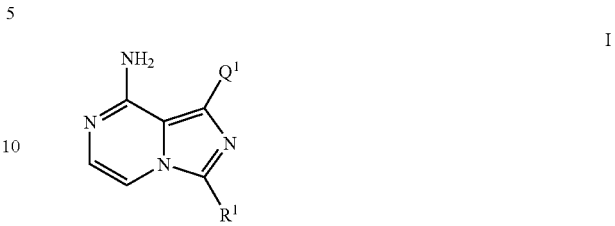

or a pharmaceutically acceptable salt thereof. The compounds of Formula I inhibit the IGF-1R enzyme and are useful for the treatment and/or prevention of various diseases and conditions that respond to treatment by inhibition of IGF-1R. The compounds of this invention are useful as inhibitors of serine/threonine and tyrosine kinases. In particular, compounds of this invention are useful as inhibitors of tyrosine kinases that are important in hyperproliferative diseases, especially cancer.

DETAILED DESCRIPTION OF THE INVENTION

The present invention relates to a compound of Formula I:

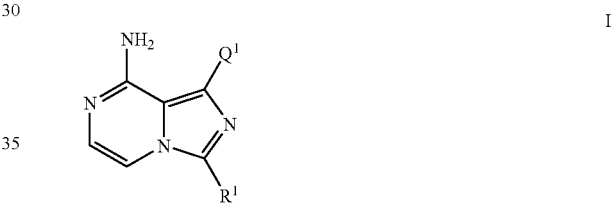

or a pharmaceutically acceptable salt thereof, wherein:

$Q^1$ is aryl$^1$, heteroaryl$^1$, cycloalkyl, heterocyclyl, cycloalkenyl, or heterocycloalkenyl, any of which is optionally substituted by one to five independent $G^1$ substituents;

$R^1$ is alkyl, cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents;

$G^1$ and $G^{41}$ are each independently halo, oxo, —$CF_3$, —$OCF_3$, —$OR^2$, —$NR^2R^3(R^{3a})_{j1}$, —$C(O)R^2$, —$CO_2R^2$, —$CONR^2R^3$, —$NO_2$, —$CN$, —$S(O)_{j1}R^2$, —$SO_2NR^2R^3$, $NR^2(C=O)R^3$, $NR^2(C=O)OR^3$, $NR^2(C=O)NR^2R^3$, $NR^2S(O)_{j1}R^3$, —(C=S)$OR^2$, —(C=O)$SR^2$, —$NR^2(C=NR^3)NR^{2a}R^{3a}$, —$NR^2(C=NR^3)OR^{2a}$, —$NR^2(C=NR^3)SR^{3a}$, —$O(C=O)OR^2$, —$O(C=O)NR^2R^3$, —$O(C=O)SR^2$, —$S(C=O)OR^2$, —$S(C=O)NR^2R^3$, $C_{0-10}$alkyl, $C_{2-10}$alkenyl, $C_{2-10}$alkynyl, $C_{1-10}$alkoxyC$_{1-10}$alkyl, $C_{1-10}$alkoxyC$_{2-10}$alkenyl, $C_{1-10}$alkoxyC$_{2-10}$alkynyl, $C_{1-10}$alkylthioC$_{1-10}$alkyl, $C_{1-10}$alkylthioC$_{2-10}$alkenyl, $C_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —$CF_3$, —$OCF_3$, —$OR^{222}$, —$NR^{222}R^{333}$ ($R^{333a})_{j1a}$, —$C(O)R^{222}$, —$CO_2R^{222}$, —$CONR^{222}R^{333}$, —NO$_2$, —CN, —S(O)$_{j1a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, —S(C=O)NR$^{222}$R$^{333}$ substituents; or —(X$^1$)$_n$—(Y$^1$)$_m$—R$^4$; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j2a}$, —C(O)R$^{222}$, —CO$_2$R$^{222}$, —CONR$^{222}$R$^{333}$, —NO$_2$, —CN, —S(O)$_{j2a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j3a}$, —C(O)R$^{222}$, —CO$_2$R$^{222}$, —CONR$^{222}$R$^{333}$, —NO$_2$, —CN, —S(O)$_{j3a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents;

G$^{11}$ is halo, oxo, —CF$_3$, —OCF$_3$, —OR$^{21}$, —NR$^{21}$R$^{31}$(R$^{3a1}$)$_{j4}$, —C(O)R$^{21}$, —CO$_2$R$^{21}$, —CONR$^{21}$R$^{31}$, —NO$_2$, —CN, —S(O)$_{j4}$R$^{21}$, —SO$_2$NR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —(C=S)OR$^{21}$, —(C=O)SR$^{21}$, —NR$^{21}$(C=NR$^{31}$)NR$^{2a1}$R$^{3a1}$, —NR$^{21}$(C=NR$^{31}$)OR$^{2a1}$, —NR$^{21}$(C=NR$^{31}$)SR$^{3a1}$, —O(C=O)OR$^{21}$, —O(C=O)NR$^{21}$R$^{31}$, —O(C=O)SR$^{21}$, —S(C=O)OR$^{21}$, —S(C=O)NR$^{21}$R$^{31}$, —P(O)OR$^{21}$OR$^{31}$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2211}$S(O)$_{j4a}$R$^{3331}$, —(C=S)OR$^{2221}$, —(C=O)SR$^{2221}$, NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j5a}$, —C(O)R$^{2221}$, —CO$_2$R$^{2221}$, —CONR$^{2221}$R$^{3331}$, —NO$_2$, —CN, —S(O)$_{j5a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j5a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j6a}$, —C(O)R$^{2221}$, —CO$_2$R$^{2221}$, —CONR$^{2221}$R$^{3331}$, —NO$_2$, —CN, —S(O)$_{j6a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j6a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or G$^{11}$ is taken together with the carbon to which it is attached to form a double bond which is substituted with R$^5$ and G$^{111}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{333a1}$ are each independently equal to C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted by one or more G$^{111}$ substituents; or aryl-C$_{0-10}$alkyl, aryl-C$_{2-10}$alkenyl, or aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more G$^{111}$ substituents; or in the case of —NR$^2$R$^3$(R$^{3a}$)$_{j1}$ or —NR$^{222}$R$^{333}$(R$^{333a}$)$_{j1a}$ or —NR$^{222}$R$^{333}$(R$^{333a}$)$_{j2a}$ or —NR$^{2221}$R$^{3331}$(R$^{333a1}$)$_{j3a}$ or —NR$^{2221}$R$^{3331}$(R$^{333a1}$)$_{j4a}$ or —NR$^{2221}$R$^{3331}$(R$^{333a1}$)$_{j5a}$ or —NR$^{2221}$R$^{3331}$(R$^{333a1}$)$_{j6a}$, R$^2$ and R$^3$ or R$^{222}$ and R$^{333}$ or R$^{2221}$ and R$^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more G$^{111}$ substituents;

X$^1$ and Y$^1$ are each independently —O—, —NR$^7$—, —S(O)$_{j7}$—, —CR$^5$R$^6$—, —N(C(O)OR$^7$)—, —N(C(O)R$^7$)—, —N(SO$_2$R$^7$)—, —CH$_2$O—, —CH$_2$S—, —CH$_2$N(R$^7$)—, —CH(NR$^7$)—, —CH$_2$N(C(O)R$^7$)—, —CH$_2$N(C(O)OR$^7$)—, —CH$_2$N(SO$_2$R$^7$)—, —CH(NHR$^7$)—, —CH(NHC(O)R$^7$)—, —CH(NHSO$_2$R$^7$)—, —CH(NHC(O)OR$^7$)—, —CH(OC(O)R$^7$)—, —CH(OC(O)NHR$^7$)—, —CH=CH—, —C≡C—, —C(=NOR$^7$)—, —C(O)—, —CH(OR$^7$)—, —C(O)N(R$^7$)—, —N(R$^7$)C(O)—, —N(R$^7$)S(O)—, —N(R$^7$)S(O)$_2$—, —OC(O)N(R$^7$)—, —N(R$^7$)C(O)N(R$^7$)—, —NR$^7$C(O)O—, —S(O)N(R$^7$)—, —S(O)$_2$N(R$^7$)—, —N(C(O)R$^7$)S(O)—, —N(C(O)R$^7$)S(O)$_2$—, —N(R$^7$)S(O)N(R$^7$)—, —N(R$^7$)S(O)$_2$N(R$^7$)—, —C(O)N(R$^7$)C(O)—, —S(O)N(R$^7$)C(O)—, —S(O)$_2$N(R$^7$)C(O)—, —OS(O)N(R$^7$)—, —OS(O)$_2$N(R$^7$)—, —N(R$^7$)S(O)O—, —N(R$^7$)S(O)$_2$O—, —N(R$^7$)S(O)C(O)—, —N(R$^7$)S(O)$_2$C(O)—, —SON(C(O)R$^7$)—, —SO$_2$N(C(O)R$^7$)—, —N(R$^7$)SON(R$^7$)—, —N(R$^7$)SO$_2$N(R$^7$)—, —C(O)O—, —N(R$^7$)P(OR$^8$)O—, —N(R$^7$)P(OR$^8$)—, —N(R$^7$)P(O)(OR$^8$)O—, —N(R$^7$)P(O)(OR$^8$)—, —N(C(O)R$^7$)P(OR$^8$)O—, —N(C(O)R$^7$)P(OR$^8$)—, —N(C(O)R$^7$)P(O)(OR$^8$)O—, —N(C(O)R$^7$)P(OR$^8$)—, —CH(R$^7$)S(O)—, —CH(R$^7$)S(O)$_2$—, —CH(R$^7$)N(C(O)OR$^7$)—, —CH(R$^7$)N(C(O)R$^7$)—, —CH(R$^7$)N $(SO_2R^7)$—, —$CH(R^7)O$—, —$CH(R^7)S$—, —$CH(R^7)N(R^7)$—, —$CH(R^7)N(C(O)R^7)$—, —$CH(R^7)N(C(O)OR^7)$—, —$CH(R^7)N(SO_2R^7)$—, —$CH(R^7)C(=NOR^7)$—, —$CH(R^7)C(O)$—, —$CH(R^7)CH(OR^7)$—, —$CH(R^7)C(O)N(R^7)$—, —$CH(R^7)N(R^7)C(O)$—, —$CH(R^7)N(R^7)S(O)$—, —$CH(R^7)N(R^7)S(O)_2$—, —$CH(R^7)OC(O)N(R^7)$—, —$CH(R^7)N(R^7)C(O)N(R^7)$—, —$CH(R^7)NR^7C(O)O$—, —$CH(R^7)S(O)N(R^7)$—, —$CH(R^7)S(O)_2N(R^7)$—, —$CH(R^7)N(C(O)R^7)S(O)$—, —$CH(R^7)N(C(O)R^7)S(O)$—, —$CH(R^7)N(R^7)S(O)N(R^7)$—, —$CH(R^7)N(R^7)S(O)_2N(R^7)$—, —$CH(R^7)C(O)N(R^7)C(O)$—, —$CH(R^7)S(O)N(R^7)C(O)$—, —$CH(R^7)S(O)_2N(R^7)C(O)$—, —$CH(R^7)OS(O)N(R^7)$—, —$CH(R^7)OS(O)_2N(R^7)$—, —$CH(R^7)N(R^7)S(O)O$—, —$CH(R^7)N(R^7)S(O)_2O$—, —$CH(R^7)N(R^7)S(O)C(O)$—, —$CH(R^7)N(R^7)S(O)_2C(O)$—, —$CH(R^7)SON(C(O)R^7)$—, —$CH(R^7)SO_2N(C(O)R^7)$—, —$CH(R^7)N(R^7)SON(R^7)$—, —$CH(R^7)N(R^7)SO_2N(R^7)$—, —$CH(R^7)C(O)O$—, —$CH(R^7)N(R^7)P(OR^8)O$—, —$CH(R^7)N(R^7)P(OR^8)$—, —$CH(R^7)N(R^7)P(O)(OR^8)O$—, —$CH(R^7)N(R^7)P(O)(OR^8)$—, —$CH(R^7)N(C(O)R^7)P(OR^8)O$—, —$CH(R^7)N(C(O)R^7)P(OR^8)$—, —$CH(R^7)N(C(O)R^7)P(O)(OR^8)O$—, or —$CH(R^7)N(C(O)R^7)P(OR^8)$—;

or $X^1$ and $Y^1$ are each independently represented by one of the following structural formulas:

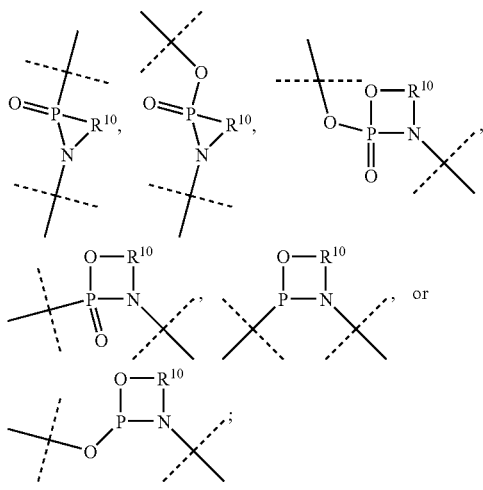

$R^{10}$, taken together with the phosphinamide or phosphonamide, is a 5-, 6-, or 7-membered aryl, heteroaryl or heterocyclyl ring system;

$R^5$, $R^6$, and $G^{111}$ are each independently a $C_{0-10}$alkyl, $C_{2-10}$alkenyl, $C_{2-10}$alkynyl, $C_{1-10}$alkoxyC$_{1-10}$alkyl, $C_{1-10}$alkoxyC$_{2-10}$alkenyl, $C_{1-10}$alkoxyC$_{2-10}$alkynyl, $C_{1-10}$alkylthioC$_{1-10}$alkyl, $C_{1-10}$alkylthioC$_{2-10}$alkenyl, $C_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C=O)R^{87}$, $NR^{77}S(O)_{j5a}R^{87}$, —$(C=S)OR^{77}$, —$(C=O)SR^{77}$, —$NR^{77}(C=NR^{87})NR^{78}R^{88}$, —$NR^{77}(C=NR^{87})OR^{78}$, —$NR^{77}(C=NR^{87})SR^{78}$, —$O(C=O)OR^{77}$, —$O(C=O)NR^{77}R^{87}$, —$O(C=O)SR^{77}$, —$S(C=O)OR^{77}$, —$P(O)OR^{77}OR^{87}$, or —$S(C=O)NR^{77}R^{87}$ substituents; or aryl-C$_{0-10}$alkyl, aryl-C$_{2-10}$alkenyl, or aryl-C$_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C=O)R^{87}$, $NR^{77}(C=O)OR^{87}$, $NR^{77}(C=O)NR^{78}R^{87}$, $NR^{77}S(O)_{j5a}R^{87}$, —$(C=S)OR^{77}$, —$(C=O)SR^{77}$, —$NR^{77}(C=NR^{87})NR^{78}R^{88}$, —$NR^{77}(C=NR^{87})OR^{78}$, —$NR^{77}(C=NR^{87})SR^{78}$, —$O(C=O)OR^{77}$, —$O(C=O)NR^{77}R^{87}$, —$O(C=O)SR^{77}$, —$S(C=O)OR^{77}$, —$P(O)OR^{77}OR^{87}$, or —$S(C=O)NR^{77}R^{87}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C=O)R^{87}$, $NR^{77}(C=O)OR^{87}$, $NR^{77}(C=O)NR^{78}R^{87}$, $NR^{77}S(O)_{j5a}R^{87}$, —$(C=S)OR^{77}$, —$(C=O)SR^{77}$, —$NR^{77}(C=NR^{87})NR^{78}R^{88}$, —$NR^{77}(C=NR^{87})OR^{78}$, —$NR^{77}(C=NR^{87})SR^{78}$, —$O(C=O)OR^{77}$, —$O(C=O)NR^{77}R^{87}$, —$O(C=O)SR^{77}$, —$S(C=O)OR^{77}$, —$P(O)OR^{77}OR^{87}$, or —$S(C=O)NR^{77}R^{87}$ substituents; or $R^5$ with $R^6$ taken together with the respective carbon atom to which they are attached, form a 3-10 membered saturated or unsaturated ring, wherein said ring is optionally substituted with $R^{69}$; or $R^5$ with $R^6$ taken together with the respective carbon atom to which they are attached, form a 3-10 membered saturated or unsaturated heterocyclic ring, wherein said ring is optionally substituted with $R^{69}$;

$R^7$ and $R^8$ are each independently H, acyl, alkyl, alkenyl, aryl, heteroaryl, heterocyclyl or cycloalkyl, any of which is optionally substituted by one or more $G^{111}$ substituents;

$R^4$ is H, alkyl, alkenyl, alkynyl, aryl, heteroaryl, cycloalkyl, heterocyclyl, cycloalkenyl, or heterocycloalkenyl, any of which is optionally substituted by one or more $G^{41}$ substituents;

$R^{69}$ is halo, —$OR^{78}$, —$SH$, —$NR^{78}R^{88}$, —$CO_2R^{78}$, —$CONR^{78}R^{88}$, —$NO_2$, —$CN$, —$S(O)_{j8}R^{78}$, —$SO_2NR^{78}R^{88}$, $C_{0-10}$alkyl, $C_{2-10}$alkenyl, $C_{2-10}$alkynyl, $C_{1-10}$alkoxyC$_{1-10}$alkyl, $C_{1-10}$alkoxyC$_{2-10}$alkenyl, $C_{1-10}$alkoxyC$_{2-10}$alkynyl, $C_{1-10}$alkylthioC$_{1-10}$alkyl, $C_{1-10}$alkylthioC$_{2-10}$alkenyl, $C_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, cyano, nitro, —$OR^{778}$, —$SO_2NR^{778}R^{888}$, or —$NR^{778}R^{888}$ substituents; or aryl-C$_{0-10}$alkyl, aryl-C$_{2-10}$alkenyl, or aryl-C$_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, haloC$_{1-10}$alkyl, haloC$_{2-10}$alkenyl, haloC$_{2-10}$alkynyl, —$COOH$, $C_{1-4}$alkoxycarbonyl, —$CONR^{778}R^{888}$, —$SO_2NR^{778}R^{888}$, or —$NR^{778}R^{888}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, haloC$_{1-10}$alkyl, haloC$_{2-10}$alkenyl, haloC$_{2-10}$alkynyl, —$COOH$, $C_{1-4}$alkoxycarbonyl, —$CONR^{778}R^{888}$, —$SO_2NR^{778}R^{888}$, or —$NR^{778}R^{888}$ substituents; or mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, or —$N(C_{1-6}$alkyl)-C$_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, haloC$_{1-}$ 10alkyl, haloC$_{2-10}$alkenyl, haloC$_{2-10}$alkynyl, —COOH, C$_{1-4}$alkoxycarbonyl, —CONR$^{778}$R$^{888}$, —SO$_2$NR$^{778}$R$^{888}$, or —NR$^{778}$R$^{888}$ substituents; or in the case of —NR$^{78}$R$^{88}$, R$^{78}$ and R$^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, C$_{1-10}$alkoxy, —SO$_2$NR$^{778}$R$^{888}$, or —NR$^{778}$R$^{888}$ substituents;

R$^{77}$, R$^{78}$, R$^{87}$, R$^{88}$, R$^{778}$, and R$^{888}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, C$_{1-10}$alkylcarbonyl, C$_{2-10}$alkenylcarbonyl, C$_{2-10}$alkynylcarbonyl, C$_{1-10}$alkoxycarbonyl, C$_{1-10}$alkoxycarbonylC$_{1-10}$alkyl, monoC$_{1-6}$alkylaminocarbonyl, diC$_{1-6}$alkylaminocarbonyl, mono(aryl)aminocarbonyl, di(aryl)aminocarbonyl, or C$_{1-10}$alkyl(aryl)aminocarbonyl, any of which is optionally substituted with one or more independent halo, cyano, hydroxy, nitro, C$_{1-10}$alkoxy, —SO$_2$N(C$_{0-4}$alkyl)(C$_{0-4}$alkyl), or —N(C$_{0-4}$alkyl)(C$_{0-4}$alkyl) substituents; or aryl-C$_{0-10}$alkyl, aryl-C$_{2-10}$alkenyl, or aryl-C$_{2-10}$alkynyl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-10}$alkyl), —SO$_2$N(C$_{0-4}$alkyl)(C$_{0-4}$alkyl), or —N(C$_{0-4}$alkyl)(C$_{0-4}$alkyl) substituents; or hetaryl-C$_{0-10}$alkyl, hetaryl-C$_{2-10}$alkenyl, or hetaryl-C$_{2-10}$alkynyl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-4}$alkyl), —SO$_2$N(C$_{0-4}$alkyl)(C$_{0-4}$alkyl), or —N(C$_{0-4}$alkyl)(C$_{0-4}$alkyl) substituents; or mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, or —N(C$_{1-6}$alkyl)-C$_{1-6}$alkyl-aryl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-4}$alkyl), —SO$_2$N(C$_{0-4}$alkyl)(C$_{0-4}$alkyl), or —N(C$_{0-4}$alkyl)(C$_{0-4}$alkyl) substituents; and n, m, j1, j1a, j2a, j3a, j4, j4a, j5a, j6a, j7, and j8 are each independently equal to 0, 1, or 2.

In an aspect of the present invention, a compound is represented by Formula I, or a pharmaceutically acceptable salt thereof, wherein R$^1$ is cycloalkyl, aryl, heteroaryl, aralkyl, or heterocyclyl, any of which is optionally substituted by one or more G$^{11}$ substituents and the other variables are described as above for Formula I.

In a second aspect of the present invention, a compound is represented by Formula I, or a pharmaceutically acceptable salt thereof, wherein R$^1$ is cycloalkyl, optionally substituted by one or more G$^{11}$ substituents and the other variables are described as above for Formula I.

In an embodiment of this second aspect, a compound is represented by Formula I, or a pharmaceutically acceptable salt thereof, wherein R$^1$ is cycloalkyl, optionally substituted by one or more G$^{11}$ substituents; Q$^1$ is aryl$^1$ or heteroaryl$^1$, any of which is substituted by one to five independent G$^1$ substituents;

G$^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C═O)R$^3$, NR$^2$(C═O)OR$^3$, NR$^2$(C═O)NR$^2$R$^3$, NR$^2$S(O)$_{j1}$R$^3$, —O(C═O)OR$^2$, —O(C═O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C═O)R$^{333}$, NR$^{222}$(C═O)OR$^{333}$, NR$^{222}$(C═O)NR$^{222}$R$^{333}$, NR$^{222}$S(O)$_{j1a}$R$^{333}$, —NR$^{222}$(C═NR$^{333}$)NR$^{222a}$R$^{333a}$, or —O(C═O)NR$^{222}$R$^{333}$ substituents; or —(X$^1$)$_n$—(Y$^1$)$_m$—R$^4$; or aryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C═O)R$^{333}$, NR$^{222}$(C═O)OR$^{333}$, NR$^{222}$(C═O)NR$^{222}$R$^{333}$, NR$^{222}$S(O)$_{j2a}$R$^{333}$, —NR$^{222}$(C═NR$^{333}$)NR$^{222a}$R$^{333a}$, or —O(C═O)NR$^{222}$R$^{333}$ substituents; or hetaryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C═O)R$^{333}$, NR$^{222}$(C═O)OR$^{333}$, NR$^{222}$(C═O)NR$^{222}$R$^{333}$, NR$^{222}$S(O)$_{j3a}$R$^{333}$, —NR$^{222}$(C═NR$^{333}$)NR$^{222a}$R$^{333a}$, or —O(C═O)NR$^{222}$R$^{333}$ substituents;

and the other variables are described as above for Formula I.

In another embodiment of this second aspect, a compound is represented by Formula I, or a pharmaceutically acceptable salt thereof, wherein R$^1$ is cycloalkyl, optionally substituted by one or more G$^{11}$ substituents; Q$^1$ is aryl$^1$ or heteroaryl$^1$, any of which is substituted by one to five independent G$^1$ substituents;

G$^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C═O)R$^3$, NR$^2$(C═O)OR$^3$, NR$^2$(C═O)NR$^2$R$^3$, NR$^2$S(O)$_{j1}$R$^3$, —O(C═O)OR$^2$, —O(C═O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C═O)R$^{333}$, NR$^{222}$(C═O)OR$^{333}$, NR$^{222}$(C═O)NR$^{222}$R$^{333}$, NR$^{222}$S(O)$_{j1a}$R$^{333}$, —NR$^{222}$(C═NR$^{333}$)NR$^{222a}$R$^{333a}$, or —O(C═O)NR$^{222}$R$^{333}$ substituents; or —(X$^1$)$_n$—(Y$^1$)$_m$—R$^4$;

and the other variables are described as above for Formula I.

In another embodiment of this second aspect, a compound is represented by Formula I, or a pharmaceutically acceptable salt thereof, wherein R$^1$ is cycloalkyl, optionally substituted by one or more G$^{11}$ substituents; Q$^1$ is aryl$^1$ or heteroaryl$^1$, any of which is substituted by one to five independent G$^1$ substituents;

at least one of said G$^1$ substituents is —(X$^1$)$_n$—(Y$^1$)$_m$—R$^4$; X$^1$ and Y$^1$ are each independently equal to —O—, —NR$^7$—, —CR$^5$R$^6$—, —S(O)$_{j7}$—, or —C(O)—;

and the other variables are described as above for Formula I.

In another embodiment of this second aspect, a compound is represented by Formula I, or a pharmaceutically acceptable salt thereof, wherein R$^1$ is cycloalkyl, optionally substituted by one or more $G^{11}$ substituents; wherein $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;
$X^1$ and $Y^1$ are each independently equal to $-O-$ or $-CR^5R^6-$;
and the other variables are described as above for Formula I.

In another embodiment of this second aspect, a compound is represented by Formula I, or a pharmaceutically acceptable salt thereof, wherein $R^1$ is cycloalkyl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;
$X^1$ and $Y^1$ are each independently equal to $-O-$ or $-CH_2-$;
and the other variables are described as above for Formula I.

In another embodiment of this second aspect, a compound is represented by Formula I, or a pharmaceutically acceptable salt thereof, wherein $R^1$ is cycloalkyl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;
$R^4$ is H, alkyl, aryl, heteroaryl, cycloalkyl, heterocyclyl, cycloalkenyl, or heterocycloalkenyl, any of which is optionally substituted by one or more independent $G^{41}$ substituents;
and the other variables are described as above for Formula I.

In another embodiment of this second aspect, a compound is represented by Formula I, or a pharmaceutically acceptable salt thereof, wherein $R^1$ is cycloalkyl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;
$R^4$ is aryl or heteroaryl, optionally substituted by one or more independent $G^{41}$ substituents;
and the other variables are described as above for Formula I.

In another embodiment of this second aspect, a compound is represented by Formula I, or a pharmaceutically acceptable salt thereof, wherein $R^1$ is cycloalkyl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;
$R^4$ is aryl or heteroaryl, optionally substituted by one or more $G^{11}$ substituents;
and the other variables are described as above for Formula I.

In another embodiment of this second aspect, a compound is represented by Formula I, or a pharmaceutically acceptable salt thereof, wherein $R^1$ is cycloalkyl substituted by one or more $G^{11}$ substituents;

$G^{11}$ is $-OR^{21}$, $-NR^{21}R^{31}(R^{31a})_{j4}$, $-C(O)R^{21}$, $-CO_2R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{333a})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)$ $OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})$ $NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)$ $NR^{2221}R^{3331}$, $-O(C=O)SR^{2221}$, $-S(C=O)OR^{2221}$, or $-S(C=O)NR^{2221}R^{3331}$ substituents; or aryl-$C_{0-10}$alkyl, aryl-$C_{2-10}$alkenyl, or aryl-$C_{2-10}$alkynyl, any of which is optionally substituted with one or more independent halo, $-CF_3$, $-OCF_3$, $-OR^{2221}$, $-NR^{2221}R^{3331}(R^{333a1})_{j5a}$, $-C(O)R^{2221}$, $-CO_2R^{2221}$, $-CONR^{2221}R^{3331}$, $-NO_2$, $-CN$, $-S(O)_{j5a}R^{2221}$, $-SO_2NR^{2221}R^{3331}$, $NR^{2221}(C=O)$ $R^{3331}$, $NR^{2221}(C=O)OR^{3331}$, $NR^{2221}(C=O)NR^{2221}R^{3331}$, $NR^{2221}S(O)_{j5a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)$ $SR^{2221}$, $-S(C=O)OR^{2221}$, or $-S(C=O)NR^{2221}R^{3331}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, $-CF_3$, $-OCF_3$, $-OR^{2221}$, $-NR^{2221}R^{3331}(R^{333a1})_{j6a}$, $-C(O)R^{2221}$, $-CO_2R^{2221}$, $-CONR^{2221}R^{3331}$, $-NO_2$, $-CN$, $-S(O)_{j6a}$ $R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j6a}$ $R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})$ $OR^{222a1}$, $-NR^{2221}(C=NR^{3331})SR^{333a1}$, $-O(C=O)$ $OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents;

and the other variables are described as above for Formula I.

In another embodiment of this second aspect, a compound is represented by Formula I, or a pharmaceutically acceptable salt thereof, wherein $R^1$ is cycloalkyl substituted by one or more independent $G^{11}$ substituents;

$G^{11}$ is $-OR^{21}$, $-NR^{21}R^{31}$, $-CO_2R^{21}$, $-C(O)R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{333a})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)$ $OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})$ $NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)$ $NR^{2221}R^{3331}$, $-O(C=O)SR^{2221}$, $-S(C=O)OR^{2221}$, or $-S(C=O)NR^{2221}R^{3331}$ substituents;

and the other variables are described as above for Formula I.

In another embodiment of this second aspect, a compound is represented by Formula I, or a pharmaceutically acceptable salt thereof, wherein $R^1$ is cis- or trans-cyclobutyl substituted at the 3-position by $G^{11}$;

$G^{11}$ is $-OH$, $-NH_2$, $-N(CH_3)_2$, $-NHAc$, $-NH(CO)$ $NHCH_3$, $-NH(CO)OCH_3$, $-CH_2OH$, $-CH_2NH_2$, $-CH_2NHAc$, $CO_2H$, $CONH_2$, $-CH_2N(CH_3)_2$, $-CH_2NH$ $(CO)NHMe$, $-CH_2NH(CO)OCH_3$, $CO_2CH_3$, $CONHCH_3$,

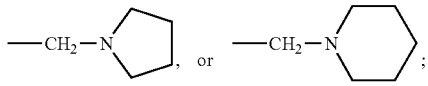

and the other variables are described as above for Formula I.

In another embodiment of this second aspect, a compound is represented by Formula I, or a pharmaceutically acceptable salt thereof, wherein $R^1$ is cis- or trans-cyclohexyl substituted at the 4-position by $G^{11}$;

$G^{11}$ is —OH, —$NH_2$, —$N(CH_3)_2$, —NHAc, —NH(CO)NHCH$_3$, —NH(CO)OCH$_3$, —CH$_2$OH, —CH$_2$NH$_2$, —CH$_2$NHAc, CO$_2$H, CONH$_2$, —CH$_2$N(CH$_3$)$_2$, —CH$_2$NH(CO)NHMe, —CH$_2$NH(CO)OCH$_3$, CO$_2$CH$_3$, CONHCH$_3$,

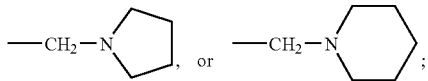

and the other variables are described as above for Formula I.

In another embodiment of this second aspect, a compound is represented by Formula I, or a pharmaceutically acceptable salt thereof, wherein $Q^1$ is aryl$^1$ substituted by one to five independent $G^1$; at least one of said $G^1$ substituents is —$(X^1)_n$—$(Y^1)_m$—$R^4$; n and m are both equal to 1;

$X^1$ is —O—;

$Y^1$ is —CH$_2$—;

$R^4$ is aryl, optionally substituted by one or more $G^{41}$ substituents;

$R^1$ is cis- or trans-cyclohexyl substituted at the 4-position by $G^{11}$;

$G^{11}$ is —OH, —$NH_2$, —$N(CH_3)_2$, —NHAc, —NH(CO)NHCH$_3$, —NH(CO)OCH$_3$, —CH$_2$OH, —CH$_2$NH$_2$, —CH$_2$NHAc, CO$_2$H, CONH$_2$, —CH$_2$N(CH$_3$)$_2$, —CH$_2$NH(CO)NHMe, —CH$_2$NH(CO)OCH$_3$, CO$_2$CH$_3$, CONHCH$_3$,

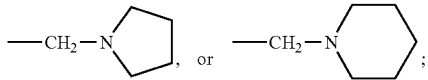

and the other variables are described as above for Formula I.

In still another embodiment of this second aspect, a compound is represented by Formula I, or a pharmaceutically acceptable salt thereof, wherein $Q^1$ is aryl$^1$ substituted by one to five independent $G^1$; at least one of said $G^1$ substituents is —$(X^1)_n$—$(Y^1)_m$—$R^4$; n and m are both equal to 1;

$X^1$ is —O—;

$Y^1$ is —CH$_2$—;

$R^4$ is aryl, optionally substituted by one or more $G^{41}$ substituents;

$R^1$ is cis- or trans-cyclobutyl substituted at the 3-position by $G^{11}$;

$G^{11}$ is —OH, —$NH_2$, —$N(CH_3)_2$, —NHAc, —NH(CO)NHCH$_3$, —NH(CO)OCH$_3$, —CH$_2$OH, —CH$_2$NH$_2$, —CH$_2$NHAc, CO$_2$H, CONH$_2$, —CH$_2$N(CH$_3$)$_2$, —CH$_2$NH(CO)NHMe, —CH$_2$NH(CO)OCH$_3$, CO$_2$CH$_3$, CONHCH$_3$,

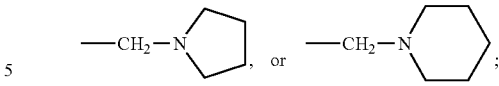

and the other variables are described as above for Formula I.

In a third aspect of the present invention, a compound is represented by Formula I, or a salt thereof, wherein $R^1$ is aryl, optionally substituted by one or more $G^{11}$ substituents, and the other variables are described as above for Formula I.

In an embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

$G^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, NR$^{222}$(C=NR$^{333}$)NR$^{222a}$R$^{333a}$, or —O(C=O)NR$^{222}$R$^{333}$ substituents; or —$(X^1)_n$—$(Y^1)_m$—$R^4$; or aryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —NR$^{222}$(C=NR$^{333}$)NR$^{222a}$R$^{333a}$, or —O(C=O)NR$^{222}$R$^{333}$ substituents; or hetaryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —NR$^{222}$(C=NR$^{333}$)NR$^{222a}$R$^{333a}$, or —O(C=O)NR$^{222}$R$^{333}$ substituents;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

$G^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —NR$^{222}$(C=NR$^{333}$)NR$^{222a}$R$^{333a}$, or —O(C=O)NR$^{222}$R$^{333}$ substituents; or —$(X^1)_n$—$(Y^1)_m$—$R^4$;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;

$X^1$ and $Y^1$ are each independently equal to $-O-$, $-NR^7-$, $-CR^5R^6-$, $-S(O)_{j7}-$, or $-C(O)-$;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;

$X^1$ and $Y^1$ are each independently equal to $-O-$ or $-CR^5R^6-$;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;

$X^1$ and $Y^1$ are each independently equal to $-O-$ or $-CH_2-$;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;

$R^4$ is H, alkyl, aryl, heteroaryl, cycloalkyl, heterocyclyl, cycloalkenyl, or heterocycloalkenyl, any of which is optionally substituted by one or more independent $G^{41}$ substituents;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;

$R^4$ is aryl or heteroaryl, optionally substituted by one or more independent $G^{41}$ substituents;

and the other variables are described as above for Formula I.

In another embodiment of this third aspect, a compound is represented by Formula I, or a pharmaceutically acceptable salt thereof, wherein $R^1$ is aryl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is $-(X^1)_n-(Y^1)_m-R^4$;

$R^4$ is aryl or heteroaryl, optionally substituted by one or more $G^{41}$ substituents;

and the other variables are described as above for Formula I.

In another embodiment of this third aspect, a compound is represented by Formula I, or a pharmaceutically acceptable salt thereof, wherein $R^1$ is cycloalkyl substituted by one or more independent $G^{11}$ substituents, $G^{11}$ is $-OR^{21}$, $-NR^{21}R^{31}(R^{31a})_{j4}$, $-C(O)R^{21}$, $-CO_2R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{333a})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents; or aryl-C$_{0-10}$alkyl, aryl-C$_{2-10}$alkenyl, or aryl-C$_{2-10}$alkynyl, any of which is optionally substituted with one or more independent halo, $-CF_3$, $-OCF_3$, $-OR^{2221}$, $-NR^{2221}R^{3331}(R^{333a1})_{j5a}$, $-C(O)R^{2221}$, $-CO_2R^{2221}$, $-CONR^{2221}R^{3331}$, $-NO_2$, $-CN$, $-S(O)_{j5a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j5a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, $-CF_3$, $-OCF_3$, $-OR^{2221}$, $-NR^{2221}R^{3331}(R^{333a1})_{j6a}$, $-C(O)R^{2221}$, $-CO_2R^{2221}$, $-CONR^{2221}R^{3331}$, $-NO_2$, $-CN$, $-S(O)_{j6a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j6a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents;

and the other variables are described as above for Formula I.

In another embodiment of this third aspect, a compound is represented by Formula I, or a pharmaceutically acceptable salt thereof, wherein $R^1$ is cycloalkyl substituted by one or more independent $G^{11}$ substituents;

$G^{11}$ is $-OR^{21}$, $-NR^{21}R^{31}$, $-CO_2R^{21}$, $-C(O)R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, $-CF_3$, $-OCF_3$, $-OR^{2221}$, $-NR^{2221}R^{3331}(R^{333a1})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)$ $NR^{2221}R^{3331}$, —O(C=O)$SR^{2221}$, —S(C=O)$OR^{2221}$, or —S(C=O)$NR^{2221}R^{3331}$ substituents;

and the other variables are described as above for Formula I.

In another embodiment of this third aspect, a compound is represented by Formula I, or a pharmaceutically acceptable salt thereof, wherein $R^1$ is phenyl optionally substituted by one or more independent $G^{11}$ substituents;

and the other variables are described as above for Formula I.

In still another embodiment of this third aspect, a compound is represented by Formula I, or a pharmaceutically acceptable salt thereof, wherein $Q^1$ is aryl$^1$ substituted by one to five $G^1$ substituents; at least one of said $G^1$ substituents is —(X$^1$)$_n$—(Y$^1$)$_m$—R$^4$;

$X^1$ is —O—;

$Y^1$ is —CH$_2$—;

$R^4$ is aryl, optionally substituted by one or more $G^{41}$ substituents;

$R^1$ is phenyl substituted by one or more independent $G^{11}$ substituents;

and the other variables are described as above for Formula I.

In a fourth aspect of the present invention, a compound is represented by Formula I, or a salt thereof, wherein $R^1$ is heterocyclyl, optionally substituted by one or more $G^{11}$ substituents and the other variables are described as above for Formula I.

In an embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

$G^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, NR$^{222}$(C=NR$^{333}$)NR$^{222a}$R$^{333a}$, or —O(C=O)NR$^{222}$R$^{333}$ substituents; or —(X$^1$), —(Y$^1$)$_m$—R$^4$; or aryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —NR$^{222}$(C=NR$^{333}$)NR$^{222a}$R$^{333a}$, or —O(C=O)NR$^{222}$R$^{333}$ substituents; or hetaryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —NR$^{222}$(C=NR$^{333}$)NR$^{222a}$R$^{333a}$, or —O(C=O)NR$^{222}$R$^{333}$ substituents;

and the other variables are described as above for Formula I.

In another embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

$G^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —NR$^{222}$(C=NR$^{333}$)NR$^{222a}$R$^{333a}$, or —O(C=O)NR$^{222}$R$^{333}$ substituents; or —(X$^1$)$_n$—(Y$^1$)$_m$—R$^4$;

and the other variables are described as above for Formula I.

In another embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

wherein at least one of said $G^1$ substituents is —(X$^1$)$_n$—(Y$^1$)$_m$—R$^4$;

$X^1$ and $Y^1$ are each independently equal to —O—, —NR$^7$—, —CR$^5$R$^6$—, —S(O)$_{j7}$—, or —C(O)—;

and the other variables are described as above for Formula I.

In another embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

at least one of said $G^1$ substituents is —(X$^1$)$_n$—(Y$^1$)$_m$—R$^4$;

$X^1$ and $Y^1$ are each independently equal to —O— or —CR$^5$R$^6$—;

and the other variables are described as above for Formula I.

In another embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

wherein at least one of said $G^1$ substituents is —(X$^1$)$_n$—(Y$^1$)$_m$—R$^4$;

$X^1$ and $Y^1$ are each independently equal to —O— or —CH$_2$—;

and the other variables are described as above for Formula I.

In another embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

wherein at least one of said $G^1$ substituents is —(X$^1$)$_n$—(Y$^1$)$_m$—R$^4$;

$R^4$ is H, alkyl, aryl, heteroaryl, cycloalkyl, heterocyclyl, cycloalkenyl, or heterocycloalkenyl, any of which is optionally substituted by one or more independent $G^{41}$ substituents;

and the other variables are described as above for Formula I.

In another embodiment of this fourth aspect, a compound is represented by Formula I, or a pharmaceutically acceptable salt thereof, wherein $R^1$ is heterocyclyl, optionally substituted by one or more $G^{11}$ substituents; $Q^1$ is aryl$^1$ or heteroaryl$^1$, any of which is substituted by one to five independent $G^1$ substituents;

wherein at least one of said $G^1$ substituents is $-(X^1)_n-(Y^1)_m-R^4$;

$R^4$ is aryl or heteroaryl, optionally substituted by one or more independent $G^{41}$ substituents;

and the other variables are described as above for Formula I.

In another embodiment of this fourth aspect, a compound is represented by Formula I, or a pharmaceutically acceptable salt thereof, wherein $Q^1$ is aryl$^1$ or heteroaryl$^1$, any of which is substituted by one to five independent $G^1$ substituents;

wherein at least one of said $G^1$ substituents is $-(X^1)_n-(Y^1)_m-R^4$;

$R^4$ is aryl or heteroaryl, optionally substituted by one or more $G^{41}$ substituents;

and the other variables are described as above for Formula I.

In another embodiment of this fourth aspect, a compound is represented by Formula I, or a pharmaceutically acceptable salt thereof, wherein $R^1$ is heterocyclyl represented by the structural formula:

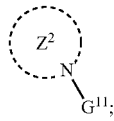

and the other variables are described as above for Formula I.

In another embodiment of this fourth aspect, a compound is represented by Formula I, or a pharmaceutically acceptable salt thereof, wherein $R^1$ is heterocyclyl represented by the structural formula:

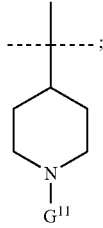

wherein $G^{11}$ is equal to $-C(O)R^2$, $-CO_2R^2$, $-CONR^2R^3$, $-SO_2NR^2R^3$, $-S(O)_{j1}R^3$, $C_{0-10}$alkyl, $C_{2-10}$alkenyl, $C_{1-10}$alkoxyC$_{1-10}$alkyl, $C_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, $-NR^{222}(C=NR^{333})NR^{222a}R^{333a}$, or $-O(C=O)NR^{222}R^{333}$ substituents; or aryl-C$_{0-10}$alkyl, optionally substituted with one or more independent halo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j2a}R^{333}$, $-NR^{222}(C=NR^{333})NR^{222a}R^{333a}$, or $-O(C=O)NR^{222}R^{333}$ substituents; or hetaryl-C$_{0-10}$alkyl, optionally substituted with one or more independent halo, $-CF_3$, $-OCF_3$, $-OR^{222}$, $-NR^{222}R^{333}$, $-C(O)R^{222}$, $-CO_2R^{222}R^{222}$, $-CONR^{222}R^{333}$, $-SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j3a}R^{333}$, $NR^{222}(C=NR^{333})NR^{222a}R^{333a}$, or $-O(C=O)NR^{222}R^{333}$ substituents;

and the other variables are described as above for Formula I.

In another embodiment of this fourth aspect, a compound is represented by Formula I, or a pharmaceutically acceptable salt thereof, wherein $R^1$ is heterocyclyl represented by the structural formula:

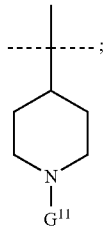

wherein $G^{11}$ is equal to $-C(O)R^2$, $-CO_2R^3$, $-CONR^2R^3$, $-SO_2NR^2R^3$, $-S(O)_{j1}R^3$, $C_{0-10}$alkyl, $C_{2-10}$alkenyl, $C_{1-10}$alkoxyC$_{1-10}$alkyl, $C_{1-10}$alkylthio C$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, $-NR^{222}(C=NR^{333})NR^{222a}R^{333a}$, or $-O(C=O)NR^{222}R^{333}$ substituents; or $-(X^1)_n-(Y^1)_m-R^4$;

and the other variables are described as above for Formula I.

In another embodiment of this fourth aspect, a compound is represented by Formula I, or a pharmaceutically acceptable salt thereof, wherein $R^1$ is heterocyclyl represented by the structural formula:

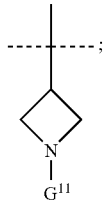

wherein $G^{11}$ is equal to $-C(O)R^2$, $-CO_2R^2$, $-CONR^2R^3$, $-SO_2NR^2R^3$, $-S(O)_{j1}R^3$, $C_{0-10}$alkyl, $C_{2-10}$alkenyl, $C_{1-10}$alkoxyC$_{1-10}$alkyl, $C_{1-10}$alkylthio C$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, $-CF_3$, $-OCF_3$, $-OR^{222}$, $-NR^{222}R^{333}$, $-C(O)R^{222}$, $-CO_2R^{222}$, $-CONR^{222}R^{333}$, $-SO_2$ $NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, $-NR^{222}(C=NR^{333})$ NR$^{222a}$R$^{333a}$, or —O(C=O)NR$^{222}$R$^{333}$ substituents; or —(X$^1$)$_n$—(Y$^1$)$_m$—R$^4$; or aryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$R$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —NR$^{222}$(C=NR$^{333}$)NR$^{222a}$R$^{333a}$, or —O(C=O)NR$^{222}$R$^{333}$ substituents; or hetaryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —NR$^{222}$(C=NR$^{333}$)NR$^{222a}$R$^{333a}$, or —O(C=O)NR$^{222}$R$^{333}$ substituents;

and the other variables are described as above for Formula I.

In still another embodiment of this fourth aspect, a compound is represented by Formula I, or a pharmaceutically acceptable salt thereof, wherein R$^1$ is heterocyclyl represented by the structural formula:

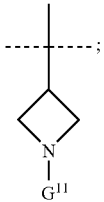

wherein G$^{11}$ is equal to —C(O)R$^2$, —CO$_2$R$^2$, —CONR$^2$R$^3$, —SO$_2$NR$^2$R$^3$, —S(O)$_{j1}$R$^3$, C$_{0-10}$alkyl, C$_{2-10}$alkenyl, C$_{1-10}$alkoxyC$_{1-10}$alkyl, C$_{1-10}$alkylthioC$_{1-10}$alkyl, cycloC$_{3-8}$alkyl, cycloC$_{3-8}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —NR$^{222}$(C=NR$^{333}$)NR$^{222a}$R$^{333a}$, or —O(C=O)NR$^{222}$R$^{333}$ substituents; or —(X$^1$)$_n$—(Y$^1$)$_m$—R$^4$;

and the other variables are described as above for Formula I.

The compounds of the present invention include compounds represented by Formula I, or a pharmaceutically salt thereof, wherein Q$^1$ is aryl$^1$ or heteroaryl$^1$, any of which is optionally substituted by one or more independent G$^1$ substituents; or wherein Q$^1$ is heteroaryl$^1$, any of which is optionally substituted by one or more independent G$^1$ substituents; or wherein Q$^1$ is aryl$^1$, any of which is optionally substituted by one or more independent G$^1$ substituents; or wherein G$^1$ is halo, —CF$_3$, —OCF$_3$, —OR$^2$, —NR$^2$R$^3$, —C(O)R$^2$, —CO$_2$R$^2$, —CONR$^2$R$^3$, —S(O)$_{j1}$R$^2$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{222}$, —NR$^{222}$R$^{333}$ (R$^{333a}$)$_{j1a}$, —C(O)R$^{222}$, —CO$_2$R$^{222}$, —CONR$^{222}$R$^{333}$, —NO$_2$, —CN, —S(O)$_{j1a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, —S(C=O)NR$^{222}$R$^{333}$ substituents; or —(X$^1$)$_n$—(Y$^1$)$_m$—R$^4$; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j2a}$, —C(O)R$^{222}$, —CO$_2$R$^{222}$, —CONR$^{222}$R$^{333}$, —NO$_2$, —CN, —S(O)$_{j2a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or hetaryl-C$_{010}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j3a}$, —C(O)R$^{222}$, —CO$_2$R$^{222}$, —CONR$^{222}$R$^{333}$, —NO$_2$, —CN, —S(O)$_{j3a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or wherein G$^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, C$_{1-10}$alkoxyC$_{1-10}$alkyl, C$_{1-10}$alkoxyC$_{2-10}$alkenyl, C$_{1-10}$alkylthioC$_{1-10}$alkyl, C$_{1-10}$alkylthioC$_{2-10}$alkenyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, or heterocyclyl-C$_{0-10}$alkyl, or heterocyclyl-C$_{2-10}$alkenyl, any of which is optionally substituted with one or more independent oxo, —CF$_3$, —OCF$_3$, —OR$^{222}$, —NR$^{222}$R$^{333}$, —C(O)R$^{222}$, CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —NR$^{222}$(C=NR$^{333}$)NR$^{222a}$R$^{333a}$, or —O(C=O)NR$^{222}$R$^{333}$ substituents; or —(X$^1$)$_n$—(Y$^1$)$_m$—R$^4$; or aryl-C$_{0-10}$alkyl optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —NR$^{222}$(C=NR$^{333}$)NR$^{222a}$R$^{333a}$, or —O(C=O)NR$^{222}$R$^{333}$ substituents; or hetaryl-C$_{0-10}$alkyl, optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —NR$^{222}$(C=NR$^{333}$)NR$^{222a}$R$^{333a}$, or —O(C=O)NR$^{222}$R$^{333}$ substituents; or wherein G$^1$ is halo, —OR$^2$, —NR$^2$R$^3$, —C(O)R$^2$, —CO$_2$R$^2$, —CONR$^2$R$^3$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —O(C=O)OR$^2$, —O(C=O)NR$^2$R$^3$, C$_{0-10}$alkyl, C$_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, or heterocyclyl-$C_{0-10}$alkyl, or heterocyclyl-$C_{2-10}$alkenyl, any of which is optionally substituted with one or more independent oxo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, —$NR^{222}(C=NR^{333})NR^{222a}R^{333a}$, or —$O(C=O)NR^{222}R^{333}$ substituents; or —$(X^1)_n$—$(Y^1)_m$—$R^4$; or aryl-$C_{0-10}$alkyl, optionally substituted with one or more independent halo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j2a}R^{333}$, —$NR^{222}(C=NR^{333})NR^{222a}R^{333a}$, or —$O(C=O)NR^{222}R^{333}$ substituents; or hetaryl-$C_{0-10}$alkyl, optionally substituted with one or more independent halo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j3a}R^{333}$, —$NR^{222}(C=NR^{333})NR^{222a}R^{333a}$, or —$O(C=O)NR^{222}R^{333}$ substituents; or wherein $G^1$ is halo, —$OR^2$, —$NR^2R^3$, —$C(O)R^2$, —$CO_2R^2$, —$CONR^2R^3$, —$SO_2NR^2R^3$, $NR^2(C=O)R^3$, $NR^2(C=O)OR^3$, $NR^2(C=O)NR^2R^3$, $NR^2S(O)_{j1}R^3$, —$O(C=O)OR^2$, —$O(C=O)NR^2R^3$, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, or heterocyclyl-$C_{0-10}$alkyl, or heterocyclyl-$C_{2-10}$alkenyl, any of which is optionally substituted with one or more independent oxo, —$CF_3$, —$OCF_3$, —$OR^{222}$, —$NR^{222}R^{333}$, —$C(O)R^{222}$, —$CO_2R^{222}$, —$CONR^{222}R^{333}$, —$SO_2NR^{222}R^{333}$, $NR^{222}(C=O)R^{333}$, $NR^{222}(C=O)OR^{333}$, $NR^{222}(C=O)NR^{222}R^{333}$, $NR^{222}S(O)_{j1a}R^{333}$, —$NR^{222}(C=NR^{333})NR^{222a}R^{333a}$, or —$O(C=O)NR^{222}R^{333}$ substituents; or —$(X^1)_n$—$(Y^1)_m$—$R^4$; or wherein $X^1$ and $Y^1$ are each independently —O—, —$NR^7$—, —$S(O)_{j7}$—, —$CR^5R^6$—, —$N(C(O)OR^7)$—, —$N(C(O)R^7)$—, —$N(SO_2R^7)$—, —$CH_2O$—, —$CH_2S$—, —$CH_2N(R^7)$—, —$CH(NR^7)$—, —$CH_2N(C(O)R^7)$—, —$CH_2N(C(O)OR^7)$—, —$CH_2N(SO_2R^7)$—, —$CH(NHR^7)$—, —$CH(NHC(O)R^7)$—, —$CH(NHSO_2R^7)$—, —$CH(NHC(O)OR^7)$—, —$CH(OC(O)R^7)$—, —$CH(OC(O)NHR^7)$—, —$C(O)$—, —$CH(OR^7)$—, —$C(O)N(R^7)$—, —$N(R^7)C(O)$—, —$N(R^7)S(O)$—, —$N(R^7)S(O)_2$—, —$OC(O)N(R^7)$—, —$N(R^7)C(O)N(R^7)$—, —$NR^7C(O)O$—, —$S(O)N(R^7)$—, —$S(O)_2N(R^7)$—, —$N(C(O)R^7)S(O)$—, —$N(C(O)R^7)S(O)_2$—, —$N(R^7)S(O)N(R^7)$—, —$N(R^7)S(O)_2N(R^7)$—, —$C(O)N(R^7)C(O)$—, —$S(O)N(R^7)C(O)$—, —$S(O)_2N(R^7)C(O)$—, —$OS(O)N(R^7)$—, —$OS(O)_2N(R^7)$—, —$N(R^7)S(O)O$—, —$N(R^7)S(O)_2O$—, —$N(R^7)S(O)C(O)$—, —$N(R^7)S(O)_2C(O)$—, —$SON(C(O)R^7)$—, —$SO_2N(C(O)R^7)$—, —$N(R^7)SON(R^7)$—, —$N(R^7)SO_2N(R^7)$—, —$C(O)O$—, —$CH(R^7)S(O)$—, —$CH(R^7)S(O)_2$—, —$CH(R^7)N(C(O)OR^7)$—, —$CH(R^7)N(C(O)R^7)$—, —$CH(R^7)N(SO_2R^7)$—, —$CH(R^7)O$—, —$CH(R^7)S$—, —$CH(R^7)N(R^7)$—, —$CH(R^7)N(C(O)R^7)$—, —$CH(R^7)N(C(O)OR^7)$—, —$CH(R^7)N(SO_2R^7)$—, —$CH(R^7)C(=NOR^7)$—, —$CH(R^7)C(O)$—, —$CH(R^7)CH(OR^7)$—, —$CH(R^7)C(O)N(R^7)$—, —$CH(R^7)N(R^7)C(O)$—, —$CH(R^7)N(R^7)S(O)$—, —$CH(R^7)N(R^7)S(O)_2$—, —$CH(R^7)OC(O)N(R^7)$—, —$CH(R^7)N(R^7)C(O)N(R^7)$—, —$CH(R^7)NR^7C(O)O$—, —$CH(R^7)S(O)N(R^7)$—, —$CH(R^7)S(O)_2N(R^7)$—, —$CH(R^7)N(C(O)R^7)S(O)$—, —$CH(R^7)N(C(O)R^7)S(O)$—, —$CH(R^7)N(R^7)S(O)N(R^7)$—, —$CH(R^7)N(R^7)S(O)_2N(R^7)$—, —$CH(R^7)C(O)N(R^7)C(O)$—, —$CH(R^7)S(O)N(R^7)C(O)$—, —$CH(R^7)S(O)_2N(R^7)C(O)$—, —$CH(R^7)OS(O)N(R^7)$—, —$CH(R^7)OS(O)_2N(R^7)$—, —$CH(R^7)N(R^7)S(O)O$—, —$CH(R^7)N(R^7)S(O)_2O$—, —$CH(R^7)N(R^7)S(O)C(O)$—, —$CH(R^7)N(R^7)S(O)_2C(O)$—, —$CH(R^7)SON(C(O)R^7)$—, —$CH(R^7)SO_2N(C(O)R^7)$—, —$CH(R^7)N(R^7)SON(R^7)$—, —$CH(R^7)N(R^7)SO_2N(R^7)$—, or —$CH(R^7)C(O)O$—; or wherein $Q^1$ is substituted by said one to five independent $G^1$ substituents wherein at least one of said $G^1$ substituents is —$(X^1)_n$—$(Y^1)_m$—$R^4$, and wherein $X^1$ and $Y^1$ are each independently equal to —O—, —$NR^7$—, —$CR^5R^6$—, —$S(O)_{j7}$—, or —$C(O)$—, and wherein n and m are both equal to 1 and j7 is equal to 1 or 2; or wherein $Q^1$ is substituted by said one to five independent $G^1$ substituents wherein at least one of said $G^1$ substituents is —$(X^1)_n$—$(Y^1)_m$—$R^4$, and wherein $X^1$ and $Y^1$ are each independently —O— or —$CR^5R^6$—, and wherein n and m are equal to 1; or wherein $R^1$ is cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents; or wherein $R^1$ is cycloalkyl, aryl, heteroaryl, aralkyl, heteroaralkyl, or heterocyclyl, any of which is optionally substituted by one or more independent $G^{11}$ substituents; or wherein $R^1$ is cycloalkyl or heterocyclyl, any of which is optionally substituted by one or more independent $G^{11}$ substituents; or wherein $R^1$ is cycloalkyl optionally substituted by one or more independent $G^{11}$ substituents; or wherein $R^1$ is heterocyclyl optionally substituted by one or more independent $G^{11}$ substituents; or wherein $R^1$ is aryl, heteroaryl, aralkyl, or heteroaralkyl, any of which is optionally substituted by one or more independent $G^{11}$ substituents; or wherein $R^1$ is aryl or heteroaryl, any of which is optionally substituted by one or more independent $G^{11}$ substituents; or wherein $G^{11}$ is —$OR^{21}$, —$NR^{21}R^{31}(R^{31a})_{j4}$, —$C(O)R^{21}$, —$CO_2R^{21}$, —$CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, —$O(C=O)OR^{21}$, —$O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{333a})_{j4a}$, —$C(O)R^{2221}$, —$CO_2R^{2221}$, —$CONR^{2221}R^{3331}$, —$NO_2$, —$CN$, —$S(O)_{j4a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$ substituents; or aryl-$C_{0-10}$alkyl, aryl-$C_{2-10}$alkenyl, or aryl-$C_{2-10}$alkynyl, any of which is optionally substituted with one or more independent halo, —$CF_3$, —$OCF_3$, —$OR^{2221}$, —$NR^{2221}R^{3331}(R^{333a1})_{j5a}$, —$C(O)R^{2221}$, —$CO_2R^{2221}$, —$CONR^{2221}R^{3331}$, —$NO_2$, —$CN$, —$S(O)_{j5a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j5a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$, substituents; or hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{2221}$, —$NR^{2221}R^{3331}(R^{333a1})_{j6a}$, —$C(O)R^{2221}$, —$CO_2R^{2221}$, —$CONR^{2221}R^{3331}$, —$NO_2$, —$CN$, —$S(O)_{j6a}$ $R^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j6a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, or —S(C=O)NR$^{2221}$R$^{3331}$ substituents; or wherein G$^{11}$ is —OR$^{21}$, —NR$^{21}$R$^{31}$, —CO$_2$R$^{21}$, —C(O)R$^{21}$, —CONR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —O(C=O)OR$^{21}$, —O(C=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j4a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, or —S(C=O)NR$^{2221}$R$^{3331}$ substituents; or wherein R$^4$ is H, alkyl, aryl, heteroaryl, cycloalkyl, heterocyclyl, cycloalkenyl, or heterocycloalkenyl, any of which is optionally substituted by one or more independent G$^{41}$ substituents; or wherein R$^4$ is alkyl, aryl, heteroaryl, cycloalkyl, heterocyclyl, cycloalkenyl, or heterocycloalkenyl, any of which is optionally substituted by one or more independent G$^{41}$ substituents; or wherein R$^4$ is alkyl, aryl, heteroaryl, cycloalkyl, heterocyclyl, cycloalkenyl, or heterocycloalkenyl, any of which is optionally substituted by one or more independent G$^{41}$ substituents; or wherein Q$^1$ is phenyl substituted by said one to five independent G$^1$ substituents wherein at least one of said G$^1$ substituents is —(X$^1$)$_n$—(Y$^1$)$_m$—R$^4$, and wherein n=1 and X$^1$ is 3-(—O—), m=1 and Y$^1$ is —(—CH$_2$—), and R$^4$ is aryl optionally substituted by one or more independent G$^{41}$ substituents; or wherein R$^1$ is aryl, heteroaryl, cycloalkyl or heterocyclyl, optionally substituted by one or more independent G$^{11}$ substituents; or wherein R$^1$ is cycloalkyl or heterocyclyl, optionally substituted by one or more independent G$^{11}$ substituents; or wherein R$^1$ is cycloalkyl, optionally substituted by one or more independent G$^{11}$ substituents; or wherein R$^1$ is cyclobutyl, cyclopentyl or cyclohexyl, optionally substituted by one or more independent G$^{11}$ substituents; or wherein G$^{11}$ is —OR$^{21}$, —NR$^{21}$R$^{31}$, —CO$_2$R$^{21}$, —C(O)R$^{21}$, —CONR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —O(C=O)OR$^{21}$, —O(C=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j4a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, or —S(C=O)NR$^{2221}$R$^{3331}$ substituents; or wherein Q$^1$ is phenyl substituted by said one to five independent G$^1$ substituents wherein at least one of said G$^1$ substituents is (X$^1$)$_n$—(Y$^1$)$_m$—R$^4$, and wherein n=1 and X$^1$ is 4-(—O—), m=1 and Y$^1$ is —(—CH$_2$—), and R$^4$ is aryl optionally substituted by one or more independent G$^{41}$ substituents; or wherein R$^1$ is aryl, heteroaryl, cycloalkyl or heterocyclyl, optionally substituted by one or more independent G$^{11}$ substituents; or wherein R$^1$ is cycloalkyl or heterocyclyl, optionally substituted by one or more independent G$^{11}$ substituents;

wherein R$^1$ is cycloalkyl, optionally substituted by one or more independent G$^{11}$ substituents; or wherein R$^1$ is cyclobutyl, cyclopentyl or cyclohexyl, optionally substituted by one or more independent G$^{11}$ substituents; or wherein G$^{11}$ is —OR$^{21}$, —NR$^{21}$R$^{31}$, —CO$_2$R$^{21}$, —C(O)R$^{21}$, —CONR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —O(C=O)OR$^{21}$, —O(C=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j4a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$ or —S(C=O)NR$^{2221}$R$^{3331}$ substituents; or wherein Q$^1$ is phenyl substituted by said one to five independent G$^1$ substituents wherein at least one of said G$^1$ substituents is —(X$^1$)$_n$—(Y$^1$)$_m$—R$^4$, and wherein n=1 and X$^1$ is 3-(—O—), m=0, and R$^4$ is (C$_0$-C$_8$)alkyl or cycloalkyl optionally substituted by one or more independent G$^{41}$ substituents; or wherein R$^1$ is aryl, heteroaryl, cycloalkyl or heterocyclyl, optionally substituted by one or more independent G$^{11}$ substituents; or wherein R$^1$ is cycloalkyl or heterocyclyl, optionally substituted by one or more independent G$^{11}$ substituents; or wherein R$^1$ is cycloalkyl, optionally substituted by one or more independent G$^{11}$ substituents; or wherein R$^1$ is cyclobutyl, cyclopentyl or cyclohexyl, optionally substituted by one or more independent G$^{11}$ substituents; or wherein G$^{11}$ is —OR$^{21}$, —NR$^{21}$R$^{31}$, —CO$_2$R$^{21}$, —C(O)R$^{21}$, —CONR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —O(C=O)OR$^{21}$, —O(C=O)NR$^{21}$R$^{31}$, C$_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —CF$_3$, —OCF$_3$, —OR$^{2221}$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j4a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$ or —S(C=O)NR$^{2221}$R$^{3331}$ substituents; or wherein R$^4$ is (C$_0$-C$_6$)alkyl; or wherein R$^4$ is H or methyl; or wherein R$^4$ is H or methyl; or wherein $Q^1$ is phenyl substituted by said one to five independent $G^1$ substituents wherein at least one of said $G^1$ substituents is $—(X^1)_n—(Y^1)_m—R^4$, and wherein n=1 and $X^1$ is 3-(—O—), m=0, and $R^4$ is aryl optionally substituted by one or more independent $G^{41}$ substituents; or wherein $R^1$ is aryl, heteroaryl, cycloalkyl or heterocyclyl, optionally substituted by one or more independent $G^{11}$ substituents; or wherein $R^1$ is cycloalkyl or heterocyclyl, optionally substituted by one or more independent $G^{11}$ substituents; or wherein $R^1$ is cyclobutyl, cyclopentyl or cyclohexyl, optionally substituted by one or more independent $G^{11}$ substituents; or wherein $G^{11}$ is $—OR^{21}$, $—NR^{21}R^{31}$, $—CO_2R^{21}$, $—C(O)R^{21}$, $—CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $—O(C=O)OR^{21}$, $—O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $—CF_3$, $—OCF_3$, $—OR^{2221}$, $—NR^{2221}R^{3331}(R^{333a1})_{j4a}$, $—C(O)R^{2221}$, $—CO_2R^{2221}$, $—CONR^{2221}R^{3331}$, $—NO_2$, $—CN$, $—S(O)_{j4a}R^{2221}$, $—SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $—(C=S)OR^{2221}$, $—(C=O)SR^{2221}$, $—NR^{2221}(C=NR^{3331})NR^{222a1}R^{333a1}$, $—NR^{2221}(C=NR^{3331})OR^{222a1}$, $—NR^{2221}(C=NR^{3331})SR^{333a1}$, $—O(C=O)OR^{2221}$, $—O(C=O)NR^{2221}R^{3331}$, $—O(C=O)SR^{2221}$, $—S(C=O)OR^{2221}$, or $—S(C=O)NR^{2221}R^{3331}$ substituents; or wherein $R^4$ is phenyl optionally substituted with $G^{41}$; or wherein $Q^1$ is phenyl substituted by said one to five independent $G^1$ substituents wherein at least one of said $G^1$ substituents is $—(X^1)_n—(Y^1)_m—R^4$, and wherein n=1 and $X^1$ is 3- or 4-(—NH—), m=1 and $Y^1$ is —(—SO_2—), and $R^4$ is aryl optionally substituted by one or more independent $G^{41}$ substituents; or wherein $R^1$ is aryl, heteroaryl, cycloalkyl or heterocyclyl, optionally substituted by one or more independent $G^{11}$ substituents; or wherein $R^1$ is cycloalkyl or heterocyclyl, optionally substituted by one or more independent $G^{11}$ substituents; or wherein $R^1$ is cyclobutyl, cyclopentyl or cyclohexyl, optionally substituted by one or more independent $G^{11}$ substituents; or wherein $G^{11}$ is $—OR^{21}$, $—NR^{21}R^{31}$, $—CO_2R^{21}$, $—C(O)R^{21}$, $—CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $—O(C=O)OR^{21}$, $—O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $—CF_3$, $—OCF_3$, $—OR^{2221}$, $—NR^{2221}R^{3331}(R^{333a1})_{j4a}$, $—C(O)R^{2221}$, $—CO_2R^{2221}$, $—CONR^{2221}R^{3331}$, $—NO_2$, $—CN$, $—S(O)_{j4a}R^{2221}$, $—SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $—(C=S)OR^{2221}$, $—(C=O)SR^{2221}$, $—NR^{2221}(C=NR^{3331})NR^{222a1}R^{333a1}$, $—NR^{2221}(C=NR^{3331})OR^{222a1}$, $—NR^{2221}(C=NR^{3331})SR^{333a1}$, $—O(C=O)OR^{2221}$, $—O(C=O)NR^{2221}R^{3331}$, $—O(C=O)SR^{2221}$, $—S(C=O)OR^{2221}$, or $—S(C=O)NR^{2221}R^{3331}$ substituents; or wherein $R^1$ is cis- or trans-cyclobutyl substituted at the 3-position by $G^{11}$ wherein $G^{11}$ is —OH, $—NH_2$, $—N(CH_3)_2$, —NHAc, $—NH(CO)NHCH_3$, $—NH(CO)OCH_3$, $—CH_2OH$, $—CH_2NH_2$, $—CH_2NHAc$, $CO_2H$, $CONH_2$, $—CH_2N(CH_3)_2$, $—CH_2NH(CO)NHMe$, $—CH_2NH(CO)OCH_3$, $CO_2CH_3$, $CONHCH_3$,

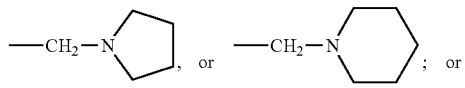

wherein $R^1$ is cis- or trans-cyclohexyl substituted at the 4-position by $G^{11}$ wherein $G^{11}$ is —OH, $—NH_2$, $—N(CH_3)_2$, —NHAc, $—NH(CO)NHCH_3$, $—NH(CO)OCH_3$, $—CH_2OH$, $—CH_2NH_2$, $—CH_2NHAc$, $CO_2H$, $CONH_2$, $—CH_2N(CH_3)_2$, $—CH_2NH(CO)NHMe$, $—CH_2NH(CO)OCH_3$, $CO_2CH_3$, $CONHCH_3$,

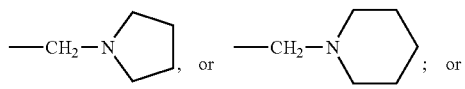

wherein the compound of Formula I is selected from the group consisting of:
[1-(3-Benzyloxy-phenyl)-3-cyclobutyl-imidazo[1,5-a]pyrazin-8-ylamine],
1-(3-Benzyloxyphenyl)-3-phenyl-imidazo[1,5-a]pyrazin-8-ylamine,
3-Benzyl-1-(3-benzyloxyphenyl)-imidazo[1,5-a]pyrazin-8-ylamine,
1-(3-Benzyloxyphenyl)-3-naphthalen-1-yl-imidazo[1,5-a]pyrazin-8-ylamine,
1-(3-Benzyloxyphenyl)-3-naphthalen-2-yl-imidazo[1,5-a]pyrazin-8-ylamine,
1-(3-Benzyloxy-phenyl)-3-cyclopentyl-imidazo[1,5-a]pyrazin-8-ylamine,
1-(3-Benzyloxy-phenyl)-3-cyclohexyl-imidazo[1,5-a]pyrazin-8-ylamine,
1-(3-Benzyloxy-phenyl)-3-cycloheptyl-imidazo[1,5-a]pyrazin-8-ylamine,
1-(3-Benzyloxy-phenyl)-3-(tetrahydro-furan-3-yl)-imidazo[1,5-a]pyrazin-8-ylamine,
trans-3-[8-Amino-1-(3-benzyloxy-phenyl)-imidazo[1,5-a]pyrazin-3-yl]-cyclobutanol,
1-(3-Benzyloxy-phenyl)-3-(1-methyl-piperidin-4-yl)-imidazo[1,5-a]pyrazin-8-ylamine,
cis-4-[8-Amino-1-(3-benzyloxy-phenyl)-imidazo[1,5-a]pyrazin-3-yl]-cyclohexanecarboxylic acid amide,
trans-4-[8-Amino-1-(3-benzyloxy-phenyl)-imidazo[1,5-a]pyrazin-3-yl]-cyclohexanecarboxylic acid amide,
cis-{4-[8-Amino-1-(3-benzyloxy-phenyl)-imidazo[1,5-a]pyrazin-3-yl]-cyclohexyl}-methanol,
trans-{4-[8-Amino-1-(3-benzyloxy-phenyl)-imidazo[1,5-a]pyrazin-3-yl]-cyclohexyl}-methanol,
cis-2-{4-[8-Amino-1-(3-benzyloxy-phenyl)-imidazo[1,5-a]pyrazin-3-yl]-cyclohexylmethyl}-isoindole-1,3-dione,
trans-2-{4-[8-Amino-1-(3-benzyloxy-phenyl)-imidazo[1,5-a]pyrazin-3-yl]-cyclohexylmethyl}-isoindole-1,3-dione,
cis-3-(4-Aminomethyl-cyclohexyl)-1-(3-benzyloxy-phenyl)-imidazo[1,5-a]pyrazin-8-ylamine,
trans-3-(4-Aminomethyl-cyclohexyl)-1-(3-benzyloxy-phenyl)-imidazo[1,5-a]pyrazin-8-ylamine,
cis-N-{4-[8-Amino-1-(3-benzyloxy-phenyl)-imidazo[1,5-a]pyrazin-3-yl]-cyclohexylmethyl}-acetamide, or
trans-N-{4-[8-Amino-1-(3-benzyloxy-phenyl)-imidazo[1,5-a]pyrazin-3-yl]-cyclohexylmethyl}-acetamide; or
and the other variables are as defined above for Formula I.

The present invention includes a method of inhibiting protein kinase activity comprising administering a compound of Formula I or a pharmaceutically acceptable salt thereof.

The present invention includes a method of inhibiting IGF-IR activity comprising administering a compound of Formula I or a pharmaceutically acceptable salt thereof.

The present invention includes a method of inhibiting protein kinase activity wherein the activity of said protein kinase affects hyperproliferative disorders comprising administering a compound of Formula I or a pharmaceutically acceptable salt thereof.

The present invention includes a method of inhibiting protein kinase activity wherein the activity of said protein kinase influences angiogenesis, vascular permeability, immune response, cellular apoptosis, tumor growth, or inflammation comprising administering a compound of Formula I or a pharmaceutically acceptable salt thereof.

The present invention includes a method of treating a patient having a condition which is mediated by protein kinase activity, said method comprising administering to the patient a therapeutically effective amount of a compound of Formula I or a pharmaceutically acceptable salt thereof.

The present invention includes a method of treating a patient having a condition which is mediated by IGF-1R activity, said method comprising administering to the patient a therapeutically effective amount of a compound of Formula I or a pharmaceutically acceptable salt thereof.

The present invention includes a method of treating a patient having a hyperproliferative disorder, said method comprising administering to the patient a therapeutically effective amount of a compound of Formula I or a pharmaceutically acceptable salt thereof.

The present invention includes a method of treating a patient having a condition which is mediated by protein kinase activity wherein the activity of said protein kinase influences angiogenesis, vascular permeability, immune response, cellular apoptosis, tumor growth, or inflammation, said method comprising administering to the patient a therapeutically effective amount of a compound of Formula I or a pharmaceutically acceptable salt thereof.

The present invention includes a method of treating a patient having a condition which is mediated by protein kinase activity wherein the protein kinase is a protein serine/threonine kinase or a protein tyrosine kinase, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is one or more ulcers, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is one or more ulcers wherein the ulcer or ulcers are caused by a bacterial or fungal infection; or the ulcer or ulcers are Mooren ulcers; or the ulcer or ulcers are a symptom of ulcerative colitis, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is Lyme disease, sepsis or infection by Herpes simplex, Herpes Zoster, human immunodeficiency virus, parapoxvirus, protozoa, or toxoplasmosis, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is Lyme disease, sepsis or infection by Herpes simplex, Herpes Zoster, human immunodeficiency virus, parapoxvirus, protozoa, or toxoplasmosis, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is von Hippel Lindau disease, pemphigoid, psoriasis, Paget's disease, or polycystic kidney disease, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is fibrosis, sarcoidosis, cirrhosis, thyroiditis, hyperviscosity syndrome, Osler-Weber-Rendu disease, chronic occlusive pulmonary disease, asthma, exudtaes, ascites, pleural effusions, pulmonary edema, cerebral edema or edema following burns, trauma, radiation, stroke, hypoxia, or ischemia, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is ovarian hyperstimulation syndrome, preeclainpsia, menometrorrhagia, or endometriosis, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase-activity is chronic inflammation, systemic lupus, glomerulonephritis, synovitis, inflammatory bowel disease, Crohn's disease, glomerulonephritis, rheumatoid arthritis and osteoarthritis, multiple sclerosis, or graft rejection, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is sickle cell anaemia, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is an ocular condition, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is an ocular condition wherein the ocular condition is ocular or macular edema, ocular neovascular disease, seleritis, radial keratomy, uveitis, vitritis, myopia, optic pits, chronic retinal detachment, post-laser treatment complications, conjunctivitis, Stargardt's disease, Eales disease, retinopathy, or macular degeneration, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is a cardiovascular condition, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is atherosclerosis, restenosis, ischemia/reperfusion injury, vascular occlusion, venous malformation, or carotid obstructive disease, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is cancer, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is cancer wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, or malignant ascites, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is cancer wherein the cancer is Kaposi's sarcoma, Hodgkin's disease, lymphoma, myeloma, or leukemia, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is Crow-Fukase (POEMS) syndrome or a diabetic condition, said method comprising administering to the patient a therapeutically effective amount of a compound of Formula I or a pharmaceutically acceptable salt thereof.

The present invention includes a method of treating a patient having a condition which is mediated by protein kinase activity wherein the condition mediated by protein kinase activity is Crow-Fukase (POEMS) syndrome or a diabetic condition wherein the diabetic condition is insulin-dependent diabetes mellitus glaucoma, diabetic retinopathy, or microangiopathy, said method comprising administering to the patient a therapeutically effective amount of a compound of Formula I or a pharmaceutically acceptable salt thereof.

The present invention includes a method of treating a patient having a condition which is mediated by protein kinase activity wherein the protein kinase activity is involved in T cell activation, B cell activation, mast cell degranulation, monocyte activation, signal transduction, apoptosis, the potentiation of an inflammatory response or a combination thereof, said method comprising administering to the patient a therapeutically effective amount of a compound of Formula I or a pharmaceutically acceptable salt thereof.

The present invention includes a composition comprising a compound according to Formula I, or a pharmaceutically acceptable salt thereof; and a pharmaceutically acceptable carrier.

The present invention includes a composition comprising a compound according to Formula I, or a pharmaceutically acceptable salt thereof; and an anti-neoplastic, anti-tumor, anti-angiogenic, or chemotherapeutic agent.

The present invention includes a composition comprising a compound according to Formula I, or a pharmaceutically acceptable salt thereof; and a cytotoxic cancer therapeutic agent.

The present invention includes a composition comprising a compound according to Formula I, or a pharmaceutically acceptable salt thereof; and an angiogenesis inhibiting cancer therapeutic agent.

The present invention includes a method of treating a patient having a condition which is mediated by protein kinase activity, said method comprising administering to the patient a therapeutically effective amount of a pharmaceutical composition comprising a compound according to Formula I, or a pharmaceutically acceptable salt thereof; and a pharmaceutically acceptable carrier.

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

The term "halo" refers to fluoro, chloro, bromo or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "cycloalkyl" refers to a cyclic aliphatic ring structure, optionally substituted with alkyl, hydroxy and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl and the like.

The term "alkylcarbonyloxyalkyl" refers to an ester moiety, for example acetoxymethyl, n-butyryloxyethyl and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl and the like.

The term "alkylsulfonylalkyl" refers to an alkyl group substituted with an alkylsulfonyl moiety, for example mesylmethyl, isopropylsulfonylethyl and the like.

The term "alkylsulfonyl" refers to a sulfonyl moiety substituted with an alkyl group, for example mesyl, n-propylsulfonyl and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl and the like.

The term "haloalkenyl" refers to an alkenyl group substituted with one or more halo groups.

The term "cycloalkenyl" refers to a cyclic aliphatic ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl and the like.

The term "alkynyl" refers to an unsaturated hydrocarbon group, straight or branched, having 1 or 2 acetylenic bonds, for example ethynyl, propargyl and the like.

The term "haloalkynyl" refers to an alkynyl group substituted with one or more halo groups.

The term "alkylcarbonyl" refers to an alkylketo functionality, for example acetyl, n-butyryl and the like.

The term "alkenylcarbonyl" refers to an alkenylketo functionality, for example, propenoyl and the like.

The term "aryl" refers to phenyl or naphthyl which may be optionally substituted. Typical aryl substituents include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl and 2-iodo-4-methylphenyl.

The term "aryl$^1$" refers to phenyl which may be optionally substituted. Typical aryl$^1$ substituents include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, 2,4-dimethoxyphenyl, 4-(trifluoromethyl)phenyl and 2-iodo-4-methylphenyl.

The terms "heteroaryl" or "hetaryl" refer to a substituted or unsubstituted 5- or 6-membered unsaturated ring containing one, two, three or four heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of hetaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heterocyclic ring may be optionally substituted with up to two substituents.

The terms "heteroaryl$^1$" or "hetaryl$^1$" refer to a substituted or unsubstituted 5- or 6-membered unsaturated ring containing one, two, three or four heteroatoms, preferably one or two heteroatoms independently selected from oxygen, nitrogen and sulfur. Examples of hetaryl$^1$'s include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, and thiadiazolyl. The heterocyclic ring may be optionally substituted with up to two substituents.

The terms "aryl-alkyl" or "arylalkyl" are used to describe a group wherein the alkyl chain can be branched or straight chain with the aryl portion, as defined hereinbefore, forming a bridging portion of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxyphenyl)butyl and 10-phenyldecyl.

The terms "aryl-cycloalkyl" or "arylcycloalkyl" are used to describe a group wherein the aryl group is attached to a cycloalkyl group, for example phenylcyclopentyl and the like.

The terms "aryl-alkenyl" or "arylalkenyl" are used to describe a group wherein the alkenyl chain can be branched or straight chain with the aryl portion, as defined hereinbefore, forming a bridging portion of the aralkenyl moiety, for example styryl (2-phenylvinyl), phenpropenyl and the like.

The terms "aryl-alkynyl" or "arylalkynyl" are used to describe a group wherein the alkynyl chain can be branched or straight chain with the aryl portion, as defined hereinbefore, forming a bridging portion of the aryl-alkynyl moiety, for example 3-phenyl-1-propynyl and the like.

The terms "aryl-oxy" or "aryloxy" are used to describe a terminal aryl group attached to a bridging oxygen atom. Typical aryl-oxy groups include phenoxy, 3,4-dichlorophenoxy and the like.

The terms "aryl-oxyalkyl" or "aryloxyalkyl" are used to describe a group wherein an alkyl group is substituted with an aryl-oxy group, for example pentafluorophenoxymethyl and the like.

The terms "hetaryl-oxy" or "heteroaryl-oxy" or "hetaryloxy" or "heteroaryloxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetaryl-alkyl" or "heteroaryl-alkyl" are used to describe a group wherein the alkyl chain can be branched or straight chain with the heteroaryl portion, as defined hereinbefore, forming a bridging portion of the heteroaralkyl moiety, for example 3-furylmethyl, thenyl, furfuryl and the like.

The terms "hetarylalkenyl" or "heteroarylalkenyl" or "hetaryl-alkenyl" or "heteroaryl-alkenyl" are used to describe a group wherein the alkenyl chain can be branched or straight chain with the heteroaryl portion, as defined hereinbefore, forming a bridging portion of the heteroaralkenyl moiety, for example 3-(4-pyridyl)-1-propenyl.

The terms "hetarylalkynyl" or "heteroarylalkynyl" or "hetaryl-alkynyl" or "heteroaryl-alkynyl" are used to describe a group wherein the alkynyl chain can be branched or straight chain with the heteroaryl portion, as defined hereinbefore, forming a bridging portion of the heteroaralkynyl moiety, for example 4-(2-thienyl)-1-butynyl.

The term "heterocyclyl" refers to a substituted or unsubstituted 5 or 6 membered saturated ring containing one, two or three heteroatoms, preferably one or two heteroatoms independently selected from oxygen, nitrogen and sulfur or to a bicyclic ring system containing up to 10 atoms including one heteroatom selected from oxygen, nitrogen and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, 5-methyl-6-chromanyl and

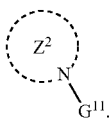

The terms "heterocyclylalkyl" or "heterocyclyl-alkyl" are used to describe a group wherein the alkyl chain can be branched or straight chain with the heterocyclyl portion, as defined hereinabove, forming a bridging portion of the heterocyclylalkyl moiety, for example 3-piperidinylmethyl and the like.

The terms "heterocyclylalkenyl" or "heterocyclyl-alkenyl" are used to describe a group wherein the alkenyl chain can be branched or straight chain with the heterocyclyl portion, as defined hereinbefore, forming a bridging portion of the heterocyclylalkenyl moiety, for example 2-morpholinyl-1-propenyl.

The terms "heterocyclylalkynyl" or "heterocyclyl-alkynyl" are used to describe a group wherein the alkynyl chain can be branched or straight chain with the heterocyclyl portion, as defined hereinbefore, forming a bridging portion of the heterocyclylalkynyl moiety, for example 2-pyrrolidinyl-1-butynyl.

The term "carboxylalkyl" includes both branched and straight chain alkyl groups as defined hereinbefore attached to a carboxyl (—COOH) group.

The term "carboxylalkenyl" includes both branched and straight chain alkenyl groups as defined hereinbefore attached to a carboxyl (—COOH) group.

The term "carboxylalkynyl" includes both branched and straight chain alkynyl groups as defined hereinbefore attached to a carboxyl (—COOH) group.

The term "carboxylcycloalkyl" refers to a carboxyl (—COOH) group attached to a cyclic aliphatic ring structure as defined hereinbefore.

The term "carboxylcycloalkenyl" refers to a carboxyl (—COOH) group attached to a cyclic aliphatic ring structure having 1 or 2 ethylenic bonds as defined hereinbefore.

The terms "cycloalkylalkyl" or "cycloalkyl-alkyl" refer to a cycloalkyl group as defined hereinbefore attached to an alkyl group, for example cyclopropylmethyl, cyclohexylethyl and the like.

The terms "cycloalkylalkenyl" or "cycloalkyl-alkenyl" refer to a cycloalkyl group as defined hereinbefore attached to an alkenyl group, for example cyclohexylvinyl, cycloheptylallyl and the like.

The terms "cycloalkylalkynyl" or "cycloalkyl-alkynyl" refer to a cycloalkyl group as defined hereinbefore attached to an alkynyl group, for example cyclopropylpropargyl, 4-cyclopentyl-2-butynyl and the like.

The terms "cycloalkenylalkyl" or "cycloalkenyl-alkyl" refer to a cycloalkenyl group as defined hereinbefore attached to an alkyl group, for example 2-(cyclopenten-1-yl)ethyl and the like.

The terms "cycloalkenylalkenyl" or "cycloalkenyl-alkenyl" refer to a cycloalkenyl group as defined hereinbefore attached to an alkenyl group, for example 1-(cyclohexen-3-yl)allyl and the like.

The terms "cycloalkenylalkynyl" or "cycloalkenyl-alkynyl" refer to a cycloalkenyl group as defined hereinbefore attached to an alkynyl group, for example 1-(cyclohexen-3-yl)propargyl and the like.

The term "carboxylcycloalkylalkyl" refers to a carboxyl (—COOH) group attached to the cycloalkyl ring portion of a cycloalkylalkyl group as defined hereinbefore.

The term "carboxylcycloalkylalkenyl" refers to a carboxyl (—COOH) group attached to the cycloalkyl ring portion of a cycloalkylalkenyl group as defined hereinbefore.

The term "carboxylcycloalkylalkynyl" refers to a carboxyl (—COOH) group attached to the cycloalkyl ring portion of a cycloalkylalkynyl group as defined hereinbefore.

The term "carboxylcycloalkenylalkyl" refers to a carboxyl (—COOH) group attached to the cycloalkenyl ring portion of a cycloalkenylalkyl group as defined hereinbefore.

The term "carboxylcycloalkenylalkenyl" refers to a carboxyl (—COOH) group attached to the cycloalkenyl ring portion of a cycloalkenylalkenyl group as defined hereinbefore.

The term "carboxylcycloalkenylalkynyl" refers to a carboxyl (—COOH) group attached to the cycloalkenyl ring portion of a cycloalkenylalkynyl group as defined hereinbefore.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy and the like.

The term "alkoxyalkoxyalkyl" refers to an alkyl group substituted with an alkoxy moiety which is in turn substituted with a second alkoxy moiety, for example methoxymethoxymethyl, isopropoxymethoxyethyl and the like.

The term "alkylthio" includes both branched and straight chain alkyl groups attached to a bridging sulfur atom, for example methylthio.

The term "haloalkylthio" refers to an alkylthio group substituted with one or more halo groups, for example trifluoromethylthio.

The term "alkoxyalkyl" refers to an alkyl group substituted with an alkoxy group, for example isopropoxymethyl.

The term "alkoxyalkenyl" refers to an alkenyl group substituted with an alkoxy group, for example 3-methoxyallyl.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined hereinbefore substituted with an alkoxycarbonyl, for example 4-(ethoxycarbonyl)-2-butenyl and the like.

The term "alkoxycarbonylalkynyl" refers to a straight chain or branched alkynyl as defined hereinbefore substituted with an alkoxycarbonyl, for example 4-(ethoxycarbonyl)-2-butynyl and the like.

The term "haloalkoxyalkyl" refers to a straight chain or branched alkyl as defined hereinbefore substituted with a haloalkoxy, for example 2-chloroethoxymethyl, trifluoromethoxymethyl and the like.

The term "haloalkoxyalkenyl" refers to a straight chain or branched alkenyl as defined hereinbefore substituted with a haloalkoxy, for example 4-(chloromethoxy)-2-butenyl and the like.

The term "haloalkoxyalkynyl" refers to a straight chain or branched alkynyl as defined hereinbefore substituted with a haloalkoxy, for example 4-(2-fluoroethoxy)-2-butynyl and the like.

The term "alkylthioalkyl" refers to a straight chain or branched alkyl as defined hereinbefore substituted with an alkylthio group, for example methylthiomethyl, 3-(isobutylthio)heptyl and the like.

The term "alkylthioalkenyl" refers to a straight chain or branched alkenyl as defined hereinbefore substituted with an alkylthio group, for example 4-(methylthio)-2-butenyl and the like.

The term "alkylthioalkynyl" refers to a straight chain or branched alkynyl as defined hereinbefore substituted with an alkylthio group, for example 4-(ethylthio)-2-butynyl and the like.

The term "haloalkylthioalkyl" refers to a straight chain or branched alkyl as defined hereinbefore substituted with an haloalkylthio group, for example 2-chloroethylthiomethyl, trifluoromethylthiomethyl and the like.

The term "haloalkylthioalkenyl" refers to a straight chain or branched alkenyl as defined hereinbefore substituted with an haloalkylthio group, for example 4-(chloromethylthio)-2-butenyl and the like.

The term "haloalkylthioalkynyl" refers to a straight chain or branched alkynyl as defined hereinbefore substituted with a haloalkylthio group, for example 4-(2-fluoroethylthio)-2-butynyl and the like.

The term "dialkoxyphosphorylalkyl" refers to two straight chain or branched alkoxy groups as defined hereinbefore attached to a pentavalent phosphorous atom, containing an oxo substituent, which is in turn attached to an alkyl, for example diethoxyphosphorylmethyl.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above (or a pharmaceutically acceptable salt thereof).

Moreover, within this preferred embodiment, the invention encompasses a pharmaceutical composition for the treatment of disease by inhibiting kinases, comprising a pharmaceutically acceptable carrier and a non-toxic therapeutically effective amount of compound of Formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, allergy/asthma, disease and conditions of the immune system, disease and conditions of the central nervous system (CNS), cardiovascular disease, dermatology, and angiogenesis may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above, or a pharmaceutically acceptable salt thereof.

Moreover, within this preferred embodiment, the invention encompasses a pharmaceutical composition for the treatment of disease by inhibiting tyrosine kinase enzymes, resulting in cell proliferation, growth, differentiation, metabolism, cell cycle events, apoptosis, motility, transcription, phosphorylation, translation and other signaling processes, comprising a pharmaceutically acceptable carrier and a non-toxic therapeutically effective amount of compound of formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a compound represented by formula I, or a pharmaceutically acceptable salt thereof, as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. He suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, allergy/asthma, disease and conditions of the immune system, disease and conditions of the central nervous system (CNS), cardiovascular disease, dermatology, and angiogenesis may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biological Assays

The efficacy of the Examples of the invention, compounds of Formula I, as inhibitors of insulin-like growth factor-1 receptor (IGF-1R) were demonstrated and confirmed by a number of pharmacological in vitro assays. The following assays and their respective methods have been carried out with the compounds according to the invention. Activity possessed by compounds of Formula I may be demonstrated in vivo.

In Vitro Tyrosine Kinase Assay

The IGF-1R inhibitory of a compound of formula I can be shown in a tyrosine kinase assay using purified GST fusion protein containing the cytoplasmic kinase domain of human IGF-1R expressed in Sf9 cells. This assay is carried out in a final volume of 90 μL containing 1-100 nM (depending on the specific activity) in an Immulon-4 96-well plate (Thermo Lab systems) pre-coated with 1 μg/well of substrate poly-glu-tyr (4:1 ratio) in kinase buffer (50 mM Hepes, pH 7.4, 125 mM NaCl, 24 mM $MgCl_2$, 1 mM $MnCl_2$, 1% glycerol, 200 μM $Na_3VO_4$, and 2 mM DTT). The enzymatic reaction was initiated by addition of ATP at a final concentration of 100 μM.

After incubation at room temperature for 30 minutes, the plates were washed with 2 mM Imidazole buffered saline with 0.02% Tween-20. Then the plate was incubated with anti-phosphotyrosine mouse monoclonal antibody pY-20 conjugated with horse radish peroxidase (HRP) (Calbiochem) at 167 ng/mL diluted in phosphate buffered saline (PBS) containing 3% bovine serum albumin (BSA), 0.5% Tween-20 and 200 μM $Na_3VO_4$ for 2 hours at room temperature. Following 3×250 μL washes, the bound anti-phosphotyrosine antibody was detected by incubation with 100 μl/well ABTS (Kirkegaard & Perry Labs, Inc.) for 30 minutes at room temperature. The reaction was stopped by the addition of 100 μl/well 1% SDS, and the phosphotyrosine dependent signal was measured by a plate reader at 405/490 nm.

Examples 1-21 showed inhibition of IGF-1R. Examples 1-21 showed efficacy and activity by inhibiting IGF-1R in the biochemical assay with $IC_{50}$ values less than 15 μM. Preferably the $IC_{50}$ value is less than 5 μM. More advantageously, the $IC_{50}$ value is less than 1 μM. Even more advantageously, the $IC_{50}$ value is less than 200 nM.

The most preferred Examples are selective towards IGF-1R.

Cell-based Autophosphotyrosine Assay

NIH 3T3 cells stably expressing full-length human IGF-1R were seeded at $1\times10^4$ cells/well in 0.1 ml Dulbecco's minimal essential medium (DMEM) supplemented with 10% fetal calf serum (FCS) per well in 96-well plates. On Day 2, the medium is replaced with starvation medium (DMEM containing 0.5% FCS) for 2 hours and a compound was diluted in 100% dimethyl sulfoxide (DMSO), added to the cells at six final concentrations in duplicates (20, 6.6, 2.2, 0.74, 0.25 and 0.082 μM), and incubated at 37° C. for additional 2 hours. Following addition of recombinant human IGF-1 (100 ng/mL) at 37° C. for 15 minutes, the media was then removed and the cells were washed once with PBS (phosphate-buffered saline), then lysed with cold TGH buffer (1% Triton-100, 10% glycerol, 50 mM Hepes [pH 7.4]) supplemented with 150 mM NaCl, 1.5 mM MgCl, 1 mM EDTA and fresh protease and phosphatase inhibitors [10 μg/ml leupeptin, 25 μg/ml aprotinin, 1 mM phenyl methyl sulphonyl fluoride (PMSF), and 200 μM $Na_3VO_4$]. Cell lysates were transferred to a 96-well microlite2 plate (Corning CoStar #3922) coated with 10 ng/well of IGF-1R antibody (Calbiochem, Cat#GR31L) and incubated at 4° C. overnight. Following washing with TGH buffer, the plate was incubated with anti-phosphotyrosine mouse monoclonal antibody pY-20 conjugated with horse radish peroxidase (HRP) for 2 hours at room temperature. The autophosphotyrosine was then detected by addition of Super Signal ELISA Femto Maximum Sensitivity Substrate (Pierce) and chemiluminescence was read on a Wallac Victor² 1420 Multilabel Counter. The $IC_{50}$ curves of the compounds were plotted using an ExcelFit program.

The following Examples showed efficacy and activity by inhibiting IGF-1R in the above assay with $IC_{50}$ values between 100 μM-about 8 nM, with selectivity over insulin receptor expected to be in a range from 1-15 fold. The selectivity is preferably 5 fold, even more preferably the selectivity is 10 fold. Preferably the $IC_{50}$ value is less than 5 μM. More advantageously, the $IC_{50}$ value is less than 1 μM. Even more advantageously, the $IC_{50}$ value is less than 200 nM. Insulin receptor autophosphotyrosine assays are performed essentially as described above for IGF-1R cell-based assays, but use insulin (10 nM) as activating ligand and an insulin receptor antibody as capture antibody with HepG2 cells expressing endogenous human insulin receptor.

EXPERIMENTAL

Schemes 1-13 below, as well as the Examples that follow, show how to synthesize compounds of this invention and utilize the following abbreviations: Me for methyl, Et for ethyl, $^i$Pr or $^i$Pr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, (p-$CH_3O$)Ph for p-methoxyphenyl, (p-$NO_2$)Ph for p-nitrophenyl, 4Br-Ph or (4Br)Ph for 4-bromophenyl, 2-$CF_3$-Ph or (2$CF_3$)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, CDI for 1,1'-carbonyldiimidazole, NMO for 4-methylmorpholine N-oxide, DEAD for diethlyl azodicarboxylate, DIAD for diisopropyl azodicarboxylate, DBAD for di-tert-butyl azodicarboxylate, HPFC for high performance flash chromatography, rt for room temperature, min for minute, h for hour, and Bn for benzyl.

Accordingly, the following are compounds which are useful as intermediates in the formation of IGF-1R inhibiting Examples.

The compounds of Formula I of this invention and the intermediates used in the synthesis of the compounds of this invention were prepared according to the following methods. Method A was used when preparing compounds of Formula I as shown below in Scheme 1:

Method A:

Scheme 1

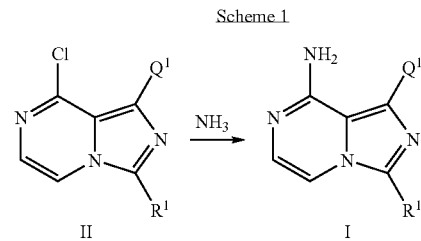

where $Q^1$ and $R^1$ are as defined previously for compound of Formula I.

In a typical preparation of compounds of Formula I, compound of Formula II was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcoholics such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II of Scheme 1 were prepared as shown below in Scheme 2.

Scheme 2

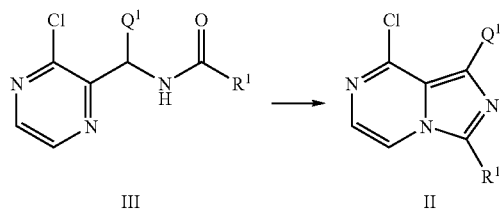

III          II where $Q^1$ and $R^1$ are as defined previously for compound of Formula I.

In a typical preparation of a compound of Formula II, an intermediate of Formula III was treated with $POCl_3$ in a suitable solvent at a suitable reaction temperature. Suitable solvents for use in the above process included, but were not limited to, ethers such as tetrahydrofuran (THF), glyme, and the like; and chlorinated solvents such as methylene chloride ($CH_2Cl_2$) or chloroform ($CHCl_3$). If desired, mixtures of these solvents were used. The preferred solvent was methylene chloride. The above process was carried out at temperatures between about $-78°$ C. and about $120°$ C. Preferably, the reaction was carried out between $40°$ C. and about $70°$ C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III of Scheme 2 were prepared as shown below in Scheme 3:

Scheme 3

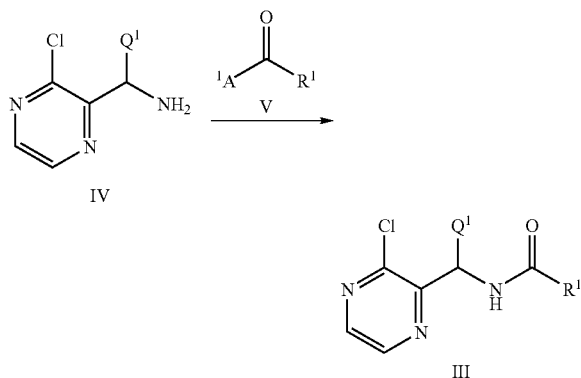

where $Q^1$ and $R^1$ are as defined previously for compound of Formula I and $A^1$=OH, alkoxy, or a leaving group such as chloro or imidazole.

In a typical preparation, of a compound of Formula III, a compound of Formula IV and compound of Formula V were reacted under suitable amide coupling conditions. Suitable conditions include but are not limited to treating compounds of Formula IV and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about $0°$ C. and about $80°$ C. Preferably, the reaction was carried out between $22°$ C. The above process to produce compounds of the present invention was preferably carried out at about atmospheric pressure although higher or lower pressures were used if desired. Substantially, equimolar amounts of reactants were preferably used although higher or lower amounts were used if desired. Additionally, other suitable reaction conditions for the conversion of $RNH_2$ to CONHR can be found in Larock, R. C. *Comprehensive Organic Transformations*, $2^{nd}$ ed.; Wiley and Sons: New York, 1999, pp 1941-1949.

The compounds of Formula IV of Scheme 3 were prepared as shown below in Scheme 4:

Scheme 4

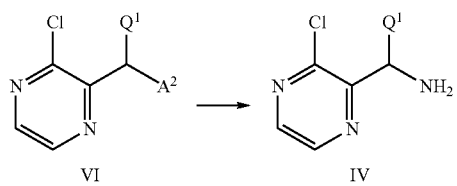

VI          IV where $Q^1$ is as defined previously for compound of Formula I and $A^2$=phthalimido or $N^3$.

In a typical preparation, of a compound of Formula IV, a compound of Formula VI is reacted under suitable reaction conditions in a suitable solvent. When $A^2$=phthalimido, suitable conditions include treatment of compound of Formula VI with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about $0°$ C. and about $80°$ C. Preferably, the reaction was carried out between $22°$ C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula IV of Scheme 3 can alternatively be prepared as shown below in Scheme 4a:

Scheme 4a $Q^1$—CHO $\longrightarrow$ $Q^1$—C≡N—$Si(CH_3)_3$ $\longrightarrow$

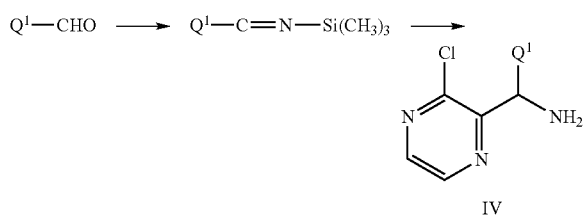

IV where $Q^1$ is as defined previously for compound of Formula I.

In a typical preparation, of a compound of Formula IV, an aldehyde $Q^1$-CHO was reacted under suitable reaction conditions in a suitable solvent with lithium hexamethyldisilazide to give an N-TMS imine $Q^1$-C=N—Si(CH$_3$)$_3$. Suitable solvents for use in the above process included, but were not limited to, ethers such as tetrahydrofuran (THF), glyme, and the like. The preferred solvent was THF. The above process was carried out at temperatures between about −78° C. and about 20° C. The preferred temperature was about 0° C. The imine $Q^1$-C=N—Si(CH$_3$)$_3$ thus obtained was then cooled to about −78° C. and treated with a lithiated 2-chloropyrazine under suitable reaction conditions in a suitable solvent to give a compound of Formula IV. Lithiated 2-chloropyrazine may be obtained by treating 2-chloropyrazine with a base such as lithium tetramethylpiperidide (Li-TMP). Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula VI of Scheme 4 were prepared as shown below in Scheme 5:

Scheme 5

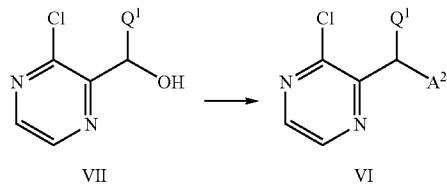

VII    VI where $Q^1$ is as defined previously for compound of Formula I and $A^2$=phthalimido or $N^3$.

In a typical preparation of a compound of Formula VI (when $A^2$=phthalimido), a compound of Formula VII was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like and an azodicarboxylate (DIAD, DEAD, DBAD). The desired reactants were triphenylphosphine and DIAD. The above process may be carried out at temperatures between about −78° C. and about 100° C. Preferably, the reaction was carried out at 22° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphospine, DIAD and phthalimide was used per equivalent of compound of Formula VII. The compounds of Formula VII were prepared according to known procedures (Ple, N.; et. al. *Tetrahedron*, 1998, 54, 9701-9710) from aldehydes $Q^1$-CHO. Additionally, compound of Formula VII can be reacted with Ts$_2$O, Ms$_2$O, Tf$_2$O, TsCl, MsCl, or SOCl$_2$ in which the hydroxy group is converted to a leaving group such as its respective tosylate, mesylate triflate or halogen such as chloro and subsequently reacted with an amine equivalent such as NH(Boc)$_2$, phthalimide, or azide. Conversion of the amine equivalents by known methods such as by treating under acidic conditions (NH(Boc)$_2$), with hydrazine (phthalimide) as shown in Scheme 4, or with triphenylphosphine/water (azide) will afford the desired amine as shown in Scheme 4.

The compounds of Formula I-A (compounds of Formula I where $R^1$=Z-CONR$^2$R$^3$) were prepared as shown below in Scheme 6:

Scheme 6

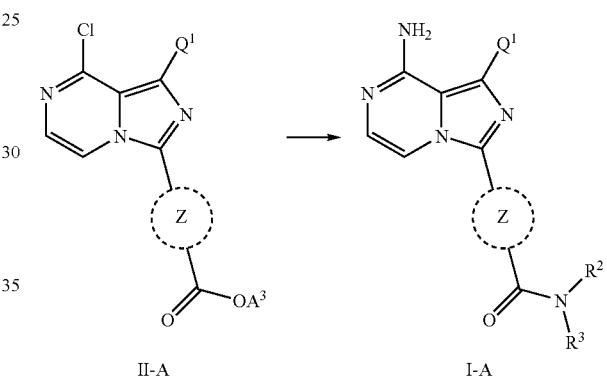

II-A    I-A where $Q^1$, $R^2$, and $R^3$ are as defined previously for compound of Formula I and $A^3$=hydrogen or alkyl such as methyl or ethyl.

In a typical preparation of compound of Formula I-A (compounds of Formula I where $R^1$=Z-CONR$^2$R$^3$), when $A^3$=alkyl and $R^2$ and $R^3$ were both equal to H, reaction of compound of Formula II-A with ammonia in a suitable solvent, afforded compound of Formula I-A. Suitable solvents for use in the above process included, but were not limited to, ethers such as tetrahydrofuran (THF), glyme, and the like; dimethylformamide (DMF); dimethyl sulfoxide (DMSO); acetonitrile; alcoholics such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired. Additionally, in a typical preparation of compound of Formula I-A (compounds of Formula I where $R^1$=Z-CONR$^2$R$^3$), compound of Formula II-A (compounds of Formula II where $R^1$=Z-CO$_2$A$^3$) was reacted with HNR²R³ followed by ammonia in a suitable solvent. When A³=H, typical coupling procedures as described in Scheme 3 (conversion of CO₂H to COCl via treatment with SOCl₂ or oxalyl chloride followed by reaction with HNR²R³ or treatment of CO₂H and HNR²R³ with EDC or DCC in conjunction with DMAP, HOBT, or HOAt and the like) were employed to afford the transformation of a carboxylic acid to an amide. When A³=alkyl such as methyl or ethyl, treatment of the ester with Al(NR²R³) afforded conversion of $CO_2A^3$ to $CO(NR^2R^3)$. Subsequent treatment with ammonia afforded compounds of Formula I-A.

The compounds of Formula II-B (compounds of Formula II where R¹=Z-CH₂OH) and I-B (compounds of Formula I where R¹=Z-CH₂OH) were prepared as shown below in Scheme 7:

between about −78° C. and about 120° C. Preferably, the reaction was carried out between 80° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II-B (compounds of Formula II where R¹=Z-CH₂OH), II-C (compounds of Formula II where R¹=Z-CH₂A⁴), II-D (compounds of Formula II where R¹=Z-A⁵(R²)(R³)$_d$), I-B (compounds of Formula I where R¹=Z-CH₂OH) and I-C (compounds of Formula I where R¹=Z-A⁵(R²)(R³)$_d$) were prepared as shown below in Scheme 8:

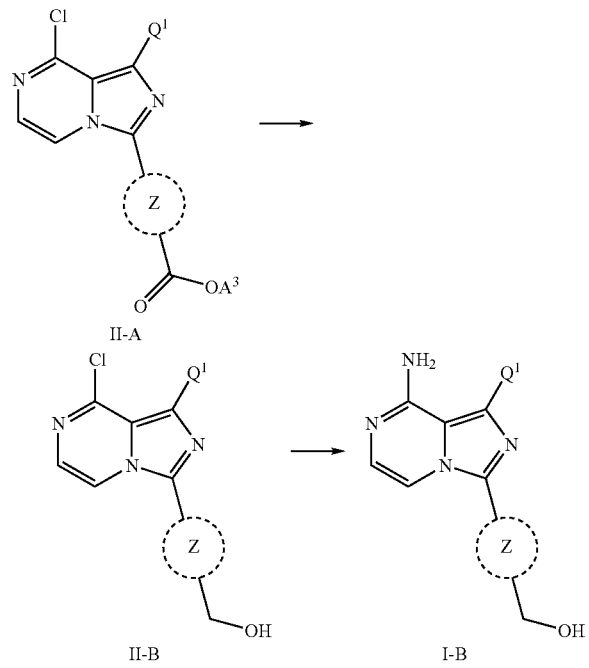

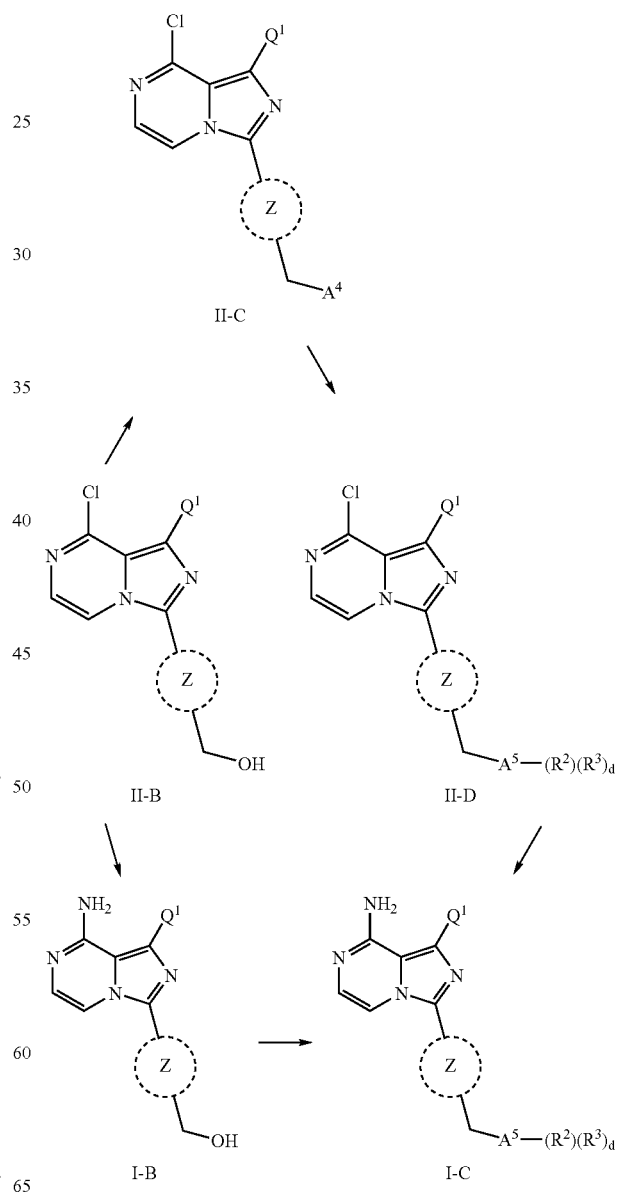

where Q¹ is as defined previously for compound of Formula I and A³=hydrogen or alkyl such as methyl or ethyl.

In a typical preparation of compound of Formula I-B (compounds of Formula I where R¹=Z-CH₂OH), compound of Formula II-A (compounds of Formula II where R¹=Z-CO₂A³) is treated with a suitable reducing agent such as lithium aluminum hydride in a suitable solvent, such as THF to afford compound of Formula II-B (compounds of Formula II where R¹=Z-CH₂OH). Subsequent treatment of compound of Formula II-B (compounds of Formula II where R¹=Z-CH₂OH) with ammonia in a suitable solvent, afforded compound of Formula I-B (compounds of Formula I where R¹=Z-CH₂OH). Suitable solvents for use in the above process included, but were not limited to, ethers such as tetrahydrofuran (THF), glyme, and the like; dimethylformamide (DMF); dimethyl sulfoxide (DMSO); acetonitrile; alcoholics such as methanol, ethanol, isopropanol, trifluoroethanol, and the like; and chlorinated solvents such as methylene chloride (CH₂Cl₂) or chloroform (CHCl₃). If desired, mixtures of these solvents were used. The preferred solvent was isopropanol. The above process was carried out at temperatures where $Q^1$, $R^2$, and $R^3$ are as defined previously for compound of Formula I; $A^4$=suitable leaving group such as OTs, OMs, OTf, or halo such as chloro, bromo, or iodo; d=0 or 1; and $A^5$=N, O or S.

In a typical preparation of compound of Formula I-C (compounds of Formula I where $R^1$=Z-$A^5$($R^2$)($R^3$)$_d$), the hydroxy group of compound of Formula II-B (compounds of Formula II where $R^1$=Z-$CH_2$OH) was converted to a suitable leaving group, $A^4$, such as Cl or OTs, OMs, or OTf, by reaction with $SOCl_2$ or $Ts_2O$, $Ms_2O$, or $Tf_2O$ to afford compound of Formula II-C (compounds of Formula II where $R^1$=Z-$CH_2A^4$). Reaction of compound of Formula II-C (compounds of Formula II where $R^1$=Z-$CH_2A^4$) with $HA^5(R^2)(R^3)_d$ afforded compound of Formula II-D (compounds of Formula II where $R^1$=Z-$A^5(R^2)(R^3)_d$). Subsequent reaction of compound of Formula II-D (compounds of Formula II where $R^1$=Z-$A^5(R^2)(R^3)_d$) with ammonia in a suitable solvent such as isopropanol or methanol, afforded compound of Formula I-C (compounds of Formula I where $R^1$=Z-$A^5(R^2)(R^3)_d$). Additionally, compound of Formula II-B (compounds of Formula II where $R^1$=Z-$CH_2$OH) was converted to compound of Formula I-B (compounds of Formula I where $R^1$=Z-$CH_2$OH) as described previously in Scheme 7. Further reaction of compound of Formula I-B (compounds of Formula I where $R^1$=Z-$CH_2$OH) to compound of Formula I-C (compounds of Formula I where $R^1$=Z-$A^5(R^2)(R^3)_d$) was accomplished by following the previously described conditions for the conversion of compound of Formula II-B (compounds of Formula II where $R^1$=Z-$CH_2$OH) to compound of Formula II-C (compounds of Formula II where $R^1$=Z-$CH_2A^4$) and the further conversion of compound of Formula II-C (compounds of Formula II where $R^1$=Z-$CH_2A^4$) to compound of Formula II-D (compounds of Formula II where $R^1$=Z-$A^5(R^2)(R^3)_d$) (in the net conversion of OH to $A^5(R^2)(R^3)_d$). Furthermore, compound of Formula II-B (compounds of Formula II where $R^1$=Z-$CH_2$OH) can be directly converted to compound of Formula II-D (compounds of Formula II where $R^1$=Z-$A^5(R^2)(R^3)_d$) by treating compound of Formula II-B with various alkylating agent or with phenols via the Mitsunobu reaction to afford compounds Formula II-D (compounds of Formula II where $R^1$=Z-$A^5(R^2)(R^3)_d$) in which $A^5$=O, d=0, and $R^2$=alkyl or aryl.

The compounds of Formula I-C' (compounds of Formula I where $R^1$=Z-$CH_2$-$A^2$), I-C" (compounds of Formula I where $R^1$=Z-$CH_2$—$NH_2$), and I-C''' (compounds of Formula I where $R^1$=Z-$CH_2$—N($R^2$)($R^3$)) were prepared as shown below in Scheme 8a:

Scheme 8a

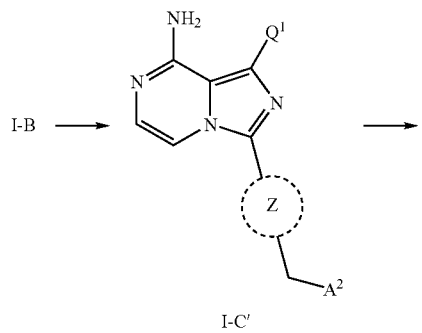

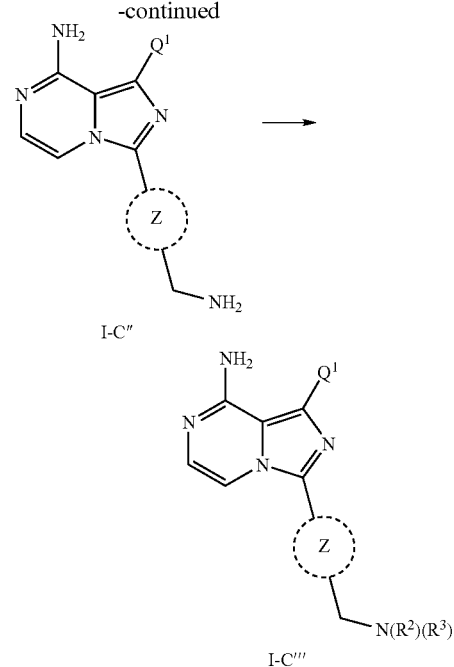

where $Q^1$, $R^2$, and $R^3$ are as defined previously for compound of Formula I and $A^2$=phthalimido.

In a typical preparation of compounds of Formula I-C' (compounds of Formula I where $R^1$=Z-$CH_2$-$A^2$), I-C" (compounds of Formula I where $R^1$=Z-$CH_2$—$NH_2$), and I-C''' (compounds of Formula I where $R^1$=Z-$CH_2$—N($R^2$)($R^3$)), the hydroxy group of compound of Formula I-B (compounds of Formula I where $R^1$=Z-$CH_2$OH) was converted to $A^2$, a phthalimide group, following the procedures as described in Scheme 5 for the conversion of compound of Formula VII to compound of Formula VI. Reaction of compound of Formula I-C' under conditions described in Scheme 4 afforded compound of Formula I-C". Reaction of compound of Formula I-C" with but not limited to various alkylating agents, various aldehydes/ketones under reductive amination conditions, various acylating agents such as acetic anhydride, benzoyl chlorides, or with carboxylic acids in the presence of EDC or DCC with HOBT or HOAT, or with sulphonylating agents such as $Ts_2O$ or $MeSO_2Cl$ afforded compounds of Formula I-C'''. For example, in a typical preparation of compounds of Formula I-C''' (compounds of Formula I where $R^1$=Z-$CH_2$—N($R^2$)($R^3$)), a compound of Formula I-C" is treated with a suitable acylating agent in the presence of a suitable base in a suitable solvent. Suitable solvents for use in the above process included, but were not limited to, ethers such as tetrahydrofuran (THF), glyme, and the like; and chlorinated solvents such as methylene chloride ($CH_2Cl_2$) or chloroform ($CHCl_3$). If desired, mixtures of these solvents were used, however, the preferred solvent was chloroform. Suitable bases for use in the above process included, but were not limited to, trialkylamines such as diisopropylethylamine, triethylamine, or resion bound trialkylamines such as PS-DIEA. The preferred base was PS-DIEA. In the case where the suitable acylating agent was acetic anhydride, the conversion of compound of Formula I-C" to compound of Formula I-C''' where $R^2$=H and $R^3$=$COCH_3$ was accomplished. The above process was carried out at temperatures between about −78° C. and about 120° C. Preferably, the reaction was carried out between 0° C. and about 20° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I-D (compounds of Formula I where $R^1=Z^2$-H and $Z^2$ is a heterocyclyl ring containing a nitrogen atom connected to H) and I-E (compounds of Formula I where $R^1=Z^2$-$R^2$ and $Z^2$ is a heterocyclyl ring containing a nitrogen atom connected to $R^2$) were prepared as shown below in Scheme 9:

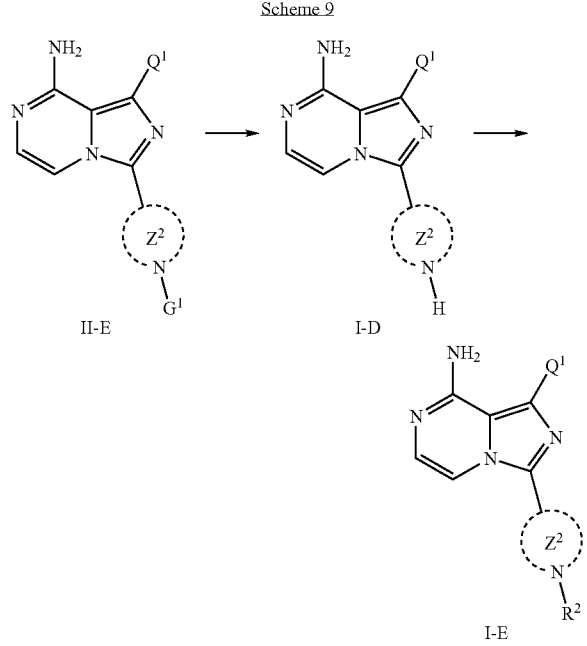

where $Q^1$ and $R^2$ are as defined previously for compound of Formula I, $G^1$ is C(=O)A or $CO_2A^6$, and $A^6$=alkyl, aryl, or aralkyl.

In a typical preparation of compound of Formula I-E (compounds of Formula I where $R^1=Z^2$-$R^2$ and $Z^2$ is a heterocyclyl ring containing a nitrogen atom connected to $R^2$), compound of Formula II-E (compounds of Formula II where $R^1=Z^2$-$G^1$ and $Z^2$ is a heterocyclyl ring containing a nitrogen atom connected to $G^1$) is treated with suitable reagents capable of deprotecting $G^1$ to H and therefore afford compound of Formula I-D (compounds of Formula I where $R^1=Z^2$-H and $Z^2$ is a heterocyclyl ring containing a nitrogen atom connected to H). For example, treatment of compound of Formula II-E (compounds of Formula II where $R^1=Z^2$-$G^1$ and $Z^2$ is a heterocyclyl ring containing a nitrogen atom connected to $G^1$) when $G^1$ is equal to C(=O)$CF_3$ with ammonia in methanol affords compound of Formula I-D (compounds of Formula I where $R^1=Z^2$-H and $Z^2$ is a heterocyclyl ring containing a nitrogen atom connected to H). Compound of Formula I-D (compounds of Formula I where $R^1=Z^2$-H and $Z^2$ is a heterocyclyl ring containing a nitrogen atom connected to H) can be subjected to various conditions including but not limited to reductive aminations, alkylations and ar(hetar)ylations, and acylations to afford amides, ureas, guanidines, carbamates, thiocarbamates, and variously substituted nitrogen adducts to afford the net conversion of NH to $NR^2$.

The compounds of Formula II-G (compounds of Formula II where $R^1=Z^3$-OH), II-H (compounds of Formula II where $R^1=Z^3$-$A^5(R^2)(R^3)_d$), I-F (compounds of Formula I where $R^1=Z^{31}$-OH), and I-G (compounds of Formula I where $R^1=Z^3$-$A^5(R^2)(R^3)_d$) were prepared as shown below in Scheme 10:

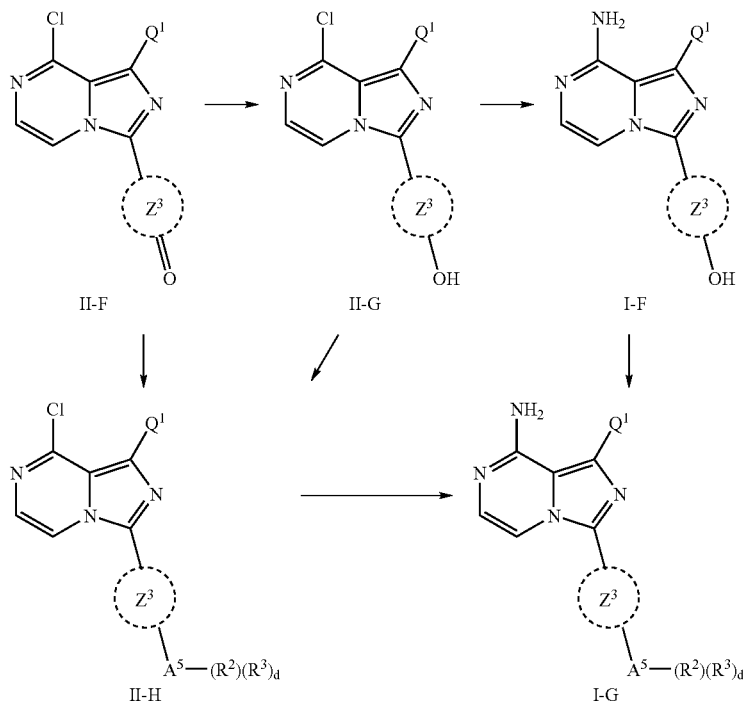

where $Q^1$, $R^2$, and $R^3$ are as defined previously for compound of Formula I; d=0 or 1; and $A^5$=N, O or S.

In a typical preparation of compound of Formula I-F (compounds of Formula I where $R^1=Z^3$-OH) and I-G (compounds of Formula I where $R^1=Z^3$-$A^5(R^2)(R^3)_d$), the following transformations occurred: Compound of Formula II-F (compounds of Formula I where $R^1=Z^3$-C=O) was reduced with a suitable reducing agent in a suitable solvent, such as sodium borohydride in methanol to afford compound of Formula II-G (compounds of Formula II where $R^1=Z^3$-OH). Compound of Formula II-G (compounds of Formula II where $R^1=Z^3$-OH) was subjected to ammonia in methanol to afford compound of Formula I-F (compounds of Formula I where $R^1=Z^3$-OH). Additionally, compounds of Formula II-F (compounds of Formula I where $R^1=Z^3$-C=O) can be reacted with various amines under reductive amination conditions (NaBH$_3$CN with $HA^5(R^2)(R^3)_d$ where d=0, $A^5$=N, and $R^2$ and $R^3$ are as previously described for compound of Formula I) to afford compounds of Formula II-H (compounds of Formula II where $R^1=Z^3$-$A^5(R^2)(R^3)_d$) where d=0, $A^5$=N, and $R^2$ and $R^3$ are as previously described for compound of Formula I. Subsequent reaction of compounds of Formula II-H (compounds of Formula II where $R^1=Z^3$-$A^5(R^2)(R^3)_d$ where d=0, $A^5$=N, and $R^2$ and $R^3$ are as previously described for compound of Formula I) with ammonia in methanol afforded compounds of Formula I-G (compounds of Formula I where $R^1=Z^3$-$A^5(R^2)(R^3)_d$). Furthermore, compounds of Formula II-H from II-G and I-G from I-F can be synthesized according to the conditions described in Scheme 8 for the transformations of II-B to II-D and I-B to I-C, respectively.

The compounds of Formula II-F (compounds of Formula II where $R^1=Z^3$=O) and II-B (compounds of Formula II where $R^1$=Z-CH$_2$OH) were prepared as shown below in Scheme 11:

Scheme 11

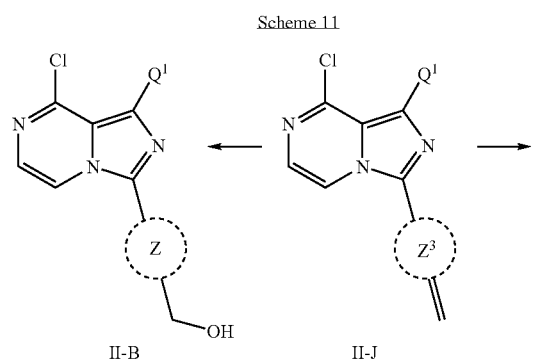

II-B          II-J

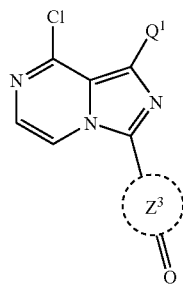

II-F where $Q^1$ is as defined previously for compound of Formula I.

In a typical preparation of compound of Formula II-F (compounds of Formula II where $R^1=Z^3$=O), compounds of Formula II-J (compounds of Formula II where $R^1=Z^3$=CH$_2$) were treated under suitable oxidizing conditions to afford the conversion of the exocyclic methylene moiety to its respective ketone (see 3-[1-(3-Benzyloxy-phenyl)-8-chloro-imidazo[1,5-a]pyrazin-3-yl]-cyclobutanone (compound of Formula II-F where $Z^3$=3-cyclobutyl and $Q^1$=Ph-(3-OBn)) in the Example section). Additionally, compound of Formula II-B (compounds of Formula II where $R^1$=Z-CH$_2$OH) can be prepared by reacting compounds of Formula II-J (compounds of Formula II where $R^1=Z^3$=CH$_2$) under suitable hydroboration-oxidation conditions (see {3-[1-(3-Benzyloxyphenyl)-8-chloro-imidazo[1,5-a]pyrazin-3-yl]cyclobutyl}methanol in the Example section). It should be noted that compounds of Formula II-B (compounds of Formula II where $R^1$=Z-CH$_2$OH) can be treated under suitable oxidative conditions such as those described within Example 65(a) to afford compounds of Formula II-A (compounds of Formula II where $R^1$=Z-CO$_2A^3$).

The compounds of Formula I-H (compounds of Formula I where $R^1=Z^3$-OH(CH$_2$OH)), I-J (compounds of Formula I where $R^1=Z^3$-OH(CH$_2$A$^4$)), and I-K (compounds of Formula I where $R^1=Z^3$-OH(CH$_2$$A^5(R^2)(R^3)_d$)), were prepared as shown below in Scheme 12:

Scheme 12

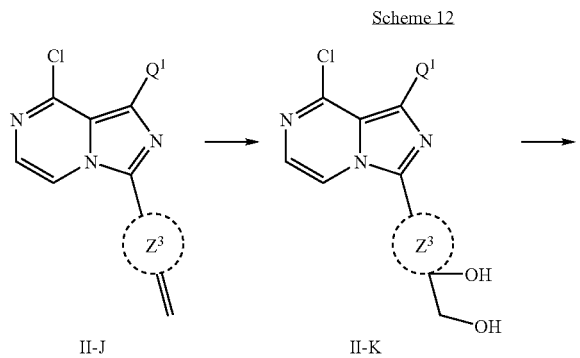

II-J          II-K

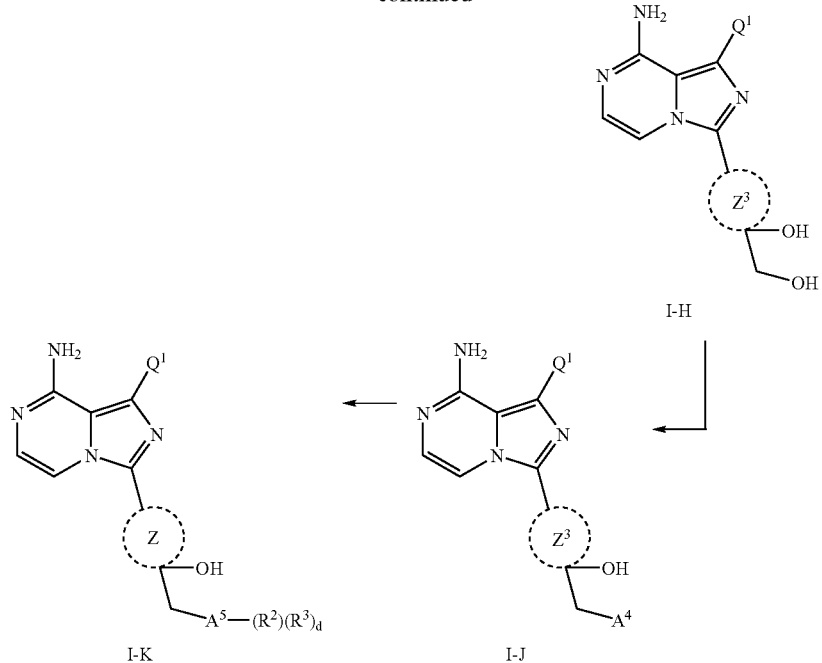

where $Q^1$, $R^2$, and $R^3$ are as defined previously for compound of Formula I; $A^4$=suitable leaving group such as OTs, OMs, or OTf; d=0 or 1; and $A^5$=N, O or S.

In a typical preparation of compounds of Formula I-H (compounds of Formula I where $R^1=Z^3$-OH(CH$_2$OH)), I-J (compounds of Formula I where $R^1=Z^3$-OH(CH$_2A^4$)) and I-K (compounds of Formula I where $R^1=Z^3$-OH(CH$_2A^5(R^2)$)$(R^3)_d$)), the exocyclic olefinic moiety of compound of Formula II-J (compounds of Formula II where $R^1=Z^3$=CH$_2$) was reacted with a suitable dihydroxylating agent such as osmium tetraoxide in the presence of NMO in a suitable solvent such as THF to afford compound of Formula II-K (compounds of Formula II where $R^1=Z^3$-OH(CH$_2$OH)) as a mixture of cis and trans isomers. Compound of Formula II-K (compounds of Formula II where $R^1=Z^3$-OH(CH$_2$OH)) was reacted under ammonolysis conditions in a suitable solvent such as isopropanol in a sealed pressure vessel at 110° C. to afford compound of Formula I-H (compounds of Formula I where $R^1=Z^3$-OH(CH$_2$OH)). The primary hydroxy group of compound of Formula I-H (compounds of Formula I where $R^1=Z^3$-OH(CH$_2$OH)) was converted to a suitable leaving group, $A^4$, such as OTs, OMs, or OTf, by reaction with Ts$_2$O, Ms$_2$O, or Tf$_2$O in the presence of a suitable base such as diisopropylamine or pyridine and solvent such as THF or methylene chloride to afford compound of Formula I-J (compounds of Formula I where $R^1=Z^3$-OH(CH$_2A^4$)). Reaction of compound of Formula I-J (compounds of Formula I where $R^1=Z^3$-OH(CH$_2A^4$)) with HA$^5(R^2)(R^3)_d$ in a suitable solvent such as THF or methylene chloride afforded compound of Formula I-K (compounds of Formula I where $R^1=Z^3$-OH (CH$_2A^5(R^2)(R^3)_d$).

The compounds of Formula I-L (compounds of Formula I where $R^1=Z^3$-OH(G$^{11}$)) were prepared as shown below in Scheme 13:

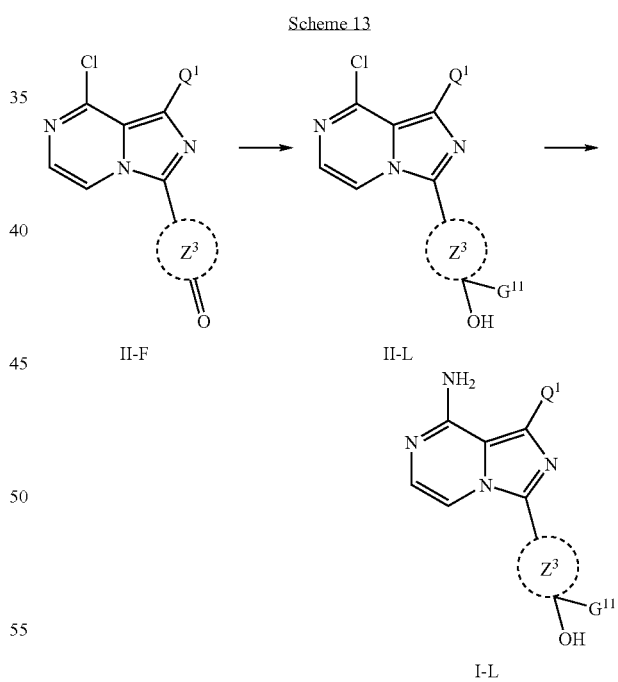

Scheme 13 where $Q^1$ and $G^{11}$ are as defined previously for compound of Formula I.

In a typical preparation of compounds of Formula I-L (compounds of Formula I where $R^1=Z^3$-OH(G$^{11}$)), the ketone moiety of compound of Formula II-F (compounds of Formula II where $R^1=Z^3$=O) was reacted with a suitable nucleophilic reagent such as MeMgBr or MeLi in a suitable solvent such as THF to afford compound of Formula II-L (compounds of Formula II where $R^1=Z^3$-OH($G^{11}$)) as a mixture of cis and trans isomers. Compound of Formula II-L (compounds of Formula II where $R^1=Z^3$-OH($G^{11}$)) was reacted under previously described ammonolysis conditions in a sealed pressure vessel at 110° C. to afford compound of Formula I-L (compounds of Formula I where $R^1=Z^3$-OH($G^{11}$)).

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Green and P. G. M. Wutz, John Wiley and Sons, 1989.

The following examples are intended to illustrate and not to limit the scope of the present invention.

Analytical HPLC Conditions:

Unless otherwise stated, all HPLC analyses were run on a Micromass system with a XTERRA MS C18 5μ 4.6×50 mm column and detection at 254 nm. Table A below lists the mobile phase, flow rate, and pressure.

TABLE A

| Time (min) | % CH$_3$CN | 0.01% HCOOH in H$_2$O % | Flow (mL/min) | Pressure (psi) |
|---|---|---|---|---|
| 0.00 | 5 | 95 | 1.3 | 400 |
| 4.00 | 100 | 0 | 1.3 | 400 |
| 5.50 | 100 | 0 | 1.3 | 400 |
| 6.00 | 5 | 95 | 1.3 | 400 |
| 7.00 | 5 | 95 | 1.3 | 400 |

Semipreparative HPLC Conditions:

Where indicated as "purified by Gilson HPLC", the compounds of interest were purified by a preparative/semi-preparative Gilson HPLC workstation with a Phenomenex Luna 5μ C18 (2) 60×21 20 MM 5μ column and Gilson 215 liquid handler (806 manometric module, 811C dynamic mixer, detection at 254 nm). Table B lists the gradient, flow rate, time, and pressure.

TABLE B

| Time (min) | % CH$_3$CN | 0.01% HCOOH in H$_2$O % | Flow (mL/min) | Pressure (psi) |
|---|---|---|---|---|
| 0.00 | 5 | 95 | 15 | 1000 |
| 15.00 | 60 | 40 | 15 | 1000 |
| 15.10 | 100 | 0 | 15 | 1000 |
| 19.00 | 100 | 0 | 15 | 1000 |
| 20.00 | 5 | 95 | 15 | 1000 |

Example 1

[1-(3-Benzyloxy-phenyl)-3-cyclobutyl-imidazo[1,5-a]pyrazin-8-ylamine] (compound of Formula I where $R^1$=cyclobutyl and $Q^1$=Ph-(3-OBn)): A methanolic solution (1.0 mL) of 1-(3-benzyloxy-phenyl)-8-chloro-3-cyclobutyl-imidazo[1,5-a]pyrazine (compound of Formula II where $R^1$=cyclobutyl and $Q^1$=Ph-(3-OBn)) (47.0 mg, 0.12 mmol) in a sealed tube was charged with 3.0 mL of 7N NH$_3$ in MeOH and heated to 110° C. for 48 h. The reaction was concentrated in vacuo, taken up into CH$_2$Cl$_2$ and purified using HPFC with a 2 g Jones silica gel column, (30% EtOAc:Hex) to yield the desired product as a off-white solid; $^1$H NMR (CDCl$_3$, 400 MHz) δ 1.99-2.18 (m, 2H), 2.47-2.52 (m, 2H), 2.61-2.66 (m, 2H), 3.81 (q, 1H, J=8.6 Hz), 5.15 (s, 4H), 7.02-7.05 (m, 2H), 7.10 (d, 1H, J=5.0 Hz), 7.24-7.52 (m, 8H); MS (ES) 371.30 (M+1), 372.31 (M+2), 373.31 (M+3).

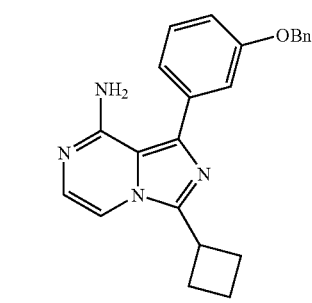

a) 1-(3-Benzyloxy-phenyl)-8-chloro-3-cyclobutyl-imidazo[1,5-a]pyrazine (compound of Formula II where $R^1$=cyclobutyl and $Q^1$=Ph-(3-OBn)): Cyclobutanecarboxylic Acid [(3-benzyloxy-phenyl)-(3-chloro-pyrazin-2-yl)-methyl]Amide (100.0 mg, 0.25 mmol) was dissolved in POCl$_3$ (0.8 mL) and CH$_2$Cl$_2$ (0.2 mL) and allowed to stir at 45° C. for 24 h. The reaction mixture was concentrated in vacuo to a yellow oil, dissolved in EtOAc and neutralized with cold sat. NaHCO$_3$. The aqueous layer was extracted with EtOAc (3×) and the combined organic layers were dried over Na$_2$SO$_4$, filtered and concentrated in vacuo, to yield the desired product as a yellow gum; $^1$H NMR (CDCl$_3$, 400 MHz) δ 2.18-2.21 (m, 1H), 2.49-2.53 (m, 2H), 2.63-2.69 (m, 2H), 3.82 (q, 1H, J=8.5 Hz), 5.14 (s, 2H), 7.03-7.05 (m, 1H), 7.29-7.49 (m, 9H); MS (ES) 390.21 (M+1), 392.20 (M+3), 393.21 (M+4).

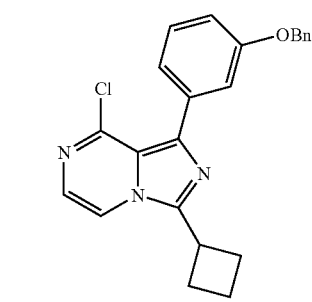

b) Cyclobutanecarboxylic Acid [(3-benzyloxy-phenyl)-(3-chloro-pyrazin-2-yl)-methyl]Amide (compound of Formula III where $R^1$=cyclobutyl and $Q^1$=Ph-(3-OBn)): Cyclobutanecarboxylic acid (21.2 mg, 0.2 mmol), EDC (61.0 mg, 0.3) and HOBt (32.5 mg, 0.2 mmol) were dissolved in CH$_2$Cl$_2$ (1.0 mL) and allowed to stir at rt for 10 min. A CH$_2$Cl$_2$ solution (1.0 mL) of C-(3-benzyloxy-phenyl)-C-(3-chloro-pyrazin-2-yl)-methylamine (compound of Formula IV where $Q^1$=Ph-(3-OBn)) (69.0 mg, 0.2 mmol) was added to the reaction mixture and allowed to react at rt for 24 h. Purification via HPFC using a 5 g Jones silica gel column (30% EtOAc:Hex) yielded the desired product as a yellow solid; $^1$H NMR (CDCl$_3$, 400 MHz) δ 1.57 (s, 1H), 1.87-2.13 (m, 1H), 2.13-2.18 (m, 3H), 3.06 (q, 1H, J=8.5 Hz), 5.05 (s, 2H), 6.54 (d, 1H, J=7.9 Hz), 6.86-6.94 (m, 3H), 7.20-7.58 (m, 5H), 8.31 (d, 1H, J=2.5 Hz), 8.53 (d, 1H, J=2.5 Hz); MS (ES) 408.26 (M+1), 410.26 (M+3), 411.27 (M+4).

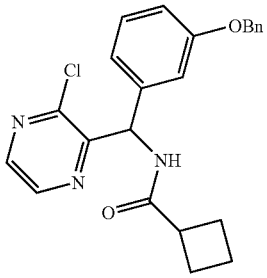

c) C-(3-Benzyloxy-phenyl)-C-(3-chloro-pyrazin-2-yl)-methylamine (compound of Formula IV where $Q^1$=Ph-(3-OBn)): 2-[(3-Benzyloxy-phenyl)-(3-chloro-pyrazin-2-yl)-methyl]-isoindole-1,3-dione (compound of Formula VI where $Q^1$=Ph-(3-OBn) and $A^2$=phthalimido) (2.76 g, 6.05 mmol) was dissolved in EtOH (12 mL) and $CH_2Cl_2$ (4 mL) charged with $N_2H_4$ (0.57 mL, 18.16 mmol) and allowed to react for 16 h at rt. The white precipitate that was formed was filtered and washed with EtOAc. The filtrate and organic washings were concentrated in vacuo, and purified via HPFC using a 100 g Jones silica gel column (50% EtOAc:Hex to 5% MeOH:$CH_2Cl_2$) to yield the desired product as a reddish oil; $^1$H NMR (CDCl$_3$, 400 MHz) δ 5.04 (s, 2H), 5.52 (s, 1H), 6.85-6.98 (m, 2H), 7.21-7.26 (m, 2H), 7.30-7.41 (m, 5H), 8.26 (d, 1H, J=2.5 Hz), 8.52 (d, 1H, J=2.5 Hz); MS (ES) 326.25 (M+1), 328.23 (M+3), 329.24 (M+4). An alternative preparation of this compound is as follows: To a solution of 3-benzyloxybenzaldehyde (compound of Formula $Q^1$-CHO where $Q^1$=Ph-(3-OBn) (1.00 g, 4.71 mmol) in dry THF (5 mL), cooled by ice/water, was added LiHMDS (1 M solution in THF; 4.8 mL, 4.8 mmol). After 30 min at 0° C., this solution of (3-Benzyloxybenzylidene)-trimethylsilylamine (compound of Formula $Q^1$-C=N—Si(CH$_3$)$_3$ where $Q^1$=Ph-(3-OBn) was cooled by CO$_2$(s)/acetone. To a solution of 2,2,6,6-tetramethylpiperidine (0.90 mL, 0.75 g, 5.3 mmol) in dry THF (10 mL), cooled by CO$_2$(s)/acetone, was added nBuLi (2.5 M in hexanes; 2.2 mL, 5.5 mmol). The cooling bath was replaced with an ice/water bath for 15 min, and then the solution was re-cooled to −78° C. After 15 min, 2-chloropyrazine (0.39 mL, 0.50 g, 4.4 mmol) was added. The cooled solution of (3-Benzyloxybenzylidene)-trimethylsilylamine (vide supra) was transferred into this solution of lithiochloropyrazine 2 by cannula 30 min later, and the mixture is stirred at −78° C. for 2.5 h and at 0° C. for 0.5 h. The reaction was quenched by adding water and EtOAc. The mixture was filtered through Celite, the layers were separated, the aqueous layer was extracted with EtOAc (4×30 mL), and the combined EtOAc extracts were washed with water and brine and dried over MgSO$_4$. The crude material was adsorbed onto Hydromatrix and chromatographed on silica gel [Jones Flashmaster, 50 g/150 mL cartridge, eluting with hexanes:EtOAc 4:1 (1-44)→1:1 (45-64)→EtOAc (65-97)], yielding the target compound as an orange foam.

d) 2-[(3-Benzyloxy-phenyl)-(3-chloro-pyrazin-2-yl)-methyl]-isoindole-1,3-dione (compound of Formula VI where $Q^1$=Ph-(3-OBn) and $A^2$=phthalimido): (3-Chloro-pyrazin-2-yl)-(3-benxyloxy-phenyl)-methanol (2.00 g, 6.12 mmol), triphenylphosphine (1.80 g, 6.70 mmol), and phthalimide (986 mg, 6.70 mmol) were dissolved in THF (20.0 mL) at rt. The reaction mixture was charged with DIAD (1.30 mL, 6.70 mmol) dropwise and allowed to react for 24 h at rt (TLC analysis (20% EtOAc:Hex)). The crude product was purified by applying HPFC with a 100 g Jones silica gel column (20% EtOAc:Hex) to yield the desired product as a pale yellow solid; $^1$H NMR (CDCl$_3$, 400 MHz) δ 5.02 (s, 2H), 6.41 (brs, 1H), 6.87-6.97 (m, 3H), 7.26-7.40 (m, 3H), 7.72-7.76 (m, 2H), 7.83-7.86 (m, 2H), 8.34 (d, 1H, J=2.4 Hz), 8.55 (d, 1H, J=2.4 Hz).

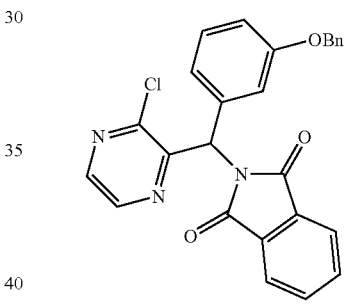

e) (3-Chloro-pyrazin-2-yl)-(3-benzyloxy-phenyl)-methanol [Compound of Formula VII where $Q^1$=Ph-(3-OBn)]: A THF (20 mL) solution of 2M n-BuLi in cyclohexanes was cooled to −78° C. and charged with 2,2,6,6-tetramethylpiperidine (1.8 mL, 10.48 mmol). The reaction vessel was removed from the cooling bath and allowed to warm to 0° C. for 15 min, then cooled back to −78° C. and charged with 2-chloropyrazine (1.0 g, 8.73 mmol) dropwise. The reaction was allowed to react for 15 min, and charged with a 10.0 mL THF solution of 3-benzyloxybenzaldehyde (2.0 g, 9.60 mmol) slowly at −78° C. The reaction was allowed to react for 2 h (TLC analysis (30% EtOAc:Hex)) and quenched with HCl$_{conc.}$ (2.0 mL), and H$_2$O (30.0 mL). The crude product was extracted from the aqueous/THF layer 4× with CH$_2$Cl$_2$. The organic layers were combined and washed 1× with H$_2$O, 1× brine, dried over Na$_2$SO$_4$ and concentrated in vacuo, to yield the crude product as a brown oil. High performance flash chromatography (HPFC) with a 70 g Jones silica gel column (30% EtOAc:Hex) was applied to yield the desired product as a pale yellow solid; $^1$H NMR (CDCl$_3$, 400 MHz) δ 5.01 (s, 3H), 6.00 (s, 2H), 6.90-6.96 (m, 3H), 7.23-7.41 (m, 6H), 8.36 (d, 1H, J=2.4 Hz), 8.54 (d, 1H, J=2.5 Hz); MS (ES) 327.16 (M+1), 329.16 (M+3).

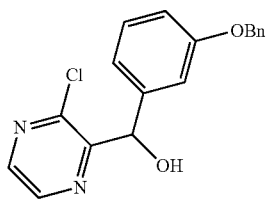

Example 2

1-(3-Benzyloxyphenyl)-3-phenyl-imidazo[1,5-a]pyrazin-8-ylamine (compound of Formula I where R[1]=phenyl and Q[1]=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R[1]=cyclobutyl and Q[1]=Ph-(3-OBn)) with 1-(3-benzyloxyphenyl)-8-chloro-3-phenylimidazo[1,5-a]pyrazine (compound of Formula II where R[1]=phenyl and Q[1]=Ph-(3-OBn)); white solid; $^1$H NMR (DMSO-d6, 400 MHz) δ 5.12 (s, 2H), 6.12 (bs, 2H), 7.04-7.06 (m, 2H), 7.20 (d, 1H, J=7.6 Hz), 7.25-7.55 (m, 10H), 7.70 (d, 1H, J=4.8 Hz), 7.79 (d, 2H, J=8.0 Hz).

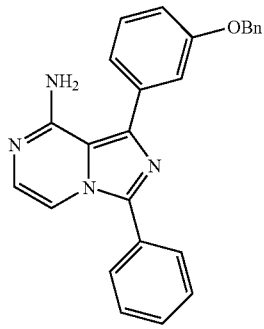

a) 1-(3-Benzyloxyphenyl)-8-chloro-3-phenylimidazo[1,5-a]pyrazine (compound of Formula II where R[1]=phenyl and Q[1]=Ph-(3-OBn)) was prepared according to the procedures described for 1-(3-benzyloxy-phenyl)-8-chloro-3-cyclobutyl-imidazo[1,5-a]pyrazine (compound of Formula II where R[1]=cyclobutyl and Q[1]=Ph-(3-OBn)) above except for the substitution of cyclobutanecarboxylic acid [(3-benzyloxy-phenyl)-(3-chloro-pyrazin-2-yl)-methyl]amide with N-[(3-benzyloxyphenyl)-(3-chloropyrazin-2-yl)methyl]benzamide (compound of Formula III where R[1]=phenyl and Q[1]=Ph-(3-OBn)); yellow solid; $^1$H NMR (DMSO-d6, 400 MHz) δ 5.12 (s, 2H), 6.98 (ddd, 1H, J=1.2, 2.8, 8.2 Hz), 7.21-7.43 (m, 8H), 7.52-7.59 (m, 4H), 7.84-7.87 (m, 2H), 8.37 (d, 1H, J=5.2 Hz).

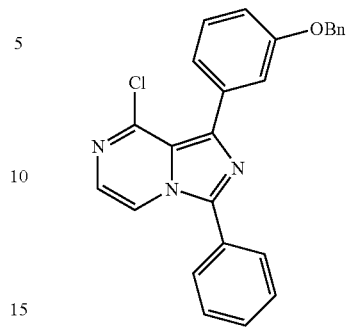

b) N-[(3-Benzyloxyphenyl)-(3-chloropyrazin-2-yl)methyl]benzamide (compound of Formula III where R[1]=phenyl and Q[1]=Ph-(3-OBn)) was prepared according to the procedures described for the synthesis of cyclobutanecarboxylic Acid [(3-benzyloxy-phenyl)-(3-chloro-pyrazin-2-yl)-methyl]amide (compound of Formula III where R[1]=cyclobutyl and Q[1]=Ph-(3-OBn)) above except for the substitution of benzoic acid for cyclobutanecarboxylic acid; $^1$H NMR (DMSO-d6, 400 MHz) δ 5.02 (s, 2H), 6.58 (d, 1H, J=7.6 Hz), 6.91-6.93 (m, 2H), 6.99 (s, 1H), 7.21-7.49 (m, 9H), 7.85 (d, 2H, J=7.2 Hz), 8.43 (d, 1H, J=2.4 Hz), 8.63 (d, 1H, J=2.4 Hz), 9.23 (d, 1H, J=7.6 Hz).

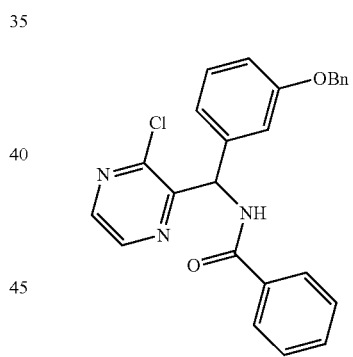

Example 3

3-Benzyl-1-(3-benzyloxyphenyl)-imidazo[1,5-a]pyrazin-8-ylamine (compound of Formula I where R[1]=benzyl and Q[1]=Ph-(3OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R[1]=cyclobutyl and Q[1]=Ph-(3-OBn)) with 3-benzyl-1-(3-benzyloxyphenyl)-8-chloroimidazo[1,5-a]pyrazine (compound of Formula II where R[1]=benzyl and Q[1]=Ph-(3-OBn)); white solid; $^1$H NMR (DMSO-d6, 400 MHz) δ 4.40 (s, 2H), 5.12 (s, 2H), 6.08 (bs, 2H), 7.03 (d, 1H, J=4.8 Hz), 7.08 (ddd, 1H, J=1.2, 2.8, 8.2 Hz), 7.19-7.49 (m, 13H), 7.57 (d, 1H, J=5.2 Hz).

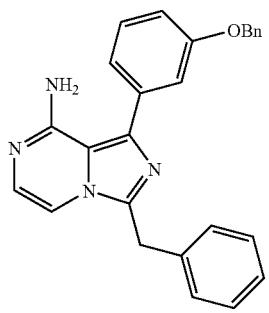

a) 3-Benzyl-1-(3-benzyloxyphenyl)-8-chloroimidazo[1,5-a]pyrazine (compound of Formula II where R¹=benzyl and Q¹=Ph-(3-OBn)) was prepared according to the procedures described for 1-(3-benzyloxy-phenyl)-8-chloro-3-cyclobutyl-imidazo[1,5-a]pyrazine (compound of Formula II where R¹=cyclobutyl and Q¹=Ph-(3-OBn)) above except for the substitution of cyclobutanecarboxylic acid [(3-benzyloxyphenyl)-(3-chloro-pyrazin-2-yl)-methyl]amide with N-[(3-benzyloxyphenyl)-(3-chloropyrazin-2-yl-methyl]-2-phenylacetamide (compound of Formula III where R¹=benzyl and Q¹=Ph-(3-OBn)); yellow solid; ¹H NMR (DMSO-d₆, 400 MHz) δ 5.12 (s, 2H), 6.98 (ddd, 1H, J=1.2 Hz, 2.8 Hz, 8.2 Hz), 7.21-7.43 (m, 8H), 7.52-7.59 (m, 4H), 7.84-7.87 (m, 2H), 8.37 (d, 1H, J=5.2 Hz).

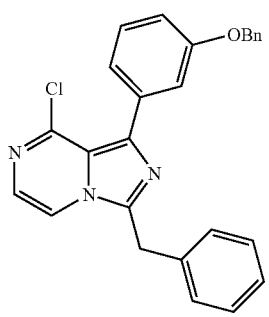

b) N-[(3-Benzyloxyphenyl)-(3-chloropyrazin-2-yl-methyl]-2-phenylacetamide (compound of Formula III where R¹=benzyl and Q¹=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where R¹=cyclobutyl and Q¹=Ph-(3-OBn)) above except for the substitution of phenylacetic acid for cyclobutanecarboxylic acid.

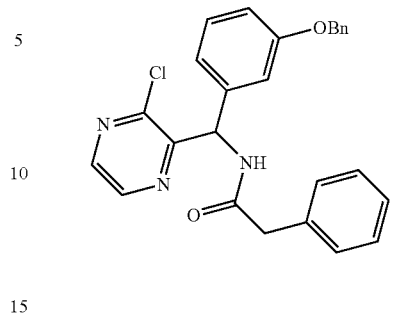

Example 4

1-(3-Benzyloxyphenyl)-3-naphthalen-1-yl-imidazo[1,5-a]pyrazin-8-ylamine (compound of Formula I where R¹=naphthalen-1-yl and Q¹=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R¹=cyclobutyl and Q¹=Ph-(3-OBn)) with 1-(3-benzyloxy-phenyl)-8-chloro-3-naphthalen-1-yl-imidazo[1,5-a]pyrazine (compound of Formula II where R¹=naphthalen-1-yl and Q¹=Ph-(3-OBn)); White solid; ¹H NMR (DMSO-d₆, 400 MHz) δ 5.20 (s, 2H), 6.27 (bs, 2H), 7.05 (d, 1H, J=4.8 Hz), 7.13 (m, 1H), 7.21 (d, 1H, J=5.2 Hz), 7.33-7.51 (m, 8H), 7.55-7.65 (m, 3H), 7.70-7.72 (m, 1H), 7.82-7.85 (m, 2H), 8.09 (d, 1H, J=7.6 Hz), 8.16 (d, 1H, J=8.4 Hz).

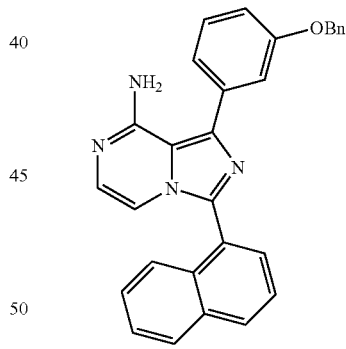

a) 1-(3-benzyloxy-phenyl)-8-chloro-3-naphthalen-1-yl-imidazo[1,5-a]pyrazine (compound of Formula II where R¹=naphthalen-1-yl and Q¹=Ph-(3-OBn)) was prepared according to the procedures described for 1-(3-benzyloxy-phenyl)-8-chloro-3-cyclobutyl-imidazo[1,5-a]pyrazine (compound of Formula II where R¹=cyclobutyl and Q¹=Ph-(3-OBn)) above except for the substitution of cyclobutanecarboxylic acid [(3-benzyloxy-phenyl)-(3-chloro-pyrazin-2-yl)-methyl]amide with naphthalene-1-carboxylic acid [(3-benzyloxyphenyl)-(3-chloropyrazin-2-yl)-methyl]-amide (compound of Formula II where R¹=naphthalen-1-yl and Q¹=Ph-(3-OBn)); MS (ES) 462.46 (M+1), 464.46 (M+3).

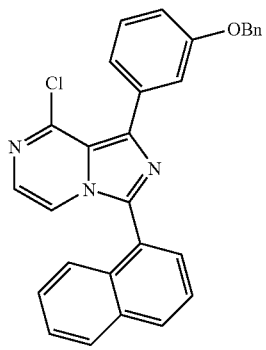

b) Naphthalene-1-carboxylic acid [(3-benzyloxyphenyl)-(3-chloropyrazin-2-yl)-methyl]-amide (compound of Formula II where $R^1$=naphthalen-1-yl and $Q^1$=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where $R^1$=cyclobutyl and $Q^1$=Ph-(3-OBn)) above except for the substitution of 1-naphthanoic acid for cyclobutanecarboxylic acid; White solid; $^1$H NMR (DMSO-$d_6$, 400 MHz) δ 5.12 (s, 2H), 6.72 (d, 1H, J=7.4 Hz), 6.98 (dd, 1H, J=2.4 Hz, 8.2 Hz), 7.06 (d, 1H, J=7.6 Hz), 7.12 (bs, 1H), 7.29-7.44 (m, 5H), 7.53-7.57 (m, 4H), 7.65 (d, 1H, J=7.0 Hz), 7.97-8.03 (m, 2H), 8.13-8.15 (m, 1H), 8.52 (d, 1H, J=2.5 Hz), 8.73 (d, 1H, J=2.5 Hz).

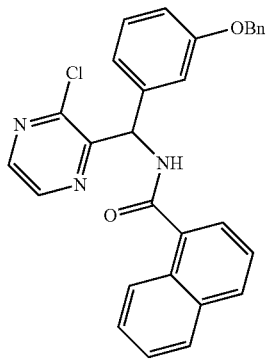

Example 5

1-(3-Benzyloxyphenyl)-3-naphthalen-2-yl-imidazo[1,5-a]pyrazin-8-ylamine (compound of Formula I where $R^1$=naphthalen-2-yl and $Q^1$=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where $R^1$=cyclobutyl and $Q^1$=Ph-(3-OBn)) with 1-(3-benzyloxy-phenyl)-8-chloro-3-naphthalen-2-yl-imidazo[1,5-a]pyrazine (compound of Formula II where $R^1$=naphthalen-2-yl and $Q^1$=Ph-(3-OBn)); White solid; $^1$H NMR (DMSO-$d_6$, 400 MHz) δ 5.18 (s, 2H), 6.18 (bs, 2H), 7.11-7.47 (m, 9H), 7.58-7.61 (m, 2H), 7.94-8.10 (m, 5H), 8.44 (s, 2H).

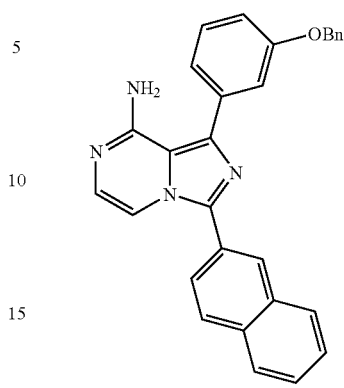

a) 1-(3-benzyloxy-phenyl)-8-chloro-3-naphthalen-2-yl-imidazo[1,5-a]pyrazine (compound of Formula II where $R^1$=naphthalen-2-yl and $Q^1$=Ph-(3-OBn)) was prepared according to the procedures described for 1-(3-benzyloxy-phenyl)-8-chloro-3-cyclobutyl-imidazo[1,5-a]pyrazine (compound of Formula II where $R^1$=cyclobutyl and $Q^1$=Ph-(3-OBn)) above except for the substitution of cyclobutanecarboxylic acid [(3-benzyloxy-phenyl)-(3-chloro-pyrazin-2-yl)-methyl]amide with naphthalene-2-carboxylic acid [(3-benzyloxyphenyl)-(3-chloropyrazin-2-yl)-methyl]-amide (compound of Formula II where $R^1$=naphthalen-2-yl and $Q^1$=Ph-(3-OBn)); MS (ES) 462.49 (M+1), 464.48 (M+3).

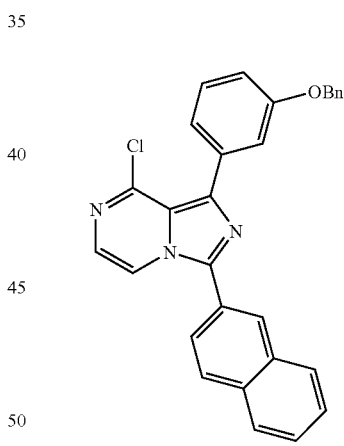

b) Naphthalene-2-carboxylic acid [(3-benzyloxyphenyl)-(3-chloropyrazin-2-yl)-methyl]-amide (compound of Formula II where $R^1$=naphthalen-2-yl and $Q^1$=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where $R^1$=cyclobutyl and $Q^1$=Ph-(3-OBn)) above except for the substitution of 2-naphthanoic acid for cyclobutanecarboxylic acid; Off white solid, $^1$H NMR (DMSO-$d_6$, 400 MHz) δ 5.12 (s, 2H), 6.70 (d, 1H, J=7.5 Hz), 6.89-7.09 (m, 3H), 7.29-7.44 (m, 6H), 7.60-7.63 (m, 2H), 7.97-8.11 (m, 4H), 8.50 (d, 1H, J=2.5 Hz), 8.58 (s, 1H), 8.72 (d, 1H, J=2.5 Hz).

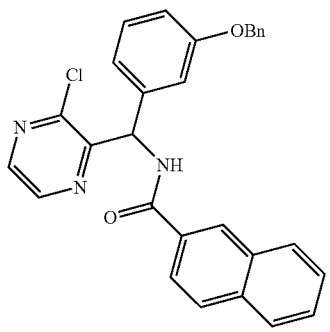

Example 6

1-(3-Benzyloxy-phenyl)-3-cyclopentyl-imidazo[1,5-a]pyrazin-8-ylamine (compound of Formula I where R¹=cyclopentyl and Q¹=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R¹=cyclobutyl and Q¹=Ph-(3-OBn)) with 1-(3-benzyloxy-phenyl)-8-chloro-3-cyclopentyl-imidazo[1,5-a]pyrazine (compound of Formula II where R¹=cyclopentyl and Q¹=Ph-(3-OBn)); MS (ES) 385.5 (M+1).

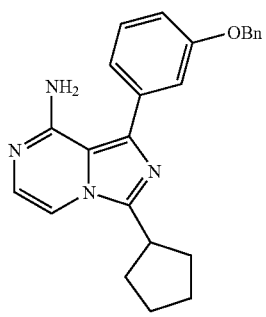

a) 1-(3-Benzyloxy-phenyl)-8-chloro-3-cyclopentyl-imidazo[1,5-a]pyrazine (compound of Formula II where R¹=cyclopentyl and Q¹=Ph-(3-OBn)) was prepared according to the procedures described for 1-(3-benzyloxy-phenyl)-8-chloro-3-cyclobutyl-imidazo[1,5-a]pyrazine (compound of Formula II where R¹=cyclobutyl and Q¹=Ph-(3-OBn)) above except for the substitution of cyclobutanecarboxylic acid [(3-benzyloxy-phenyl)-(3-chloro-pyrazin-2-yl)-methyl]amide with cyclopentanecarboxylic acid [(3-benzyloxy-phenyl)-(3-chloro-pyrazin-2-yl)-methyl]-amide (compound of Formula II where R¹=cyclopentyl and Q¹=Ph-(3-OBn)); MS (ES) 404.2 (M+1), 406.2 (M+3).

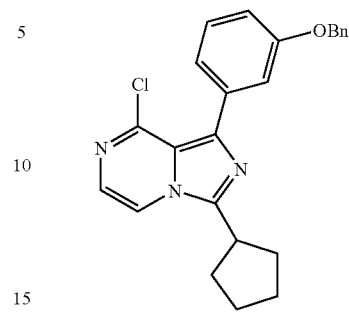

b) Cyclopentanecarboxylic acid [(3-benzyloxy-phenyl)-(3-chloro-pyrazin-2-yl)-methyl]-amide (compound of Formula II where R¹=cyclopentyl and Q¹=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where R¹=cyclobutyl and Q¹=Ph-(3-OBn)) above except for the substitution of cyclopentane carboxylic acid for cyclobutanecarboxylic acid; MS (ES) 422.2 (M+1), 424.2 (M+3).

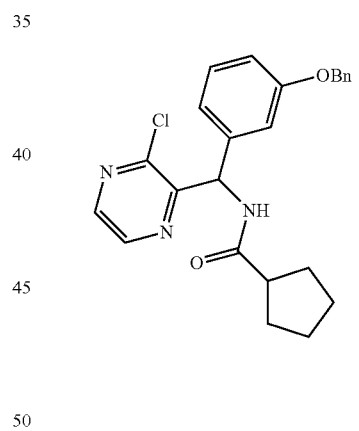

Example 7

1-(3-Benzyloxy-phenyl)-3-cyclohexyl-imidazo[1,5-a]pyrazin-8-ylamine (compound of Formula I where R¹=cyclohexyl and Q¹=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R¹=cyclobutyl and Q¹=Ph-(3-OBn)) with 1-(3-benzyloxy-phenyl)-8-chloro-3-cyclohexyl-imidazo[1,5-a]pyrazine (compound of Formula II where R¹=cyclohexyl and Q¹=Ph-(3-OBn)); MS (ES) 399.3 (M+1).

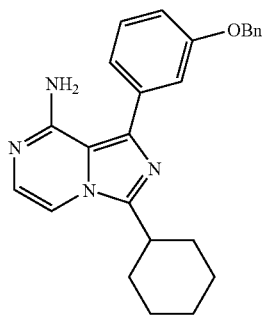

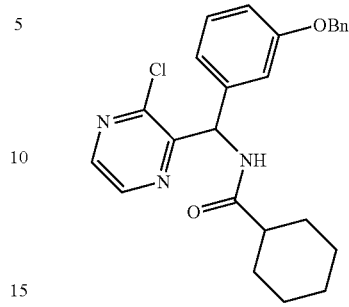

Example 8

1-(3-Benzyloxy-phenyl)-3-cycloheptyl-imidazo[1,5-a]pyrazin-8-ylamine (compound of Formula I where R¹=cycloheptyl and Q¹=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R¹=cyclobutyl and Q¹=Ph-(3-OBn)) with 1-(3-benzyloxy-phenyl)-8-chloro-3-cycloheptyl-imidazo[1,5-a]pyrazine (compound of Formula II where R¹=cycloheptyl and Q¹=Ph-(3-OBn)); MS (ES) 413.3 (M+1).

a) 1-(3-Benzyloxy-phenyl)-8-chloro-3-cyclohexyl-imidazo[1,5-a]pyrazine (compound of Formula II where R¹=cyclohexyl and Q¹=Ph-(3-OBn)) was prepared according to the procedures described for 1-(3-benzyloxy-phenyl)-8-chloro-3-cyclobutyl-imidazo[1,5-a]pyrazine (compound of Formula II where R¹=cyclobutyl and Q¹=Ph-(3-OBn)) above except for the substitution of cyclobutanecarboxylic acid [(3-benzyloxy-phenyl)-(3-chloro-pyrazin-2-yl)-methyl]amide with cyclohexylcarboxylic acid [(3-benzyloxy-phenyl)-(3-chloro-pyrazin-2-yl)-methyl]-amide (compound of Formula II where R¹=cyclohexyl and Q¹=Ph-(3-OBn)); MS (ES) 418.2 (M+1), 420.2 (M+3).

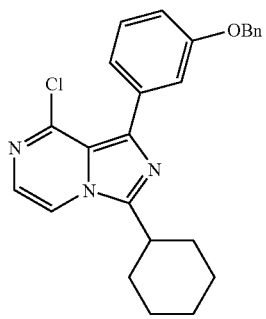

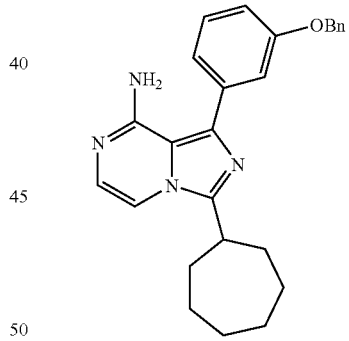

b) Cyclohexane carboxylic acid [(3-benzyloxy-phenyl)-(3-chloro-pyrazin-2-yl)-methyl]-amide (compound of Formula II where R¹=cyclohexyl and Q¹=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where R¹=cyclobutyl and Q¹=Ph-(3-OBn)) above except for the substitution of cyclohexane carboxylic acid for cyclobutanecarboxylic acid; MS (ES) 436.2 (M+1), 438.2 (M+3).

a) 1-(3-Benzyloxy-phenyl)-8-chloro-3-cycloheptyl-imidazo[1,5-a]pyrazine (compound of Formula II where R¹=cycloheptyl and Q¹=Ph-(3-OBn)) was prepared according to the procedures described for 1-(3-benzyloxy-phenyl)-8-chloro-3-cyclobutyl-imidazo[1,5-a]pyrazine (compound of Formula II where R¹=cyclobutyl and Q¹=Ph-(3-OBn)) above except for the substitution of cyclobutanecarboxylic acid [(3-benzyloxy-phenyl)-(3-chloro-pyrazin-2-yl)-methyl]amide with cycloheptylcarboxylic acid [(3-benzyloxy-phenyl)-(3-chloro-pyrazin-2-yl)-methyl]-amide (compound of Formula II where R¹=cycloheptyl and Q¹=Ph-(3-OBn)); MS (ES) 432.2 (M+1), 434.2 (M+3).

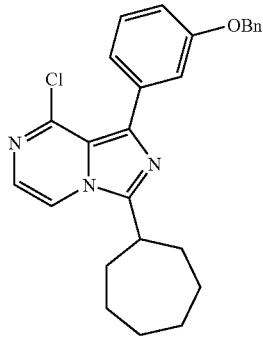

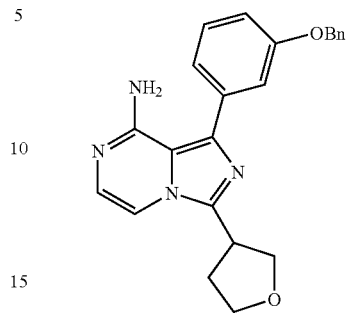

a) 1-(3-Benzyloxy-phenyl)-8-chloro-3-(tetrahydro-furan-3-yl)-imidazo[1,5-a]pyrazine (compound of Formula II where R¹=tetrahydrofuran-3-yl and Q¹=Ph-(3-OBn)) was prepared according to the procedures described for 1-(3-benzyloxy-phenyl)-8-chloro-3-cyclobutyl-imidazo[1,5-a]pyrazine (compound of Formula II where R¹=cyclobutyl and Q¹=Ph-(3-OBn)) above except for the substitution of cyclobutanecarboxylic acid [(3-benzyloxy-phenyl)-(3-chloro-pyrazin-2-yl)-methyl]amide with tetrahydro-furan-3-carboxylic acid [(3-benzyloxy-phenyl)-(3-chloro-pyrazin-2-yl)-methyl]-amide (compound of Formula II where R¹=tetrahydrofuran-3-yl and Q¹=Ph-(3-OBn)); MS (ES) 406.2 (M+1), 408.2 (M+3).

b) Cycloheptane carboxylic acid [(3-benzyloxy-phenyl)-(3-chloro-pyrazin-2-yl)-methyl]-amide (compound of Formula II where R¹=cycloheptyl and Q¹=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where R¹=cyclobutyl and Q¹=Ph-(3-OBn)) above except for the substitution of cycloheptane carboxylic acid for cyclobutanecarboxylic acid; MS (ES) 450.2 (M+1), 452.2 (M+3).

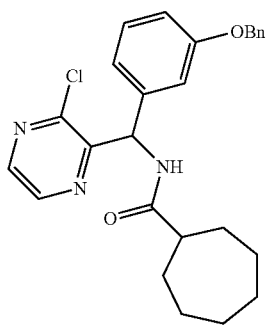

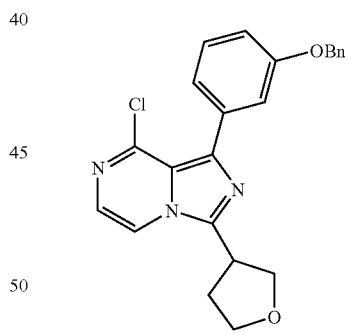

Example 9

1-(3-Benzyloxy-phenyl)-3-(tetrahydro-furan-3-yl)-imidazo[1,5-a]pyrazin-8-ylamine (compound of Formula I where R¹=tetrahydrofuran-3-yl and Q¹=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where R¹=cyclobutyl and Q¹=Ph-(3-OBn)) with 1-(3-benzyloxy-phenyl)-8-chloro-3-(tetrahydro-furan-3-yl)-imidazo[1,5-a]pyrazine (compound of Formula II where R¹=tetrahydrofuran-3-yl and Q¹=Ph-(3-OBn)); MS (ES) 387.5 (M+1).

b) Tetrahydro-furan-3-carboxylic acid [(3-benzyloxy-phenyl)-(3-chloro-pyrazin-2-yl)-methyl]-amide (compound of Formula II where R¹=3-tetrahydrofuranyl and Q¹=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where R¹=cyclobutyl and Q¹=Ph-(3-OBn)) above except for the substitution of tetrahydro-furan-3-carboxylic acid for cyclobutanecarboxylic acid; MS (ES) 424.2 (M+1), 426.2 (M+3).

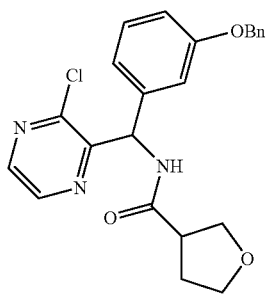

Example 10 trans-4-[8-Amino-1-(3-benzyloxy-phenyl)-imidazo[1,5-a]pyrazin-3-yl]-cyclohexanecarboxylic acid amide (compound of Formula I-A where Z=cyclohexyl, C(=O)NR$^2$R$^3$=4-trans-C(=O)NH$_2$, and Q$^1$=Ph-(3-OBn)) was prepared as follows: A 0.2 M 2-propanol solution of trans-4-[1-(3-benzyloxyphenyl)-8-chloro-imidazo[1,5-a]pyrazin-3-yl]cyclohexane carboxylic acid methyl ester (compound of Formula II-A where Z=cyclohexyl, CO$_2$A$^3$=4-trans-CO$_2$Me, and Q$^1$=Ph-(3-OBn)) (150 mg, 0.32 mmol) in a 15 mL sealed tube was cooled to −78° C. and charged with ammonia for 30 sec. The reaction was heated to 110° C. for 4d, after which time the reaction mixture was charged with EtOAc and sat. NaHCO$_3$. The EtOAc layer washed with sat. NaHCO$_3$ (3×) and brine (1×) and the organic layer was dried over Na$_2$SO$_4$, filtered, and concentrated in vacuo to afford the desired product as an off-white solid. The product was dry-loaded and purified by silica gel chromatography, eluting with 2% MeOH/CH$_2$Cl$_2$ to 5% MeOH/CH$_2$Cl$_2$. The resulting white solid was recrystallized with CH$_2$Cl$_2$, CH$_3$CN, and hexanes to afford the title compound as a white powder; $^1$H NMR (DMSO-d$_6$, 400 MHz) δ 1.57-1.66 (m, 4H), 1.86-1.88 (m, 2H), 1.98-2.00 (m, 2H), 2.17-2.23 (m, 1H), 3.07-3.13 (m, 1H), 5.17 (s, 1H), 6.02 (bs, 2H), 6.70 (bs, 2H), 7.03 (d, 1H, J=5.2 Hz), 7.07 (ddd, 1H, J=0.8, 2.4, 8.4 Hz), 7.18 (d, 1H, J=7.6 Hz), 7.21-7.22 (m, 1H), 7.32-7.37 (m, 1H), 7.40 (d, 1H, J=1.6 Hz), 7.41-7.44 (m, 2H), 7.46 (s, 1H), 7.50 (d, 1H, J=1.6 Hz), 7.66 (d, 1H, J=4.8 Hz); MS (ES) 442.5 (M+1).

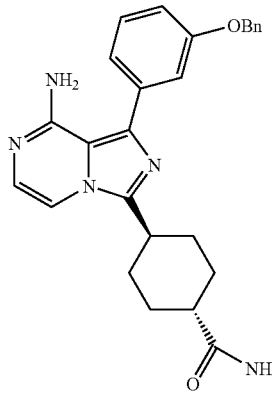

a) trans-4-[1-(3-Benzyloxy-phenyl)-8-chloro-imidazo[1,5-a]pyrazin-3-yl]-cyclohexanecarboxylic acid methyl (compound of Formula II-A where Z=cyclohexyl, CO$_2$A$^3$=4-trans-CO$_2$Me, and Q$^1$=Ph-(3-OBn)) was prepared according to the procedures described for 1-(3-benzyloxy-phenyl)-8-chloro-3-cyclobutyl-imidazo[1,5-a]pyrazine (compound of Formula II where R$^1$=cyclobutyl and Q$^1$=Ph-(3-OBn)) above except for the substitution of cyclobutanecarboxylic acid [(3-benzyloxy-phenyl)-(3-chloro-pyrazin-2-yl)-methyl]amide (compound of Formula III where R$^1$=cyclobutyl and Q$^1$=Ph-(3-OBn)) with trans-4-{[(3-benzyloxy-phenyl)-(3-chloro-pyrazin-2-yl)-methyl]-carbamoyl}-cyclohexanecarboxylic acid methyl ester (compound of Formula III where R$^1$=trans-4-cyclohexane carboxylic acid methyl ester and Q$^1$=Ph-(3-OBn)); MS (ES) 476.2 (M+1), 478.2 (M+3).

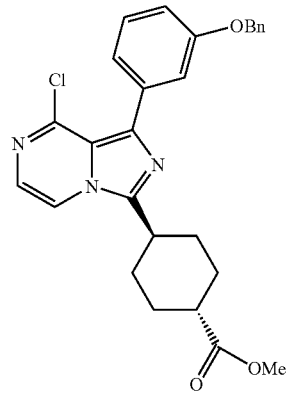

b) trans-4-{[(3-Benzyloxy-phenyl)-(3-chloro-pyrazin-2-yl)-methyl]-carbamoyl}-cyclohexanecarboxylic acid methyl ester (compound of Formula III where R$^1$=trans-4-cyclohexane carboxylic acid methyl ester and Q$^1$=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where R$^1$=cyclobutyl and Q$^1$=Ph-(3-OBn)) above except for the substitution of trans-cyclohexane-1,4-dicarboxylic acid monomethyl ester for cyclobutanecarboxylic acid; MS (ES) 494.3 (M+1), 496.3 (M+3).

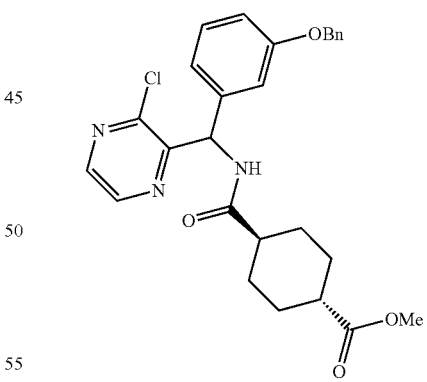

Example 11 trans-{4-[8-Amino-1-(3-benzyloxy-phenyl)-imidazo[1,5-a]pyrazin-3-yl]-cyclohexyl}-methanol (compound of Formula I-B where Z=cyclohexyl and Q$^1$=Ph-(3-OBn)) was prepared according to the procedures described for the synthesis of 4-[8-amino-1-(3-benzyloxy-phenyl)-imidazo[1,5-a]pyrazin-3-yl]-cyclohexanecarboxylic acid amide except for the substitution of trans-4-[1-(3-benzyloxyphenyl)-8-chloroimidazo[1,5-a]pyrazin-3-yl]cyclohexane carboxylic acid methyl ester (compound of Formula II-A where Z=cyclohexyl, $CO_2A^3$=4-trans-$CO_2Me$, and $Q^1$=Ph-(3-OBn)) with {4-[1-(3-benzyloxy-phenyl)-8-chloro-imidazo[1,5-a]pyrazin-3-yl]-cyclohexyl}-methanol (compound of Formula II-B where Z=cyclohexyl and $Q^1$=Ph-(3-OBn)); $^1$H NMR (CDCl$_3$, 400 MHz) δ 1.21 (ddd, 2H, J=25.2 Hz, 12.8 Hz, 3.6 Hz), 1.65-1.71 (m, 1H), 1.91 (ddd, 2H, J=29.6 Hz, 13.2 Hz, 3.6 Hz), 2.00-2.05 (m, 2H), 2.12-2.16 (m, 2H), 2.93 (tt, 1H, J=11.6 Hz, 4.0 Hz), 3.56 (d, 2H, J=6.0 Hz), 5.11 (bs, 2H), 5.16 (s, 2H), 7.05 (ddd, 1H, J=8.0 Hz, 2.8 Hz, 1.2 Hz), 7.07 (d, 1H, J=5.2 Hz), 7.20-7.22 (m, 2H), 7.23-7.24 (m, 2H), 7.31-7.35 (m, 1H), 7.36-7.41 (m, 2H), 7.42-7.45 (m, 2H); MS (ES) 429.5 (M+1).

Example 12 cis-3-[8-Amino-1-(3-benzyloxy-phenyl)-imidazo[1,5-a]pyrazin-3-yl]-cyclobutanol (compound of Formula I-F where $Z^3$=cis-3-cyclobutyl and $Q^1$=Ph-(3-OBn)): 3-[1-(3-Benzyloxy-phenyl)-8-chloro-imidazo[1,5-a]pyrazin-3-yl]-cyclobutanol (compound of Formula II-G where $Z^3$=cis-3-cyclobutyl and $Q^1$=Ph-(3-OBn)) (84.0 mg, 0.2 mmol) was placed in a sealed tube and charged with 3.0 mL of 7N NH$_3$ in MeOH and heated to 110° C. for 60 h. The reaction was concentrated in vacuo, taken up into CH$_2$Cl$_2$ and purified using HPFC with a 5 g Jones silica gel column (2% MeOH:CH$_2$Cl$_2$) to yield the desired product as a off-white solid; $^1$H NMR (CDCl$_3$, 400 MHz) δ 2.45-2.51 (m, 2H), 2.90-2.97 (m, 2H), 3.31 (q, 1H, J=8.0 Hz), 4.39 (q, 1H, J=7.0 Hz), 5.03 (brs, 1H), 5.15 (s, 2H), 7.03-7.13 (m, 2H), 7.23-7.52 (m, 9H); MS (ES) 387.3 (M+1), 389.3 (M+3).

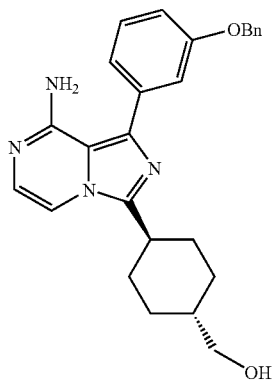

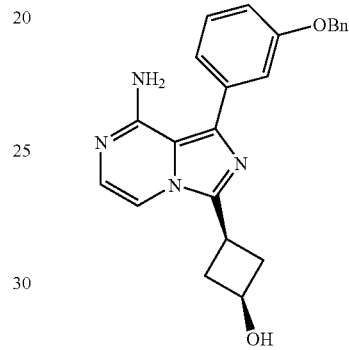

a) trans-{4-[1-(3-Benzyloxy-phenyl)-8-chloro-imidazo[1,5-a]pyrazin-3-yl]-cyclohexyl}-methanol (compound of Formula II-B where Z=cyclohexyl and $Q^1$=Ph-(3-OBn)): A 0.2 M THF solution of trans-4-[1-(3-benzyloxyphenyl)-8-chloro-imidazo[1,5-a]pyrazin-3-yl]cyclohexane carboxylic acid methyl ester (800 mg, 1.68 mmol) was cooled to −78° C. and charged with LiAlH$_4$ (63.8 mg, 1.68 mmol) portionwise; the reaction vessel was removed from the −78° C. cooling bath and allowed to warm to rt. After 2 h, the reaction mixture was charged with EtOAc, Na$_2$SO$_4$.10H$_2$O, and silica gel and concentrated in vacuo to yellow solids. The material was purified by silica gel chromatography, eluting with EtOAc, to afford the desired product as a yellow solid; MS (ES) 448.2 (M+1), 450.2 (M+3).

a) cis-[1-(3-Benzyloxy-phenyl)-8-chloro-imidazo[1,5-a]pyrazin-3-yl]-cyclobutanol (compound of Formula II-G where $Z^3$=cis-3-cyclobutyl and $Q^1$=Ph-(3-OBn)): A methanolic-CH$_2$Cl$_2$ solution (1.0 mL) of 3-[1-(3-benzyloxy-phenyl)-8-chloro-imidazo[1,5-a]pyrazin-3-yl]-cyclobutanone (compound of Formula II-F where $Z^3$=cis-3-cyclobutyl and $Q^1$=Ph-(3-OBn)) (80.0 mg, 0.2 mmol) was cooled to 0° C. and charged with MP-borohydride (200.0 mg, 2.0 eq.). The reaction mixture was allowed to warm up to rt over a 24 h period. The resin-bound reducing agent was filtered and washed with EtOAc. The combined filtrate was concentrated in vacuo to yield the desired product as a light yellow solid; $^1$H NMR (CDCl$_3$, 400 MHz) δ 2.61-2.68 (m, 2H), 2.94-3.01 (m, 2H), 3.36 (q, 1H, J=8.0 Hz), 4.42 (q, 1H, J=7.3 Hz), 5.15 (s, 2H), 7.00-7.09 (m, 1H), 7.30-7.47 (m, 9H), 7.56 (d, 1H, J=5.0 Hz); MS (ES) 407.2 (M+1), 409.2 (M+3).

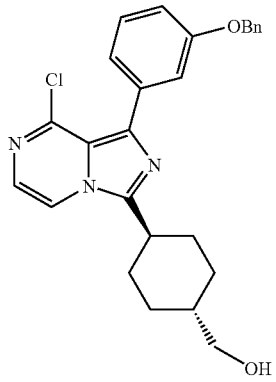

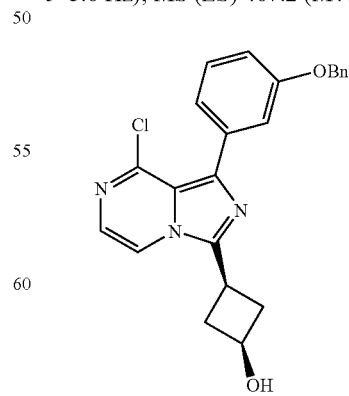

b) 3-[1-(3-Benzyloxy-phenyl)-8-chloro-imidazo[1,5-a]pyrazin-3-yl]-cyclobutanone (compound of Formula II-F where $Z^3$=3-cyclobutyl and $Q^1$=Ph-(3-OBn)): 3-Oxo-cyclobutanecarboxylic Acid [(3-benzyloxy-phenyl)-(3-chloro-pyrazin-2-yl)-methyl]-amide (compound of Formula III where $R^1$=3-cyclobutanone and $Q^1$=Ph-(3-OBn)) (614.0 mg, 1.5 mmol) was dissolved in $POCl_3$ (8.0 mL) and $CH_2Cl_2$ (2.0 mL) and allowed to stir at 55° C. for 24 h. The reaction mixture was concentrated in vacuo to a yellow solid, dissolved in cold EtOAc and neutralized with cold sat. $NaHCO_3$. The aqueous layer was extracted with EtOAc (3×) and the combined organic layers were dried over $Na_2SO_4$, filtered and concentrated in vacuo. Purification via HPFC using a 20 g Jones silica gel column (50% EtOAc:Hex to 1% MeOH: $CH_2Cl_2$) followed by a recrystalization from hot EtOH yielded the desired product as a light yellow solid; $^1H$ NMR ($CDCl_3$, 400 MHz) δ 3.61-3.68 (m, 2H), 3.86-3.95 (m, 3H), 5.15 (s, 2H), 7.00-7.09 (m, 1H), 7.30-7.47 (m, 9H), 7.61 (d, 1H, J=5.0 Hz); MS (ES) 404.2 (M+1), 406.2 (M+3). Alternatively, 3-[1-(3-Benzyloxy-phenyl)-8-chloro-imidazo[1,5-a]pyrazin-3-yl]-cyclobutanone can be prepared from 1-(3-benzyloxyphenyl)-8-chloro-3-(3-methylenecyclobutyl)-imidazo[1,5-a]pyrazine (Example 44b) as follows: To a solution of 1-(3-benzyloxyphenyl)-8-chloro-3-(3-methylenecyclobutyl)-imidazo[1,5-a]pyrazine (100 mg, 0.25 mmol) in THF (3 mL) and water (1 mL) were added NMO (0.1 mL, 0.5 mmol, 50% aq. solution) and $K_2OsO_4 \cdot H_2O$ (5 mg, 0.013 mmol). The resulting mixture was stirred at rt overnight. TLC showed the reaction was complete. The reaction was quenched with $Na_2SO_3$ (160 mg, 1.25 mmol), then diluted with EtOAc (40 mL) and water (5 mL), washed with brine (20 mL), and dried over anhydrous sodium sulfate. The filtrate was concentrated under reduced pressure to give 3-[1-(3-benzyloxy-phenyl)-8-chloro-imidazo[1,5-a]pyrazin-3-yl]-1-hydroxymethyl-cyclobutanol as a yellow solid (100 mg). LC-MS (ES, Pos.): m/z 436/438 (3/1) [MH$^+$]. The solution of 3-[1-(3-benzyloxy-phenyl)-8-chloro-imidazo[1,5-a]pyrazin-3-yl]-1-hydroxymethyl-cyclobutanol in THF (3 mL) and water (1 mL) was cooled to 0° C. and charged with sodium periodate (64 mg, 0.3 mmol). The resulting mixture was slowly warmed to rt in 2 h. TLC showed the reaction was complete. The mixture was diluted with EtOAc (40 mL) and water (5 mL), washed with brine (20 mL), and dried over anhydrous sodium sulfate. The filtrate was concentrated under reduced pressure and the crude product was purified by silica gel column chromatography (Hexanes:EtOAc=50: 50→30:70) to give the title compound as a yellow solid (70 mg, 70% yield over two steps); LC-MS (ES, Pos.): m/z 404/406 (3/1) [MH$^+$]; $^1H$ NMR ($CDCl_3$, 400 MHz) δ 3.60-3.67 (m, 2H), 3.81-3.94 (m, 3H), 5.14 (s, 2H), 3.81-3.94 (m, 3H), 7.06 (m, 1H), 7.27-7.47 (m, 9H), 7.59 (d, J=4.9 Hz, 1H).

c) 3-Oxo-cyclobutanecarboxylic Acid [(3-benzyloxy-phenyl)-(3-chloro-pyrazin-2-yl)-methyl]-amide (compound of Formula III where $R^1$=3-cyclobutanone and $Q^1$=Ph-(3-OBn)): 3-Oxo-cyclobutanecarboxylic acid (184.2 mg, 1.8 mmol), EDC (529.1 mg, 2.8 mmol) and HOBt (281.8 mg, 1.8 mmol) were dissolved in $CH_2Cl_2$ (18.0 mL) and allowed to stir at rt for 10 min. A $CH_2Cl_2$ solution (1.0 mL) of C-(3-Benzyloxy-phenyl)-C-(3-chloro-pyrazin-2-yl)-methylamine (600.0 mg, 1.8 mmol) was added to the reaction mixture, which was allowed to stir at rt for 24 h. Purification via HPFC using a 20 g Jones silica gel column (30% EtOAc:Hex to 50% EtOAc:Hex) yielded the desired product as a white solid; $^1H$ NMR ($CDCl_3$, 400 MHz) δ 3.07-3.22 (m, 3H), 3.42-3.48 (m, 2H), 5.03 (s, 2H), 6.55 (d, 1H, J=7.8 Hz), 6.89-6.96 (m, 3H), 7.22-7.39 (m, 5H,), 8.35 (d, 1H, J=2.5 Hz), 8.50 (d, 1H, J=2.5 Hz); MS (ES) 422.2 (M+1), 424.2 (M+3).

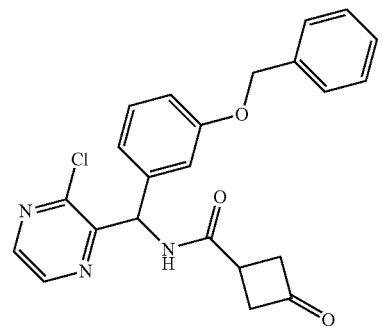

Example 13

1-(3-Benzyloxy-phenyl)-3-(1-methyl-piperidin-4-yl)-imidazo[1,5-a]pyrazin-8-ylamine (compound of Formula I where $R^1$=4-N-methylpiperidine and $Q^1$=Ph-(3-OBn)) was prepared according to the procedures described for Example 1 above except for the substitution of 1-(3-benzyloxy-phenyl)-8-chloro-3-cyclobutyl-imidazo[1,5-a]pyrazine (compound of Formula II where $R^1$=cyclobutyl and $Q^1$=Ph-(3-OBn)) with 1-(3-benzyloxy-phenyl)-8-chloro-3-(1-methyl-piperidin-4-yl)-imidazo[1,5-a]pyrazine (compound of Formula II where $R^1$=4-N-methylpiperidine and $Q^1$=Ph-(3-OBn)); white solid, purified by Gilson HPLC to yield the desired product as the formic acid salt as a colorless gum; $^1H$ NMR ($CD_3OD$, 400 MHz) δ 2.24-2.27 (m, 4H), 2.94 (s, 3H), 3.24 (m, 1H), 3.55-3.66 (m, 4H), 5.17 (s, 2H), 7.05-7.49 (m, 10H), 7.65 (d, 1H, J=5.1 Hz); MS (ES) 414.3 (M+1).

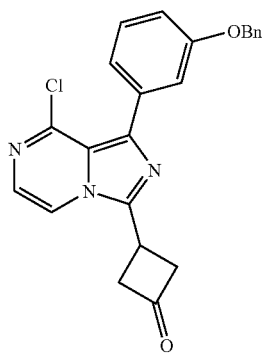

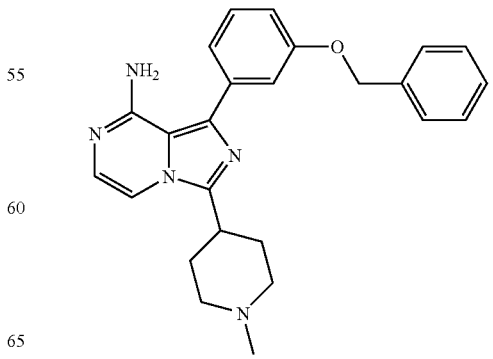

a) 1-(3-Benzyloxy-phenyl)-8-chloro-3-(1-methyl-piperidin-4-yl)-imidazo[1,5-a]pyrazine (compound of Formula II where $R^1$=4-N-methylpiperidine and $Q^1$=Ph-(3-OBn)) was prepared according to the procedures described for 1-(3-benzyloxy-phenyl)-8-chloro-3-cyclobutyl-imidazo[1,5-a]pyrazine (compound of Formula II where $R^1$=cyclobutyl and $Q^1$=Ph-(3-OBn)) above except for the substitution of cyclobutanecarboxylic acid [(3-benzyloxy-phenyl)-(3-chloro-pyrazin-2-yl)-methyl]amide with 1-methyl-piperidine-4-carboxylic acid [(3-benzyloxy-phenyl)-(3-chloro-pyrazin-2-yl)-methyl]-amide (compound of Formula III where $R^1$=4-N-methylpiperidine and $Q^1$=Ph-(3-OBn)); Yellow oil; MS (ES) 433.2 (M+1), 435.2 (M+3).

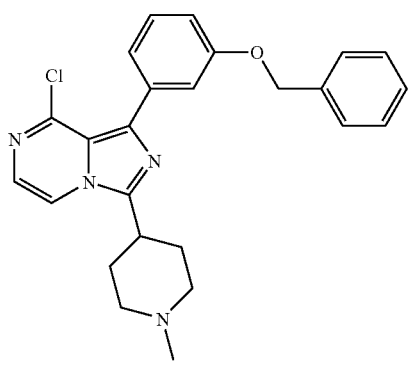

b) 1-Methyl-piperidine-4-carboxylic acid [(3-benzyloxy-phenyl)-(3-chloro-pyrazin-2-yl)-methyl]-amide (compound of Formula III where $R^1$=4-N-methylpiperidine and $Q^1$=Ph-(3-OBn)) was prepared according to the procedures described for the synthesis of cyclobutanecarboxylic acid [(3-benzyloxy-phenyl)-(3-chloro-pyrazin-2-yl)-methyl]amide (compound of Formula III where $R^1$=cyclobutyl and $Q^1$=Ph-(3-OBn)) above except for the substitution of 1-methyl-piperidine-4-carboxylic acid for cyclobutanecarboxylic acid; $^1$H NMR (CDCl$_3$, 400 MHz) δ 1.25-2.33 (brm, 10H), 2.95 (brs, 2H), 5.02 (s, 1H), 6.50 (d, 1H, J=7.8 Hz), 6.87-6.94 (m, 3H), 7.19-7.38 (m, 5H), 8.33 (d, 1H, J=2.5 Hz), 8.50 (d, 1H, J=2.5 Hz); MS (ES) 451.2 (M+1), 453.2 (M+3).

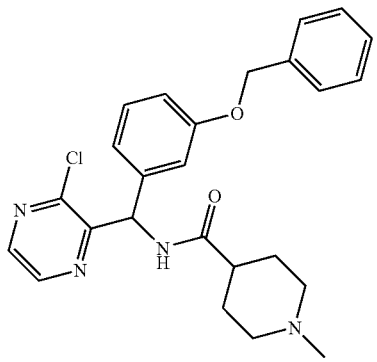

Example 14 cis-4-[8-Amino-1-(3-benzyloxy-phenyl)-imidazo[1,5-a]pyrazin-3-yl]-cyclohexanecarboxylic acid amide (compound of Formula I-A where Z=cyclohexyl, C(=O)NR$^2$R$^3$=4-cis-C(=O)NH$_2$, and $Q^1$=Ph-(3-OBn)) was prepared according to the procedures described for Example 10 except for the substitution of trans-4-[1-(3-benzyloxyphenyl)-8-chloro-imidazo[1,5-a]pyrazin-3-yl]cyclohexane carboxylic acid methyl ester (compound of Formula II-A where Z=cyclohexyl, CO$_2$A$^3$=4-trans-CO$_2$Me, and $Q^1$=Ph-(3-OBn)) with cis-4-[1-(3-benzyloxyphenyl)-8-chloro-imidazo[1,5-a]pyrazin-3-yl]cyclohexane carboxylic acid methyl ester (compound of Formula II-A where Z=cyclohexyl, CO$_2$A$^3$=4-cis-CO$_2$Me, and $Q^1$=Ph-(3-OBn)); MS (ES) 442.4 (M+1).

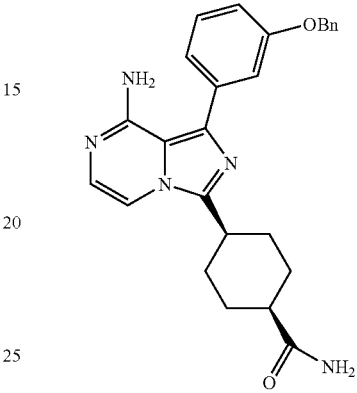

a) cis-4-[1-(3-Benzyloxy-phenyl)-8-chloro-imidazo[1,5-a]pyrazin-3-yl]-cyclohexanecarboxylic acid methyl ester (compound of Formula II-A where Z=cyclohexyl, CO$_2$A$^3$=4-cis-CO$_2$Me, and $Q^1$=Ph-(3-OBn)) was prepared according to the procedures described for 1-(3-benzyloxy-phenyl)-8-chloro-3-cyclobutyl-imidazo[1,5-a]pyrazine (compound of Formula II where $R^1$=cyclobutyl and $Q^1$=Ph-(3-OBn)) above except for the substitution of cyclobutanecarboxylic acid [(3-benzyloxy-phenyl)-(3-chloro-pyrazin-2-yl)-methyl]amide (compound of Formula III where $R^1$=cyclobutyl and $Q^1$=Ph-(3-OBn)) with cis-4-{[(3-benzyloxy-phenyl)-(3-chloro-pyrazin-2-yl)-methyl]-carbamoyl}-cyclohexanecarboxylic acid methyl ester (compound of Formula III where $R^1$=trans-4-cyclohexane carboxylic acid methyl ester and $Q^1$=Ph-(3-OBn)); MS (ES) 476.2 (M+1), 478.2 (M+3).

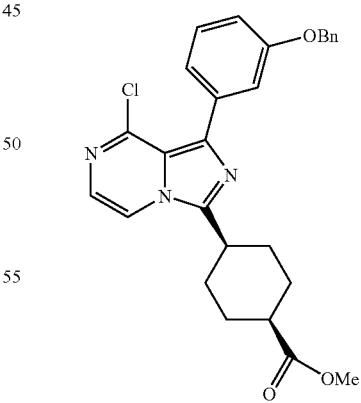

b) cis-4-{[(3-Benzyloxy-phenyl)-(3-chloro-pyrazin-2-yl)-methyl]-carbamoyl}-cyclohexanecarboxylic acid methyl ester (compound of Formula III where $R^1$=cis-4-cyclohexane carboxylic acid methyl ester and $Q^1$=Ph-(3-OBn)) was prepared according to the procedures described for the synthesis of cyclobutanecarboxylic acid [(3-benzyloxy-phenyl)-(3- chloro-pyrazin-2-yl)-methyl]amide (compound of Formula III where R¹=cyclobutyl and Q¹=Ph-(3-OBn)) above except for the substitution of cis-cyclohexane-1,4-dicarboxylic acid monomethyl ester for cyclobutanecarboxylic acid; MS (ES) 494.3 (M+1), 496.3 (M+3).

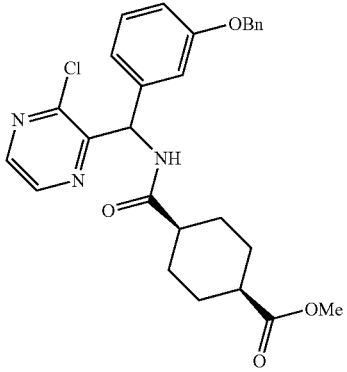

Example 15 cis-{4-[8-Amino-1-(3-benzyloxy-phenyl)-imidazo[1,5-a]pyrazin-3-yl]-cyclohexyl}-methanol (compound of Formula I-B where Z=cyclohexyl and Q¹=Ph-(3-OBn)) was prepared according to the procedures described for the synthesis of trans-4-[8-amino-1-(3-benzyloxy-phenyl)-imidazo[1,5-a]pyrazin-3-yl]-cyclohexanecarboxylic acid amide except for the substitution of cis-4-[1-(3-benzyloxyphenyl)-8-chloro-imidazo[1,5-a]pyrazin-3-yl]cyclohexane carboxylic acid methyl ester (compound of Formula II-A where Z=cyclohexyl, $CO_2A^3$=4-cis-$CO_2$Me, and Q¹=Ph-(3-OBn)) with {4-[1-(3-benzyloxy-phenyl)-8-chloro-imidazo[1,5-a]pyrazin-3-yl]-cyclohexyl}-methanol (compound of Formula II-B where Z=cyclohexyl and Q¹=Ph-(3-OBn)); MS (ES) 429.2 (M+1).

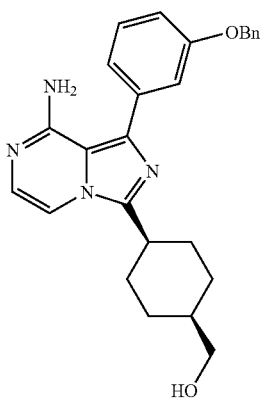

a) cis-{4-[1-(3-Benzyloxy-phenyl)-8-chloro-imidazo[1,5-a]pyrazin-3-yl]-cyclohexyl}-methanol (compound of Formula II-B where Z=cyclohexyl and Q¹=Ph-(3-OBn)) was prepared as described for the synthesis of trans-{4-[1-(3-benzyloxy-phenyl)-8-chloro-imidazo[1,5-a]pyrazin-3-yl]-cyclohexyl}-methanol (compound of Formula II-B where Z=trans-1,4-cyclohexyl and Q¹=Ph-(3-OBn)) except for the substitution of trans-4-[1-(3-benzyloxyphenyl)-8-chloro-imidazo[1,5-a]pyrazin-3-yl]cyclohexane carboxylic acid methyl ester with cis-4-[1-(3-benzyloxyphenyl)-8-chloro-imidazo[1,5-a]pyrazin-3-yl]cyclohexane carboxylic acid methyl ester; MS (ES) 448.2 (M+1), 450.2 (M+3).

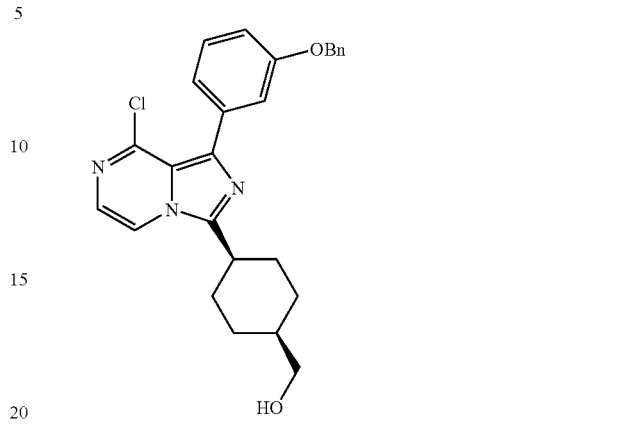

Example 16 cis-2-{4-[8-Amino-1-(3-benzyloxy-phenyl)-imidazo[1,5-a]pyrazin-3-yl]-cyclohexylmethyl}-isoindole-1,3-dione (compound of Formula I-C' where Z=cis-1,4-cyclohexyl, A²=phthalimido and Q¹=Ph-(3-OBn)) was prepared as follows: cis-{4-[8-Amino-1-(3-benzyloxy-phenyl)-imidazo[1,5-a]pyrazin-3-yl]-cyclohexyl}-methanol (compound of Formula I-B where Z=cis-1,4-cyclohexyl and Q¹=Ph-(3-OBn)) (175 mg, 0.41 mmol), phthalimide (72 mg, 0.49 mmol), and resin-bound triphenylphosphine (PS-Ph₃P [Argonaut, 2.33 mmol/g]) (263 mg) were dissolved in 2 mL of THF, evacuated, placed under nitrogen atmosphere and charged with DIAD (97 μL, 0.49 mmol). After stirring for 16 h, the reaction mixture was filtered through a cotton pipet plug, washed 6× with EtOAc, concentrated in vacuo, and purified by silica gel column chromatography (gradient of 30% EtOAc/hexanes to 70% EtOAc/hexanes) to afford the desired product as a foamy yellow solid; MS (ES+): m/z 558.5 (M+1).

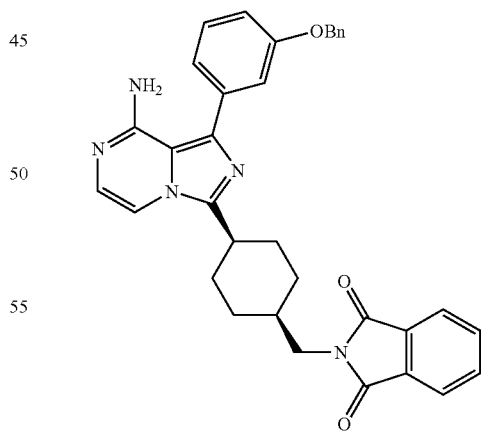

Example 17 trans-2-{4-[8-Amino-1-(3-benzyloxy-phenyl)-imidazo[1,5-a]pyrazin-3-yl]-cyclohexylmethyl}-isoindole-1,3-dione (compound of Formula I-C' where Z=4-trans-cyclohexyl, A²=phthalimido and Q¹=Ph-(3-OBn)) was prepared according to the procedures described in Example 16 above except for the replacement of cis-{4-[8-amino-1-(3-benzyloxy-phenyl)-imidazo[1,5-a]pyrazin-3-yl]-cyclohexyl}-methanol with trans-{4-[8-amino-1-(3-benzyloxy-phenyl)-imidazo[1,5-a]pyrazin-3-yl]-cyclohexyl}-methanol; MS (ES+): m/z 558.4 [MH⁺].

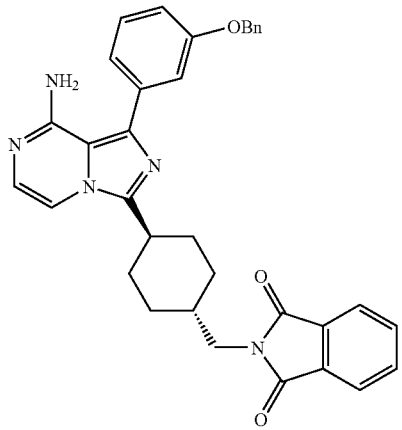

Example 18 cis-3-(4-Aminomethyl-cyclohexyl)-1-(3-benzyloxy-phenyl)-imidazo[1,5-a]pyrazin-8-ylamine (compound of Formula I-C" where Z=cis-1,4-cyclohexyl and Q¹=Ph-(3-OBn)) was prepared as follows: An ethanolic solution of cis-2-{4-[8-amino-1-(3-benzyloxy-phenyl)-imidazo[1,5-a]pyrazin-3-yl]-cyclohexylmethyl}-isoindole-1,3-dione (compound of Formula I-C' where Z=cis-1,4-cyclohexyl, A²=phthalimido and Q¹=Ph-(3-OBn)) (490 mg, 0.92 mmol) was charged with an excess of hydrazine (10 μL) and allowed to stir at rt for 16 h. The solution was filtered through a fritted glass funnel and the solids washed with EtOH (4×). The filtrate was concentrated in vacuo and the crude product was purified by High Pressure Flash Chromatography (HPFC) (dry loaded, gradient of CH₂Cl₂ to 2% ~7N NH₃ in MeOH/CH₂Cl₂) to afford the desired product as a white foamy solid; ¹H NMR (400 MHz, CDCl₃) δ 1.66-1.72 (m, 4H), 1.77-1.86 (m, 4H), 2.00-2.07 (m, 3H), 2.75 (d, 2H, J=8.0 Hz), 3.10-3.13 (m, 1H), 5.10 (bs, 2H), 5.14 (s, 2H), 7.00-7.04 (m, 2H), 7.18-7.25 (m, 3H), 7.33-7.46 (m, 6H); MS (ES+): m/z 428.4 [MH⁺].

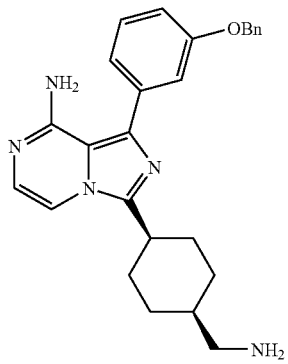

Example 19 trans-3-(4-Aminomethyl-cyclohexyl)-1-(3-benzyloxy-phenyl)-imidazo[1,5-a]pyrazin-8-ylamine (compound of Formula I-C" where Z=trans-1,4-cyclohexyl and Q¹=Ph-(3-OBn)) was prepared according to the procedures described for the synthesis of cis-3-(4-aminomethyl-cyclohexyl)-1-(3-benzyloxy-phenyl)-imidazo[1,5-a]pyrazin-8-ylamine (compound of Formula I-C" where Z=cis-1,4-cyclohexyl and Q¹=Ph-(3-OBn)) above except for the replacement of cis-2-{4-[8-amino-1-(3-benzyloxy-phenyl)-imidazo[1,5-a]pyrazin-3-yl]-cyclohexylmethyl}-isoindole-1,3-dione (compound of Formula I-C' where Z=cis-1,4-cyclohexyl, A²=phthalimido and Q¹=Ph-(3-OBn)) with trans-2-{4-[8-amino-1-(3-benzyloxy-phenyl)-imidazo[1,5-a]pyrazin-3-yl]-cyclohexylmethyl}-isoindole-1,3-dione (compound of Formula I-C' where Z=trans-1,4-cyclohexyl, A²=phthalimido and Q¹=Ph-(3-OBn)); ¹H NMR (400 MHz, CDCl₃) δ 1.13 (ddd, 2H, J=25.2 Hz, 12.8 Hz, 3.6 Hz), 1.31-1.52 (m, 3H), 1.88 (ddd, 2H, J=29.6 Hz, 13.2 Hz, 3.6 Hz), 2.00-2.05 (m, 2H), 2.12-2.16 (m, 2H), 2.62 (d, 2H, J=6.4 Hz), 2.93 (tt, 1H, J=11.6 Hz, 4.0 Hz), 5.02 (bs, 2H), 5.14 (s, 2H), 7.01 (ddd, 1H, J=8.0 Hz, 2.8 Hz, 1.2 Hz), 7.04 (d, 1H, J=5.2 Hz), 7.21-7.22 (m, 2H), 7.23-7.24 (m, 2H), 7.34-7.36 (m, 1H), 7.36-7.41 (m, 2H), 7.42-7.45 (m, 2H); MS (ES) 428.5 (M+1).

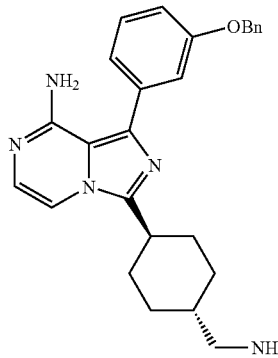

Example 20 cis-N-{4-[8-Amino-1-(3-benzyloxy-phenyl)-imidazo[1,5-a]pyrazin-3-yl]-cyclohexylmethyl}-acetamide (compound of Formula I-C''' where Z=cis-1,4-cyclohexyl, R²=H, R³=C(═O)CH₃, and Q¹=Ph-(3-OBn)) was prepared as follows: cis-3-(4-Aminomethyl-cyclohexyl)-1-(3-benzyloxy-phenyl)-imidazo[1,5-a]pyrazin-8-ylamine (compound of Formula I-C" where Z=cis-1,4-cyclohexyl and Q¹=Ph-(3-OBn)) (10.8 mg, 0.03 mmol) was dissolved in 0.3 mL of chloroform and charged with PS-DIEA (10 mg, 0.04 mmol) followed by acetic anhydride (2.1 μL, 0.02 mmol) and allowed to stir for 0.5 h. The solution was filtered through a cotton pipet plug and the solids washed with chloroform (4×). The filtrate was concentrated in vacuo and the crude product was purified by silica gel chromatography (2% ~7N NH₃ in MeOH/CH₂Cl₂) to afford the desired product as a foamy white solid; MS (ES) 470.5 (M+1).

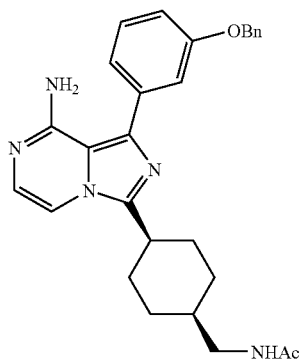

Example 21 trans-N-{4-[8-Amino-1-(3-benzyloxy-phenyl)-imidazo[1,5-a]pyrazin-3-yl]-cyclohexylmethyl}-acetamide (compound of Formula I-C''' where Z=trans-1,4-cyclohexyl, R²=H, R³=C(=O)CH₃, and Q¹=Ph-(3-OBn)) was prepared according to the procedures described for cis-N-{4-[8-amino-1-(3-benzyloxy-phenyl)-imidazo[1,5-a]pyrazin-3-yl]-cyclohexylmethyl}-acetamide (compound of Formula I-C''' where Z=cis-1,4-cyclohexyl, R²=H, R³=C(=O)CH₃, and Q¹=Ph-(3-OBn)) above except for the replacement of cis-3-(4-aminomethyl-cyclohexyl)-1-(3-benzyloxy-phenyl)-imidazo[1,5-a]pyrazin-8-ylamine (compound of Formula I-C'' where Z=cis-1,4-cyclohexyl and Q¹=Ph-(3-OBn)) with trans-3-(4-aminomethyl-cyclohexyl)-1-(3-benzyloxy-phenyl)-imidazo[1,5-a]pyrazin-8-ylamine (compound of Formula I-C'' where Z=trans-1,4-cyclohexyl and Q¹=Ph-(3-OBn)); ¹H NMR (400 MHz, CDCl₃) δ 1.18 (ddd, 2H, J=25.2 Hz, 12.8 Hz, 3.6 Hz), 1.60-1.66 (m, 1H), 1.85 (ddd, 2H, J=29.6 Hz, 13.2 Hz, 3.6 Hz), 1.94-1.98 (m, 2H), 2.01 (s, 3H), 2.08-2.12 (m, 2H), 2.90 (tt, 1H, J=11.6 Hz, 4.0 Hz), 3.20 (dd, 2H, J=6.4 Hz, 6.4 Hz), 5.07 (bs, 2H), 5.14 (s, 2H), 5.49 (m, 1H), 7.02 (ddd, 1H, J=8.0 Hz, 2.8 Hz, 1.2 Hz), 7.04 (d, 1H, J=5.2 Hz), 7.19-7.22 (m, 2H), 7.23-7.24 (m, 2H), 7.31-7.36 (m, 1H), 7.36-7.41 (m, 2H), 7.43-7.46 (m, 2H); MS (ES) 470.5 (M+1).

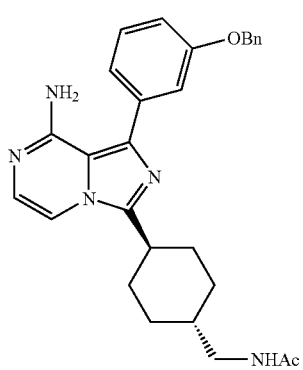

The following examples were synthesized according to the procedures described in Examples 1-22 unless stated otherwise.

Example 22

1-Biphenyl-3-yl-3-cyclobutylimidazo[1,5-a]pyrazin-8-ylamine: Prepared according to the procedures for 1-(3-Benzyloxy-phenyl)-3-cyclobutyl-imidazo[1,5-a]pyrazin-8-ylamine, white solid, MS (ES) 341.38 (M+1).

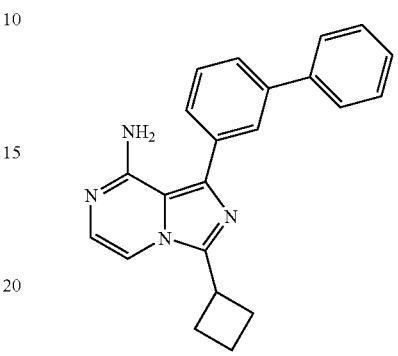

a) 1-Biphenyl-3-yl-8-chloro-3-cyclobutylimidazo[1,5-a]pyrazine: Prepared according to the procedures for 1-(3-Benzyloxy-phenyl)-8-chloro-3-cyclobutyl-imidazo[1,5-a]pyrazine, yellow solid, MS (ES) 360.36 (M+1).

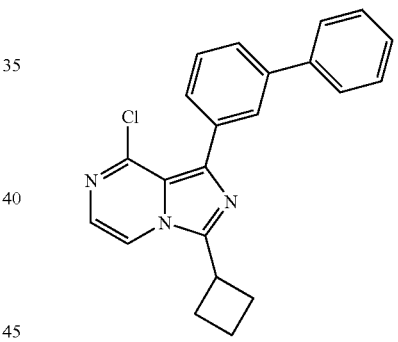

b) Cyclobutanecarboxylic Acid [biphenyl-3-yl-(3-chloro-pyrazin-2-yl)methyl]amide: Prepared according to the procedures for Cyclobutanecarboxylic Acid [(3-benzyloxy-phenyl)-(3-chloro-pyrazin-2-yl)-methyl]Amide, off-white oil, MS (ES) 378.37 (M+1).

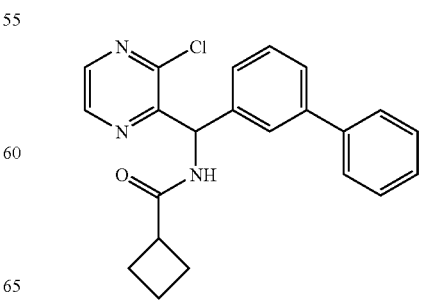

c) C-Biphenyl-3-yl-C-(3-chloropyrazin-2-yl)-methylamine: Prepared according to the procedures for C-(3-Benzyloxy-phenyl)-C-(3-chloro-pyrazin-2-yl)-methylamine, orange oil, MS (ES) 296.18 (M+1), 279.18 (M–17).

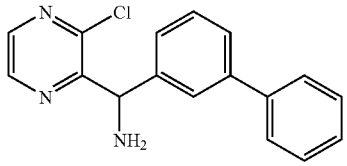

d) 2-[Biphenyl-3-yl-(3-chloropyrazin-2-yl)-methyl]-isoindole-1,3-dione: Prepared according to the procedures for 2-[(3-Benzyloxy-phenyl)-(3-chloro-pyrazin-2-yl)-methyl]-isoindole-1,3-dione, orange oil, MS (ES) 426.92 (M+1).

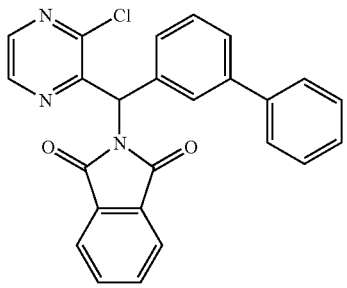

e) Biphenyl-3-yl-(3-chloropyrazin-2-yl)-methanol: Prepared according to the procedures for (3-Chloro-pyrazin-2-yl)-(3-benzyloxy-phenyl)-methanol, orange oil, MS (ES) 297.11 (M+1), 278.13 (M–17).

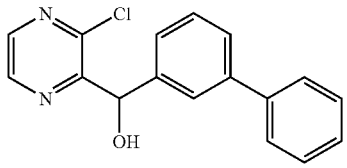

f) Biphenyl-3-carbaldehyde: Prepared from 3-bromo-benzaldehyde and phenylboronic acid utilizing Pd(PPh$_3$)$_4$, K$_2$CO$_3$, 4:1 DMF:H$_2$O (see detailed description under the General synthesis to Suzuki analogues in Examples 24-26), following standard Suzuki Coupling procedures as described in the following reference: Strongin, R. M.; et. al. *Org. Lett.*, 2000, 20, 3201-3204; Clear oil, $^1$H NMR (CDCl$_3$, 400 MHz) δ 7.38-7.51 (m, 3H), 7.60-7.65 (m, 3H), 7.87 (dd, 2H, J=2.8 Hz, 8.4 Hz), 8.11-8.12 (m, 1H), 10.0 (s, 1H); MS (ES) 183.28 (M+1).

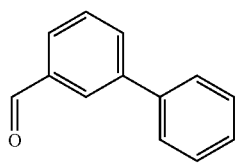

Example 23

1-(3-Bromo-phenyl)-3-cyclobutylimidazo[1,5-a]pyrazin-8-ylamine: Prepared according to the procedures for 1-(3-Benzyloxy-phenyl)-3-cyclobutyl-imidazo[1,5-a]pyrazin-8-ylamine, Light pink solid, $^1$H NMR (CDCl$_3$, 400 MHz) δ 2.02-2.21 (m, 2H), 2.45-2.65 (m, 4H), 3.81 (p, 1H, J=8.8 Hz), 5.03 (bs, 2H), 7.07 (d, 1H, J=4.8 Hz), 7.13 (d, 1H, J=4.8 Hz), 7.33-7.37 (m, 1H), 7.53 (d, 1H, J=7.2 Hz), 7.60 (d, 1H, J=7.2 Hz), 7.88 (d, 1H, J=1.6 Hz).

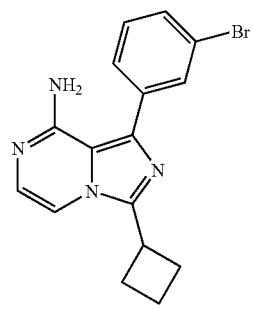

a) 1-(3-Bromophenyl)-8-chloro-3-cyclobutylimidazo[1,5-a]pyrazine: Prepared according to the procedures for 1-(3-Benzyloxy-phenyl)-8-chloro-3-cyclobutyl-imidazo[1,5-a]pyrazine, Yellow solid, $^1$H NMR (CDCl$_3$, 400 MHz) δ 2.04-2.22 (m, 2H), 2.50-2.67 (m, 4H), 3.84 (p, 1H, J=8.8 Hz), 7.29-7.33 (m, 2H), 7.51 (d, 1H, J=4.8 Hz), 7.52-7.55 (m, 1H), 7.61-7.64 (m, 1H), 7.86-7.87 (m, 1H).

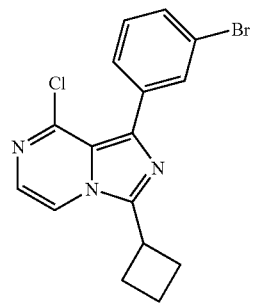

b) Cyclobutanecarboxylic Acid [(3-bromophenyl)-(3-chloropyrazin-2-yl)methyl]amide: Prepared according to the procedures for Cyclobutanecarboxylic Acid [(3-benzyloxy-phenyl)-(3-chloro-pyrazin-2-yl)-methyl]Amide, White solid, $^1$H NMR (CDCl$_3$, 400 MHz) δ 1.83-2.02 (m, 2H), 2.13-2.29 (m, 4H), 3.09 (p, 1H, J=8.8 Hz), 6.53 (d, 1H, J=8.0 Hz), 7.08 (d, 1H, J=8.0 Hz), 7.16-7.20 (m, 1H), 7.34-7.43 (m, 3H), 7.37 (d, 1H, J=2.8 Hz), 8.53 (d, 1H, J=2.8 Hz).

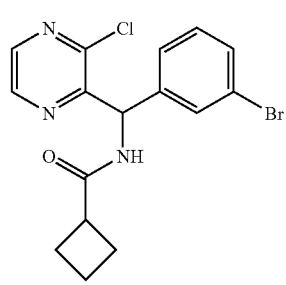

c) C-(3-Bromophenyl)-C-(3-chloropyrazin-2-yl)-methylamine: Prepared according to the procedures for C-(3-Benzyloxy-phenyl)-C-(3-chloro-pyrazin-2-yl)-methylamine, Orange oil, $^1$H NMR (CDCl$_3$, 400 MHz) δ 5.54 (s, 1H), 7.17-7.21 (m, 1H), 7.31 (d, 1H, J=8.0 Hz), 7.39 (d, 1H, J=8.4 Hz), 7.51-7.53 (d, 1H, J=8.4 Hz), 8.31 (d, 1H, J=2.8 Hz), 8.56 (d, 1H, J=2.4 Hz).

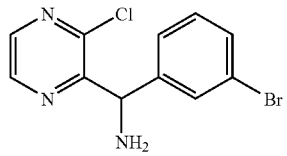

d) 2-[(3-Bromophenyl)-(3-chloropyrazin-2-yl)-methyl]-isoindole-1,3-dione: Prepared according to the procedures for 2-[(3-Benzyloxy-phenyl)-(3-chloro-pyrazin-2-yl)-methyl]-isoindole-1,3-dione, Orange oil, $^1$H NMR (CDCl$_3$, 400 MHz) δ 6.84 (s, 1H), 7.47-7.53 (m, 2H), 7.74-7.86 (m, 6H), 8.37 (dd, 1H, J=1.2 Hz, 2.6 Hz), 8.48 (d, 1H, J=2.4 Hz).

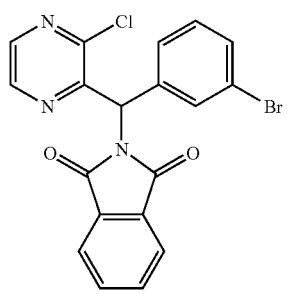

e) (3-Bromophenyl)-(3-chloropyrazin-2-yl)-methanol: Prepared according to the procedures for (3-Chloro-pyrazin-2-yl)-(3-benzyloxy-phenyl)-methanol, Light yellow solid, $^1$H NMR (CDCl$_3$, 400 MHz) δ 4.66 (d, 1H, J=8.0 Hz), 5.98 (d, 1H, J=8.0 Hz), 7.18-7.23 (m, 1H), 7.29-7.49 (m, 3H), 8.40 (d, 1H, J=2.4 Hz), 8.57 (d, 1H, J=2.4 Hz).

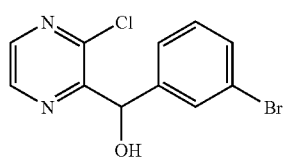

General Synthesis to Suzuki Analogues Examples 24-26.

A 4:1 DMF:H$_2$O solution was purged with N$_2$ for 45 minutes prior to the reaction. 1-(3-Bromo-phenyl)-3-cyclobutyl-imidazo[1,5-a]pyrazin-8-ylamine (1.0 equiv), the suitable boronic acid (1.1 equiv), K$_2$CO$_3$ (2.25 equiv), and PS-Pd(Ph$_3$)$_4$ (0.05 equiv) were slurried in enough 4:1 DMF:H$_2$O to give a 0.25 M solution. The reaction mixture was heated to 90° C. overnight with stirring, cooled, diluted with CH$_2$Cl$_2$, filtered through Celite, and the resin washed with additional CH$_2$Cl$_2$. The filtrate was concentrated in vacuo, redissolved in DCM, and purified by chromatography (Jones Flashmaster Personal, 50:50 Hexane:EtOAc to 100% EtOAc) to afford desired imidazopyrazines Examples 24-26.

Example 24

1-(4'-t-Butylbiphenyl-3-yl)-3-cyclobutylimidazo[1,5-a]pyrazin-8-ylamine: Light brown solid, $^1$H NMR (CDCl$_3$, 400 MHz) δ 1.34 (s, 9H), 2.02-2.21 (m, 2H), 2.45-2.68 (m, 4H), 3.83 (p, 1H, J=8.8 Hz), 5.18 (bs, 2H), 7.06 (d, 1H, J=5.2 Hz), 7.13 (d, 1H, J=5.2 Hz), 7.50-7.65 (m, 7H), 7.89 (d, 1H, J=1.6 Hz).

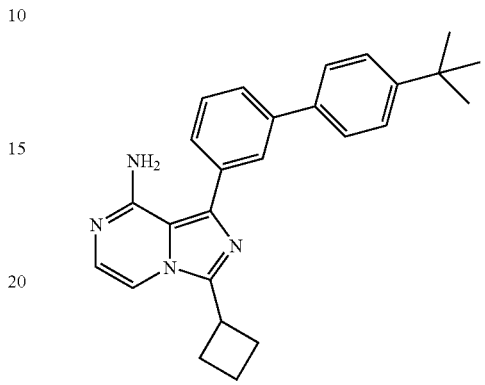

Example 25

3-Cyclobutyl-1-(4'-methylbiphenyl-3-yl)-imidazo[1,5-a]pyrazin-8-ylamine: Off-white solid, MS (ES) 355.37 (M+1).

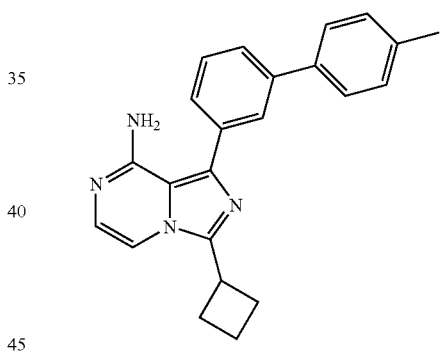

Example 26

3-Cyclobutyl-1-(4'-methoxybiphenyl-3-yl)-imidazo[1,5-a]pyrazin-8-ylamine: White solid, MS (ES) 371.21 (M+1).

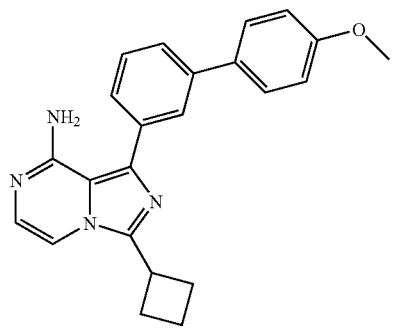

Example 27

1-(3-Benzyloxyphenyl)-3-cyclopentylmethylimidazo[1,5-a]pyrazin-8-ylamine: Prepared according to the procedures for 1-(3-Benzyloxy-phenyl)-3-cyclobutyl-imidazo[1,5-a]pyrazin-8-ylamine, Clear oil, MS (ES) 399.20 (M+1).

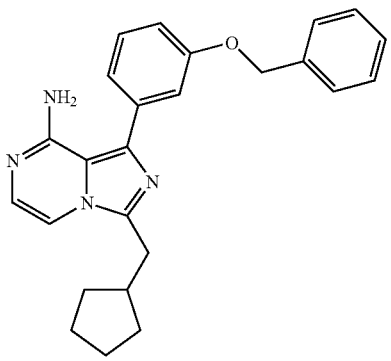

a) 1-(3-Benzyloxphenyl)-8-chloro-3-cyclopentylmethylimidazo[1,5-a]pyrazine: Prepared according to the procedures for 1-(3-Benzyloxy-phenyl)-8-chloro-3-cyclobutyl-imidazo[1,5-a]pyrazine, Yellow oil, MS (ES) 418.37 (M+1).

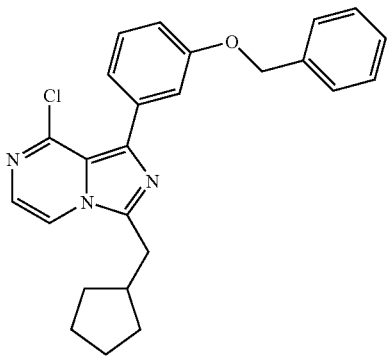

b) N-[(3-Benzyloxyphenyl)-(3-chloropyrazin-2-yl)-methyl]-2-cyclopentyl-acetamide: Prepared according to the procedures for Cyclobutanecarboxylic Acid [(3-benzyloxy-phenyl)-(3-chloro-pyrazin-2-yl)-methyl]Amide, White solid, MS (ES) 436.32 (M+1).

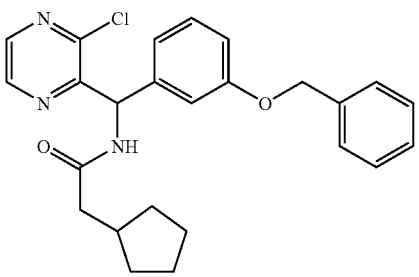

Example 28

1-(3-Benzyloxyphenyl)-3-cyclohexylmethylimidazo[1,5-a]pyrazin-8-ylamine: Prepared according to the procedures for 1-(3-Benzyloxy-phenyl)-3-cyclobutyl-imidazo[1,5-a]pyrazin-8-ylamine, White solid, $^1$H NMR (CDCl$_3$, 400 MHz) δ 1.07-1.27 (m, 5H), 1.64-1.73 (m, 5H), 1.83-1.93 (m, 1H), 2.86 (d, 1H, J=6.8 Hz), 5.02 (bs, 2H), 5.15 (s, 2H), 7.01-7.06 (m, 2H), 7.19 (d, 1H, J=2.0 Hz, 4.8 Hz), 7.23-7.25 (m, 2H), 7.33-7.46 (m, 7H).

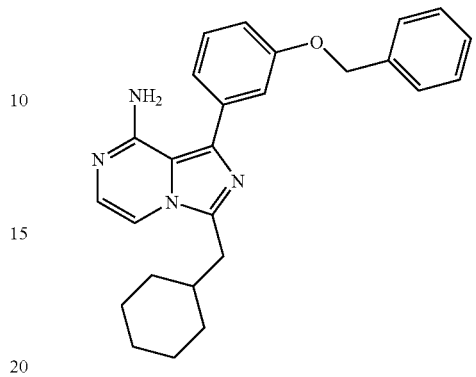

a) 1-(3-Benzyloxyphenyl)-8-chloro-3-cyclohexylmethylimidazo[1,5-a]pyrazine: Prepared according to the procedures for 1-(3-Benzyloxy-phenyl)-8-chloro-3-cyclobutyl-imidazo[1,5-a]pyrazine, Yellow oil, $^1$H NMR (CDCl$_3$, 400 MHz) δ 1.08-1.26 (m, 5H), 1.66-1.73 (m, 5H), 1.85-1.93 (m, 1H), 2.92 (d, 1H, J=7.2 Hz), 5.14 (s, 2H), 7.03 (dd, 1H, J=2.0 Hz, 7.8 Hz), 7.29-7.41 (m, 6H), 7.44-7.46 (m, 2H), 8.32 (d, 1H, J=2.0 Hz), 7.59 (d, 1H, J=4.8 Hz).

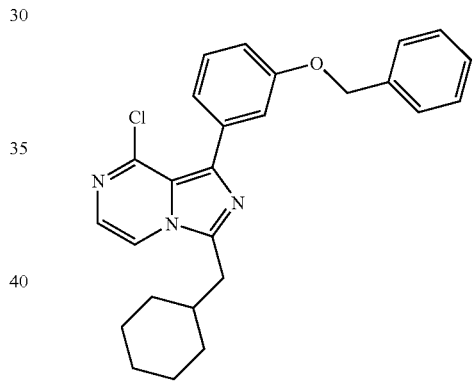

b) N-[(3-Benzyloxyphenyl)-(3-chloropyrazin-2-yl)-methyl]-2-cyclohexyl-acetamide: Prepared according to the procedures for Cyclobutanecarboxylic Acid [(3-benzyloxy-phenyl)-(3-chloro-pyrazin-2-yl)-methyl]Amide, White solid, $^1$H NMR (CDCl$_3$, 400 MHz) δ 0.88-0.97 (m, 2H), 1.09-1.29 (m, 3H), 1.63-1.82 (m, 6H), 2.11 (d, 1H, J=7.2 Hz), 5.02 (s, 2H), 6.55 (d, 1H, J=7.6 Hz), 6.86-6.94 (m, 3H), 7.03 (d, 1H, J=7.6 Hz), 7.19-7.25 (m, 1H), 7.30-7.40 (m, 6H), 8.32 (d, 1H, J=2.0 Hz), 8.49 (d, 1H, J=2.0 Hz).

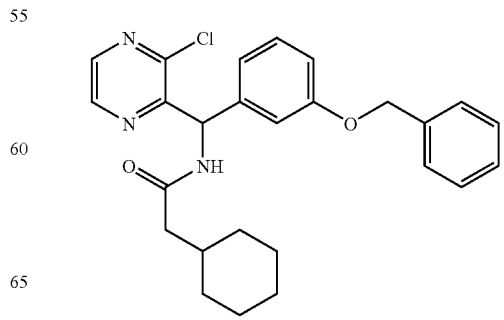

Example 29

1-(3-Benzyloxyphenyl)-imidazo[1,5-a]pyrazin-8-ylamine: Prepared according to the procedures for 1-(3-Benzyloxy-phenyl)-3-cyclobutyl-imidazo[1,5-a]pyrazin-8-ylamine, White solid, $^1$H NMR (CDCl$_3$, 400 MHz) δ 5.09 (bs, 2H), 5.15 (s, 2H), 7.05-7.10 (m, 3H), 7.34-7.45 (m, 8H), 8.11 (s, 1H).

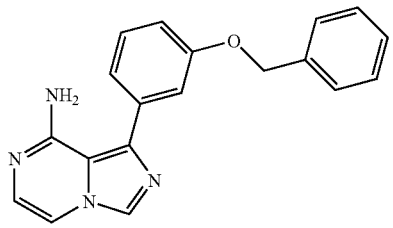

a) 1-(3-Benzyloxyphenyl)-8-chloroimidazo[1,5-a]pyrazine: Prepared according to the procedures for 1-(3-Benzyloxy-phenyl)-8-chloro-3-cyclobutyl-imidazo[1,5-a]pyrazine, Yellow oil, MS (ES) 336.06 (M+1).

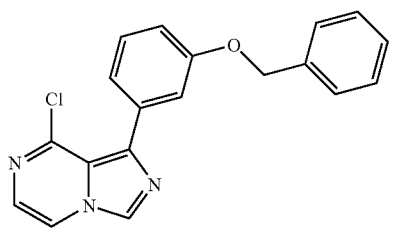

b) N-[(3-Benzyloxyphenyl)-(3-chloropyrazin-2-yl)-methyl]-formamide: Prepared according to the procedures for Cyclobutanecarboxylic Acid [(3-benzyloxy-phenyl)-(3-chloro-pyrazin-2-yl)-methyl]Amide, White solid, $^1$H NMR (CDCl$_3$, 400 MHz) δ 5.03 (s, 2H), 6.62 (d, 1H, J=8.0 Hz), 6.88-6.97 (m, 3H), 7.22-7.24 (m, 1H), 7.32-7.41 (m, 5H), 8.29 (bs, 1H), 8.35 (d, 1H, J=2.4 Hz), 8.51 (d, 1H, J=2.0 Hz).

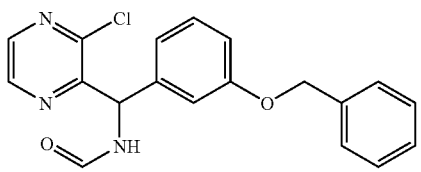

Example 30

1-(3-Benzyloxyphenyl)-3-trifluoromethylimidazo[1,5a]pyrazin-8-ylamine: Prepared according to the procedures for 1-(3-Benzyloxy-phenyl)-3-cyclobutyl-imidazo[1,5-a]pyrazin-8-ylamine, Pink solid, $^1$H NMR (CDCl$_3$, 400 MHz) δ 5.15 (s, 2H), 5.25 (bs, 2H), 7.08-7.11 (m, 1H), 7.23-7.29 (m, 3H), 7.34-7.45 (m, 6H), 7.54 (d, 1H, J=4.8 Hz).

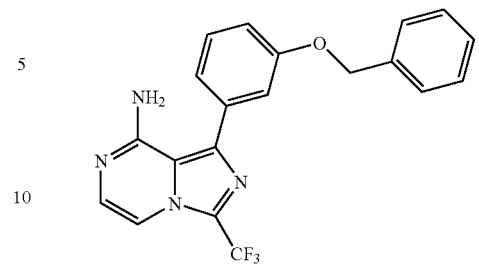

a) 1-(3-Benzyloxyphenyl)-8-chloro-3-trifluoromethylimidazo[1,5-a]pyrazine: Prepared according to the procedures for 1-(3-Benzyloxy-phenyl)-8-chloro-3-cyclobutyl-imidazo[1,5-a]pyrazine, Yellow oil, $^1$H NMR (CDCl$_3$, 400 MHz) δ 5.14 (s, 2H), 7.08-7.11 (m, 1H), 7.28-7.46 (m, 8H), 7.59 (d, 1H, J=4.8 Hz), 7.99 (d, 1H, J=5.2 Hz).

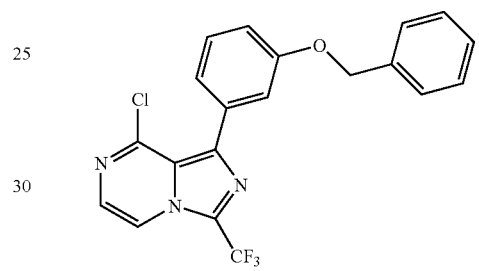

b) N-[(3-Benzyloxyphenyl)-(3-chloropyrazin-2-yl)-methyl]-2,2,2-trifluoroacetamide: Prepared according to the procedures for Cyclobutanecarboxylic Acid [(3-benzyloxy-phenyl)-(3-chloro-pyrazin-2-yl)-methyl]Amide, White solid, $^1$H NMR (CDCl$_3$, 400 MHz) δ 5.03 (s, 2H), 6.46 (d, 1H, J=7.6 Hz), 6.92-6.96 (m, 3H), 7.28-7.41 (m, 5H), 8.16 (d, 1H, J=6.4 Hz), 8.40 (d, 1H, J=2.4 Hz), 8.55 (d, 1H, J=2.4 Hz).

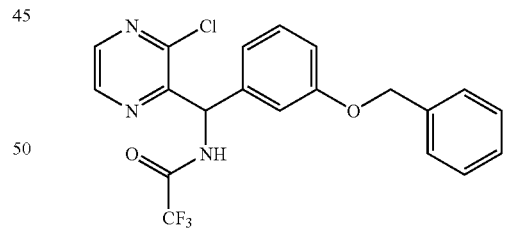

Example 31

4-[8-Amino-1-(3-benzyloxyphenyl)-imidazo[1,5-a]pyrazin-3-yl]-benzamide: Prepared according to the procedures for 1-(3-Benzyloxy-phenyl)-3-cyclobutyl-imidazo[1,5-a]pyrazin-8-ylamine, Yellow solid, $^1$H NMR (DMSO-d$_6$, 400 MHz) δ 5.20 (s, 2H), 6.23 (bs, 2H), 7.12 (dd, 1H, J=2.4 Hz, 8.2 Hz), 7.16 (d, 1H, J=2.4 Hz), 7.27 (d, 1H, J=7.6 Hz), 7.32-7.50 (m, 8H), 7.85 (d, 1H, J=5.2 Hz), 7.96 (d, 2H, J=8.8 Hz), 8.07 (d, 2H, J=8.8 Hz), 8.14 (bs, 1H).

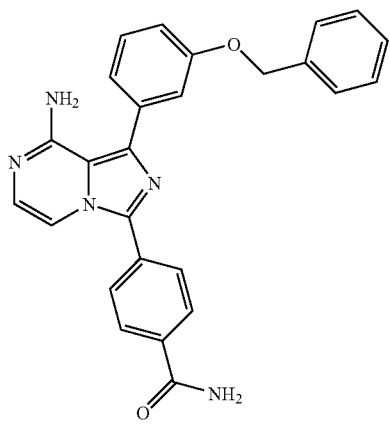

a) 4-[1-(3-Benzyloxyphenyl)-8-chloroimidazo[1,5-a]pyrazin-3-yl]-benzoic Acid Methyl Ester: Prepared according to the procedures for 1-(3-Benzyloxy-phenyl)-8-chloro-3-cyclobutyl-imidazo[1,5-a]pyrazine, Yellow solid, MS (ES) 469.90 (M+1).

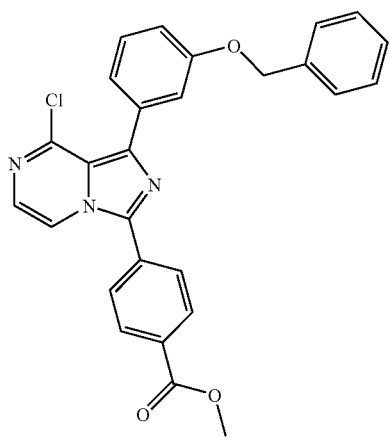

b) N-[(3-Benzyloxyphenyl)-(3-chloropyrazin-2-yl)-methyl]-terephthalamic Acid Methyl Ester: Prepared according to the procedures for Cyclobutanecarboxylic Acid [(3-benzyloxy-phenyl)-(3-chloro-pyrazin-2-yl)-methyl]Amide, Yellow solid, MS (ES) 490.01 (M+2).

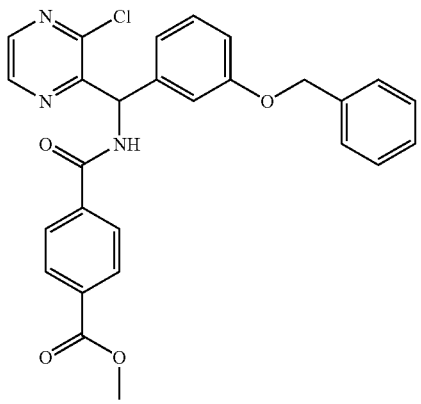

Example 32

3-Cyclobutyl-1-phenylimidazo[1,5-a]pyrazin-8-ylamine: Gaseous NH$_3$ was condensed into a cooled (−78° C.) solution of 8-chloro-3-cyclobutyl-1-phenylimidazo[1,5-a]pyrazine (602.9 mg, 2.125 mmol) in NH$_3$/i-PrOH (2M, 15 mL) in a pressure tube until the volume had doubled. The tube was sealed and heated to 110° C. for 2 d. After excess NH$_3$/i-PrOH was removed in vacuo, the residue was extracted with CH$_2$Cl$_2$ (3×30 mL), and the combined organic layers were washed with brine (3×30 mL), dried over anhydrous MgSO$_4$, filtered, and concentrated. The material obtained (670 mg) was recrystallized from EtOAc, granting 393.3 mg (70%, 1.488 mmol) of the title compound, as pale pink crystals. The mother liquor was reduced ca. 50% in vacuo and again recrystallized from EtOAc, affording an additional 38.4 mg (7%, 0.145 mmol) of the title compound, as pink crystals, >99% pure by HPLC; mp. 164-166° C.; $^1$H NMR (CDCl$_3$, 400 MHz) δ 1.98-2.09 (m, 1H), 2.11-2.23 (m, 1H), 2.44-2.54 (m, 2H), 2.58-2.70 (m, 2H), 3.82 (quint, J=8.4 Hz, 1H), 5.02 (s, br, —NH$_2$), 7.05 (d, J=4.8 Hz, 1H), 7.12 (d, J=5.2 Hz, 1H), 7.38-7.43 (m, 1H), 7.46-7.53 (m, 2H), 7.65-7.70 (m, 2H). $^{13}$C NMR (CDCl$_3$, 100.6 MHz, DEPT135): δ 18.87 (−), 26.94 (2C, −), 31.48 (+), 106.61 (+), 113.93 (C$_{quart}$), 127.43 (+), 128.08 (+), 128.81 (2C, +), 129.67 (2C, +), 134.87 (C$_{quart}$), 135.32 (C$_{quart}$), 143.90 (C$_{quart}$), 151.75 (C$_{quart}$). MS (ES+): m/z 265.2 (100) [MH$^+$].

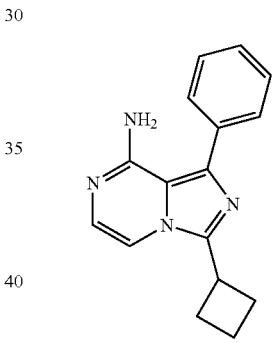

a) 8-Chloro-3-cyclobutyl-1-phenylimidazo[1,5-a]pyrazine: A mixture of cyclobutanecarboxylic acid [(3-chloropyrazin-2-yl)-phenylmethyl]-amide (710 mg, 2.35 mmol) and POCl$_3$ (15 mL, 25 g, 163 mmol) was heated to 55° C., under N$_2$ atmosphere, for 21 h. POCl$_3$ was evaporated in vacuo, a cold solution of NH$_3$ in i-PrOH (2M, 15 mL) was added until pH was basic, and rotary evaporation was used to remove excess solvent. The crude material was suspended between EtOAc and dH$_2$O, the layers were separated, and the aqueous layer was extracted with EtOAc (4×50 mL). The combined organic layers were washed with NaHCO$_3$ sat. aq. sol. (2×50 mL) and brine (1×50 mL), dried over anhydrous MgSO$_4$, and filtered. Sample was purified by filtration through a silica gel plug with 10% EtOAc:CH$_2$Cl$_2$ (250 mL) and filtrate was concentrated in vacuo, affording 602.9 mg (90%, 2.125 mmol) of the title compound, containing ≈0.5 equivalents of reduced DIAD and ≦0.06 equivalents of cyclobutanecarboxylic acid [(3-chloropyrazin-2-yl)-phenylmethyl]-amide (4), as a gold-colored solid; $^1$H NMR (CDCl$_3$, 400 MHz) δ 2.00-2.11 (m, 1H), 2.13-2.26 (m, 1H), 2.47-2.57 (m, 2H), 2.60-2.72 (m, 2H), 3.85 (quint, J=8.4 Hz, 1H), 7.30 (d, J=5.2 Hz, 1H), 7.38-7.47 (m, 3H), 7.50 (d, J=5.2 Hz, 1H), 7.67-7.71 (m, 2H). MS (ES+): m/z 284.1/286.1 (100/55) [MH$^+$].

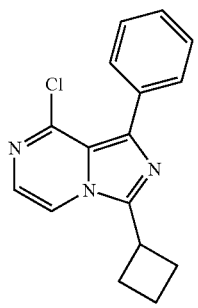

b) Cyclobutanecarboxylic acid [(3-chloropyrazin-2-yl)-phenylmethyl]-amide: To a solution of C-(3-chloropyrazin-2-yl)-C-phenylmethylamine (610.7 mg, 2.780 mmol), DMAP (17 mg, 0.139 mmol), and (iPr)$_2$EtN (726 μL, 539 mg, 4.17 mmol) in dry CH$_2$Cl$_2$ (10 mL), cooled to 0° C., cyclobutanecarbonyl chloride (350 μL, 363 mg, 3.058 mmol) was added under N$_2$ atmosphere, the cooling bath was removed, and the reaction mixture stirred at ambient temperature for 2 h. The reaction mixture was quenched with dH$_2$O, taken up by CH$_2$Cl$_2$ (3×20 mL), washed (1×30 mL each) with 0.25M citric acid (pH 2-3), dH$_2$O, NaHCO$_3$ sat. aq. sol., and brine, dried over anhydrous MgSO$_4$, and filtered. Sample was purified by filtration through a silica gel plug with 10% EtOAc:CH$_2$Cl$_2$ (250 mL) and filtrate was concentrated in vacuo, yielding the title compound as a gold-colored solid; $^1$H NMR (CDCl$_3$, 400 MHz) δ 1.80-2.02 (m, 2H), 2.10-2.22 (m, 2H), 2.22-2.34 (m, 2H), 3.09 (quint, J=8.4 Hz, 1H), 6.58 (d, J=7.6 Hz, 1H), 7.01 (d, J=8.0 Hz, 1H), 7.24-7.36 (m, 5H), 8.33 (d, J=2.4 Hz, 1H), 8.52 (d, J=2.0 Hz, 1H).

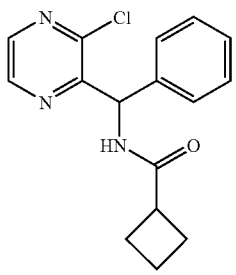

c) C-(3-Chloropyrazin-2-yl)-C-phenylmethylamine: To a solution of 2-[(3-chloropyrazin-2-yl)-phenylmethyl]-isoindole-1,3-dione (7.70 g, 22 mmol), containing ≈0.77 eq. of reduced DIAD, in EtOH (10 mL) and co-solvent CH$_2$Cl$_2$ (15 mL), N$_2$H$_4$ (10 mL, 7.91 g, 0.172 mol) was added and the reaction solution was stirred at rt, under N$_2$, for 1 d. The suspension was filtered, the orange solid was washed several times with CH$_2$Cl$_2$, and the filtrate was concentrated in vacuo. The residue was suspended between HCl (2M)/EtOAc and the EtOAc layer was discarded. The aqueous layer was brought to a basic pH using NaOH and extracted with CH$_2$Cl$_2$ (5×60 mL), washed with brine (2×50 mL), dried over MgSO$_4$, filtered, and concentrated, giving 2.1923 g (45%; 9.9795 mmol) of the title compound, containing ≈0.1 eq. of reduced DIAD, as a brown oil; $^1$H NMR (CDCl$_3$, 400 MHz) δ 2.24 (s, br, 2H), 5.56 (s, 1H), 7.26-7.38 (m, 5H), 8.27 (s, 1H), 8.55 (s, 1H). MS (ES+): m/z 203.2/205.2 (100/73) [MH$^+$-NH$_3$].

C-(3-Chloropyrazin-2-yl)-C-phenylmethylamine hydrochloride (2-HCl): To a solution of C-(3-chloropyrazin-2-yl)-C-phenylmethylamine (1.582 g, 7.20 mmol) in 1,4-dioxane (≦5 mL), HCl (2 mL, 7.55 mmol, 4M soln. in 1,4-dioxane) was added and left for approx. 5 min. The reaction mixture was filtered and the solid was washed several times with 1,4-dioxane, yielding the title compound as a tan solid. Sample contains ≈0.1 eq. of 1,4-dioxane by $^1$H NMR; $^1$H NMR (d-MeOH, 400 MHz) δ 5.85 (s, 1H), 7.35 (s, 1H), 8.44 (d, J=2.4 Hz, 1H), 8.65 (d, J=2.4 Hz, 1H).

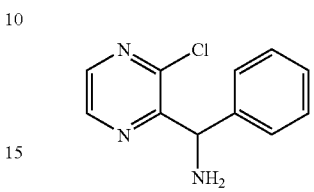

d) 2-[(3-Chloropyrazin-2-yl)-phenylmethyl]isoindole-1,3-dione: Prepared according to the procedures for 2-[(3-Benzyloxy-phenyl)-(3-chloro-pyrazin-2-yl)-methyl]-isoindole-1,3-dione, Yellow oil, MS (ES) 350.04 (M+1).

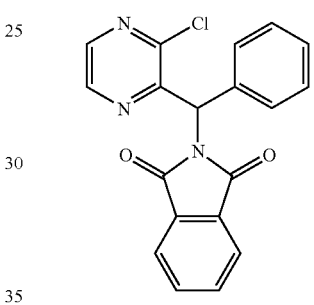

e) (3-Chloropyrazin-2-yl)-phenylmethanol: Prepared according to the procedures for (3-Chloro-pyrazin-2-yl)-(3-benzyloxy-phenyl)-methanol, Yellow solid, $^1$H NMR (CDCl$_3$, 400 MHz) δ 4.62 (d, 1H, J=8.0 Hz), 6.04 (d, 1H, J=8.0 Hz), 7.29-7.36 (m, 5H), 8.37 (d, 1H, J=2.4 Hz), 8.56 (d, 1H, J=2.4 Hz).

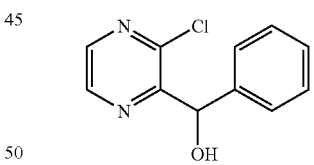

General procedure to Examples 33 and 34: A THF solution (3 mL) of trans-toluene-4-sulfonic acid 4-[8-amino-1-(3-benzyloxy-phenyl)imidazo[1,5-a]pyrazin-3-yl]-cyclohexylmethyl ester (200 mg, 0.34 mmol) in a sealed tube was charged with azetidine (8.92 mmol, 510 mg) and stirred at 50° C. for 24 h. The reaction mixture concentrated in vacuo and partitioned b/w EtOAc and sat. NaHCO$_3$. The organic layer was washed with sat. NaHCO$_3$ (2×), water (1×), brine (1×), dried over Na$_2$SO$_4$, filtered, and concentrated to a yellow oil. The crude material was purified by silica gel column chromatography [Jones Flashmaster, 5 g/25 mL cartridge, eluting with CH$_2$Cl$_2$ to 2% ~7 N NH$_3$ in MeOH/CH$_2$Cl$_2$] to afford trans-3-(4-azetidin-1-ylmethyl-cyclohexyl)-1-(3-benzyloxy-phenyl)-imidazo[1,5-a]pyrazin-8-ylamine as a white solid (130 mg, 82%).

Example 33

(trans-3-(4-Azetidin-1-ylmethyl-cyclohexyl)-1-(3-benzyloxy-phenyl)-imidazo[1,5-a]pyrazin-8-ylamine: MS (ES+): m/z 468.1.

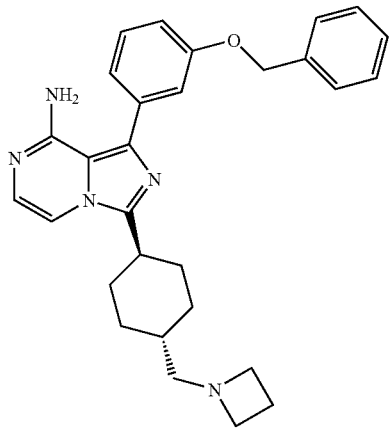

Example 34 trans-1-(3-Benzyloxy-phenyl)-3-(4-pyrrolidin-1ylmethyl-cyclohexyl)-imidazo[1,5-a]pyrazin-8-ylamine): MS (ES+): m/z 482.3.

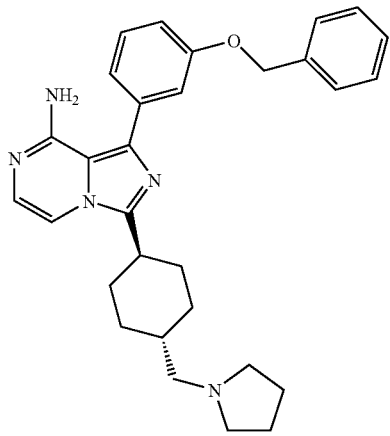

a) trans-Toluene-4-sulfonic acid 4-[8-amino-1-(3-benzyloxy-phenyl)imidazo[1,5-a]pyrazin-3-yl]-cyclohexylmethyl ester: A pyridine solution (23 mL) of trans-{4-[8-amino-1-(3-benzyloxy-phenyl)-imidazo[1,5-a]pyrazin-3-yl]-cyclohexyl}-methanol (2.00 g, 4.67 mmol) was cooled to −20° C. and charged with Ts$_2$O (1.52 g, 4.67 mmol). The reaction was allowed to warm to rt and stirred for 16 h. The mixture was concentrated in vacuo to a tan foam and partitioned between CHCl$_3$ and water. The organic layer was washed with 1M NaOH (2×), water (1×), brine (1×), dried over Na$_2$SO$_4$, filtered, and concentrated to tan foam. The crude material was purified by silica gel column chromatography [Jones Flashmaster, 50 g/150 mL cartridge, eluting with 50% EtOAc/Hexanes to 5% MeOH/EtOAc] to afford trans-toluene-4-sulfonic acid 4-[8-amino-1-(3-benzyloxy-phenyl)imidazo[1,5-a]pyrazin-3-yl]-cyclohexylmethyl ester as a tan foam (1.90 g, 70%); MS (ES+): m/z 583.1

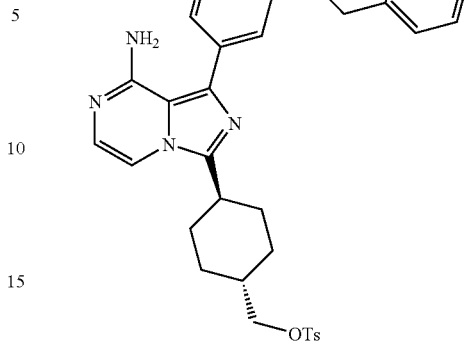

Example 35 trans-4-[8-Amino-1-(3-benzyloxy-phenyl)-imidazo[1,5-a]pyrazin-3-yl]-cyclohexanecarboxylic acid methyl ester: An isopropanol solution (42 mL) of trans-4-[1-(3-benzyloxy-phenyl)-8-chloro-imidazo[1,5-a]pyrazin-3-yl]-cyclohexanecarboxylic acid methyl ester (4.00 g, 8.4 mmol) in a sealed tube was cooled to −78° C. Ammonia was bubbled into the solution for 2 min; the tube was capped and heated to 110° C. for 1 d. The reaction mixture was concentrated in vacuo and partitioned b/w EtOAc and water. The organic layer was washed with water (2×), brine (1×), dried over Na$_2$SO$_4$, filtered, and concentrated to a yellow oil. The crude material was purified by silica gel column chromatography [Jones Flashmaster, 20 g/70 mL cartridge, eluting with 50% EtOAc/Hexanes to 2% ~7 N NH$_3$ in MeOH/EtOAc] to afford trans-4-[8-amino-1-(3-benzyloxy-phenyl)-imidazo[1,5-a]pyrazin-3-yl]-cyclohexanecarboxylic acid methyl ester as a tan foam (1.50 g, 39%); recovered trans-4-[1-(3-benzyloxy-phenyl)-8-chloro-imidazo[1,5-a]pyrazin-3-yl]-cyclohexanecarboxylic acid methyl ester (1.20 g, 30%); MS (ES+): m/z 457.1.

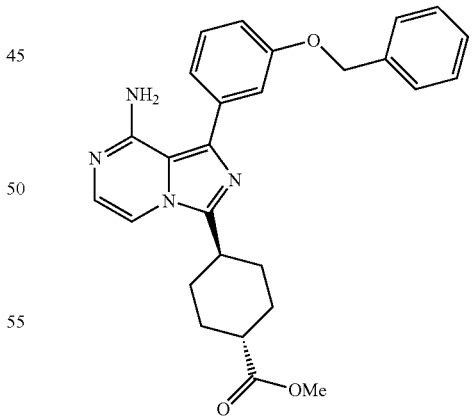

Example 36

(trans-4-[8-Amino-1-(3-benzyloxy-phenyl)-imidazo[1,5-a]pyrazin-3-yl]-cyclohexanecarboxylic acid): A THF solution (11 mL) of trans-4-[8-amino-1-(3-benzyloxy-phenyl)-imidazo[1,5-a]pyrazin-3-yl]-cyclohexanecarboxylic acid methyl ester (1.50 g, 3.28 mmol) was charged with 10 M NaOH (1.64 mL, 16.42 mmol); a minimal amount of methanol was added to make the reaction mixture homogeneous. The reaction stirred at rt for 2 h. The reaction mixture was concentrated to solids and acidified to pH 5 with 2 M HCl. The resulting ppt was filtered, washed with water, and dried in a vacuum oven overnight at 50° C. to afford acid trans-4-[8-Amino-1-(3-benzyloxy-phenyl)-imidazo[1,5-a]pyrazin-3-yl]-cyclohexanecarboxylic acid as an off-white solid (1.10 g, 76%); MS (ES+): m/z 443.1.

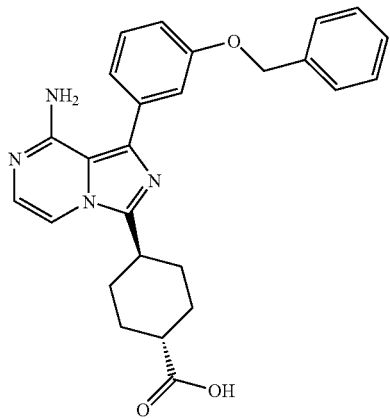

General procedure to EXAMPLES 37 and 38: A DMF solution (2 mL) of acid trans-4-[8-amino-1-(3-benzyloxy-phenyl)-imidazo[1,5-a]pyrazin-3-yl]-cyclohexanecarboxylic acid (100 mg, 0.23 mmol) and methylamine hydrochloride (153 mg, 2.26 mmol) in a sealed tube was charged with DIEA (394 μL, 2.26 mmol), 0.6 M HOAt in DMF (377 μL, 0.23 mmol), and then EDC (65 mg, 0.34 mmol). The reaction mixture stirred at rt for 16 h. The reaction mixture was concentrated to solids, taken up in CH$_2$Cl$_2$, charged with silica, and concentrated to brown solids. The crude material was purified by silica gel column chromatography [Jones Flashmaster, 20 g/70 mL cartridge, eluting with 2% ~7 N NH$_3$ in MeOH/CH$_2$Cl$_2$ to 5% ~7 N NH$_3$ in MeOH/CH$_2$Cl$_2$] to afford trans-4-[8-amino-1-(3-benzyloxy-phenyl)-imidazo[1,5-a]pyrazin-3-yl]-cyclohexanecarboxylic acid methylamide as an off-white solid (60 mg, 57%).

Example 37

(trans-4-[8-Amino-1-(3-benzyloxy-phenyl)-imidazo[1,5-a]pyrazin-3-yl]-cyclohexanecarboxylic acid methylamide: MS (ES+): m/z 456.3.

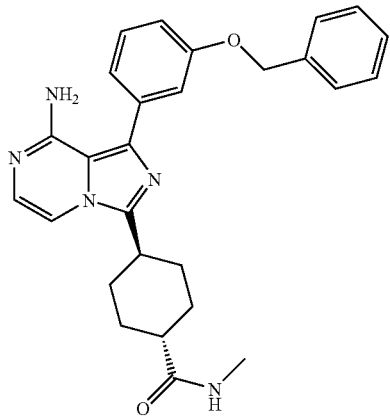

Example 38

4-[8-Amino-1-(3-benzyloxy-phenyl)-imidazo[1,5-a]pyrazin-3-yl]-cyclohexanecarboxylic acid ethylamide: MS (ES+): m/z 470.4.

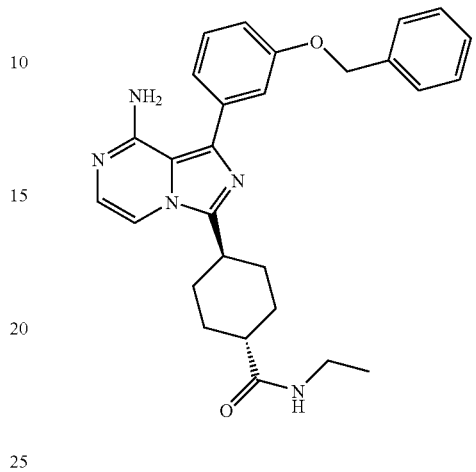

General Reductive Amination Procedures:

3-[8-Amino-1-(3-benzyloxy-phenyl)-imidazo[1,5-a]pyrazin-3-yl]-cyclobutanecarbaldehyde (225 mg, 565 mmol) was dissolved in dichloroethane (DCE) (4.0 mL) followed by the addition of resin bound-BH(OAc)$_3$ (562 mg, 1.129 mmol), AcOH (70 μL, 1.186 mmol) and pyrrolidine (0.14 mL, 1.694 mmol). After stirring for 24 h at rt the resin was filtered and washed with CH$_2$Cl$_2$ and the filtrate combined and concentrated in vacuo. The crude oil was purified by silica gel column chromatography (2-5% 7N NH$_3$ in MeOH:CH$_2$Cl$_2$) to yield the desired compounds. The more polar spot is the cis isomer, which is the major isomer.

Example 39 trans-1-(3-Benzyloxy-phenyl)-3-(3-pyrrolidin-1-ylmethyl-cyclobutyl)-imidazo[1,5-a]pyrazin-8-ylamine: Followed general reductive amination conditions; $^1$H NMR (400 MHz, CDCl$_3$) δ 1.75 (brs, 4H), 2.35 (brs, 2H), 2.66 (brm, 9H), 3.68-3.75 (m, 1H), 4.94 (brs, 2H), 5.08 (s, 2H), 6.98-6.99 (m, 3H), 7.20-7.42 (m, 8H); MS (ES+): 454.15 (M+1), 455.15 (M+2), 456.17 (M+3);

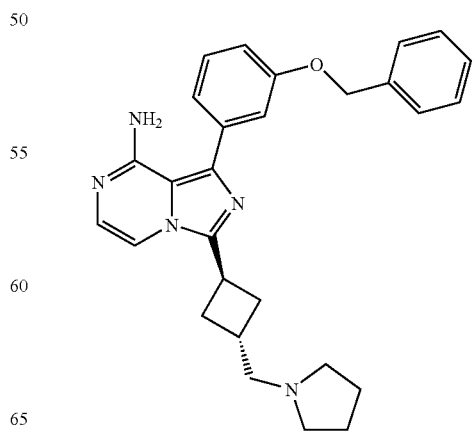

Example 40 cis-1-(3-Benzyloxy-phenyl)-3-(3-pyrrolidin-1-ylmethyl-cyclobutyl)-imidazo[1,5-a]pyrazin-8-ylamine: Followed general reductive amination conditions; $^1$H NMR (400 MHz, CDCl$_3$) δ 1.88-1.91 (m, 4H), 2.39-2.43 (m, 2H), 2.64-2.82 (m, 9H), 3.73-3.90 (m, 1H), 5.20 (brs, 2H), 5.26 (s, 2H), 7.13-7.15 (m, 1H), 7.22 (d, 1H, J=5.0 Hz), 7.35-7.57 (m, 8H); MS (ES+): 454.11 (M+1), 455.06 (M+2), 456.20 (M+3);

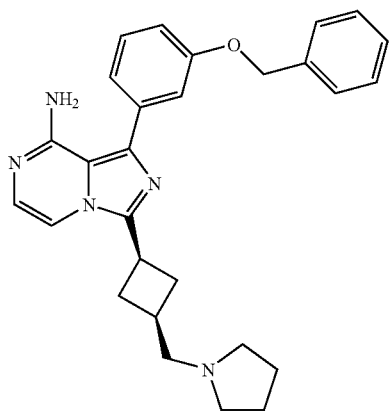

Example 41 trans-3-(3-Azetidin-1-ylmethylcyclobutyl)-1-(3-benzyloxyphenyl)-imidazo[1,5-a]pyrazin-8-ylamine: Followed general reductive amination conditions; $^1$H NMR (400 MHz, CDCl$_3$) δ 2.07-2.11 (m, 2H), 2.20-44 (m, 2H), 2.51 (brm, 1H), 2.63-2.71 (m, 4H), 3.25 (t, 4H, J=7.04 Hz), 3.71-3.75 (m, 1H), 5.00 (brs, 2H), 5.11 (s, 2H), 6.98-6.99 (m, 3H), 7.20-7.42 (m, 8H).

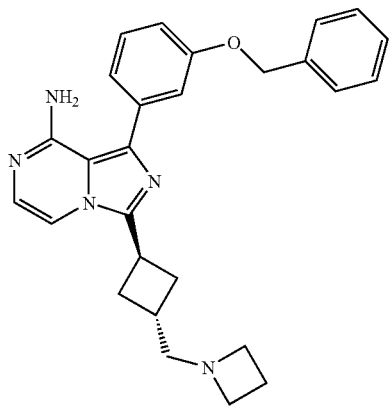

Example 42 cis-3-(3-Azetidin-1-ylmethylcyclobutyl)-1-(3-benzyloxyphenyl)-imidazo[1,5-a]pyrazin-8-ylamine: Followed general reductive amination conditions; $^1$H NMR (400 MHz, CDCl$_3$) δ 1.98-2.02 (m, 2H), 2.18-2.21 (m, 2H), 2.44-2.54 (m, 4H), 3.12 (t, 4H, J=7.0 Hz), 3.52-3.57 (m, 1H), 4.98 (brs, 4H), 6.95-6.97 (m, 2H), 7.03 (d, 1H, J=5.0 Hz), 7.16-7.45 (m, 8H); MS (ES+): 440.08 (M+1), 441.08 (M+2), 442.13 (M+3). Alternatively, cis-3-(3-Azetidin-1-ylmethylcyclobutyl)-1-(3-benzyloxyphenyl)-imidazo[1,5-a]pyrazin-8-ylamine could be prepared as follows: A sealed tube containing a solution of toluene-4-sulfonic acid 3-[8-amino-1-(3-benzyloxyphenyl)-imidazo[1,5-a]pyrazin-3-yl]cyclobutylmethyl ester (15 mg, 0.027 mmol) in THF (3 mL) was charged with azetidine (0.04 mL, 0.54 mmol), sealed, and heated at 50° C. overnight. The mixture was concentrated and the residue was diluted with ethyl acetate (20 mL), washed with sat. aq. NaHCO$_3$ (2×10 mL) and brine (2×10 mL), and dried over anhydrous sodium sulfate. The filtrate was concentrated under reduced pressure to afford a white solid.

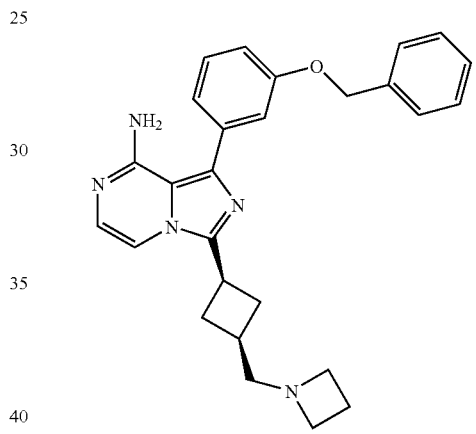

Example 43

Toluene-4-sulfonic acid 3-[8-amino-1-(3-benzyloxyphenyl)-imidazo[1,5-a]pyrazin-3-yl]cyclobutylmethyl ester: A solution of {3-[8-amino-1-(3-benzyloxyphenyl)-imidazo[1,5-a]pyrazin-3-yl]cyclobutyl}methanol (23 mg, 0.057 mmol) in dry methylene chloride (3 mL) was charged with pyridine (0.1 mL) and Ts$_2$O (21 mg, 0.063 mmol) at −20° C. under N$_2$ atmosphere. The mixture was slowly warmed to rt overnight. The reaction was quenched with water (1 mL), diluted with ethyl acetate (20 mL), washed with sat. aq. NaHCO$_3$ (10 mL) and brine (2×10 mL), and dried over anhydrous sodium sulfate. The filtrate was concentrated under reduced pressure, and the crude material was purified by silica gel column chromatography (eluting with EtOAc:MeOH=98:2→96:4), yielding the title compound as a white solid. Partial trans isomer was removed by chromatography and the ratio of cis and trans isomers raised to 8:1; MS (ES, Pos.): m/z 555 [MH$^+$]. $^1$H NMR (CDCl$_3$, 400 MHz) δ 2.27-2.35 (m, 2H), 2.41 (s, 3H), 2.55-2.62 (m, 2H), 2.80 (m, 1H), 3.66 (m, 1H), 4.07 (d, J=6.7 Hz, 2H), 5.01 (br s, 2H, NH$_2$), 5.15 (s, 2H), 7.02-7.85 (m, 15H). Anal. Calcd for C$_{31}$H$_{30}$N$_4$O$_4$S.1/3H$_2$O: C, 66.41; H, 5.51; N, 9.99. Found: C, 66.43; H, 5.44; N, 10.07.

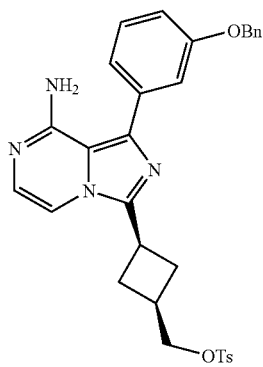

Example 44

{3-[8-Amino-1-(3-benzyloxyphenyl)-imidazo[1,5-a]pyrazin-3-yl]cyclobutyl}methanol: A solution of {3-[1-(3-benzyloxyphenyl)-8-chloro-imidazo[1,5-a]pyrazin-3-yl]cyclobutyl}methanol (40 mg, 0.095 mmol) in 5 mL of 2N NH$_3$/$^i$PrOH was cooled to −78° C. and charged with NH$_3$ gas for 1 min. This sealed tube was equipped with a teflon O-ring, sealed and heated at 110° C. overnight. The mixture was cooled to rt and the cap was removed. The solution was concentrated under reduced pressure and the crude material was purified by silica gel column chromatography (eluting with 100% ethyl acetate→EtOAc:$^i$PrOH=80:20), yielding the title compound as a white solid, a mixture of cis and trans isomers. MS (ES, Pos.): m/z 401 [MH$^+$]. $^1$H NMR (CDCl$_3$, 400 MHz) δ 2.37-2.44 (m, 2H), 2.61-2.74 (m, 3H), 3.65-3.82 (m, 3H), 5.03 (br s, 2H, NH$_2$), 5.14 (s, 2H), 7.01-7.46 (m, 11H).

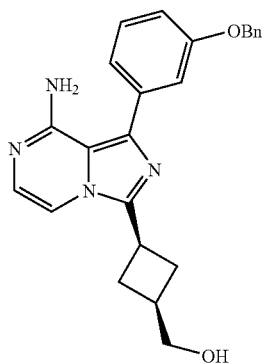

a) {3-[1-(3-Benzyloxyphenyl)-8-chloro-imidazo[1,5-a]pyrazin-3-yl]cyclobutyl}methanol: To a solution of 1-(3-benzyloxyphenyl)-8-chloro-3-(3-methylenecyclobutyl)-imidazo[1,5-a]pyrazine (345 mg, 0.86 mmol) in dry THF (5 mL) was added 9-BBN (2.6 mL, 1.3 mmol, 0.5 M in THF) dropwise at 0° C. under nitrogen atmosphere. The temperature was slowly warmed to rt overnight. Upon which time TLC showed the reaction was complete. The mixture was cooled to 0° C., and 2 mL 1N aq. NaOH and 0.4 mL 30% aq. H$_2$O$_2$ were added, the resulting mixture was stirred at 0° C. for 10 min, then rt for 30 min. The resulting white solid was filtered off, the filtrate was diluted with ethyl acetate (60 mL), washed with brine (3×20 mL), and dried over anhydrous sodium sulfate. The filtrate was concentrated under reduced pressure, and the crude material was purified by silica gel column chromatography (eluting with 100% ethyl acetate), yielding the title compound as a yellow viscous oil, a mixture of cis and trans isomers. MS (ES, Pos.): MS (ES, Pos.): m/z 420/422 (3/1) [MH$^+$]. $^1$H NMR (CDCl$_3$, 400 MHz) δ 2.32 (br s, 1H), 2.60-2.85 (m, 5H), 3.88-4.11 (m, 3H), 5.36 (s, 2H), 7.27 (m, 1H), 7.48-7.69 (m, 9H), 7.77 (d, J=5.0 Hz, 1H).

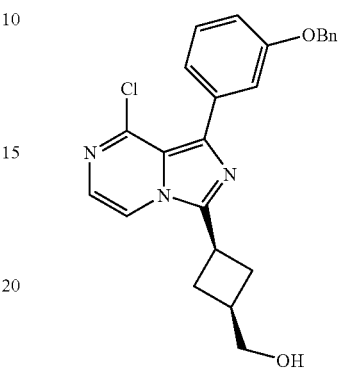

b) 1-(3-Benzyloxyphenyl)-8-chloro-3-(3-methylenecyclobutyl)-imidazo[1,5-a]pyrazine: A mixture of 3-methylenecyclobutanecarboxylic acid [(3-benzyloxyphenyl)-(3-chloropyrazin-2-yl)methyl]amide (190 mg, 0.45 mmol) and POCl$_3$ (2 mL) was heated at 55° C. under N$_2$ atmosphere overnight. The mixture was concentrated under reduced pressure, the residue was cooled to 0° C., quenched with 2N NH$_3$/$^i$PrOH to pH>10, and the solid was filtered off and washed with methylene chloride. The filtrate was concentrated and the crude material was purified by silica gel column chromatography (eluting with hexanes:EtOAc=80:20→60:40), yielding the title product as a yellow solid; MS (ES, Pos.): m/z 402/404 (3/1) [MH$^+$]; $^1$H NMR (CDCl$_3$, 400 MHz) δ 3.26-3.44 (m, 4H), 3.86 (m, 1H), 4.94 (m, 2H), 5.16 (s, 2H), 7.07 (ddd, J=8.2, 2.6, 1.1 Hz, 1H), 7.30-7.50 (m, 9H), 7.54 (d, J=5.0 Hz, 1H).

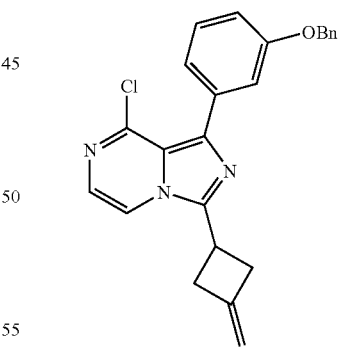

c) 3-Methylenecyclobutanecarboxylic acid [(3-benzyloxyphenyl)-(3-chloropyrazin-2-yl)methyl]amide: To a suspension of C-(3-benzyloxyphenyl)-C-(3-chloropyrazin-2-yl)methylamine hydrochloride (724 mg, 2.0 mol) in methylene dichloride (10 mL) was added $^i$Pr$_2$NEt (1.7 mL, 10.0 mmol), at which time the solid dissolved. The reaction was charged with 3-methylenecyclobutanecarboxylic acid (560 mg, 5.0 mmol), EDC (1.15 g, 6.0 mmol) and HOBt (270 mg, 2.0 mmol) and the resulting mixture was stirred at rt overnight. The mixture was diluted with ethyl acetate (50 mL), washed with sat. aq. NaHCO$_3$ (2×20 mL) and brine (2×20 mL), and dried over anhydrous sodium sulfate. The filtrate was concentrated under reduced pressure, and the crude material was purified by silica gel column chromatography (eluting with hexanes:EtOAc=80:20→60:40), yielding the title product as a light-yellow viscous oil; MS (ES, Pos.): m/z 420/422 (3/1) [MH$^+$]; $^1$H NMR (CDCl$_3$, 400 MHz) δ 2.85-3.09 (m, 5H), 4.78 (m, 2H), 5.03 (s, 2H), 6.55 (d, J=7.9 Hz, 1H), 6.87-6.95 (m, 3H), 7.08 (br d, 1H, NH), 7.21-7.41 (m, 6H), 8.33 (d, J=2.5 Hz, 1H), 8.49 (d, J=2.5 Hz, 1H).

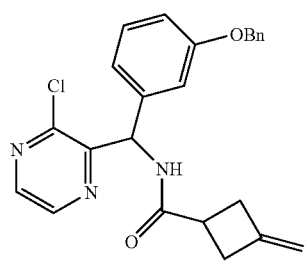

d) 3-Methylenecyclobutanecarboxylic acid: To a solution of 3-methylenecyclobutanecarbonitrile (10.0 g, 107.4 mmol) in ethanol (100 mL) and water (100 mL) was added potassium hydroxide (28.0 g, 430 mmol, 85% pure); the resulting mixture was refluxed for 8 h. Ethanol was removed under reduced pressure, then the solution was cooled to 0° C. and acidified with conc. HCl to pH=1. The mixture was extracted with diethyl ether (4×100 mL). The combined organic phases were dried over anhydrous sodium sulfate. Concentration in vacuo afforded the desired product as a colorless oil; $^1$H NMR (CDCl$_3$, 400 MHz) δ 2.91-3.18 (m, 4H), 3.14-3.22 (m, 1H), 4.83 (m, 2H); $^{13}$C NMR (CDCl$_3$, 100 MHz) δ 32.95, 35.30, 107.14, 143.77, 181.02 ppm.

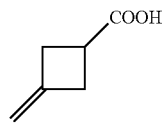

Procedures for General Grignard Reaction:

3-[1-(3-Benzyloxy-phenyl)-8-chloro-imidazo[1,5-a]pyrazin-3-yl]-cyclobutanone (100 mg, 248 mols) was dissolved in dry THF (1.0 mL) under inert atmosphere and cooled to −78° C. A solution of MeMgBr (40 μL, 322 mols) in toluene: THF (75:25) was added slowly to the cooled solution. After 24 h of reaction at rt the reaction was cooled to 0° C. and quenched with NH$_4$Cl sat. aq. solution and the aqueous layer was washed with EtOAc (2×). The organic layers where combined, dried over sodium sulfate, filtered and concentrated in vacuo. The crude oil was purified by silica gel column chromatography [Jones Flashmaster, 10 g/70 mL cartridge, eluting with 2-5% ((7N NH$_3$) in MeOH):CH$_2$Cl$_2$], yielding 3-[1-(3-Benzyloxy-phenyl)-8-chloro-imidazo[1,5-a]pyrazin-3-yl]-1-methyl-cyclobutanol as a brown solid.

Example 45

3-[8-Amino-1-(3-benzyloxy-phenyl)-imidazo[1,5-a]pyrazin-3-yl]-1-methyl-cyclobutanol: Prepared according to the procedures for 1-(3-Benzyloxy-phenyl)-3-cyclobutyl-imidazo[1,5-a]pyrazin-8-ylamine, Light brown crystals, $^1$H NMR (400 MHz, CDCl$_3$) δ 1.43 (s, 3H), 2.49-2.64 (m, 4H), 3.27-3.32 (m, 1H), 5.07 (s, 2H), 6.96-7.38 (m, 1H); MS (ES+): 401.34 (M+1), 402.41 (M+2), 403.43 (M+3).

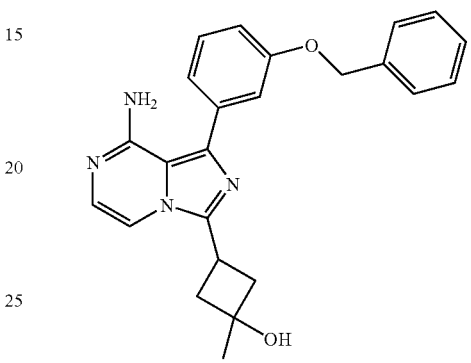

a) 3-[1-(3-Benzyloxy-phenyl)-8-chloro-imidazo[1,5-a]pyrazin-3-yl]-1-methyl-cyclobutanol was prepared according to the Procedures for General Grignard Reaction: MS (ES+): 420.35 (M+1), 422.35 (M+3), 423.47 (M+4).

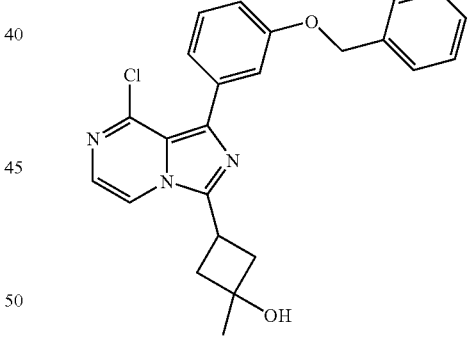

Example 46

3-[8-Amino-1-(3-benzyloxy-phenyl)-imidazo[1,5-a]pyrazin-3-yl]-1-ethyl-cyclobutanol: Prepared according to the procedures for 1-(3-Benzyloxy-phenyl)-3-cyclobutyl-imidazo[1,5-a]pyrazin-8-ylamine, Light yellow gum (7.9 mg, 22%) Light brown crystals, $^1$H NMR (400 MHz, CDCl$_3$) δ 0.94 (t, 3H, J=7.2 Hz), 1.66 (q, 2H, J=7.4 Hz), 2.41-2.46 (m, 2H), 2.60-2.65 (m, 2H), 3.26-3.32 (m, 1H), 5.06 (s, 2H), 6.95-6.97 (m, 2H), 7.05 (d, 1H, J=5.1 Hz), 7.26-7.38 (m, 8H); MS (ES+): 415.27 (M+1), 416.34 (M+2), 417.40 (M+3).

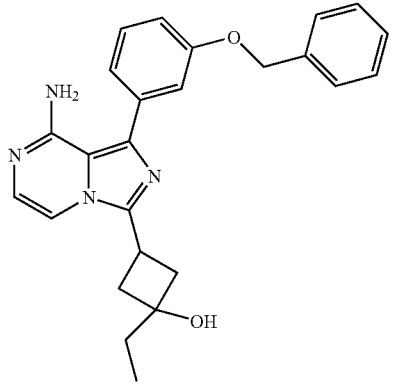

a) 3-[1-(3-Benzyloxy-phenyl)-8-chloro-imidazo[1,5-a]pyrazin-3-yl]-1-ethyl-cyclobutanol was prepared according to the Procedures for General Grignard Reaction: Light yellow gum (38 mg, 36%), $^1$H NMR (400 MHz, CDCl$_3$) δ 0.95 (t, 3H, J=7.36 Hz), 1.68 (q, 2H, J=7.36 Hz), 2.54-2.69 (m, 4H), 3.31-3.39 (m, 1H), 5.08 (s, 2H), 6.99-7.00 (m, 1H), 7.19-7.40 (m, 9H), 7.50 (d, 1H, J=5.0 Hz); MS (ES+): 434.08 (M+1), 436.09 (M+3), 437.05 (M+4).

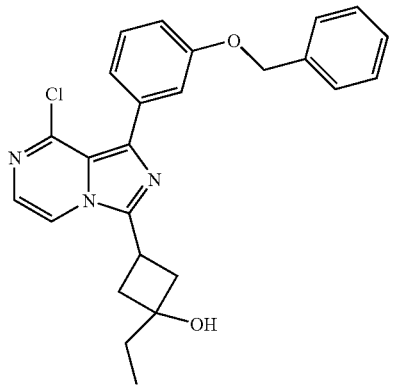

Example 47

1-Allyl-3-[8-amino-1-(3-benzyloxy-phenyl)-imidazo[1,5-a]pyrazin-3-yl]-cyclobutanol: Prepared according to the procedures for 1-(3-Benzyloxy-phenyl)-3-cyclobutyl-imidazo[1,5-a]pyrazin-8-ylamine, Light yellow foam (8.2 mg, 34%), $^1$H NMR (400 MHz, CDCl$_3$) δ 2.41 (d, 2H, J=7.2 Hz), 2.47-2.52 (m, 2H), 2.63-2.68 (m, 2H), 3.29-3.33 (m, 1H), 5.07 (s, 2H), 5.13-5.18 (m, 2H), 5.86-5.92 (m, 1H), 6.95-6.97 (m, 2H), 7.05 (d, 1H, J=5.0 Hz), 7.26-7.38 (m, 8H); MS (ES+): 427.28 (M+1), 428.34 (M+2), 429.38 (M+3).

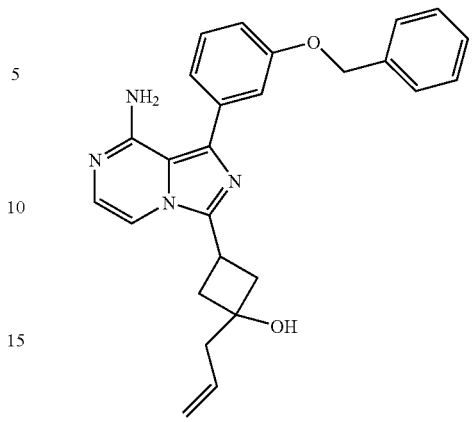

a) 1-Allyl-3-[1-(3-benzyloxy-phenyl)-8-chloro-imidazo[1,5-a]pyrazin-3-yl]-cyclobutanol was prepared according to the Procedures for General Grignard Reaction: Light yellow gum (25 mg, 23%), $^1$H NMR (400 MHz, CDCl$_3$) δ 2.40 (d, 2H, J=7.2 Hz), 2.49-2.68 (m, 4H), 3.29-3.33 (m, 1H), 5.06 (brs, 4H), 5.84 (m, 1H), 6.99-7.00 (m, 1H), 7.19-7.40 (m, 9H), 7.50 (d, 1H, J=5.0 Hz); MS (ES+): 446.08 (M+1), 448.07 (M+3), 449.05 (M+4).

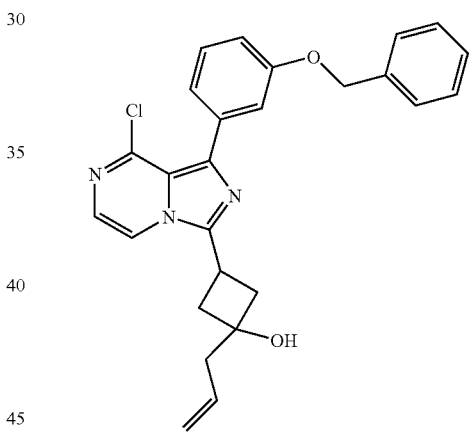

Example 48

1-(3-Benzyloxyphenyl)-3-tert-butylimidazo[1,5-a]pyrazin-8-ylamine: Gaseous NH$_3$ is condensed into a cooled (dry ice/acetone) solution of 1-(3-benzyloxyphenyl)-3-tert-butyl-8-chloroimidazo[1,5-a]pyrazine (61.8 mg, 0.158 mmol) in iPrOH (2 mL) in a pressure tube until the volume is doubled, then the tube is sealed and heated to 110° C. (bath temp.) overnight. The seal has leaked during that time, LC indicates ≈50% conversion; therefore, ammonia is condensed in and the tube is heated as described before. The crude material is purified by preparative TLC (1000 μm silica gel layer, 20×20 cm plate), eluting once with 1% MeOH in CH$_2$Cl$_2$ and then three times with hexanes:EtOAc 3:1. One obtains the title compound as pale yellow solid, >95% pure by HPLC; $^1$H NMR (CDCl$_3$, 400 MHz) δ 1.57 (s, 9H), 5.06 (brs, 2H), 5.14 (s, 2H), 6.99-7.04 (m, 2H), 7.22-7.26 (m, 2H), 7.31-7.42 (m, 4H), 7.44 (d, J=8.4 Hz, 2H), 7.46 (d, J=5.3 Hz, 1H). MS (ES+): m/z 373.1 (100) [MH$^+$].

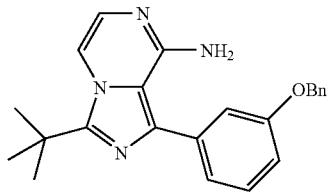

a) 1-(3-Benzyloxyphenyl)-3-tert-butyl-8-chloroimidazo[1,5-a]pyrazine: A mixture of POCl$_3$ (3 mL, 5 g, 33 mmol) and N-[(3-benzyloxyphenyl)-(3-chloropyrazin-2-yl)-methyl]-2,2-dimethylpropionamide (109 mg, 0.266 mmol) is heated to 55° C. for 6 d. POCl$_3$ is evaporated, a cold solution of NH$_3$ in iPrOH (2 M, 5 mL) is added, the suspension is filtered, and the solid is washed with iPrOH. The crude material contained in the combined filtrate and washings is adsorbed onto Hydromatrix and chromatographed on silica gel [Jones Flashmaster, 10 g/70 mL cartridge, eluting with hexanes:EtOAc 10:1 (1-22)→5:1 (23-40)], yielding the title compound as yellow oil that slowly solidifies; $^1$H NMR (CDCl$_3$, 400 MHz) δ 1.59 (s, 9H), 5.13 (s, 2H), 7.03 (d, J=8.0 Hz, 1H), 7.27-7.42 (m, 7H), 7.46 (d, J=7.2 Hz, 2H), 7.87 (d, J=4.8 Hz, 1H). MS (ES+): m/z 392.1/394.0 (12/4) [MH$^+$].

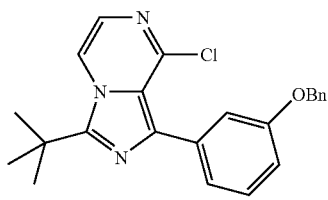

b) N-[(3-Benzyloxyphenyl)-(3-chloropyrazin-2-yl)-methyl]-2,2-dimethylpropionamide: To a solution of the crude C-(3-benzyloxyphenyl)-C-(3-chloropyrazin-2-yl)-methylamine (444 mg, max. 1.36 mmol) in CH$_2$Cl$_2$ (5 mL), cooled by ice/water, are added NEt$_3$ (210 μL, 152 mg, 1.51 mmol), DMAP (8 mg, 0.07 mmol), and pivaloyl chloride (185 μL, 181 mg, 1.50 mmol), then the cooling bath is removed, and the reaction solution is stirred at ambient temperature for 4.5 h. More pivaloyl chloride (90 μL, 88 mg, 0.73 mmol) and NEt$_3$ (100 μL, 73 mg, 0.72 mmol) are added and also after further 2.5 h, and the solution is stirred overnight at ambient temperature. The reaction mixture is taken up in EtOAc (35 mL), washed with diluted HCl, water, NaHCO$_3$ sol., and brine, dried over MgSO$_4$, filtered, and concentrated in vacuo. The crude material is chromatographed on silica gel [Jones Flashmaster, 50 g/150 mL cartridge, eluting with hexanes:EtOAc 10:1 (1-17)→3:1 (18-41)→2:1 (42-56)], yielding the title compound as orange oil; $^1$H NMR (CDCl$_3$, 400 MHz) δ 1.21 (s, 9H), 5.03 (s, 2H), 6.50 (d, J=8.0 Hz, 1H), 6.86-6.90 (m, 1H), 6.93-6.97 (m, 2H), 7.23 (t, J=7.8 Hz, 1H), 7.29-7.43 (m, 6H), 8.32 (d, J=2.4 Hz, 2H), 8.50 (d, J=2.4 Hz, 1H). MS (ES+): m/z 410.1/412.1 (100/36) [MH$^+$], 309.1/311.1 (32/12) [MH$^+$-tBuCONH$_2$].

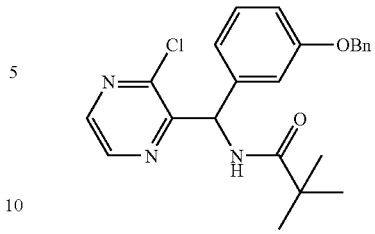

Example 49 cis-1-[3-(Benzyloxy)phenyl]-3-[3-(dimethylamino)cyclobutyl]imidazo[1,5-a]pyrazin-8-amine: A light yellow isopropanol solution (5.0 mL) of cis-[3-(8-chloro-1-phenyl-imidazo[1,5-a]pyrazin-3-yl)-cyclobutyl]-dimethyl-amine (0.21 mmol, 90 mg) in a 15 mL sealed tube was cooled to −78° C. Ammonia was bubbled into the solution for 90 sec; the tube was capped and heated to 114° C. for 10 h. The sealed tube was cooled to rt and then −78° C. before it was uncapped. The reaction mixture was filtered through a Buchner funnel to remove NH$_4$Cl salt and the remaining solid was washed with EtOAc (15 mL×2) and MeOH (15 mL×2). The combined filtrates were concentrated to provide the light yellow greasy compound (90 mg), which was purified by mass directed HPLC (gradient: 5% to 60% CH$_3$CN in water at pH 9 in 6 min). The title compound was obtained as off-white solid with >95% purity; $^1$H NMR (400 MHz, CDCl$_3$): δ 7.45 (d, J=8.0 Hz, 2H), 7.41-7.31 (m, 4H), 7.26-7.22 (m, 2H), 7.13 (d, J=5.2 Hz, 1H), 7.04 (d, J=4.0 Hz, 1H), 7.01 (d, J=2.4 Hz, 1H), 5.11 (d, J=24 Hz, 2H), 3.41 (p, J=8.0 Hz, 1H), 2.80 (p, J=8.0 Hz, 1H), 2.68-2.62 (m, 2H), 2.49-2.41 (m, 2H). MS (ES+): m/z 414 (100) [MH$^+$].

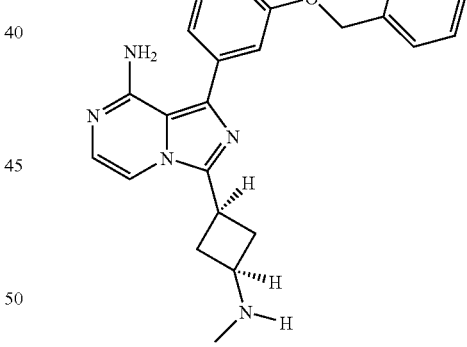

a) cis-[3-(8-Chloro-1-phenyl-imidazo[1,5-a]pyrazin-3-yl)-cyclobutyl]-dimethyl-amine: An DCE solution of 3-{1-[3-(benzyloxy)phenyl]-8-chloroimidazo[1,5-a]pyrazin-3-yl}cyclobutanone was charged with dimethylamine (0.37 mmol, 0.19 mL) and then catalytic amount of AcOH (7 μL). The mixture was stirred at rt for 30 min before resin-bound triacetoxyborohydride (0.5 mmol, 240 mg) was added. Reaction mixture was stirred at rt for 16 h before the solution was filtered through a Buchner funnel to remove the resin. The filtrate was concentrated and the obtained oil was dissolved in DCM (15 mL), washed with saturated NaHCO$_3$ solution (2×15 mL) and brine (2×15 mL). The solvent was dried over sodium sulfate and concentrated under reduced pressure. The title compound was obtained as a yellow greasy oil; MS (ES+): m/z 433 (100) [MH$^+$].

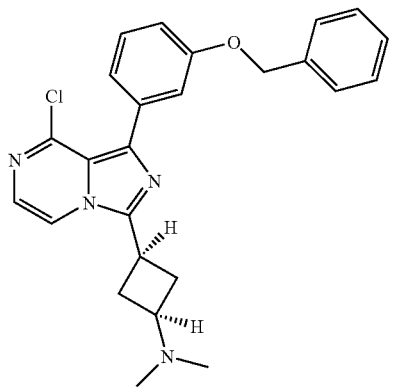

Example 50

3-(8-Amino-3-cyclobutyl-imidazo[1,5-a]pyrazin-1-yl)-phenol: A solution of 1-(3-Benzyloxy-phenyl)-3-cyclobutyl-imidazo[1,5-a]pyrazin-8-ylamine (1.82 g, 4.92 mmol) in 4M HCl in dioxane (20 mL) was heated to 75° C. in a sealed tube for 1.5 h. The reaction was allowed to cool to rt, the dioxane was decanted off and the brown gum residue was cooled to 0° C. in an ice-bath and charged with 7N $NH_3$ in MeOH until basic. The reaction mixture was concentrated in vacuo, triturated with EtOAc and $CHCl_3$, and the $NH_4Cl$ salts filtered off. The filtrate was concentrated in vacuo and purified by flash silica chromatography (8% MeOH in $CHCl_3$) resulting in an off-white solid; $^1H$ NMR (DMSO-$d_6$, 400 MHz) δ 1.84-1.99 (m, 1H), 2.00-2.16 (m, 1H), 2.34-2.48 (m, 4H), 3.86-4.00 (m, 1H), 6.08 (brs, 2H), 6.81 (dd, 1H, J=8.4 Hz, 8.0 Hz), 6.95-7.06 (m, 3H), 7.30 (t, 1H, J=8.4 Hz); 7.41 (d, 1H, J=5.2 Hz), 9.63 (brs, 1H); MS (ES+): m/z 281.39 [MH$^+$].

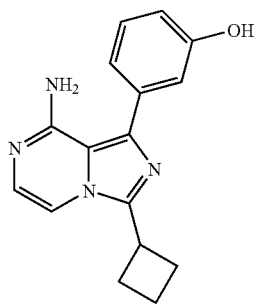

Example 51

3-Cyclobutyl-1-[3-(4-fluoro-benzyloxy)-phenyl]-imidazo[1,5-a]pyrazin-8-ylamine: An anhydrous DMF (2 mL) solution of 3-(8-amino-3-cyclobutyl-imidazo[1,5-a]pyrazin-1-yl)-phenol (50 mg, 0.179 mmol) and $K_2CO_3$ (27 mg, 0.197 mmol) was charged with 1-bromomethyl-4-fluoro-benzene (7) (24 μL, 0.197 mmol) and stirred 12 h at 40° C. The reaction mixture was partitioned between $CHCl_3$ and $H_2O$ and separated. The aqueous layer was re-extracted with $CHCl_3$ (3×) and the combined organic fractions were washed with $H_2O$ (1×), brine (1×), dried over $Na_2SO_4$, filtered and concentrated in vacuo. The crude mixture was purified by MDP resulting in a light tan/waxy solid; $^1H$ NMR (CDCl$_3$, 400 MHz) δ 1.99-2.08 (m, 1H), 2.11-2.25 (m, 1H), 2.44-2.55 (m, 2H), 2.58-2.70 (m, 2H), 3.75-3.88 (m, 1H), 5.06 (brs, 2H), 5.10 (s, 2H), 6.98-7.15 (m, 5H); 7.20-7.34 (m, 3H), 7.35-7.47 (m, 3H); MS (ES+): m/z 389.14.

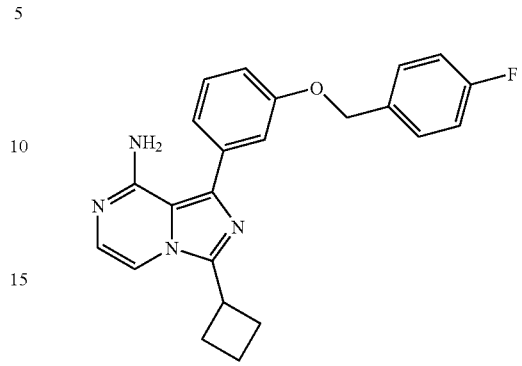

Example 52 trans-4-[8-Amino-1-(3-hydroxy-phenyl)-imidazo[1,5-a]pyrazin-3-yl]cyclohexanecarboxylic acid methyl ester: A solution of trans-4-[8-Amino-1-(3-benzyloxy-phenyl)-imidazo[1,5-a]pyrazin-3-yl]-cyclohexanecarboxylic acid methyl ester (50 mg, 0.110 mmol) in 4M HCl in dioxane (2 mL) was heated to 75° C. in a oil-bath for ~2 h. The reaction mixture was allowed to cool to rt, the dioxane was decanted off and the reaction mixture was quenched with 7N $NH_3$ in MeOH solution (~2 mL). This crude mixture was concentrated in vacuo resulting in 79 mg of an off-white solid (containing $NH_4Cl$ salts). The crude material was purified by flash silica chromatography (10% 7N $NH_3$ in MeOH in $CHCl_3$) resulting in an off-white solid; $^1H$ NMR (DMSO-$d_6$, 400 MHz) δ 1.51-1.78 (m, 4H), 1.95-2.08 (m, 4H), 2.38-2.48 (m, 1H), 3.07-3.20 (m, 1H), 3.63 (s, 3H), 6.06 (brs, 2H), 6.76-6.89 (m, 1H), 6.95-7.05 (m, 3H), 7.29 (t, 1H, J=7.8 Hz), 7.65 (d, 1H, J=5.1 Hz), 9.62 (brs, 1H); MS (ES+): m/z 367.26 [MH$^+$].

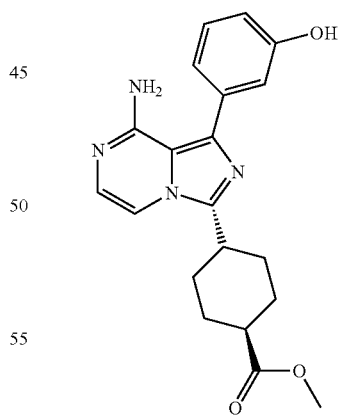

Example 53

3-[8-Amino-1-(3-benzyloxyphenyl)-imidazo[1,5-a]pyrazin-3-yl]-benzamide: Gaseous $NH_3$ was condensed into a cooled (−78° C.) solution of 3-[1-(3-benzyloxyphenyl)-8-chloroimidazo[1,5-a]pyrazin-3-yl]-benzoic acid methyl ester (102 mg, 0.216 mmol) in $NH_3$/i-PrOH (2M, 3 mL) in a pressure tube until the volume had doubled. The tube was sealed and heated to 110° C. for 2 d. After excess NH₃/i-PrOH was removed in vacuo, the crude material was taken up in CH₂Cl₂, adsorbed onto Hydromatrix, and purified by chromatography on silica gel [Jones Flashmaster, 5 g/25 mL cartridge, eluting with MeOH:CH₂Cl₂ 1%→5%], yielding the title compound, as an off-white solid; ¹H NMR (d-DMSO, 400 MHz) δ 5.18 (s, 2H), 6.30 (s, br, —NH₂), 7.10-7.18 (m, 2H), 7.25-7.58 (m, 9H), 7.67 (t, J=7.6 Hz, 1H), 7.81 (d, J=4.4 Hz, 1H), 8.00 (d, J=7.6 Hz, 2H), 8.16 (s, 1H), 8.31 (s, 1H); MS (ES+): m/z 436.0 (100) [MH⁺].

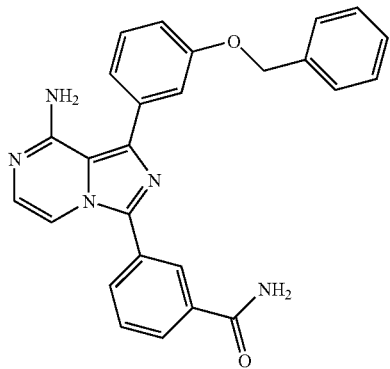

a) 3-[1-(3-Benzyloxyphenyl)-8-chloroimidazo[1,5-a]pyrazin-3-yl]-benzoic acid methyl ester: To a solution of N-[(3-benzyloxyphenyl)-(3-chloropyrazin-2-yl)-methyl]-isophthalamic acid methyl ester (610 mg, 1.25 mmol) in THF (5 mL), cooled to 0° C., KOtBu (1.6 mL, 1M, 1.6 mmol) was added under N₂ atmosphere, the cooling bath was removed, and the reaction mixture stirred at rt for 5 min. Upon addition, the color of the solution changed from yellow to brown. THF was evaporated under reduced pressure, POCl₃ (10 mL, 17 g, 109 mmol) was added, and the reaction mixture was vortexed at 55° C. for 2 d. POCl₃ was removed in vacuo, a cold solution of NH₃/i-PrOH (2M, 10 mL) was added, and excess solvent was evaporated. The residue was taken up in EtOAc (4×30 mL), washed with NaHCO₃ sat. aq. sol. (2×20 mL) and brine (1×20 mL), dried over anhydrous MgSO₄, filtered, and concentrated in vacuo. The crude material was dissolved in CH₂Cl₂, adsorbed onto Hydromatrix, and purified by chromatography on silica gel [Jones Flashmaster, 50 g/150 mL cartridge, eluting with EtOAc:CH₂Cl₂ 1%→5%], giving 264 mg (45%, 0.562 mmol) of the title compound, as a yellow solid; ¹H NMR (CDCl₃, 400 MHz) δ 3.97 (s, 3H), 5.15 (s, 2H), 7.08 (ddd, J=8.0, 2.4, 1.2 Hz, 1H), 7.30-7.43 (m, 7H), 7.44-7.48 (m, 2H), 7.67 (t, J=7.2 Hz, 1H), 8.04 (d, J=4.8 Hz, 1H), 8.05-8.09 (m, 1H), 8.19-8.22 (m, 1H), 8.50-8.52 (m, 1H); MS (ES+): m/z 469.8/471.9 (100/39) [MH⁺].

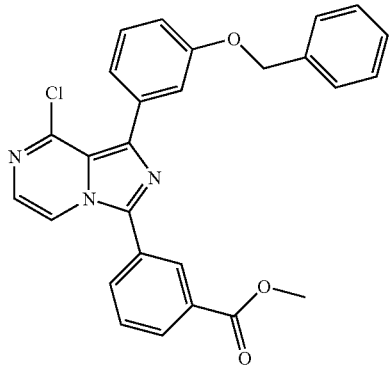

Example 54

{3-[8-Amino-1-(3-benzyloxyphenyl)-imidazo[1,5-a]pyrazin-3-yl]-phenyl}-methanol: Gaseous NH₃ was condensed into a cooled (−78° C.) solution of {3-[1-(3-benzyloxyphenyl)-8-chloroimidazo[1,5-a]pyrazin-3-yl]-phenyl}-methanol (366 mg, 0.829 mmol) in NH₃/i-PrOH (2M, 5 mL) in a pressure tube until the volume had doubled. The tube was sealed and heated to 110° C. for 19 h. After excess NH₃/i-PrOH was removed in vacuo, the residue was suspended between CH₂Cl₂ and water, the layers were separated, and the aqueous layer was extracted with CH₂Cl₂ (3×30 mL). The combined organic layers were washed with brine (3×30 mL), dried over anhydrous MgSO₄, and filtered. The crude material was purified by filtration through a plug of silica gel, eluting with 5% MeOH:CH₂Cl₂ (400 mL), concentrated in vacuo, giving 311.5 mg (89%, 0.737 mmol) of the title compound, as a yellow solid; ¹H NMR (CDCl₃, 400 MHz) δ 4.80 (s, 2H), 5.09 (s, —NH₂), 5.16 (s, 2H), 7.05-7.09 (m, 1H), 7.11 (d, J=4.8 Hz, 1H), 7.29-7.37 (m, 3H), 7.37-7.48 (m, 5H), 7.47-7.51 (m, 1H), 7.54 (t, J=7.8 Hz, 1H), 7.63 (d, J=4.8 Hz, 1H), 7.73-7.78 (m, 1H), 7.86 (s, 1H); MS (ES+): m/z 423.0 (100) [MH⁺].

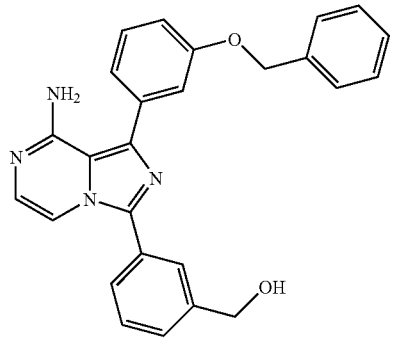

a) {3-[1-(3-Benzyloxyphenyl)-8-chloroimidazo[1,5-a]pyrazin-3-yl]-phenyl}-methanol: To a solution of 3-[1-(3-benzyloxyphenyl)-8-chloroimidazo[1,5-a]pyrazin-3-yl]-benzoic acid methyl ester (552 mg, 1.17 mmol) in THF (25 mL), cooled to 0° C., 1M LiAlH₄ (880 μL, 797 mg, 0.880 mmol) was added, under N₂, and the reaction solution was vortexed for 2 h. Upon addition, the reaction mixture changed from yellow to dark green in color. The reaction was quenched with potassium sodium tartrate sat. aq. sol. (25 mL), extracted with EtOAc (3×20 mL), washed with brine (1×40 mL), dried over MgSO₄, and filtered. The crude material was purified by filtration through a plug of silica gel plug [eluting with EtOAc:CH₂Cl₂ 1:1 (400 mL)] and concentrated, affording 366.3 mg (71%, 0.829 mmol) of the title compound, as a yellow solid; ¹H NMR (CDCl₃, 400 MHz) δ 4.82 (d, J=6.0 Hz, 2H), 5.15 (s, 2H), 7.05-7.11 (m, 1H), 7.32-7.43 (m, 7H), 7.44-7.49 (m, 2H), 7.52-7.61 (m, 2H), 7.73-7.78 (m, 1H), 7.87 (s, 1H), 8.05 (d, J=4.8 Hz, 1H); MS (ES+): m/z 441.9/443.9 (100/38) [MH⁺].

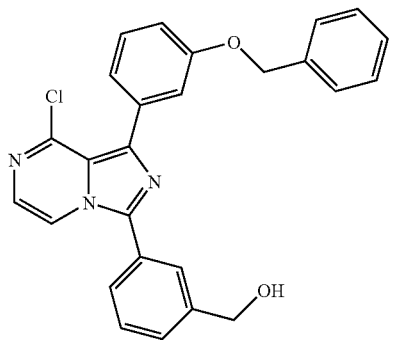

Example 55

3-(3-Aminomethylphenyl)-1-(3-benzyloxyphenyl)-imidazo[1,5-a]pyrazin-8-ylamine: To a solution of 2-{3-[8-amino-1-(3-benzyloxyphenyl)-imidazo[1,5-a]pyrazin-3-yl]-benzyl}-isoindole-1,3-dione (328 mg, 0.594 mmol) in $CH_2Cl_2$ (4 mL), $N_2H_4$ (56 μL, 57 mg, 1.78 mmol) was added and the reaction was vortexed at rt for 17 h, under $N_2$ atmosphere. Additional $N_2H_4$ (40 μL, 41 mg, 1.27 mmol) and $CH_2Cl_2$ (10 mL) were added and vortexing was continued for 3 d. The suspension was filtered, the solid was washed extensively with $CH_2Cl_2$, and the filtrate was concentrated in vacuo. The crude material (273 mg) was purified by chromatography on silica gel [Jones Flashmaster, 5 g/25 mL cartridge, eluting with MeOH (7N $NH_3$):$CH_2Cl_2$ 5%→10%], affording 107.4 mg (43%, 0.255 mmol) of the title compound, as a yellow solid, containing 0.18 eq. of DMF. Mixed fractions were also collected, giving an additional 67.4 mg (max. 16%, 0.159 mmol) of the title compound, as a yellow solid, containing 0.8 eq. of DMF; $^1$H NMR (CDCl$_3$, 400 MHz) δ 1.88 (s, br, —NH$_2$), 3.97 (s, 2H), 5.15 (s, 4H), 7.05-7.09 (m, 1H), 7.10 (d, J=4.8 Hz, 1H), 7.29-7.47 (m, 9H), 7.51 (t, J=7.8 Hz, 1H), 7.63 (d, J=5.2 Hz, 1H), 7.69 (d, J=7.6 Hz, 1H), 7.81 (s, 1H); MS (ES+): m/z 422.0 (14) [MH$^+$].

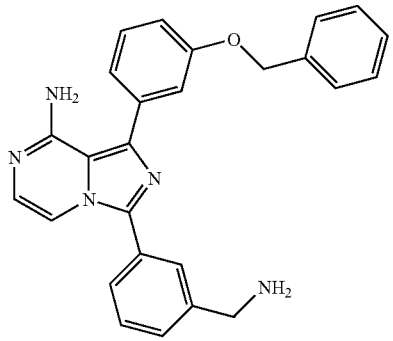

Example 56

2-{3-[8-Amino-1-(3-benzyloxyphenyl)-imidazo[1,5-a]pyrazin-3-yl]-benzyl}-isoindole-1,3-dione: To a solution/suspension of {3-[8-amino-1-(3-benzyloxy-phenyl)-imidazo[1,5-a]pyrazin-3-yl]-phenyl}-methanol (312 mg, 0.737 mmol), isoindole-1,3-dione (130 mg, 0.885 mmol), and PS-PPh$_3$ (loading 2.12 mmol/g; 696 mg, 1.47 mmol) in anhydrous THF (15 mL), cooled to 0° C., DIAD (218 μL, 224 mg, 1.11 mmol) was added dropwise, under $N_2$ atmosphere. After 10 min, the cooling bath was removed and the reaction mixture stirred at ambient temperature for 3d. The resin was filtered off on a glass frit (porosity M) and washed with large volumes of THF and then $CH_2Cl_2$. The filtrate was concentrated, adsorbed onto Hydromatrix, and the crude material (0.6843 g) was purified by chromatography on silica gel [Jones Flashmaster, 20 g/70 mL cartridge, eluting with MeOH:$CH_2Cl_2$ 0.5%→3%], yielding the title compound as a yellow solid. Sample contains ≈0.3 eq. of reduced DIAD by $^1$H NMR; $^1$H NMR (CDCl$_3$, 400 MHz) δ 4.94 (s, 2H), 5.07 (s, 2H), 5.16 (s, 2H), 7.07 (ddd, J=8.4, 2.8, 1.2 Hz, 1H), 7.11 (d, J=5.2 Hz, 1H), 7.28-7.33 (m, 3H), 7.33-7.36 (m, 1H), 7.37-7.43 (m, 2H), 7.43-7.47 (m, 2H), 7.50 (t, J=7.6 Hz, 1H), 7.53-7.56 (m, 1H), 7.62 (d, J=5.2 Hz, 1H), 7.72 (dd, J=5.6, 2.8 Hz, 2H), 7.74-7.77 (m, 1H), 7.86 (dd, J=5.2, 3.2 Hz, 2H), 7.92 (s, 1H); MS (ES+): m/z 552.3 (100) [MH$^+$].

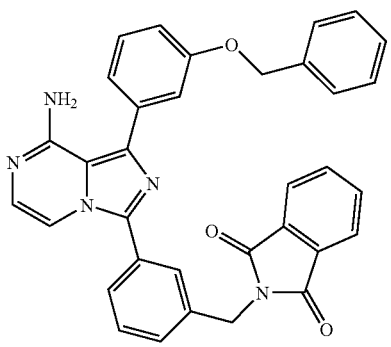

Example 57

4-{8-Amino-1-[3-(2,6-difluoro-benzyloxy)-phenyl]-imidazo[1,5-a]pyrazin-3-yl}-cyclohexanecarboxylic acid methyl ester: The procedures for 3-Cyclobutyl-1-[3-(4-fluoro-benzyloxy)-phenyl]-imidazo[1,5-a]pyrazin-8-ylamine were applied; MS (ES+): m/z 493.16 [MH$^+$].

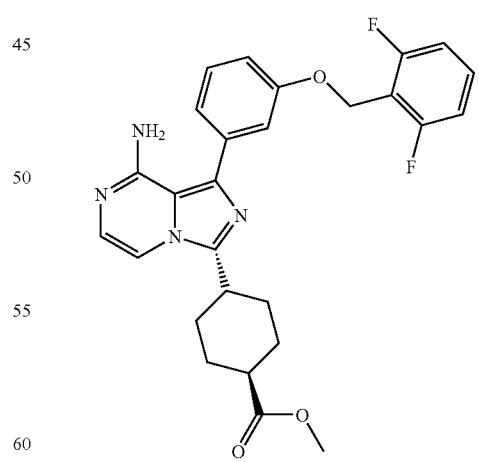

Example 58

4-{8-Amino-1-[3-(2,6-difluoro-benzyloxy)-phenyl]-imidazo[1,5-a]pyrazin-3-yl}-cyclohexanecarboxylic acid: The saponification procedures applied to the synthesis of trans-4-[8-Amino-1-(3-benzyloxy-phenyl)-imidazo[1,5-a]pyrazin-3-yl]-cyclohexanecarboxylic acid was applied to 4-{8-Amino-1-[3-(2,6-difluoro-benzyloxy)-phenyl]-imidazo[1,5-a]pyrazin-3-yl}-cyclohexanecarboxylic acid methyl ester to afford the title compound; MS (ES+): m/z 479.10 [MH+].

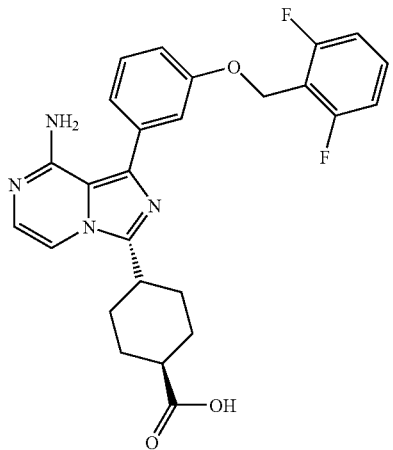

Example 59 cis-3-(3-Dimethylaminomethyl-cyclobutyl)-1-(3-benzyloxyphenyl)-imidazo[1,5-a]pyrazin-8-ylamine: A sealed tube containing a solution of cis-toluene-4-sulfonic acid 3-[8-amino-1-(3-benzyloxyphenyl)-imidazo[1,5-a]pyrazin-3-yl]cyclobutylmethyl ester (100 mg, 0.18 mmol) in THF (3 mL) was charged with dimethylamine solution (1.8 mL, 3.6 mmol, 2.0 M in THF), sealed, and heated at 50° C. overnight. The mixture was concentrated and the residue was diluted with ethyl acetate (40 mL), washed with sat. aq. NaHCO₃ (2×15 mL) and brine (2×15 mL), and dried over anhydrous sodium sulfate. The filtrate was concentrated under reduced pressure, and the residue was recrystallized to afford a white solid; LC-MS (ES, Pos.): m/z 428 [MH+]; ¹H NMR (CDCl₃, 400 MHz) δ 2.23 (s, 6H), 2.24-2.32 (m, 2H), 2.42 (d, J=6.1 Hz, 2H), 2.61-2.69 (m, 3H), 3.64 (m, 1H), 4.98 (br s, 2H, NH₂), 5.15 (s, 2H), 7.00-7.04 (m, 2H), 7.12 (d, J=5.0 Hz, 1H), 7.23-7.27 (m, 2H), 7.31-7.46 (m, 6H).

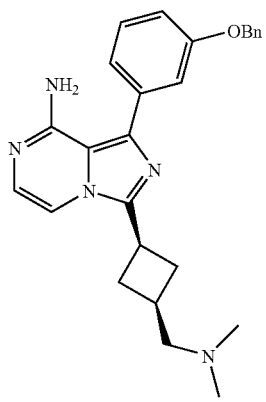

Example 60 cis-3-(3-Azetidin-1-ylmethylcyclobutyl)-1-(3-benzyloxyphenyl)-imidazo[1,5-a]pyrazin-8-ylamine: Procedures for 3-(3-Dimethylaminomethyl-cyclobutyl)-1-(3-benzyloxyphenyl)-imidazo[1,5-a]pyrazin-8-ylamine were followed, replacing dimethylamine with azetidine, LC-MS (ES, Pos.): m/z 440 [MH+].

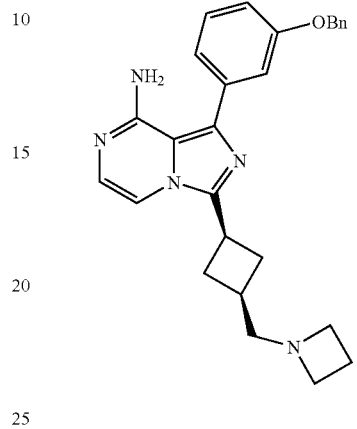

Example 61 cis-3-(3-Pyrrolidin-1-ylmethylcyclobutyl)-1-(3-benzyloxyphenyl)-imidazo[1,5-a]pyrazin-8-ylamine: Procedures for 3-(3-Dimethylaminomethyl-cyclobutyl)-1-(3-benzyloxyphenyl)-imidazo[1,5-a]pyrazin-8-ylamine were followed, replacing dimethylamine with pyrrolidine, LC-MS (ES, Pos.): m/z 454 [MH+].

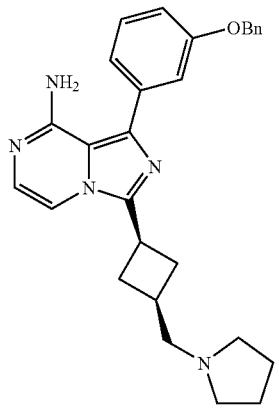

Example 62 cis-3-(3-Azidomethyl-cyclobutyl)-1-(3-benzyloxyphenyl)-imidazo[1,5-a]pyrazin-8-ylamine: A solution of cis-toluene-4-sulfonic acid 3-[8-amino-1-(3-benzyloxyphenyl)-imidazo[1,5-a]pyrazin-3-yl]cyclobutylmethyl ester (100 mg, 0.18 mmol) in DMF (2 mL) was charged with sodium azide (35 mg, 0.54 mmol), the resulting mixture was stirred at rt overnight. The mixture was diluted with water (5 mL), then extracted with ethyl acetate (3×10 mL), the combined organic phases were washed with water (2×10 mL) and brine (10 mL), and dried over anhydrous sodium sulfate. The filtrate was concentrated under reduced pressure, and the residue was purified by silica gel column chromatography (eluting with 100% ethyl acetate), yielding the title compound as a white solid; LC-MS (ES, Pos.): m/z 426 [MH+]; ¹H NMR (CDCl₃, 400 MHz) δ 2.36-2.44 (m, 2H), 2.63-2.79 (m, 3H), 3.37 (d, J=6.7 Hz, 2H), 3.69 (m, 1H), 5.14 (s, 4H, —OCH₂— and —NH₂), 7.02-7.05 (m, 2H), 7.10 (d, J=5.0 Hz, 1H), 7.25-7.45 (m, 8H).

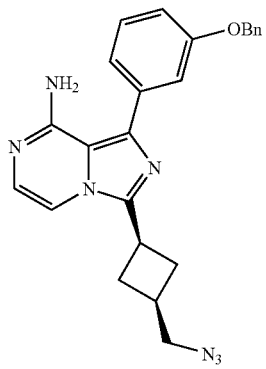

Example 63 cis-3-(3-aminomethyl-cyclobutyl)-1-(3-benzyloxyphenyl)-imidazo[1,5-a]pyrazin-8-ylamine: cis-3-(3-Azidomethyl-cyclobutyl)-1-(3-benzyloxyphenyl)-imidazo[1,5-a]pyrazin-8-ylamine (35 mg, 0.082 mmol) was dissolved in ethanol (5 mL) upon heating, the mixture was cooled to rt. and charged with Lindlar catalyst (30 mg). The mixture was hydrogenated at rt overnight. LC-MS showed the reaction was complete and clean. The catalyst was removed by filtration through a pad of celite, the filtrate was concentrated and the residue was purified by mass-directed purification to give a white solid; LC-MS (ES, Pos.): m/z 400 [MH+]; ¹H NMR (CD₃OD, 400 MHz) δ 2.17-2.24 (m, 2H), 2.56-2.67 (m, 3H), 2.79 (d, J=6.5 Hz, 2H), 3.84 (m, 1H), 5.17 (s, 2H), 6.98 (d, J=5.1 Hz, 1H), 7.15-7.47 (m, 10H).

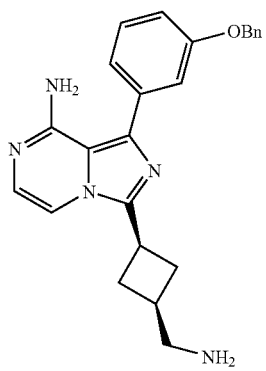

Example 64 cis-3-[8-Amino-1-(3-benzyloxy-phenyl)-imidazo[1,5-a]pyrazin-3-yl]-cyclobutane-carboxylic acid amide: A solution of cis-3-[1-(3-benzyloxy-phenyl)-8-chloro-imidazo[1,5-a]pyrazin-3-yl]-cyclobutane-carboxylic acid methyl ester (115 mg, 0.26 mmol) in 4 mL of ⁱPrOH was cooled to −78° C. and charged with NH₃ gas for 2 min. This sealed tube was equipped with a teflon O-ring, sealed and heated at 110° C. overnight. The mixture was cooled to −78° C. and the cap was removed. The mixture was diluted with EtOAc (30 mL) and washed with brine (15 mL), dried over anhydrous sodium sulfate. The filtrate was concentrated under reduced pressure and the crude product was purified by mass-directed purification to afford an off-white solid; LC-MS (ES, Pos.): m/z 414 [MH+]; ¹H NMR (CD₃OD, 400 MHz) δ 2.65-2.73 (m, 4H), 3.24 (m, 1H), 3.87 (m, 1H), 5.17 (s, 2H), 6.99 (d, J=5.2 Hz, 1H), 7.10-7.48 (m, 10H).

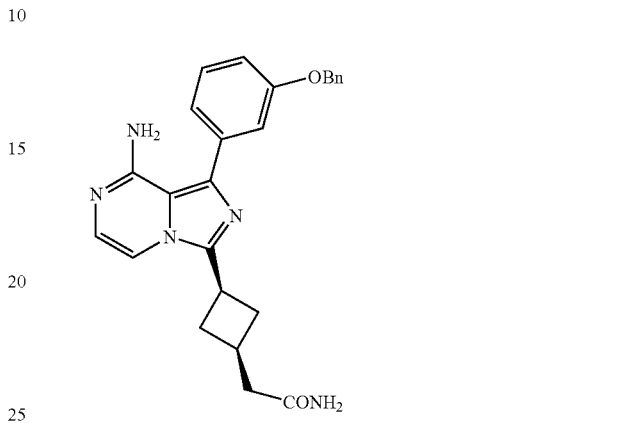

Example 65 trans-3-[8-Amino-1-(3-benzyloxy-phenyl)-imidazo[1,5-a]pyrazin-3-yl]-cyclobutane-carboxylic acid amide: The title compound was prepared according to the procedure described for cis-3-[8-Amino-1-(3-benzyloxy-phenyl)-imidazo[1,5-a]pyrazin-3-yl]-cyclobutane-carboxylic acid amide above, LC-MS (ES, Pos.): m/z 414 [MH+]; ¹H NMR (CD₃OD, 400 MHz) δ 2.70-2.78 (m, 4H), 3.28 (m, 1H), 4.03 (m, 1H), 5.18 (s, 2H), 6.99 (d, J=5.1 Hz, 1H), 7.10-7.48 (m, 10H).

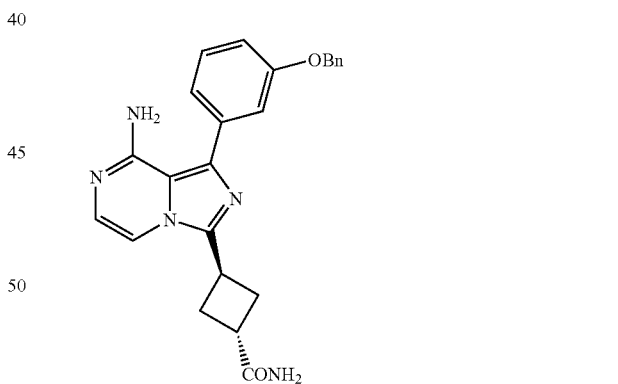

a) cis and trans-3-[1-(3-Benzyloxy-phenyl)-8-chloro-imidazo[1,5-a]pyrazin-3-yl]-cyclobutane-carboxylic acid methyl ester: A solution of (COCl)₂ (3.17 g, 2.2 mL, 25.0 mmol) in dry methylene chloride (20 mL) was charged with a solution of DMSO (3.90 g, 50.0 mmol) in methylene chloride (10 mL) dropwise at −78° C. under nitrogen. The resulting mixture was stirred at −78° C. for 30 min, followed by the addition of {3-[1-(3-benzyloxyphenyl)-8-chloro-imidazo[1,5-a]pyrazin-3-yl]cyclobutyl}methanol in methylene chloride (15 mL). The mixture was stirred at −78° C. for 30 min, then quenched with Et₃N (17.5 mL, 125 mmol) and slowly warmed to rt. The mixture was diluted with methylene chloride (100 mL), then washed with water (30 mL), sat. aq. NaHCO$_3$ (2×30 mL) and brine (30 mL), and dried over anhydrous sodium sulfate. TLC showed the reaction completed and produced the desired aldehydes (trans isomer is less polar than cis one). Evaporation afforded the crude product as a yellow oil, which was directly used to the next step. The solution of the above aldehyde in anhydrous methanol (50 mL) was charged with NIS (6.75 g, 30 mmol) and potassium carbonate (4.14 g, 30 mmol), the resulting mixture was stirred in the dark at rt overnight. TLC showed the reaction almost completed. The reaction was quenched with 20 mL of water and diluted with ethyl acetate (150 mL), then washed with sat. aq. Na$_2$S$_2$O$_3$ (2×30 mL) and brine (50 mL), and dried over anhydrous sodium sulfate. The filtrate was concentrated under reduced pressure, and the crude material was purified by silica gel column chromatography (eluting with Hexanes: EtOAc=70:30→60:40→50:50) by which the two isomers were separated. cis-3-[1-(3-Benzyloxy-phenyl)-8-chloro-imidazo[1,5-a]pyrazin-3-yl]-cyclobutane-carboxylic acid methyl ester: yellow oil; LC-MS (ES, Pos.): m/z 448/450 (3/1) [MH$^+$]; $^1$H NMR (CDCl$_3$, 400 MHz) δ 2.73-2.80 (m, 2H), 2.89-2.97 (m, 2H), 3.30 (m, 1H), 3.70 (s, 3H), 3.78 (m, 1H), 5.14 (s, 2H), 7.04 (m, 1H), 7.26-7.47 (m, 9H), 7.58 (d, J=5.0 Hz, 1H). trans-3-[1-(3-Benzyloxy-phenyl)-8-chloro-imidazo[1,5-a]pyrazin-3-yl]-cyclobutane-carboxylic acid methyl ester: yellow oil; LC-MS (ES, Pos.): m/z 448/450 (3/1) [MH$^+$]; $^1$H NMR (CDCl$_3$, 400 MHz) δ 2.76-2.83 (m, 2H), 2.88-2.95 (m, 2H), 3.33 (m, 1H), 3.77 (s, 3H), 4.03 (m, 1H), 5.14 (s, 2H), 7.05 (m, 1H), 7.26-7.47 (m, 9H), 7.50 (d, J=4.9 Hz, 1H).

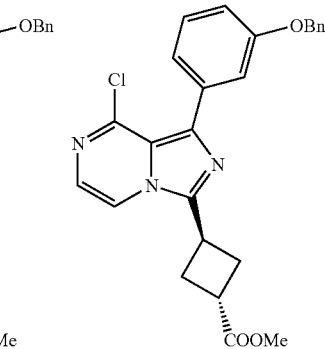

Example 66

3-[8-Amino-1-(3-benzyloxy-phenyl)-imidazo[1,5-a]pyrazin-3-yl]-1-hydroxymethyl-cyclobutanol: To a solution of 1-(3-benzyloxyphenyl)-8-chloro-3-(3-methylenecyclobutyl)-imidazo[1,5-a]pyrazine (1.0 g, 2.5 mmol) in THF (21 mL) and water (7 mL) were added NMO (1.0 mL, 5.0 mmol, 50% aq. solution) and K$_2$OsO$_4$.H$_2$O (46 mg, 0.125 mmol). The resulting mixture was stirred at rt overnight. TLC showed the reaction was complete. The reaction was quenched with Na$_2$SO$_3$ (1.60 g, 12.5 mmol). Water (15 mL) was added to dissolve the salts and the organic phase was separated. The aqueous phase was extracted with EtOAc (3×25 mL), and the combined organic phases were washed with brine (20 mL), and dried over anhydrous sodium sulfate. The filtrate was concentrated under reduced pressure to give a yellow solid, a mixture of two isomers in ca. 3:2 ratio by $^1$H NMR (CDCl$_3$, 400 MHz). LC-MS (ES, Pos.): m/z 436/438 (3/1) [MH$^+$]. The solution of the above diol (260 mg, 0.6 mmol) in 5 mL of $^i$PrOH was cooled to −78° C. and charged with NH$_3$ gas for 1 min. This sealed tube was equipped with a teflon O-ring, sealed and heated at 110° C. overnight. The mixture was cooled to −78° C. and the cap was removed. The mixture was diluted with methylene chloride (30 mL) and the salt was filtered off. The filtrate was concentrated under reduced pressure and the crude product was purified by silica gel column chromatography (100% ethyl acetate→EtOAc:MeOH=95:5 to 90:10), the title compound as a pale solid, a mixture of two isomers in ca. 3:2 ratio; LC-MS (ES, Pos.): m/z 417 [MH$^+$]; $^1$H NMR (CDCl$_3$, 400 MHz) δ 2.54-2.80 (m, 4H), 2.80, 3.85 (2×m, 1H, 2:3 ratio), 3.67, 3.71 (2×s, 2H, 3:2 ratio), 5.06 (br s, 2H), 5.14 (s, 2H), 7.03-7.45 (m, 11H).

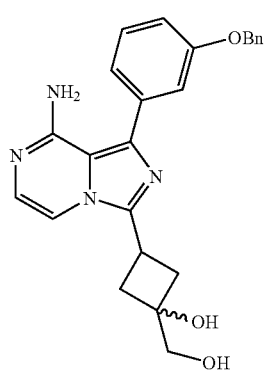

Example 67 and 68 cis- and trans-Toluene-4-sulfonic acid 3-[8-amino-1-(3-benzyloxy-phenyl)-imidazo[1,5-a]pyrazin-3-yl]-1-hydroxy-cyclobutylmethyl ester: A solution of 3-[8-amino-1-(3-benzyloxy-phenyl)-imidazo[1,5-a]pyrazin-3-yl]-1-hydroxymethyl-cyclobutanol (500 mg, 1.2 mmol) in dry methylene chloride (10 mL) and pyridine (3 mL) was charged with a solution of Ts$_2$O (470 mg, 1.44 mmol) in methylene chloride (3 mL) at −40° C. under N$_2$ atmosphere. The mixture was slowly warmed to rt overnight. TLC showed the reaction was complete. The reaction was quenched with water (2 mL), diluted with methylene chloride (40 mL), washed with sat. aq. NaHCO$_3$ (2×15 mL) and brine (15 mL), and dried over anhydrous sodium sulfate. The filtrate was concentrated under reduced pressure, and the crude material was purified by silica gel column chromatography (eluting with Hexanes: EtOAc=50:50→30:70→100% ethyl acetate, then 5% MeOH/EtOAc) afforded each pure isomer. cis-Toluene-4-sulfonic acid 3-[8-amino-1-(3-benzyloxy-phenyl)-imidazo[1,5-a]pyrazin-3-yl]-1-hydroxy-cyclobutylmethyl ester: less polar isomer, light yellow solid, LC-MS (ES, Pos.): m/z 571 [MH$^+$]; $^1$H NMR (CDCl$_3$, 400 MHz) δ 2.46 (s, 3H), 2.50-2.55 (m, 2H), 2.79-2.84 (m, 2H), 3.41 (m, 1H), 4.10 (s, 2H), 5.06 (br s, 2H), 5.14 (s, 2H), 7.03-7.11 (m, 3H), 7.21-7.23 (m, 2H), 7.33-7.45 (m, 8H), 7.85 (d, J=8.3 Hz, 2H). trans-Toluene-4-sulfonic acid 3-[8-amino-1-(3-benzyloxy-phenyl)-imidazo[1,5-a]pyrazin-3-yl]-1-hydroxy-cyclobutylmethyl ester: light yellow solid, LC-MS (ES, Pos.): m/z 571 [MH$^+$]; $^1$H NMR (CDCl$_3$, 400 MHz) δ 2.37 (s, 3H), 2.60-2.70 (m, 4H), 3.85 (m, 1H), 4.24 (s, 2H), 5.08 (br s, 2H), 5.17 (s, 2H), 6.99-7.08 (m, 3H), 7.20-7.27 (m, 3H), 7.33-7.47 (m, 7H), 7.71 (d, J=8.3 Hz, 2H).

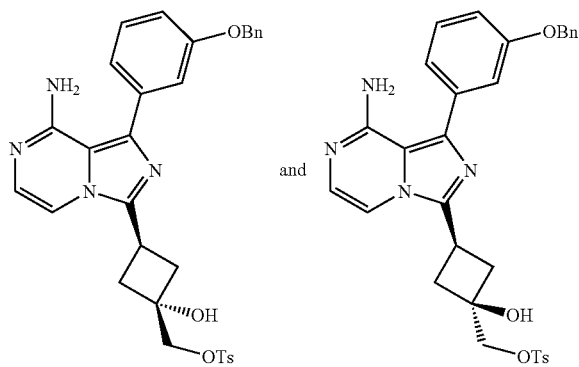 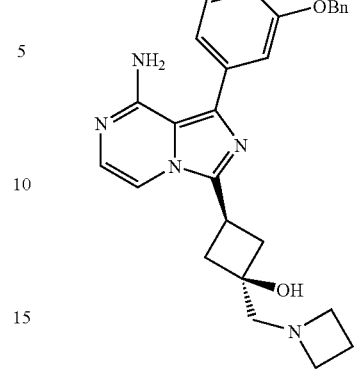

Example 69 trans-3-[8-Amino-1-(3-benzyloxy-phenyl)-imidazo[1,5-a]pyrazin-3-yl]-1-azetidin-1-ylmethyl-cyclobutanol: A sealed tube containing a solution of trans-toluene-4-sulfonic acid 3-[8-amino-1-(3-benzyloxy-phenyl)-imidazo[1,5-a]pyrazin-3-yl]-1-hydroxy-cyclobutylmethyl ester (100 mg, 0.18 mmol) in THF (5 mL) was charged with azetidine (0.24 mL, 3.6 mmol), sealed, and heated at 50° C. overnight. The mixture was concentrated and the residue was purified by mass-directed purification to afford the title compound as a white solid; LC-MS (ES, Pos.): m/z 456 [MH+]; $^1$H NMR (CDCl$_3$, 400 MHz) δ 2.05-2.12 (m, 2H), 2.50-2.63 (m, 6H), 3.30 (t, J=7.0 Hz, 4H), 3.96 (m, 1H), 4.15 (br s, 1H, —OH), 5.15 (s, 4H, —OCH$_2$— and —NH$_2$), 7.03-7.09 (m, 3H), 7.25-7.46 (m, 8H).

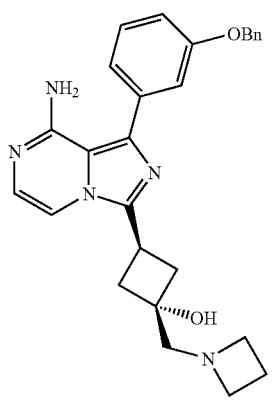

Example 70 cis-3-[8-Amino-1-(3-benzyloxy-phenyl)-imidazo[1,5-a]pyrazin-3-yl]-1-azetidin-1-ylmethyl-cyclobutanol: The title compound was prepared according to the procedure described for trans-3-[8-Amino-1-(3-benzyloxy-phenyl)-imidazo[1,5-a]pyrazin-3-yl]-1-azetidin-1-ylmethyl-cyclobutanol above, white solid; LC-MS (ES, Pos.): m/z 456 [MH+]; $^1$H NMR (CDCl$_3$, 400 MHz) δ 2.05-2.17 (m, 2H), 2.56-2.68 (m, 4H), 2.70 (s, 2H), 3.30 (m, 1H), 3.39 (t, J=7.0 Hz, 4H), 4.29 (br s, 1H, —OH), 5.10 (br s, 2H), 5.14 (s, 2H), 7.01-7.05 (m, 2H), 7.13 (d, J=5.0 Hz, 1H), 7.22-7.26 (m, 2H), 7.33-7.46 (m, 6H).

Example 71

1-[3-(4-tert-Butoxy-benzyloxy)-phenyl]-3-cyclobutyl-imidazo[1,5-a]pyrazin-8-ylamine: A solution of 3-(8-Amino-3-cyclobutyl-imidazo[1,5-a]pyrazin-1-yl)-phenol (200 mg, 0.71 mmol) in DMF (3.5 mL) was charged with Cs$_2$CO$_3$ (348 mg, 1.07 mmol) and stirred at rt for 30 min. A solution of 1-bromomethyl-4-tert-butoxy-benzene (162 mg, 0.71 mmole) in 0.5 mL of DMF, was added to the reaction mixture. After 15 h, the reaction was complete by LC/MS analysis. The product was an orange/brown solid. The crude product was chromatographed on silica gel [Jones Flashmaster, 5 g cartridge, eluting with 10% ethyl acetate]. The product was then recrystalized with ethyl acetate and hexanes yielding the title compound as a white solid; $^1$H NMR (CDCl$_3$, 400 MHz) δ 1.36 (s, 9H), 2.11-2.23 (m, 2H), 2.45-2.52 (m, 2H), 2.59-2.69 (m, 2H), 3.77-3.85 (m, 1H), 5.08 (s, 2H), 5.49 (brs, 2H), 7.01-7.04 (m, 3H), 7.05 (dd, J=4.00 Hz, 1H), 7.10 (d, J=5.02 Hz, 1H), 7.23-7.25 (m, 1H), 7.29 (q, J=40 Hz, 1H), 7.34-7.36 (m, 2H), 7.41 (t, J=16 Hz, 1H); MS (ES+): m/z 443.04 (100) [MH+].

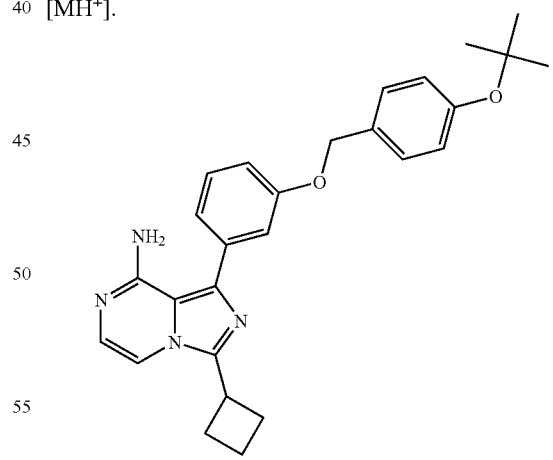

Example 72

2-[3-(8-Amino-3-cyclobutyl-imidazo[1,5-a]pyrazin-1-yl)-phenoxymethyl]-Benzonitrile: A solution of 3-(8-Amino-3-cyclobutyl-imidazo[1,5-a]pyrazin-1-yl)-phenol (500 mg, 1.78 mmol) in DMF (8.9 mL) was charged with Cs$_2$CO$_3$ (871 mg, 2.68 mmol) and stirred for 30 min. at rt. A solution of 2-cyanobenzyl bromide (500 mg, 1.78 mmol) in DMF was added to the reaction mixture. After 24 h at rt the reaction mixture was concentrated in vacuo and chromatographed on silica gel [Jones Flashmaster, 10 g cartridge, eluting with 50% EtOAc:hexanes to 100% EtOAc]. The product was then recrystalized with CH$_2$Cl$_2$ and hexanes yielding the title compound as a light red solid; $^1$H NMR (CDCl$_3$, 400 MHz) δ 2.02-2.06 (m, 1H), 2.11-2.33 (m, 1H), 2.45-2.53 (m, 2H), 2.59-2.69 (m, 2H), 3.77-3.86 (m, 1H), 5.33 (s, 2H), 7.02-7.04 (m, 1H), 7.05 (dd, J=2.4 Hz, 1H), 7.10 (d, J=5.2 Hz, 1H), 7.29-7.30 (m, 1H), 7.33 (q, J=3.6, 11H), 7.40-7.64 (m, 2H), 7.61-7.66 (m, 1H), 7.70-7.72 (m, 2H); MS (ES+): m/z 395.99 (100) [MH$^+$].

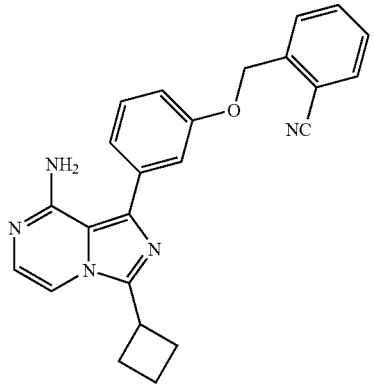

Example 73

3-Cyclobutyl-1-[3-(2-nitro-benzyloxy)-phenyl]-imidazo[1,5-a]pyrazin-8-ylamine: A solution of 3-(8-Amino-3-cyclobutyl-imidazo[1,5-a]pyrazin-1-yl)-phenol (2.00 g, 7.13 mmol) in DMF (36.7 mL) was charged with Cs$_2$CO$_3$ (3.48 g, 10.7 mmol) and stirred at rt for 30 min. A DMF solution of 2-nitrobenzyl bromide (1.54 g, 7.13 mmol), was then added to the reaction mixture. The reaction was allowed to progress at rt under nitrogen for 3.5 h. TLC analysis showed that the reaction was complete. The product was purified using silica gel column chromatography (1-3% NH$_3$ in MeOH:CH$_2$Cl$_2$). The final product was concentrated to a yellow solid; $^1$H NMR (CDCl$_3$, 400 MHz) δ 2.00-2.08 (m, 1H), 2.11-2.23 (m, 1H), 2.45-2.53 (m, 2H), 2.59-2.69 (m, 2H), 3.77-3.86 (m, 1H), 5.57 (s, 2H), 7.01-7.05 (m, 2H), 7.11 (d, J=5.6 HZ, 1H), 7.27-7.30 (m, 1H), 7.32-7.33 (m, 1H), 7.42 (t, J=16.4 Hz, 1H), 7.48-7.52 (m, 1H), 7.67-7.71 (m, 1H), 7.92 (dd, J=8.0 Hz, 1H), 8.17 (d, J=9.5 Hz, 1H); MS (ES+): m/z 416.01 (100) [MH$^+$].

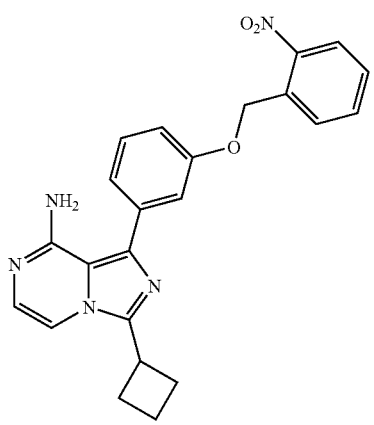

Example 74

1-[3-(2-Bromo-benzyloxy)-phenyl]-3-cyclobutyl-imidazo[1,5-a]pyrazin-8-ylamine: A solution of 3-(8-Amino-3-cyclobutyl-imidazo[1,5-a]pyrazin-1-yl)-phenol (100 mg, 0.36 mmol) in DMF (1.8 mL) was charged with Cs$_2$CO$_3$ (174 mg, 0.54 mmol) and stirred at rt for 30 min. A solution of 2-bromobenzyl bromide (89.2 mg, 0.36 mmol) in DMF was added to the reaction mixture. Reaction mixture was stirred overnight at rt under nitrogen. The crude product was left under high vacuum to remove the DMF for 2 h. The product was then purified by silica gel column chromatography (3% NH$_3$ in MeOH):CH$_2$Cl$_2$ to yield the title compound as a brown/red solid; $^1$H NMR (CDCl$_3$, 400 MHz) δ 2.02-2.08 (m, 1H), 2.14-2.21 (m, 1H), 2.45-2.53 (m, 2H), 2.59-2.69 (m, 2H), 3.77-3.85 (m, 1H), 5.21 (s, 2H), 7.00 (d, J=5.6 Hz, 1H), 7.04-7.07 (m, 1H), 7.11 (d, J=5.2 Hz, 1H), 7.18-7.23 (m, 1H), 7.25-7.30 (m, 2H), 7.33-7.37 (m, 1H), 7.42 (t, J=16 Hz, 1H), 7.55-7.61 (m, 2H); MS (ES+): m/z 450.81 (100) [MH$^+$].

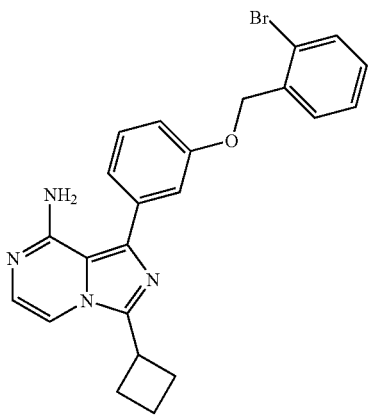

Example 75

1-[3-(3-Aminomethyl-benzyloxy)-phenyl]-3-cyclobutyl-imidazo[1,5-a]pyrazin-8-ylamine: 2-{3-[3-(8-Amino-3-cyclobutyl-imidazo[1,5-a]pyrazin-1-yl)-phenoxymethyl]-benzyl}-isoindole-1,3-dione (100 mg, 0.19 mmol) was dissolved in EtOH (0.76 mL) and charged with hydrazine (60 mg, 1.89 mmol) and stirred overnight at rt. The white ppt filtered and washed with EtOH. The filtrate was concentrated in vacuo, silica gel was added in CH$_2$Cl$_2$, and concentrated to solid. The product was chromatographed on silica gel [Jones Flashmaster, 2 g cartridge, eluting with ~2% 7N NH$_3$ MeOH:CH$_2$Cl$_2$] and isolated the title compound as a yellow solid; $^1$H NMR (CDCl$_3$, 400 MHz) δ 1.84-1.92 (m, 1H), 1.97-2.09 (m, 1H), 2.34-2.40 (m, 2H), 2.44-2.46 (m, 2H), 3.69 (s, 2H), 3.84-3.92 (m, 1H), 5.10 (s, 2H), 6.96 (d, J=5.2 Hz, 1H), 7.01-7.03 (m, 1H), 7.13-7.16 (m, 1H), 7.18-7.19 (m, 1H), 7.23-7.32 (m, 3H), 7.35-7.40 (m, 3H); MS (ES+): m/z 400.17 (100) [MH$^+$].

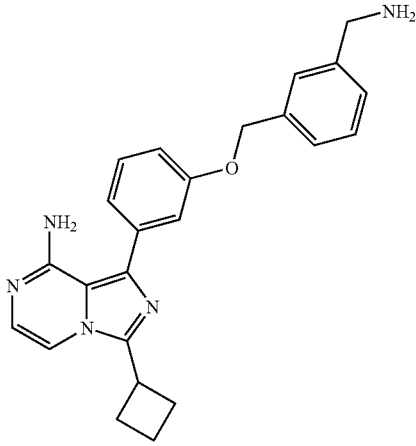

Example 76

3-[3-(8-Amino-3-cyclobutyl-imidazo[1,5-a]pyrazin-1-yl)-phenoxymethyl]-benzoic acid methyl ester. A solution of 3-(8-Amino-3-cyclobutyl-imidazo[1,5-a]pyrazin-1-yl)-phenol (2.87 g, 10.2 mmol) in DMF was charged with $Cs_2CO_3$ (4.98 g, 15.3 mmol) and stirred at rt for 30 min. A DMF solution of methyl (3-bromomethyl)benzoate (2.33 g, 10.2 mmol) was added to the reaction mixture. The reaction mixture was stirred overnight at rt under nitrogen. The crude product was placed under high vacuum to remove the residual DMF. The product was then purified using silica gel column chromatography (1% $NH_3$ in $MeOH:CH_2Cl_2$). The product was recrystalized with $CH_2Cl_2$ and hexanes to yield the title compounds as a white solid; $^1$H NMR ($CDCl_3$, 400 MHz) δ 2.00-2.07 (m, 1H), 2.11-2.22 (m, 1H), 2.45-2.52 (m, 2H), 2.58-2.68 (m, 2H), 3.76-3.85 (m, 1H), 3.93 (s, 3H), 5.18 (s, 2H), 7.01-7.04 (m, 2H), 7.10-7.11 (m, 1H), 7.24-7.29 (m, 2H), 7.38-7.49 (m, 2H), 7.65 (d, J=7.6 Hz, 1H), 8.01 (d, J=8.0 Hz, 1H), 8.13 (s, 1H); MS (ES+): m/z 429.18 (100) [MH$^+$].

Example 77

3-[3-(8-Amino-3-cyclobutyl-imidazo[1,5-a]pyrazin-1-yl)-phenoxymethyl]-Benzamide: 3-[3-(8-Amino-3-cyclobutyl-imidazo[1,5-a]pyrazin-1-yl)-phenoxymethyl]-benzoic acid methyl ester (150 mg, 0.35 mmol) was dissolved in a sealed tube with 2.0 ml of 7N $NH_3$ in MeOH and heated to 60° C. overnight. LC/MS analysis indicated that the reaction was incomplete, therefore $NH_3$ gas was bubbled into the solution and the reaction was run at 100° C. in a 100 mL Parr pressure vessel. The product was chromatographed on silica gel [Jones Flashmaster, 5 g cartridge, eluting with 2% $NH_3$ in MeOH: $CH_2Cl_2$] to yield the title compound as a white solid; $^1$H NMR ($CDCl_3$, 400 MHz) δ 1.99-2.08 (m, 1H), 2.13-2.25 (m, 1H), 2.46-2.55 (m, 2H), 2.55-2.65 (m, 2H), 3.78-3.87 (m, 1H), 5.21 (s, 2H), 6.95 (d, J=5.2 Hz, 1H), 7.08-7.11 (m, 1H), 7.13 (d, J=5.6 Hz, 1H), 7.22-7.24 (m, 2H), 7.42-7.51 (m, 2H), 7.61 (d, J=8.4 Hz, 1H), 7.80-7.83 (m, 1H), 7.94 s, 1H); MS (ES+): m/z 414.21 (100) [MH$^+$].

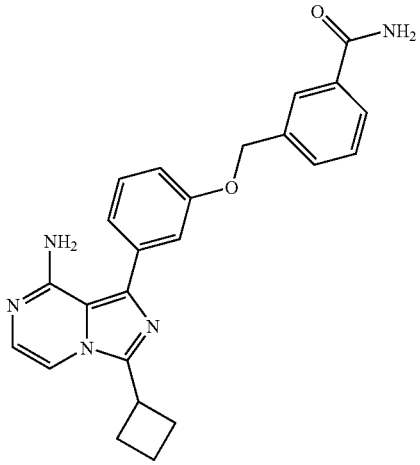

Example 78

{3-[3-(8-Amino-3-cyclobutyl-imidazo[1,5-a]pyrazin-1-yl)-phenoxymethyl]-phenyl}-methanol: A solution of 3-[3-(8-Amino-3-cyclobutyl-imidazo[1,5-a]pyrazin-1-yl)-phenoxymethyl]-benzoic acid methyl ester (600 mg, 1.40 mmol) in THF was cooled to −78° C. in an acetone/dry ice bath for 5.0 min. The reaction was purged with nitrogen and charged dropwise with 1M lithium aluminum hydride (LAH) (1.40 mL). After all the LAH was added, the solution was removed from the bath and allowed to warm to room temperature (rt). As the solution warmed, a white solid formed on the sides of the flask. The reaction mixture was then charged with ethyl acetate, $Na_2SO_4.10H_2O$ and silica. This solution was then concentrated in vacuo to a solid, and was chromatographed on silica gel [Jones Flashmaster, 50 g cartridge, eluting with 2% $NH_3$ in $MeOH:CH_2Cl_2$] to yield the title compound as a white solid; $^1$H NMR ($CDCl_3$, 400 MHz) δ 1.99-2.07 (m, 1H), 2.11-2.22 (m, 1H), 2.44-2.52 (m, 2H), 2.58-2.68 (m, 2H), 3.76-3.84 (m, 1H), 4.69 (s, 2H), 5.16 (s, 2H), 6.98 (d, J=13.2 Hz, 1H), 7.02-7.05 (m, 1H), 7.08 (d, J=4.8 Hz, 1H), 7.16-7.17 (m, 1H), 7.25-7.28 (m, 1H), 7.35-7.43 (m, 5H); MS (ES+): m/z 401.19 (100) [MH$^+$].

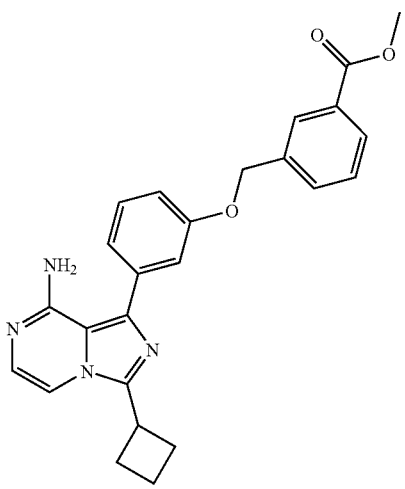

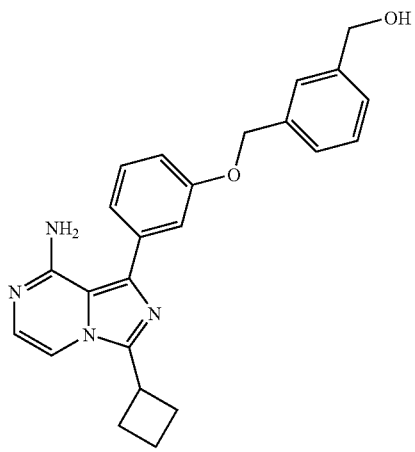

Example 79

2-{3-[3-(8-Amino-3-cyclobutyl-imidazo[1,5-a]pyrazin-1-yl)-phenoxymethyl]-benzyl}-isoindole-1,3-dione: Phthalimide (44 mg, 0.25 mmol), PS-triphenylphosphine (169 mg, 0.37 mmol) and {3-[3-(8-Amino-3-cyclobutyl-imidazo[1,5-a]pyrazin-1-yl)-phenoxymethyl]-phenyl}-methanol (100 mg, 0.25 mmol) were added to a dry rbf and dissolved with THF (1.25 mL), which was then evacuated and purged three times with nitrogen. DIAD (61 mg, 0.30 mmol) was added slowly to the reaction mixture and allowed to slowly stir for 24 h at rt. LC/MS analysis indicated that the reaction was nearly finished with some starting material left, but mostly product. Therefore, 0.2 eq. of DIAD and phthalimide were added and the reaction was left to proceed. The reaction mixture was filtered through a glass frit and washed with $CH_2Cl_2$ multiple times. The filtrate was concentrated to a red/brown oil and purified using silica gel column chromatography (1% $NH_3$ in MeOH:$CH_2Cl_2$) to afford the title compound; $^1$H NMR (CDCl$_3$, 400 MHz) δ 2.00-2.09 (m, 1H), 2.11-2.23 (m, 1H), 2.45-2.53 (m, 2H), 2.59-2.69 (m, 2H), 3.77-3.85 (m, 1H), 4.87 (s, 2H), 5.11 (s, 2H), 6.99-7.02 (m, 2H), 7.10 (d, J=5.2 Hz, 1H), 7.23-7.26 (m, 2H), 7.35-7.42 (m, 4H), 7.49 (s, 1H), 7.69-7.73 (m, 2H), 7.82-7.87 (m, 2H); MS (ES+): m/z 530.14 (100) [MH$^+$].

Example 80

3-[3-(8-Amino-3-cyclobutyl-imidazo[1,5-a]pyrazin-1-yl)-phenoxymethyl]-benzoic acid: A 5 mL methanolic solution of 3-[3-(8-Amino-3-cyclobutyl-imidazo[1,5-a]pyrazin-1-yl)-phenoxymethyl]-benzoic acid methyl ester (600 mg, 1.40 mmol) with 5 mL THF was charged with 5 mL of 10 N NaOH and the reaction mixture was heated to 60° C. After 1 h, the reaction was allowed to cool to rt and the pH of the reaction mixture was lowered to 3-4. A white precipitate formed, which was filtered and washed with hexanes to afford the title compound as a white powder; $^1$H NMR (CDCl$_3$, 400 MHz) δ 1.90-1.97 (m, 1H), 2.04-2.15 (m, 1H), 2.36-2.56 (m, 4H), 3.60-3.79 (m, 1H), 5.10 (s, 2H), 6.84 (d, J=5.2 Hz, 1H), 6.97-7.01 (m, 1H), 7.07 (d, J=5.6 Hz, 1H), 7.12-7.15 (m, 2H), 7.32-7.40 (m, 2H), 7.54 (d, J=7.2 Hz, 1H), 7.91 (d, J=7.6 Hz, 1H), 8.02 (s, 1H); MS (ES+): m/z 415.15 (100) [MH$^+$].

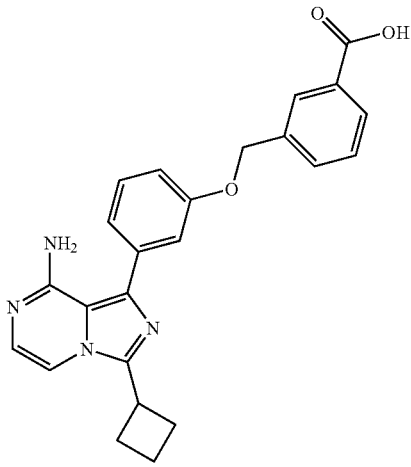

Example 81

3-[3-(8-Amino-3-cyclobutyl-imidazo[1,5-a]pyrazin-1-yl)-phenoxymethyl]-N-methyl-Benzamide: A solution of 3-[3-(8-Amino-3-cyclobutyl-imidazo[1,5-a]pyrazin-1-yl)-phenoxymethyl]-benzoic acid (100 mg, 0.24 mmol) and methylamine HCl (163 mg, 2.41 mmol) in DMF (1.2 mL) was charged with DIEA (0.42 mL, 2.41 mmol), HOBt (37.0 mg, 0.24 mmol), and EDC (69.0 mg, 0.36 mmol). The brown colored reaction mixture was allowed to stir for 18 h. LC/MS analysis indicated that the reaction was nearly complete. The reaction was heated to 50° C. and allowed to react for an additional 18 h. The DMF was removed in vacuo and the product was chromatographed on silica gel [Jones Flashmaster, 5 g cartridge, eluting with 2% 7N $NH_3$ MeOH:$CH_2Cl_2$] to yield the title compound as a pink solid; $^1$H NMR (CDCl$_3$, 400 MHz) δ 1.99-2.07 (m, 1H), 2.11-2.20 (m, 1H), 2.44-2.50 (m, 2H), 2.57-2.67 (m, 2H), 3.01 (d, J=5.2 Hz, 3H), 3.76-3.85 (m, 1H), 5.17 (s, 2H), 6.99-7.02 (m, 2H), 7.10 (d, J=5.2 Hz, 1H), 7.24-7.27 (m, 2H), 7.37-7.46 (m, 2H), 7.55 (d, J=7.6 Hz, 1H), 7.71 (d, J=7.6 Hz, 1H), 7.85 (s, 1H); MS (ES+): m/z 428.17 (100) [MH$^+$].

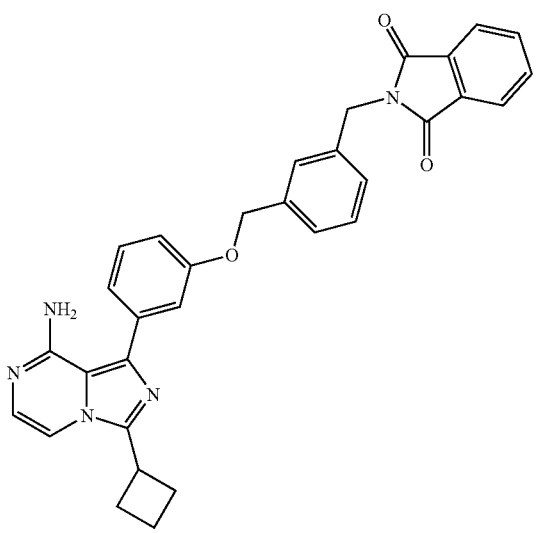

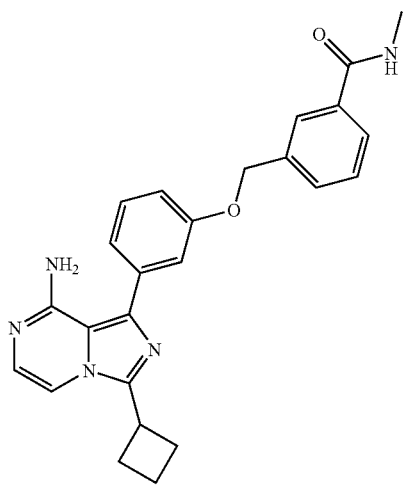

Example 82

1-(3-Benzyloxy-phenyl)-3-(3-methoxymethylene-cyclobutyl)-imidazo[1,5-a]pyrazin-8-ylamine: Prepared according to the procedures for 1-(3-Benzyloxy-phenyl)-3-cyclobutyl-imidazo[1,5-a]pyrazin-8-ylamine; Light brown foam; $^1$H NMR (CD$_3$OD, 400 MHz) δ 3.27-3.29 (m, 4H), 3.58 (s, 3H), 3.85 (q, 1H, J=7.7 Hz), 5.13 (s, 2H), 5.93 (s, 1H), 7.26-7.66 (m, 1H); MS (ES) 413.15 (M+1), 414.11 (M+2), 415.12 (M+3).

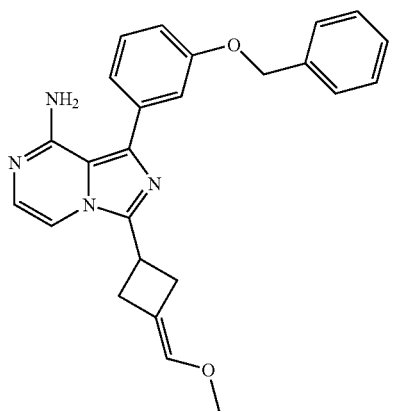

a) 1-(3-Benzyloxy-phenyl)-8-chloro-3-(3-methoxymethylene-cyclobutyl)-imidazo[1,5-a]pyrazine: To a solution of Ph$_3$PCH$_2$OMeCl (2.6 g, 7.44 mmol) in benzene (37 mL) a solution of sodium tert-amylate (819.0 mg, 7.44 mmol) in benzene (9.0 mL) was added at rt. The dark red solution was allowed to stir at rt for 10 min. at which point a solution of 3-[1-(3-Benzyloxy-phenyl)-8-chloro-imidazo[1,5-a]pyrazin-3-yl]-cyclobutanone in benzene (30.0 mL) was added dropwise at rt. The reaction mixture was then heated to 70° C. for 4 h. The reaction was then quenched with NH$_4$Cl sat. Aq. and extracted with diethyl ether (3×). The organic layers were washed with H$_2$O (1×), brine (1×), dried over Na$_2$SO$_4$, filtered and concentrated in vacuo. Purification via HPFC using a 50 g Jones silica gel column (30% EtOAc:Hex) to yield the desired product as a light yellow solid; $^1$H NMR (CDCl$_3$, 400 MHz) δ 3.29-3.33 (m, 4H), 3.59 (s, 3H), 3.90 (q, 1H, J=8.2 Hz), 5.14 (s, 2H), 5.93 (s, 1H), 7.26-7.66 (m, 11H); MS (ES) 432.05 (M+1), 434.01 (M+3), 435.02 (M+4).

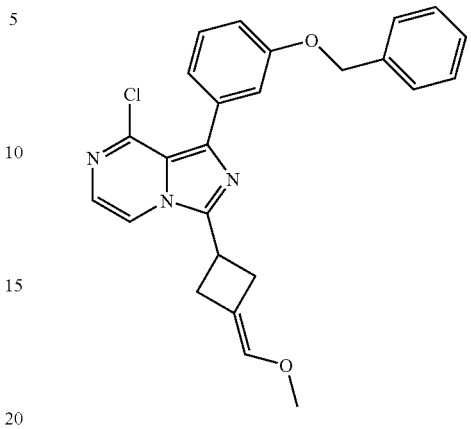

Example 83

3-[8-Amino-1-(3-benzyloxy-phenyl)-imidazo[1,5-a]pyrazin-3-yl]cyclobutanecarbaldehyde: To a methylene chloride solution (6.0 mL) of 1-(3-Benzyloxy-phenyl)-3-(3-methoxymethylene-cyclobutyl)-imidazo[1,5-a]pyrazin-8-ylamine (287.0 mg, 0.696 mmol), CF$_3$CO$_2$H (0.11 mL, 1.392 mmol) was added, followed by H$_2$O (0.5 mL). The reaction mixture was allowed to react for 1 h at rt. After which an ethanolic solution (5.0 mL) of K$_2$CO$_3$ (192.3 mg, 1.392 mmol) was added to the reaction and allowed to stir at rt for an additional 2 h. The reaction mixture extracted between water and EtOAc. The organic layers were washed with brine (1×), dried over Na$_2$SO$_4$, filtered and concentrated in vacuo to yield the desired product as a brown solid; $^1$H NMR (CDCl$_3$, 400 MHz) (mixture of cis and trans isomers) δ 2.45-2.84 (m, 4H), 3.25-3.32 (m, 1H), 3.74-3.79 (m, 1H), 5.22 (s, 2H), 6.84-6.85 (m, 1H), 7.00-7.17 (m, 5H), 7.27-7.39 (m, 6H), 9.69 (s, 1H), 9.88 (s, 1H); MS (ES) 399.07 (M+1), 400.0 (M+2), 401.0 (M+3).

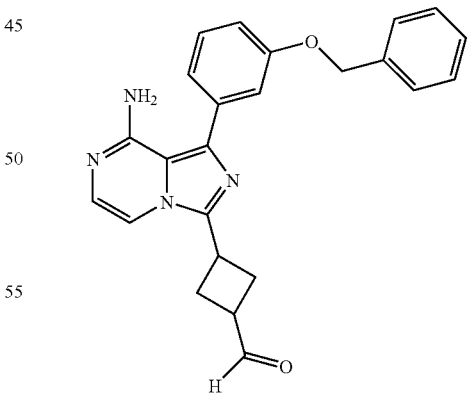

Example 84-A and 84-B cis/trans-1-(3-Benzyloxy-phenyl)-3-(4-methoxy-cyclohexyl)-imidazo[1,5-a]pyrazin-8-ylamine: Prepared according to the procedures for 1-(3-Benzyloxy-phenyl)-3-cyclobutyl-imidazo[1,5-a]pyrazin-8-ylamine. 84-A (Cis-isomer):

Off-white solid, ¹H NMR (CDCl₃, 400 MHz) δ 1.59-2.11 (m, 5H), 2.12-2.21 (brm, 3H), 3.01 (m, 1H), 3.35 (s, 3H), 3.56 (brs, 1H), 5.15 (s, 2H), 6.92 (d, 1H, J=5.4 Hz), 7.09 (dd, 1H, J=0.9 Hz), 7.20-7.52 (m, 9H); MS (ES) 430.16 (M+1), 431.11 (M+2), 432.12 (M+3). 84-B (Trans-isomer): Off-white solid, ¹H NMR (CDCl₃, 400 MHz) δ 1.30-1.34 (m, 4H), 1.80-2.22 (brm, 6H), 2.85 (tt, 1H, J=3.6 Hz), 3.18-3.31 (m, 1H), 3.33 (s, 3H), 5.03 (s, 2H), 6.93 (d, 2H, J=5.4 Hz), 7.19-7.38 (m, 9H); 6.86-7.41 (m, 7H), 8.31 (t, 1H, J=3.0 Hz), 8.53 (d, 1H, J=2.6 Hz); MS (ES) 466.41 (M+1), 468.38 (M+3), 469.45 (M+4).

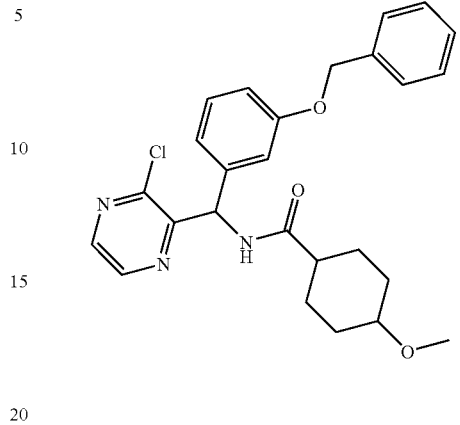

Example 85 cis-tert-Butyl ({3-[8-amino-1-(3-benzyloxyphenyl)-imidazo[1,5-a]pyrazin-3-yl]-cyclobutyl}oxy)acetate: Prepared according to the procedures for 1-(3-Benzyloxy-phenyl)-3-cyclobutyl-imidazo[1,5-a]pyrazin-8-ylamine; ¹H NMR (400 MHz, CD₃OD) δ 7.48-7.31 (m, 7H), 7.26 (t, J=1.6 Hz, 1H), 7.20 (td, J=1.2, 6.4 Hz, 1H), 7.13 (dd, J=4, 8 Hz, 1H), 6.99 (d, J=5.2 Hz, 1H), 5.18 (s, 2H), 4.21 (p, J=6.8 Hz, 1H), 3.99 (s, 2H), 3.43-3.35 (m, 1H), 2.87-2.81 (m, 2H) 2.49-2.41 (m, 2H), 1.49 (s, 9H). MS (ES+): m/z 501 (100) [MH⁺].

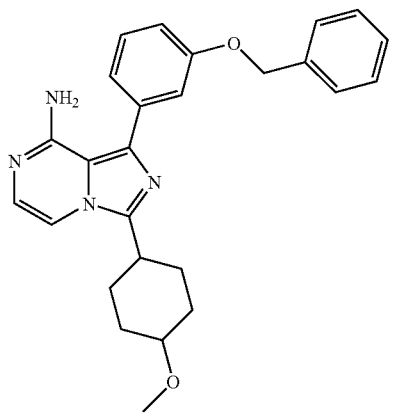

a) 1-(3-Benzyloxy-phenyl)-8-chloro-3-(4-methoxy-cyclohexyl)-imidazo[1,5-a]pyrazine: Prepared according to the procedures for 1-(3-Benzyloxy-phenyl)-8-chloro-3-cyclobutyl-imidazo[1,5-a]pyrazine utilizing 4-Methoxy-cyclohexanecarboxylic Acid [(3-benzyloxy-phenyl)-(3-chloro-pyrazin-2-yl)-methyl]-amide (331.0 mg, 0.71 mmol), POCl₃ (3.0 mL); Yellow oil; MS (ES) 448.11 (M+1), 450.13 (M+3), 451.08 (M+4).

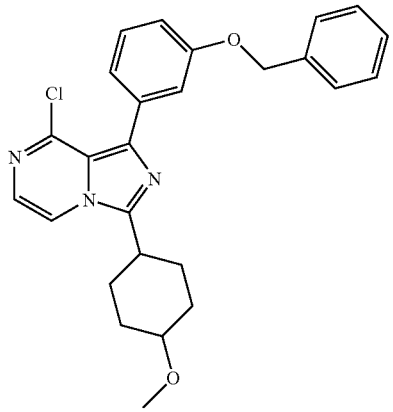

b) 4-Methoxy-cyclohexanecarboxylic Acid [(3-benzyloxy-phenyl)-(3-chloro-pyrazin-2-yl)-methyl]-amide: Prepared according to the procedures for Cyclobutanecarboxylic Acid [(3-benzyloxy-phenyl)-(3-chloro-pyrazin-2-yl)-methyl]Amide utilizing 4-methoxy-cyclohexanecarboxylic acid (145.7 mg, 0.92 mmol), EDC (264.8 mg, 1.38 mmol), HOBt (141.1 mg, 0.92 mmol) and C-(3-Benzyloxy-phenyl)-C-(3-chloro-pyrazin-2-yl)-methylamine (300.0 mg, 0.92 mmol); Purified using a 5 g Jones silica column, (30% EtOAc:Hex) to yield afford the title compound as a light yellow solid; ¹H NMR (CDCl₃, 400 MHz) δ 1.44-2.23 (m, 10H), 3.29 (s, 3H), 5.02 (s, 2H), 6.53 (t, 1H, J=8.0 Hz), 6.91-6.94 (m, 3H),

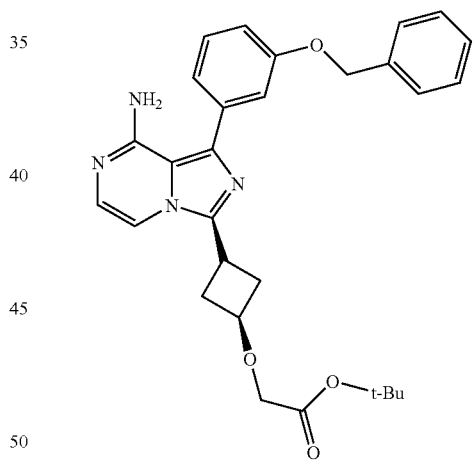

a) cis-tert-Butyl ({3-[8-chloro-1-(3-benzyloxyphenyl)imidazo[1,5-a]pyrazin-3-yl]cyclobutyl}oxy) acetate: cis-3-[1-(3-Benzyloxyphenyl)-8-chloroimidazo[1,5-a]pyrazin-3-yl] cyclobutanol (1.58 mmol, 640 mg) was dissolved in THF (8 mL) and cooled to −78° C. when it was charged with sodium bis(trimethylsilyl)amide (2.37 mmol, 2.37 mL), followed by adding tert-butyl bromoacetate (3.15 mmol, 0.47 mL) portion by portion. The reaction mixture was stirred under −20° C. for 30 min and 0° C. for 1 h before it was allowed to warm to rt slowly and stirred for 16 h. The reaction mixture was concentrated under reduced pressure, dissolved in DCM, washed with water (3×15 mL) and dried over Na₂SO₄. The crude oil was purified by silica gel column chromatography (Jones Flashmaster, 50 g/150 mL cartridge, eluting with EtOAc: Hexane (2:3)), yielding the title compound as a colorless oil;

¹H NMR (400 MHz, CDCl₃) δ 7.53 (d, J=4.8 Hz, 1H), 7.46 (d, 1H, J=8.0 Hz, 1H), 7.40-7.27 (m, 7H), 7.04 (dd, J=2.0, 8.0 Hz, 1H), 5.14 (s, 2H), 4.25 (p, J=8.0 Hz, 1H), 3.36-3.27 (m, 1H), 2.90-2.84 (m, 2H), 2.70-2.62 (m, 2H), 1.48 (s, 9H).

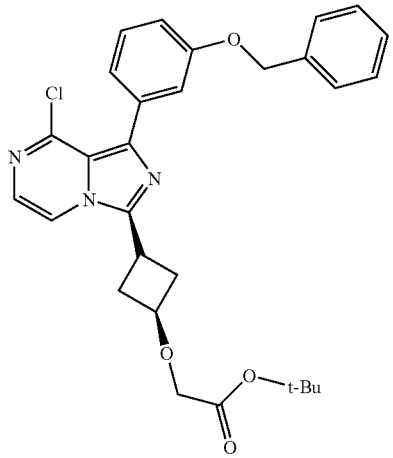

Example 86 cis-2-{3-[8-Amino-1-(3-benzyloxyphenyl)imidazo[1,5-a]pyrazin-3-yl]cyclobutoxy}ethanol: cis-tert-Butyl ({3-[8-amino-1-(3-benzyloxyphenyl)-imidazo[1,5-a]pyrazin-3-yl]cyclobutyl}oxy)acetate (0.4 mmol, 200 mg) was dissolved in THF (2 mL) and charged with LiAlH₄ (4 mmol, 4 mL, 1 M in THF) at −78° C., and stirred under rt for 1 h before the reaction mixture was heated to 50° C. for 16 h. Mixture was charged with EtOAc and allowed to stir at rt for 10 min, followed by an addition of Na₂SO₄.10H₂O. The reaction mixture was passed through a pad of Celite and concentrated under reduced pressure. The crude oil was purified by silica gel column chromatography (Jones Flashmaster, 20 g/70 mL cartridge, eluting with 1-3% MeOH in DCM), yielding the title compound as a colorless oil; NMR ¹H NMR (400 MHz, CD₃OD) δ 7.47(td, 2H), 7.43-7.42 (m, 1H), 7.39-7.36 (m, 2H), 7.33-7.29 (m, 1H), 7.25 (t, J=2.0 Hz, 1H), 7.19 (td, J=1.2 Hz, 8 Hz, 1H), 7.13 (dd, J=2.4 Hz, 8.0 Hz, 1H), 6.98 (d, J=4.8 Hz, 1H), 5.17 (s, 2H), 4.16 (p, J=7.2 Hz, 1H), 3.66-3.65 (m, 2H), 3.51 (t, J=2.4 Hz, 2H), 3.50-3.43 (m, 1H), 2.88-2.81 (m, 2H), 2.46-2.38 (m, 2H). MS (ES+): m/z 431 (100) [MH⁺].

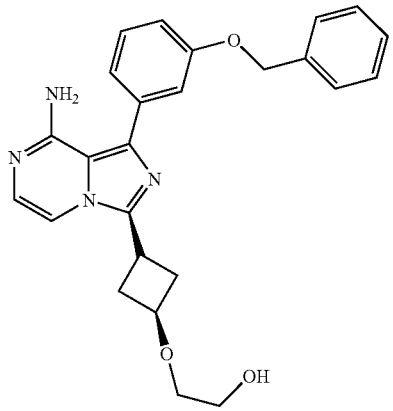

Example 87 cis-Toluene-4-sulfonic acid 2-{3-[8-amino-1-(3-benzyloxyphenyl)imidazo[1,5-a]pyrazin-3-yl]cyclobutoxy}ethyl ester: Followed tosylation procedures described for previously described Toluene-4-sulfonic acid 3-[8-amino-1-(3-benzyloxyphenyl)-imidazo[1,5-a]pyrazin-3-yl]cyclobutyl-methyl ester; ¹H NMR (400 MHz, CDCl₃) δ 7.85-7.76 (m, 2H), 7.47-7.29 (m, 9H), 7.21-7.06 (m, 4H), 6.81 (d, J=8.0 Hz, 1H), 5.19 (s, 2H), 4.20-4.10 (m, 3H), 3.65-3.60 (m, 2H), 3.34-3.27 (m, 1H), 2.84-2.80 (m, 2H), 2.57-2.44 (m, 2H), 2.44-2.41 (m, 4H). MS (ES+): m/z 585 (100) [MH⁺].

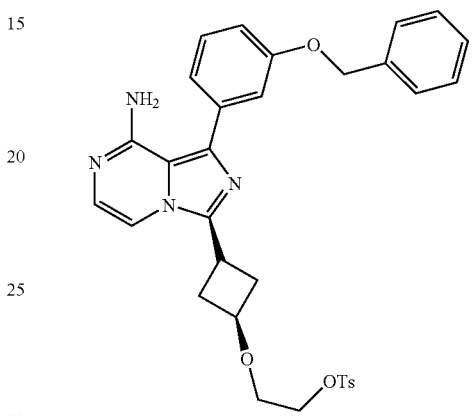

Example 88 cis-1-(3-Benzyloxyphenyl)-3-[3-(2-dimethylaminoethoxy)-cyclobutyl]imidazo[1,5-a]pyrazin-8-yl amine: Followed general procedures described in Examples 33 and 34; ¹H NMR (400 MHz, CD₃OD) δ 7.47-7.44 (m, 3H), 7.42-7.35 (m, 3H), 7.33-7.28 (m, 1H), 7.25-7.24 (m, 1H), 7.19 (td, J=0.8 Hz, 8.0 Hz, 1H), 7.12 (ddd, J=0.8 Hz, 2.8 Hz, 8.0 Hz, 1H), 6.98 (d, J=5.2 Hz, 1H), 5.17 (s, 2H), 4.12 (q, J=8.0 Hz, 1H), 3.55 (t, J=5.2 Hz, 2H), 3.49-3.40 (m, 1H), 2.85-2.82 (m, 2H), 2.61 (t, J=5.6 Hz, 2H), 2.42-2.39 (m, 2H), 2.32 (s, 6H). MS (ES+): m/z 458 (100) [MH⁺].

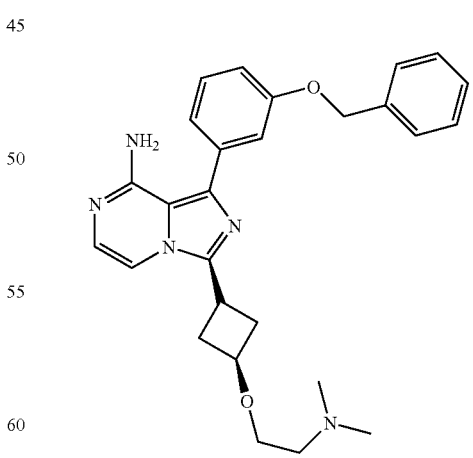

Example 89 cis-{3-[8-Amino-1-(3-benzyloxyphenyl)imidazo[1,5-a]pyrazin-3-yl]-cyclobutoxy}acetic acid: cis-tert-Butyl ({3-[8- chloro-1-(3-benzyloxyphenyl)imidazo[1,5-a]pyrazin-3-yl]cyclobutyl}oxy) acetate (0.1 mmol, 50 mg) was dissolved in 1 mL DCM and cooled in ice bath when it was charged with Et₃SiH (0.1 mmol, 15 μL) and 1 mL TFA. The reaction mixture was warmed to rt during 1 h and stirred for another hour at rt. Reaction mixture was diluted with 10 mL DCM and quenched with K₂CO₃ (20 mL) aqueous solution. The desired product was extracted in aqueous layer and reaction impurities were left in organic phase. The aqueous phase was acidified to pH 3 before it was washed with DCM (3×15 mL). DCM solution was dried over Na₂SO₄ and concentrated under reduced pressure. The crude oil was brought to next step without purification; ¹H NMR (400 MHz, CD₃OD) δ 7.65 (d, J=8.0 Hz, 2H), 7.52-7.45 (m, 4H), 7.40-7.36 (m, 2H), 7.34-7.32 (m, 2H), 7.26 (d, J=8.0 Hz, 1H), 7.25-7.19 (m, 2H), 6.96 (d, J=6.4 Hz, 1H), 5.18 (s, 2H), 4.25 (p, J=6.8 Hz, 1H), 3.50 (p, J=6.8 Hz, 1H), 2.90-2.83 (m, 2H), 2.55-2.46 (m, 2H). MS (ES+): m/z 445 (100) [MH⁺].

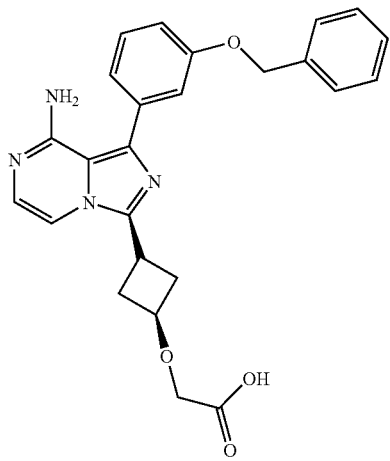

Example 90 cis-2-{3-[8-Amino-1-(3-benzyloxyphenyl)imidazo[1,5-a]pyrazin-3-yl]cyclobutoxy}-N-methylacetamide: Followed general procedures described in Example 37; ¹H NMR (400 MHz, CD₃OD) δ 7.47-7.41 (m, 4H), 7.37 (t, J=7.6 Hz, 2H), 7.32-7.28 (m, 1H), 7.25 (t, J=1.6 Hz, 1H), 7.20 (d, J=8 Hz, 1H), 7.13 (td, J=1.2 Hz, 8 Hz, 1H), 6.99 (d, J=5.2 Hz, 1H), 5.17 (s, 2H), 4.18 (p, J=8 Hz, 1H), 3.91 (s, 2H), 3.46 (p, J=8 Hz, 1H), 2.88-2.79 (m, 2H), 2.76 (s, 3H), 2.50-2.43 (m, 2H). MS (ES+): m/z 458 (100) [MH⁺].

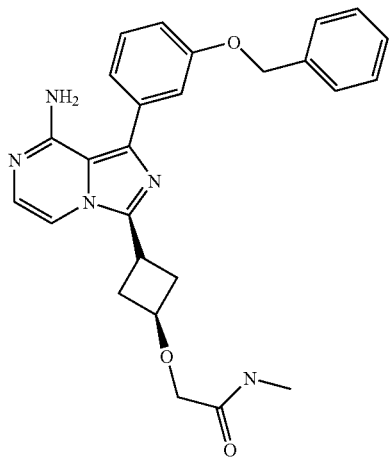

Example 91 cis-2-{3-[8-Amino-1-(3-benzyloxy-phenyl)imidazo[1,5-a]pyrazin-3-yl]cyclobutoxy}acetamide was prepared from cis-tert-Butyl ({3-[8-chloro-1-(3-benzyloxyphenyl)imidazo[1,5-a]pyrazin-3-yl]cyclobutyl}oxy) acetate following the procedures for 1-(3-Benzyloxy-phenyl)-3-cyclobutyl-imidazo[1,5-a]pyrazin-8-ylamine; ¹H NMR (400 MHz, CDCl₃) δ 7.34-7.21 (m, 6H), 7.15-7.10 (m, 3H), 6.96-6.93 (m, 1H), 6.91 (d, J=4.8 Hz, 1H), 6.50 (b, 1H), 5.74 (b, 1H), 5.19 (b, 2H), 5.04 (s, 2H), 4.02 (p, J=0.8 Hz, 1H), 3.71 (s, 2H), 3.25 (p, J=2 Hz, 1H), 2.72-2.65 (m, 2H), 2.31-2.26 (m, 2H). MS (ES+): m/z 444 (100) [MH⁺].

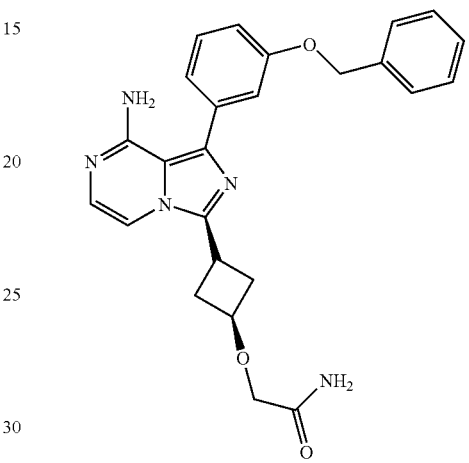

Example 92

1-(3-benzyloxy-4-methoxyphenyl)-3-cyclobutyl-imidazo[1,5-a]pyrazin-8-ylamine: An ⁱPrOH (5 ml)/DCM (4 ml) solution of 1-(3-benzyloxy-4-methoxyphenyl)-8-chloro-3-cyclobutylimidazo[1,5-a]pyrazine (290 mg, 87%, 0.601 mmol), cooled to −78° C. in a dry ice/acetone bath, was charged with liquid NH₃ for 15 min. The sealed tube was equipped with a Teflon washer, sealed and heated 110° C. for 14 h. After that time, the excess NH₃ and the solvent were evaporated. The remaining material was purified by chromatography on silica gel to obtain the title compound as a brown oil. The impurities that could not be removed by conventional methods (eg. TLC, HPLC etc.), were removed by SCX column (washed with 7 ml of DCM, 7 ml of MeOH and 7 ml of 2 N NH₃ in MeOH); ¹H NMR (CDCl₃, 400 MHz) δ 2.00-2.24 (m, 2H), 2.42-2.66 (m, 4H), 3.78 (quintet, 1H, J=8.4 Hz), 3.95 (s, 3H), 4.95 (brs, 2H), 5.23 (s, 2H), 6.98-7.02 (m, 2H), 7.07 (d, 1H, J=5.2 Hz), 7.17 (d, 1H, J=2.0 Hz), 7.23 (dd, 1H, J=2.0 and 8.0 Hz), 7.29-7.45 (m, 5H); MS (ES): 401.1 (M+1).

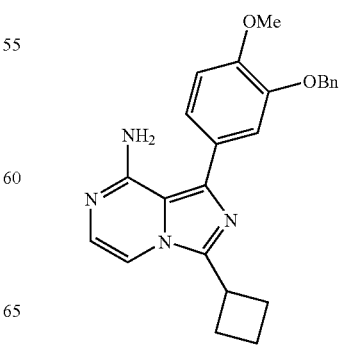

(a) 1-(3-Benzyloxy-4-methoxyphenyl)-8-chloro-3-cyclobutylimidazo[1,5-a]pyrazine: Cyclobutanecarboxylic acid [(3-benzyloxy-4-methoxyphenyl)-(3-chloropyrazin-2-yl)-methyl]-amide (308 mg, 0.703 mmol) was dissolved in $POCl_3$ (5 ml) and heated at 55° C. for 17 h. After that time, the excess $POCl_3$ was removed in vacuo and the remaining mixture was basified with $NH_3$ (2 N in $^i$PrOH). The precipitate formed was filtered off and washed with $CH_2Cl_2$, and the filtrate was purified by chromatography on silica gel to obtain a yellow-brown solid of the title compound (87% purity by LC-MS); $^1$H NMR (DMSO-$d_6$, 400 MHz) δ 2.03-2.20 (m, 2H), 2.47-2.67 (m, 4H), 3.95 (s, 3H), 5.22 (s, 2H), 7.00 (d, 1H, J=8.0 Hz), 7.25-7.47 (m, 8H); MS (ES): 420.0/422.1 (M/M+2).

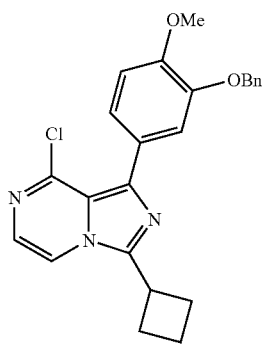

(b) Cyclobutanecarboxylic acid [(3-benzyloxy-4-methoxyphenyl)-(3-chloropyrazin-2-yl)-methyl]-amide: Into the DMF (6 ml) solution of C-(3-benzyloxy-4-methoxyphenyl)-C-(3-chloropyrazin-2-yl)-methylamine (290 mg, 0.815 mmol), cyclobutanecarboxylic acid (156 µl, 2 eq.) and $Et_3N$ (342 µl, 3 eq.), was added EDC hydrochloride (469 mg, 3 eq.) and HOBt monohydrate (250 mg, 2 eq.) at rt under $N_2$, After stirring for 24 h at rt, the mixture was poured into saturated $Na_2CO_3$ (10 ml) and $H_2O$ (10 ml), extracted with EtOAc (3×20 ml). The extracts were washed with $H_2O$ (20 ml) and brine (20 ml), and dried over $MgSO_4$. After concentration in vacuo, a brown syrup (363 mg) was obtained that was then purified by chromatography on silica gel and a brown syrup of cyclobutanecarboxylic acid [(3-benzyloxy-4-methoxyphenyl)-(3-chloropyrazin-2-yl)-methyl]-amide was obtained; $^1$H NMR (CDCl$_3$, 400 MHz) δ 1.86-1.98 (m, 2H), 2.11-2.27 (m, 4H), 3.04 (quintet, 1H, J=8.4 Hz), 3.85 (s, 3H), 5.12 (s, 2H), 6.43 (d, 1H, J=8.0 Hz), 6.79-6.90 (m, 4H), 7.28-7.38 (m, 5H), 8.29 (d, 1H, J=2.8 Hz), 8.45 (d, 1H, J=2.4 Hz); MS (ES): 438.1/440.1 (M/M+2).

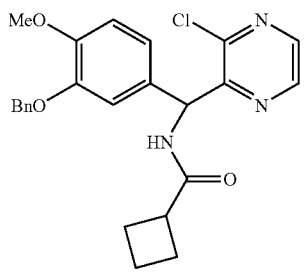

(c) C-(3-Benzyloxy-4-methoxyphenyl)-C-(3-chloropyrazin-2-yl)-methylamine: The mixture of 2-[(3-benzyloxy-4-methoxyphenyl)-(3-chloropyrazin-2-yl)-methyl]-isoindole-1,3-dione (400 mg, 0.823 mmol) and $H_2NNH_2$ (64.0 µl, 3 eq.) in EtOH (6 ml)/$CH_2Cl_2$ (2 ml) was stirred at rt under $N_2$ for 65 h. After that time, the grey solid was filtered off, and the solvent and the excess hydrazine were removed in vacuo to obtain a brown-red oil of C-(3-benzyloxy-4-methoxyphenyl)-C-(3-chloropyrazin-2-yl)-methylamine; $^1$H NMR (CD$_3$OD, 400 MHz) δ 3.84 (s, 3H), 4.96 & 5.00 (AB, 2H, J=12.0 Hz), 5.41 (s, 1H), 6.94-6.97 (m, 3H), 7.29-7.40 (m, 5H), 8.34 (d, 1H, J=2.8 Hz), 8.63 (d, 1H, J=2.4 Hz); MS (ES): 356.1/358.1 (M/M+2).

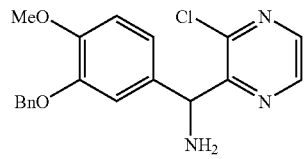

(d) 2-[(3-Benzyloxy-4-methoxyphenyl)-(3-chloropyrazin-2-yl)-methyl]-isoindole-1,3-dione: DIAD (515 µl, 1.1 eq.) was added dropwise into the THF solution (14 ml) of MS-PPh$_3$ (2.12 mmol/g, 1.24 g, 1.1 eq.), (3-benzyloxy-4-methoxyphenyl)-(3-chloropyrazin-2-yl)-methanol (849 mg, 2.38 mmol) and phthalimide (385 mg, 1.1 eq.) at 0° C. under $N_2$ over 5 min. After stirring for 20 h at rt, the mixture was separated by chromatography on silica gel and eluted incrementally with 400 ml, 10%, 20%, 30%, 40%, and 50% EtOAc/Hexane, to obtain a light-yellow oil of 2-[(3-benzyloxy-4-methoxyphenyl)-(3-chloropyrazin-2-yl)-methyl]-isoindole-1,3-dione; $^1$H NMR (CDCl$_3$, 400 MHz) δ 3.87 (s, 3H), 5.08 & 5.14 (AB, 2H, J=12.0 Hz), 6.75 (s, 1H), 6.85 (d, 1H, J=8.0 Hz), 6.88-6.92 (m, 2H), 7.17-7.35 (m, 5H), 7.72-7.75 (m, 2H), 7.82-7.84 (m, 2H), 8.31 (d, 1H, J=2.4 Hz), 8.43 (d, 1H, J=2.4 Hz); MS (ES): 486.0/487.9 (M/M+2).

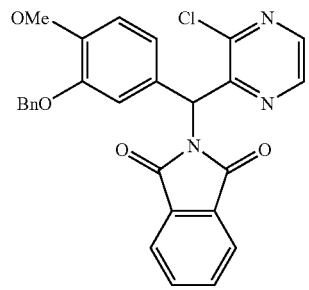

(e) (3-Benzyloxy-4-methoxyphenyl)-(3-chloropyrazin-2-yl)-methanol 2,2,6,6-Tetramethylpiperidine (1775 µl, 1.2 eq.) was added dropwise over 5 min into the THF (20 ml) solution of n-BuLi (2.5 M in cyclohexane, 4.2 ml, 1.2 eq.), which was cooled in a dry ice/acetone bath. The reaction vessel was removed from the cooling bath and allowed to warm to 0° C. for 15 min, then cooled back to −78° C. and charged with chloropyrazine (780 µl, 8.733 mmol) dropwise over 5 min. The reaction was allowed to react for 15 min, and charged with a THF (10 ml) solution of 3-benzyloxy-4-methoxybenzaldehyde (2328 mg, 1.1 eq.) over 10 min. After 2 h, the reaction mixture was warmed to rt and aqueous HCl (1 N, 15 ml) was added. The mixture was extracted with $CH_2Cl_2$ (3×50 ml). The combined extracts were washed with water (50 ml) and brine (50 ml), and dried over $MgSO_4$. After concentration in vacuo, a crude black oil (3.163 g) was obtained that was then purified by chromatography on silica gel (500 ml 10%, 30%, 40%, 50%, and 60% EtOAc/Hexane) and a brown oil of (3-benzyloxy-4-methoxyphenyl)-(3-chloropyrazin-2-yl)-methanol was obtained; ¹H NMR (DMSO-d₆, 400 MHz) δ 3.74 (s, 3H), 5.04 (s, 2H), 6.00 (d, 1H, J=6.0 Hz), 6.09 (d, 1H, J=6.0 Hz), 7.10 (s, 1H), 7.31-7.42 (m, 7H), 8.43 (d, 1H, J=2.4 Hz), 8.67 (d, 1H, J=2.4 Hz); MS (ES): 357.4/359.4 (M/M+2).

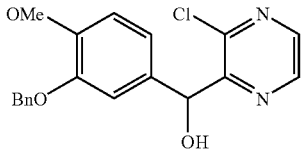

Example 93

1-(3-Benzyloxy-4-fluorophenyl)-3-cyclobutyl-imidazo[1,5-a]pyrazin-8-ylamine: Followed General Ammonolysis described in Example 92; ¹H NMR (CDCl₃, 400 MHz) δ 1.98-2.24 (m, 2H), 2.44-2.66 (m, 4H), 3.78 (quintet, 1H, J=8.4 Hz), 5.22 (s, 2H), 7.01 (d, 1H, J=4.8 Hz), 7.10 (d, 1H, J=5.2 Hz), 7.20-7.46 (m, 8H); MS (ES): 389.1 (M+1).

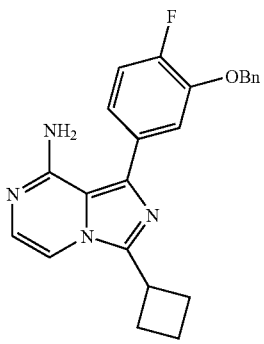

(a) 1-(3-Benzyloxy-4-fluorophenyl)-8-chloro-3-cyclobutylimidazo[1,5-a]pyrazine: Followed General Cyclization described in Example 92-(a); ¹H NMR (CDCl₃, 400 MHz) δ 2.05-2.24 (m, 2H), 2.50-2.69 (m, 4H), 3.84 (quintet, 1H, J=8.4 Hz), 5.21 (s, 2H), 7.15-7.49 (m, 9H); MS (ES): 408.0/410.0 (M/M+2).

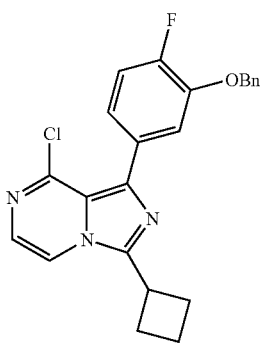

(b) Cyclobutanecarboxylic acid [(3-benzyloxy-4-fluorophenyl)-(3-chloropyrazin-2-yl)-methyl]-amide: Followed General Amide Formation described in Example 92-(b); ¹H NMR (CDCl₃, 400 MHz) δ 1.82-1.97 (m, 2H), 2.11-2.34 (m, 4H), 3.04 (quintet, 1H, J=8.0 Hz), 5.10 (s, 2H), 6.44 (d, 1H, J=7.6 Hz), 6.75-6.79 (m, 1H), 6.95-7.02 (m, 3H), 7.27-7.38 (m, 5H), 8.31 (d, 1H, J=2.4 Hz), 8.46 (d, 1H, J=2.4 Hz); MS (ES): 426.0/428.0 (M/M+2)

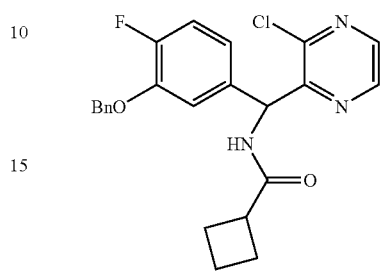

(c) C-(3-Benzyloxy-4-fluorophenyl)-C-(3-chloropyrazin-2-yl)-methylamine: Followed General Primary Amine Formation described in Example 92-(c); ¹H NMR (CD₃OD, 400 MHz) δ 5.15 & 5.19 (AB, 2H, J=12.0 Hz), 5.44 (s, 1H), 6.90-6.95 (m, 1H), 7.02-7.12 (m, 2H), 7.28-7.38 (m, 5H), 8.33 (d, 1H, J=2.4 Hz), 8.61 (d, 1H, J=2.4 Hz); MS (ES): 327.3/329.3 (M−16/M−16+2).

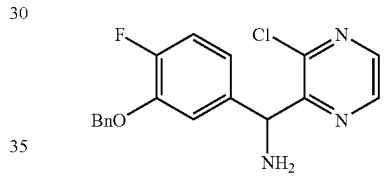

(d) 2-[(3-Benzyloxy-4-fluorophenyl)-(3-chloropyrazin-2-yl)-methyl]-isoindole-1,3-dione: Followed General Mitsunobu Reaction described in Example 92-(d); ¹H NMR (CDCl₃, 400 MHz) δ 5.07 & 5.12 (AB, 2H, J=11.6 Hz), 6.78 (s, 1H), 6.89-6.92 (m, 1H), 7.03-7.09 (m, 2H), 7.28-7.37 (m, 2H), 7.74-7.77 (m, 2H), 7.84-7.86 (m, 2H), 8.35 (d, 1H, J=2.4 Hz), 8.45 (d, 1H, J=2.8 Hz). MS (ES): 474.0/476.0 (M/M+2).

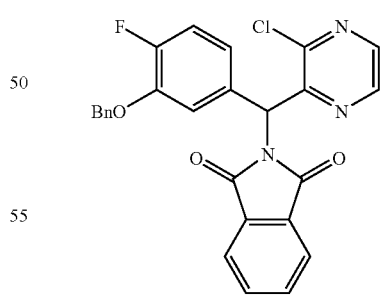

(e) (3-Benzyloxy-4-fluorophenyl)-(3-chloropyrazin-2-yl)-methanol: Followed General Lithiation described in Example 92-(e); ¹H NMR (CDCl₃, 400 MHz) δ 4.58 (d, 1H, J=8.0 Hz), 5.00 & 5.04 (AB, 2H, J=12.0 Hz), 5.94 (d, 1H, J=8.0 Hz), 6.85-6.89 (m, 1H), 6.98-7.06 (m, 2H), 7.26-7.40 (m, 5H), 8.36 (d, 1H, J=2.8 Hz), 8.53 (d, 1H, J=2.4 Hz); MS (ES): 327.1/329.1 (M−18/M−18+2).

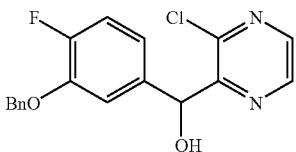

(f) 3-Benzyloxy-4-fluorobenzaldehyde: The mixture of benzyl bromide (1062 μL, 1.050 eq.), potassium carbonate (1500 mg, 1.274 eq.), 4-fluoro-3-hydroxybenzaldehyde (1193 mg, 8.515 mmol) and acetone (50 ml) was stirred at rt for 24 h. After that time, water (40 ml) was added to dissolve inorganic solid and the acetone was removed in vacuo. The mixture was extracted with ethyl acetate (3×50 ml), the combined organic extracts were washed with aqueous acetic acid (5%, 40 ml), water (2×40 ml) and brine (40 ml), and dried over MgSO$_4$. After concentration in vacuo, a brown oil of 3-benzyloxy-4-fluorobenzaldehyde was obtained; $^1$H NMR (CDCl$_3$, 400 MHz) δ 5.20 (s, 2H), 7.23-7.59 (m, 8H), 9.89 (s, 1H).

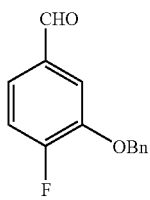

(g) 4-Fluoro-3-hydroxybenzaldehyde: BBr$_3$ (125 ml, 3.383 eq., 1 M in CH$_2$Cl$_2$) was added into the solution of 4-fluoro-3-methoxybenzaldehyde (5.695 g, 36.95 mmol) in CH$_2$Cl$_2$ (50 ml) under N$_2$ at 0° C. over 30 min. After stirring at rt for 19 h, the reaction mixture was poured into ice/water (250 ml) slowly. After separation, the oil phase was extracted with aqueous NaOH (2 N, 2×150 ml). The basic extracts were acidified by aqueous HCl (37%) until pH<2, which was then extracted with CH$_2$Cl$_2$ (3×200 ml). The organic extracts was washed with brine (100 ml) and dried over MgSO$_4$. After concentration in vacuo, a yellow-brown solid of 4-fluoro-3-hydroxybenzaldehyde was obtained; $^1$H NMR (DMSO-d$_6$, 400 MHz) δ 7.43-7.52 (m, 3H), 9.93 (s, 1H), 10.55 (brs, 1H).

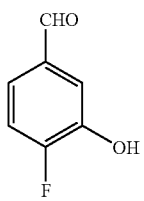

Example 94

1-(3-Benzyloxy-4-isopropoxyphenyl)-3-cyclobutylimidazo[1,5-a]pyrazin-8-ylamine: Followed General Ammonolysis described in Example 92; $^1$H NMR (CDCl$_3$, 400 MHz) δ 1.40 (d, 6H, J=6.0 Hz), 1.98-2.21 (m, 2H), 2.43-2.67 (m, 4H), 3.77 (quintet, 1H, J=8.0 Hz), 4.60 (septet, 1H, J=6.1 Hz), 4.88 (brs, 2H), 5.21 (s, 2H), 7.00 (d, 1H, J=5.2 Hz), 7.04-7.08 (m, 2H), 7.17-7.22 (m, 2H), 7.29-7.45 (m, 5H); MS (ES): 429.1 (M+1).

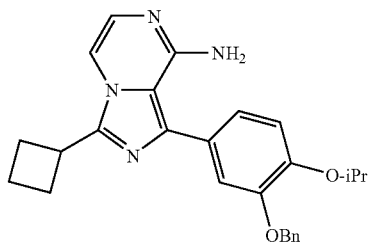

(a) 1-(3-Benzyloxy-4-isopropoxyphenyl)-8-chloro-3-cyclobutylimidazo[1,5-a]pyrazine: quantitative yield: Followed General Cyclization described in Example 92-(a); $^1$H NMR (CDCl$_3$, 400 MHz) δ 1.40 (d, 6H, J=6.0 Hz), 1.87-2.09 (m, 2H), 2.43-2.72 (m, 4H), 3.82 (quintet, 1H, J=8.4 Hz), 4.61 (septet, 1H, J=6.1 Hz), 5.19 (s, 2H), 7.03 (d, 1H, J=8.4 Hz), 7.24-7.47 (m, 9H); MS (ES): 447.9/449.9 (M/M+2).

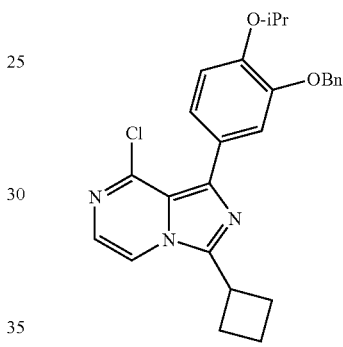

(b) Cyclobutanecarboxylic acid [(3-benzyloxy-4-isopropoxyphenyl)-(3-chloropyrazin-2-yl)-methyl]-amide: Followed General Amide Formation described in Example 92-(b); quantitative yield; $^1$H NMR (CDCl$_3$, 400 MHz) δ 1.34 (d, 6H, J=6.0 Hz), 1.84-1.98 (m, 2H), 2.11-2.30 (m, 4H), 3.05 (quintet, 1H, J=8.4 Hz), 4.48 (septet, 1H, J=5.9 Hz), 5.11 (s, 2H), 6.45 (d, 1H, J=7.6 Hz), 6.82-6.90 (m, 4H), 7.28-7.38 (m, 5H), 8.31 (d, 1H, J=2.8 Hz), 8.45 (d, 1H, J=2.8 Hz). MS (ES): 465.9/467.9 (M/M+2).

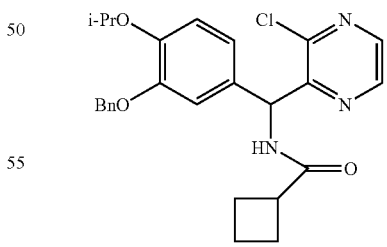

(c) C-(3-Benzyloxy-4-isopropoxyphenyl)-C-(3-chloropyrazin-2-yl)-methylamine: Followed General Primary Amine Formation described in Example 92-(c); $^1$H NMR (CDCl$_3$, 400 MHz) δ 1.34 (s, 6H, J=6.0 Hz), 4.48 (septet, 1H, J=6.2 Hz), 5.10 (s, 2H), 5.43 (s, 1H), 6.33 (brs, 2H), 6.84-6.91 (m, 3H), 7.28-7.40 (m, 5H), 8.24 (d, 1H, J=2.4 Hz), 8.49 (d, 1H, J=2.8 Hz); MS (ES): 384.0/386.0 (M/M+2).

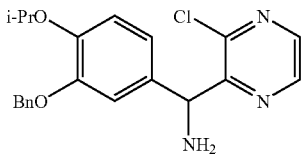

(d) 2-[(3-Benzyloxy-4-isopropoxyphenyl)-(3-chloropyrazin-2-yl)-methyl]-isoindole-1,3-dione: Followed General Mitsunobu Reaction described in Example 92-(d); $^1$H NMR (CDCl$_3$, 400 MHz) δ 1.35 (d, 6H, J=6.0 Hz), 4.53 (septet, 1H, J=6H), 5.05 & 5.10 (AB, 2H, J=12.0 Hz), 6.75 (s, 1H), 6.82-6.90 (m, 2H), 6.94 (s, 1H), 7.19-7.52 (m, 5H), 7.72-7.74 (m, 2H), 7.82-7.84 (m, 2H), 8.31 (d, 1H, J=2.4 Hz), 8.43 (d, 1H, J=2.4 Hz); MS (ES): 513.9/515.9 (M/M+2).

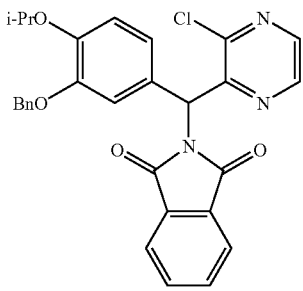

(e) (3-Benzyloxy-4-isopropoxyphenyl)-(3-chloropyrazin-2-yl)-methanol: Followed General Lithiation described in Example 92-(e); $^1$H NMR (CDCl$_3$, 400 MHz) δ 1.34 (d, 6H, J=6.4 Hz), 4.50 (septet, 1H, J=6.0 Hz), 5.10 (AB, 2H, J=12.4 Hz), 5.91 (d, 1H, J=8.0 Hz), 6.84-6.86 (m, 4H), 7.26-7.39 (m, 5H), 8.34 (d, 1H, J=2.4 Hz), 8.50 (d, 1H, J=2.4 Hz); MS (ES): 367.0/369.0 (M/M+2).

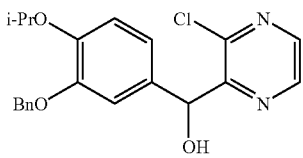

(f) 3-Benzyloxy-4-isopropoxybenzaldehyde: A mixture of 3-benzyloxy-4-hydroxybenzaldehyde (1297 mg, 5.683 mmol) and Cs$_2$CO$_3$ (2777 mg, 1.5 eq.) in DMF (5 ml) was stirred at rt for 30 min under N$_2$, and then 2-bromopropane (800 μl, 1.5 eq.) was added and heated with stirring at 75° C. overnight. The reaction mixture was cooled, and to it was added H$_2$O (20 ml), and then was extracted with EtOAc (4×20 ml). The organic extracts were washed with H$_2$O (3×20 ml) and brine (20 ml), and dried over MgSO$_4$. After concentration in vacuo, a brown oil of 3-benzyloxy-4-isopropoxybenzaldehyde was obtained, which was used without further purification. $^1$H NMR (CDCl$_3$, 400 MHz) δ 1.43 (d, 6H, J=6.4 Hz), 4.69 (septet, 1H, J=6.0 Hz), 5.18 (s, 2H), 7.01 (d, 1H, J=8.0 Hz), 7.26-7.46 (m, 7H), 9.81 (s, 1H); MS (ES): 271.1 (M+1).

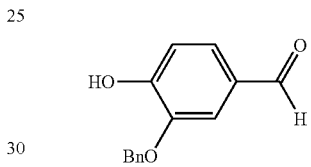

(g) 3-Benzyloxy-4-hydroxybenzaldehyde: A solution of 3-benzyloxy-4-(4-methoxybenzyloxy)-benzaldehyde (2593 mg, 7.443 mmol) in AcOH (20 ml) was heated to reflux (150° C.) for 27 h. The reaction mixture was concentrated in vacuo and the residue was dissolved in EtOAc (20 ml). The organic solution was washed with H$_2$O (20 ml) and aqueous NaOH (0.5 N, 5×20 ml). The basic extracts were combined, acidified to pH=2-3 with aqueous HCl (2 N) and back-extracted with EtOAc (2×30 ml). The organic solution was dried over MgSO$_4$, filtered and concentrated to give 3-benzyloxy-4-hydroxybenzaldehyde as a brown solid. $^1$H NMR (CDCl$_3$, 400 MHz) δ 5.18 (s, 2H), 6.22 (brs, 1H), 7.08 (d, 1H, J=8.0 Hz), 7.39-7.52 (m, 7H), 9.82 (s, 1H); MS (ES): 229.1 (M+1).

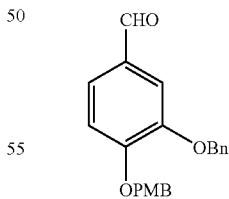

(h) 3-Benzyloxy-4-(4-methoxybenzyloxy)-benzaldehyde: Benzyl bromide (5.84 ml, 1.1 eq.) was added dropwise into the mixture of 3-hydroxy-4-(4-methoxybenzyloxy)-benzaldehyde (11.5 g, 44.6 mmol) and cesium carbonate (8.73 g, 0.6 eq.) in DMF (75 ml) at rt under N$_2$ over 15 min. After stirring at rt for 70 h, the reaction mixture was poured into water (150 ml) and was then extracted with ethyl acetate (200 ml). The organic extracts were washed with water (100 ml), aqueous NaOH (0.5 M, 100 ml), and brine (100 ml) and dried over MgSO$_4$. After concentration in vacuo, a crude brown solid of 3-benzyloxy-4-(4-methoxybenzyloxy)-benzaldehyde was obtained; $^1$H NMR (CDCl$_3$, 400 MHz) δ 3.83 (s, 3H), 5.18 (s, 2H), 5.20 (s, 2H), 6.92 (dd, 2H, J=2 and 6.8 Hz), 7.04 (d, 2H, J=8.0 Hz), 7.33-7.47 (m, 9H), 9.80 (s, 1H).

(i) 3-Hydroxy-4-(4-methoxybenzyloxy)-benzaldehyde: 4-Methoxybenzyl chloride (11.9 g, 1.05 eq.) was added dropwise into the mixture of 3,4-dihydrobenzaldehyde (10.0 g, 72.4 mmol), (n-C$_4$H$_9$)$_4$NI (21.4 g, 0.8 eq.) and cesium carbonate (17.7 g, 0.75 eq.) in DMF (100 ml) at rt under N$_2$ over 15 min. After stirring at rt for 67 h, the reaction mixture was poured into water (200 ml) and, was then extracted with ethyl acetate (3×100 ml). The organic extracts was washed with aqueous HCl (0.5 M, 200 ml), water (4×100 ml), and brine (100 ml) and dried over MgSO₄. After concentration in vacuo, a crude yellow-brown solid (18.0 g) was obtained, which was then triturated with ethyl acetate/hexane (75 ml/150 ml) to give a yellow-brown solid of 3-hydroxy-4-(4-methoxybenzyloxy)-benzaldehyde; $^1$H NMR (CDCl₃, 400 MHz) δ 3.84 (s, 3H), 5.13 (s, 2H), 5.78 (brs, 1H), 6.96 (d, 2H, J=8.0 Hz), 7.06 (d, 2H, J=8.0 Hz), 7.37 (d, 2H, J=8.4 Hz), 7.40-7.45 (m, 2H), 9.84 (s, 1H); MS (ES): 259.2 (M+1).

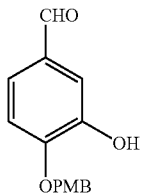

Example 95

1-(3-Benzyloxy-4-ethoxyphenyl)-3-cyclobutylimidazo[1,5-a]pyrazin-8-ylamine: Followed General Ammonolysis described in Example 92; $^1$H NMR (CDCl₃, 400 MHz) δ 1.50 (t, 3H, J=7.0 Hz), 1.99-2.19 (m, 2H), 2.42-2.67 (m, 4H), 3.78 (quintet, 1H, J=8.4 Hz), 4.19 (q, 2H, J=6.9 Hz), 4.83 (brs, 2H), 5.23 (s, 2H), 6.98-7.47 (m, 10H); MS (ES): 415.1 (M+1).

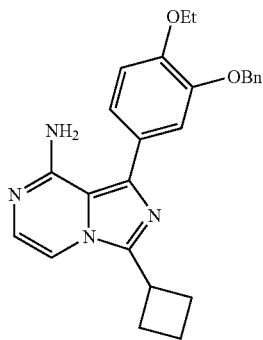

(a) 1-(3-Benzyloxy-4-ethoxyphenyl)-8-chloro-3-cyclobutylimidazo[1,5-a]pyrazine: quantitative yield: Followed General Cyclization described in Example 92-(a); $^1$H NMR (CDCl₃, 400 MHz): 1.49 (t, 3H, J=7.0 Hz), 2.01-2.22 (m, 2H), 2.48-2.70 (m, 4H), 3.82 (quintet, 1H, J=8.4 Hz), 4.17 (q, 2H, J=7.0 Hz), 5.21 (s, 2H), 7.00 (d, 1H, J=8.8 Hz), 7.25-7.47 (m, 9H); MS (ES): 433.9/435.9 (M/M+2).

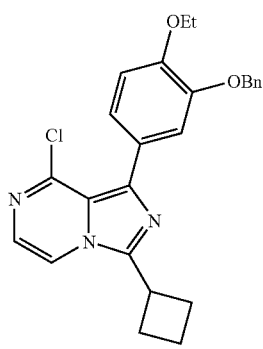

(b) Cyclobutanecarboxylic acid [(3-benzyloxy-4-ethoxyphenyl)-(3-chloropyrazin-2-yl)-methyl]-amide: A mixture of cyclobutanecarboxylic acid [(3-benzyloxy-4-hydroxyphenyl)-(3-chloropyrazin-2-yl)-methyl]-amide (162 mg, 0.382 mmol) and Cs₂CO₃ (187 mg, 0.573 mmol) in DMF (2 ml) was stirred at rt for 30 min under N₂, and then EtI (45.9 µL, 0.573 mmol) was added and heated with stirring at 50° C. for 5 h. The reaction mixture was cooled, and to it was added H₂O (15 ml), and then was extracted with EtOAc (3×15 ml). The organic extracts were washed with H₂O (3×15 ml) and brine (15 ml), and dried over MgSO₄. After concentration in vacuo, a brown oil of 3 cyclobutanecarboxylic acid [(3-benzyloxy-4-ethoxyphenyl)-(3-chloropyrazin-2-yl)-methyl]-amide was obtained, which was used without further purification. A more pure sample was obtained by Gilson HPLC purification for LC-MS and HPLC; $^1$H NMR (CDCl₃, 400 MHz) δ 1.42 (t, 3H, J=7.0 Hz), 1.84-2.11 (m, 2H), 2.12-2.18 (m, 4H), 3.04 (quintet, 1H, J=8.4 Hz), 4.04 (q, 2H, J=6.9 Hz), 5.11 (s, 2H), 6.43 (d, 1H, J=7.6 Hz), 6.78-6.88 (m, 4H), 7.25-7.38 (m, 5H), 8.29 (d, 1H, J=2.4 Hz), 8.44 (d, 1H, J=2.4 Hz); MS (ES): 451.9/453.9 (M/M+2).

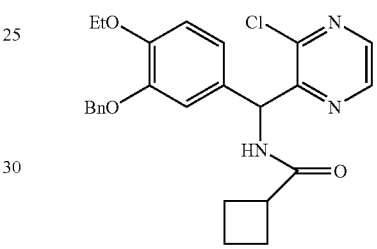

(c) Cyclobutanecarboxylic acid [(3-benzyloxy-4-hydroxyphenyl)-(3-chloropyrazin-2-yl)-methyl]-amide: A solution of cyclobutanecarboxylic acid [[3-benzyloxy-4-(4-methoxybenzyloxy)-phenyl]-(3-chloropyrazin-2-yl)-methyl]-amide (300 mg, 0.551 mmol) in AcOH (10 ml) was heated to reflux (150° C.) for 7 h. The reaction mixture was concentrated in vacuo and the residue was dissolved in EtOAc (15 ml). The organic solution was washed with saturated NaHCO₃ (10 ml), H₂O (2×10 ml) and brine (10 ml), and dried over MgSO₄, filtered and concentrated to give a brown oil. The crude oil was purified by silica gel (eluting with 200 ml of 2%, 4%, 6% MeOH/CH₂Cl₂) to obtain a light-yellow oil of cyclobutanecarboxylic acid [(3-benzyloxy-4-hydroxyphenyl)-(3-chloropyrazin-2-yl)-methyl]-amide; $^1$H NMR (CDCl₃, 400 MHz) δ 1.82-1.99 (m, 2H), 2.13-2.31 (m, 4H), 3.07 (quintet, 1H, J=8.4 Hz), 5.10 (s, 2H), 5.64 (brs, 1H), 6.47 (d, 1H, J=8.0 Hz), 6.72 (dd, 1H, J=1.6 & 8.0 Hz), 6.84 (d, 1H, J=8.0 Hz), 6.98 (d, 1H, J=7.2 Hz), 7.03 (d, 1H, J=1.6 Hz), 7.30-7.38 (m, 5H), 8.32 (d, 1H, J=2.4 Hz), 8.49 (d, 1H, J=2.8 Hz); MS (ES): 423.9/425.9 (M/M+2).

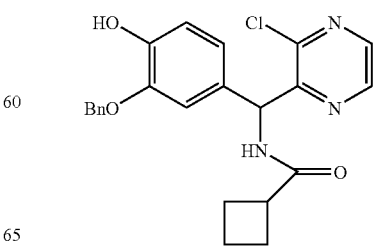

(d) Cyclobutanecarboxylic acid [[3-benzyloxy-4-(4-methoxybenzyloxy)-phenyl]-(3-chloropyrazin-2-yl)-methyl]-amide: Followed General Amide Formation described in Example 92-(b); $^1$H NMR (CDCl$_3$, 400 MHz) δ 1.84-1.98 (m, 2H), 2.11-2.26 (m, 4H), 3.04 (quintet, 1H, J=8.4 Hz), 3.80 (d, 3H, J=1.2 Hz), 5.04 (s, 2H), 5.12 (s, 2H), 6.44 (d, 1H, J=8.0 Hz), 6.78-6.89 (m, 6H), 7.26-7.38 (m, 7H), 8.29 (d, 1H, J=2.0 Hz), 8.50 (d, 1H, J=2.4 Hz); MS (ES): 544.0/546.0 (M/M+2).

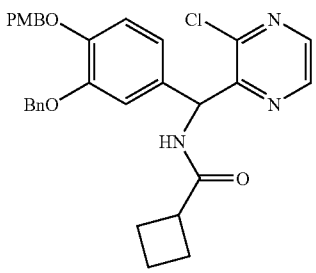

(e) C-[3-Benzyloxy-4-(4-methoxybenzyloxy)-phenyl]-C-(3-chloropyrazin-2-yl)-methylamine: Followed General Primary Amine Formation described in Example 92-(c); quantitative yield; $^1$H NMR (CD$_3$OD, 400 MHz) δ 3.80 (s, 3H), 5.04 (s, 2H), 5.12 (m, 2H), 6.89-6.92 (m, 3H), 6.98-7.00 (m, 2H), 7.30-7.39 (m, 7H), 8.34 (d, 1H, J=2.4 Hz), 8.63 (d, 1H, J=2.4 Hz); MS (ES): 461.9/463.9 (M/M+2).

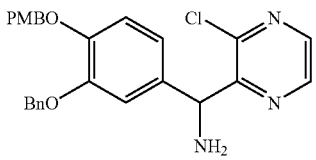

(f) 2-[[3-Benzyloxy-4-(4-methoxy-benzyloxy)-phenyl]-(3-chloro-pyrazin-2-yl)-methyl]-isoindole-1,3-dione: Followed General Mitsunobu Reaction described in Example 92-(d); $^1$H NMR (CDCl$_3$, 400 MHz) δ 3.80 (s, 3H), 4.97-5.14 (m, 4H), 6.75 (s, 1H), 6.87-6.91 (m, 4H), 6.96 (d, 1H, J=2.0 Hz), 7.19-7.24 (m, 2H), 7.33-7.36 (m, 5H), 7.72-7.74 (m, 2H), 7.82-7.84 (m, 2H), 8.31 (dd, 1H, J=0.8 and 2.4 Hz), 8.43 (d, 1H, J=2.0 Hz); MS (ES): 592.0/594.0 (M/M+2).

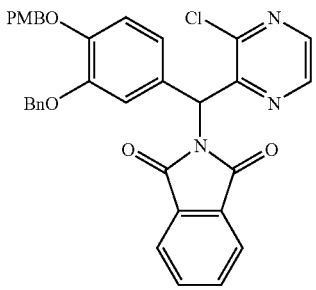

(g) [3-Benzyloxy-4-(4-methoxybenzyloxy)phenyl]-(3-chloropyrazin-2-yl)-methanol: Followed General Lithiation described in Example 92-(e); $^1$H NMR (CDCl$_3$, 400 MHz) δ 3.80 (s, 4H), 4.49 (d, 1H, J=8.0 Hz), 5.06 (s, 2H), 5.10 & 5.14 (AB, 2H, J=12.4 Hz), 5.91 (d, 1H, J=8.0 Hz), 6.82-6.88 (m, 5H), 7.27-7.38 (m, 7H), 8.33 (d, 1H, J=2.4 Hz), 8.49 (d, 1H, J=2.8 Hz); MS (ES): 444.9/446.9 (M−18/M−18+2).

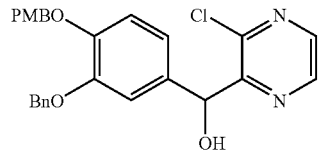

Example 96

4-(8-Amino-3-cyclobutylimidazo[1,5-a]pyrazin-1-yl)-2-benzyloxyphenol: Phosphoramidic acid 2-benzyloxy-4-(8-chloro-3-cyclobutylimidazo[1,5-a]pyrazin-1-yl)-phenyl ester isopropyl ester (300 mg, 0.569 mmol) was dissolved in 2 N NH$_3$ in $^i$PrOH (3 ml) and charged with liquid NH$_3$ (1 ml) in a dry ice/acetone bath. The above mixture was then sealed in a sealed tube and heated at 110° C. After stirring for 14 h, the excess NH$_3$ and the solvent were evaporated. THF (3 ml) was added followed by the addition of LiAlH$_4$ (88.0 mg, 2.28 mmol) at 0° C. under N$_2$. The mixture was then stirred at rt for 26 h. After that time, the reaction mixture was poured into aqueous AcOH (5%, 15 ml) and extracted with EtOAc (3×20 ml). The extracts were washed with H$_2$O (3×15 ml), brine (15 ml) and dried over MgSO$_4$. After concentrating in vacuo, a brown oil (50 mg) was obtained, which was purified by TLC eluting with 3% MeOH/CH$_2$Cl$_2$ to afford 4-(8-amino-3-cyclobutylimidazo[1,5-a]pyrazin-1-yl)-2-benzyloxyphenol as an off-white solid; $^1$H NMR (CDCl$_3$, 400 MHz) δ 1.96-2.22 (m, 2H), 2.44-2.68 (m, 4H), 3.80 (quintet, 1H, J=8.6 Hz), 5.06 (brs, 2H), 5.19 (s, 2H), 7.01 (d, 1H, J=5.2 Hz), 7.05 (d, 1H, J=8.0 Hz), 7.09 (d, 1H, J=5.2 Hz), 7.17 (dd, 1H, J=1.6 & 8.4 Hz), 7.25 (d, 1H, J=2.0 Hz), 7.35-7.44 (m, 5H); MS (ES): 387.0 (M+1).

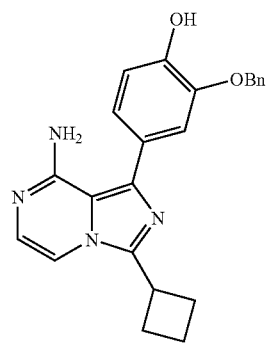

(a) Phosphoramidic acid 2-benzyloxy-4-(8-chloro-3-cyclobutylimidazo[1,5-a]pyrazin-1-yl)-phenyl ester isopropyl ester: Followed General Cyclization described in Example 92-(a) whereby Cyclobutanecarboxylic acid [[3-benzyloxy-4-(4-methoxybenzyloxy)-phenyl]-(3-chloropyrazin-2-yl)-methyl]-amide was treated with POCl$_3$ and then quenched with 2N NH$_3$ in iPrOH to afford the title compound; $^1$H NMR (CDCl$_3$, 400 MHz) δ 1.31 (d, 3H, J=6.0 Hz), 1.35 (d, 3H, J=6.4 Hz), 2.01-2.26 (m, 2H), 2.47-2.69 (m, 4H), 3.02 (d, 2H, J=4.0 Hz), 3.84 (quintet, 1H, J=8.4 Hz), 4.78 (septet, 1H, J=6.1 Hz), 5.17 (s, 2H), 7.27-7.53 (m, 10H); MS (ES): 526.9/528.9 (M/M+2).

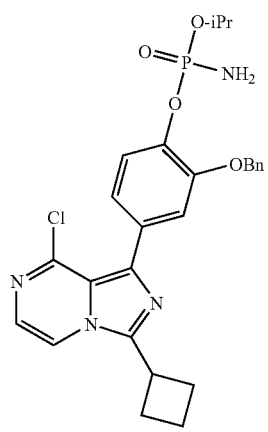

Example 97

4-{8-Amino-1-[3-(2,6-difluoro-benzyloxy)-phenyl]-imidazo[1,5-a]pyrazin-3-yl}-cyclohexanecarboxylic acid amide: The procedures for trans-4-[8-Amino-1-(3-benzyloxy-phenyl)-imidazo[1,5-a]pyrazin-3-yl]-cyclohexanecarboxylic acid amide were applied to 4-{8-Amino-1-[3-(2,6-difluoro-benzyloxy)-phenyl]-imidazo[1,5-a]pyrazin-3-yl}-cyclohexanecarboxylic acid methyl ester to afford the title compound; MS (ES+): m/z 478.02 [MH⁺].

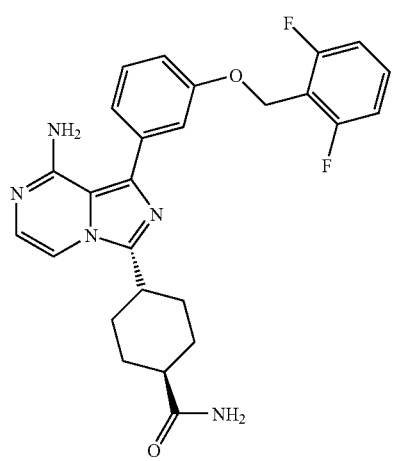

Example 98

4-{8-Amino-1-[3-(2,6-difluoro-benzyloxy)-phenyl]-imidazo[1,5-a]pyrazin-3-yl}-cyclohexanecarboxylic acid methylamide: The amide coupling procedures applied to the synthesis of (trans-4-[8-Amino-1-(3-benzyloxy-phenyl)-imidazo[1,5-a]pyrazin-3-yl]-cyclohexanecarboxylic acid methylamide was applied to 4-{8-Amino-1-[3-(2,6-difluoro-benzyloxy)-phenyl]-imidazo[1,5-a]pyrazin-3-yl}-cyclohexanecarboxylic acid to afford the title compound; MS (ES+): m/z 492.12 [MH⁺].

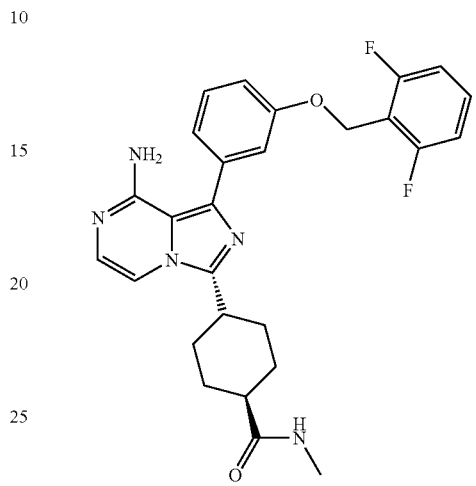

The following analytical conditions and equipment were utilized in Examples 99-293:

NMR spectra were acquired at 27° C. on a Varian Mercury 400 spectrometer operating at 400 MHz or on a Bruker AMX2 500 spectrometer operating at 500 MHz. Flow-injection samples were run on a Bruker BEST system comprising the Bruker AMX2 500 spectrometer, a Gilson 215 autosampler, a heated transfer line and a Bruker 4 mm FI-SEI NMR probe. The BEST system was controlled by XWINNMR software V2.6.

Analytical LC/MS: Samples were analyzed on a multiplexed LC/MS system consisting of a Micromass LCT mass spectrometer with a 5 channel MUX interface, a Waters 1525 binary HPLC pump, 4 Jasco PU-1585 pumps, a CTC HTS PAL autosampler with 4 injection valves, a Waters 2488 UV detector and 4 Waters Atlantis C18 columns (3.1×30 mm, 3 μm). A water/acetonitrile+0.1% formic acid gradient with a cycle time of 6 minutes and a flow rate of 0.85 ml/min was used to elute the compounds. The UV detector was set to 220 nm. The system was controlled by MassLynx 4.0 software.

Mass-directed Purification: The Mass-directed Purification system consisted of a Micromass Platform LC mass spectrometer, a Waters 600 HPLC pump, a Waters Reagent Manager, a Waters 2700 autosampler, a Waters 996 PDA detector, a Waters Fraction Collector II and Waters Xterra Prep MS C18 columns (19×50 mm). Compounds were eluted with variable water/acetonitrile+0.1% formic acid gradients running over a period of 8 minutes. The flow rate was 20 ml/min. The system was controlled by MassLynx and FractionLynx software V3.5.

UV-directed Purification: UV-directed Purification was carried out on a 4 channel Biotage Parallex Flex system equipped with 4 Waters Xterra Prep MS C18 columns (1 9×50 mm). Compounds were eluted using a water/acetonitrile+ 0.1% formic acid gradient with a cycle time of 10 minutes and a flow rate of 20 ml/min. UV detection was at 220 nm and 254 nm. The system was controlled by Biotage Parallex Flex software V2.9.

Analytical LC/MS: Compounds are analyzed using an LC/MS method using the following parameters:

HPLC Gradient:

Solvent A—HPLC grade water+0.1% Formic Acid

Solvent B—HPLC grade Acetonitrile+0.1% Formic Acid

Flow rate 0.85 ml/min 0-0.3 mins 100% A 0.3-4.25 mins 100% A to 10% A 4.25-4.40 mins 10% A to 0% A 4.40-4.90 mins hold at 100% B 4.90-5.00 mins 0% A to 100% A 5.00-6.00 mins Hold at 100% A for re-equilibration Column: Waters Atlantis C18 3u 2.1×30 mm with Phenomenex Polar RP 4.0×2.0 mm Guard column; UV Detection: 220 nm; MS conditions: 80-700 amu scan; Sample cone 30V; Capillary 3.2 kV;

Methods run using the following equipment:

Waters 1525 Binary HPLC pump

4× Jasco PU-1585 pumps

CTC HTS Pal Autosampler with 4 injection valves

Waters 2488 UV detector

Micromass LCT with 5 channel MUX interface

Data acquired using Masslynx V4.0

Mass-directed Purification

Micromass Platform LC

Masslynx V3.5

Waters 600 HPLC pump

Waters Reagent manager

Waters 2700 Autosampler

Waters Fraction Collector II

Waters 996 PDA detector

Flow rate 20 ml/min

Acetonitrile/Water+0.1% Formic Acid with Gradient running over a period of 8 minutes.

Waters Xterra Prep MS C18 columns 19×50 mm

UV-directed Purification

Biotage Parallex Flex 4 Channel UV prep system.

UV detection at 220 and 254 nm

Waters Xterra Prep MS C18 columns 19×50 mm

Acetonitrile/Water+0.1% Formic Acid with Gradient running from 95% Aqueous to 100% Organic over a period of 10 minutes.

Flex software V2.9

Example 99

N-{3-[3-(8-Amino-3-cyclobutyl-imidazo[1,5-a]pyrazin-1-yl)-phenoxymethyl]-phenyl}-acetamide

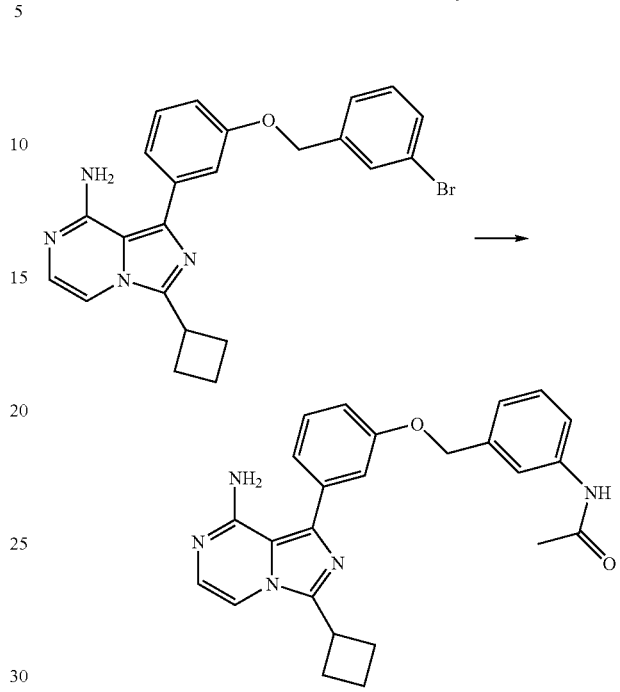

Argon was bubbled through a suspension of 1-[3-(3-bromobenzyloxy)-phenyl]-3-cyclobutyl-imidazo[1,5-a]pyrazin-8-ylamine (1, 25 mg, 0.056 mmol), potassium carbonate (15 mg, 0.109 mmol), copper(I) iodide (10 mg, 0.052 mmol), acetamide (40 mg, 0.68 mmol) and N,N'-dimethylethylenediamine (5 mg, 0.057 mmol), in dioxane (0.5 ml) in a thick walled 5 ml microwave tube. The tube was sealed and heated to 170° C. for 2 hours using the CEM Discover microwave oven at a maximum power of 250 W. The reaction mixture was then partitioned between water (3 ml) and ethyl acetate (3 ml) and the aqueous layer was extracted with further ethyl acetate (2×3 ml). The combined organic extracts were washed with water (2×3 ml) and brine (3 ml) then evaporated in vacuo. The residues after evaporation were dissolved in methanol and loaded on to 1 g SCX cartridges, then eluted with methanol and methanol/ammonia (concentrated aqueous ammonia in methanol, 3% v/v). Fractions containing product were combined and evaporated to furnish N-{3-[3-(8-Amino-3-cyclobutyl-imidazo[1,5-a]pyrazin-1-yl)-phenoxymethyl]-phenyl}-acetamide as an off white solid (10 mg, 0.023 mmol, 42%, 85% pure). This was purified further using preparative mass directed HPLC purification (conditions) to afford 2 as an off white solid (6.3 mg, 0.015 mmol, 27%; (M+H)$^+$ m/z 428.2; Retention Time; 2.87 min; $^1$H-NMR (D4-MeOH) δ 7.72 (1H, br t), 7.53 (1H, br d, J=8 Hz), 7.49 (1H, t, J=8 Hz), 7.43 (1H, d, J=5.1 Hz), 7.35 (1H, t, 7.8 Hz), 7.29 (1H, br t), 7.25-7.22 (2H, m), 7.17 (1H, dd, J=2.8, 8.2 Hz), 7.01 (1H, d, J=5.1 Hz), 5.21 (2H, s), 4.00 (1H, p, J=8.4 Hz), 2.55 (4H, m), 2.22 (1H, m), 2.15 (3H, s), 2.10-2.02 (1H, m).

The following Examples were synthesized following the method described for -{3-[3-(8-Amino-3-cyclobutyl-imidazo[1,5-a]pyrazin-1-yl)-phenoxymethyl]-phenyl}-acetamide.

| Example | Structure | Name | (M+H) ⁺m/z | Mass | HPLC Rt |
|---|---|---|---|---|---|
| 100 | 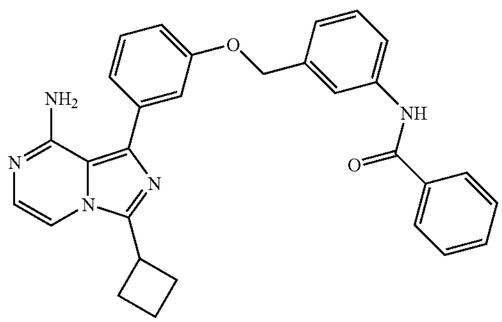 | N-{3-[3-(8-Amino-3-cyclobutyl-imidazo[1,5-a]pyrazin-1-yl)-phenoxymethyl]-phenyl}-benzamide | 490.2 | 13.1 mg | 3.21 min |
| 101 | 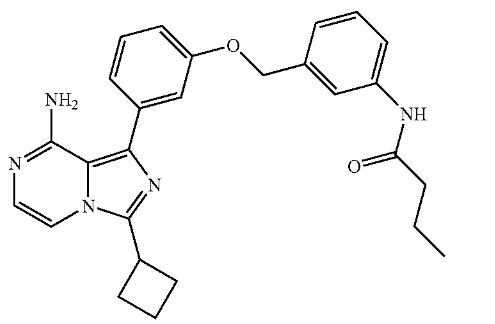 | N-{3-[3-(8-Amino-3-cyclobutyl-imidazo[1,5-a]pyrazin-1-yl)-phenoxymethyl]-phenyl}-butyramide | 456.2 | 10.2 mg | 3.09 min |
| 102 | 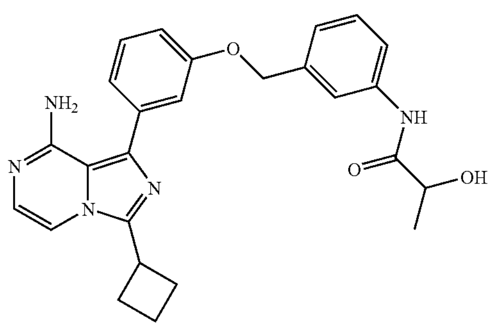 | N-{3-[3-(8-Amino-3-cyclobutyl-imidazo[1,5-a]pyrazin-1-yl)-phenoxymethyl]-phenyl}-2-hydroxy-propionamide | 458.2 | 7.5 mg | 2.74 min |
| 103 | 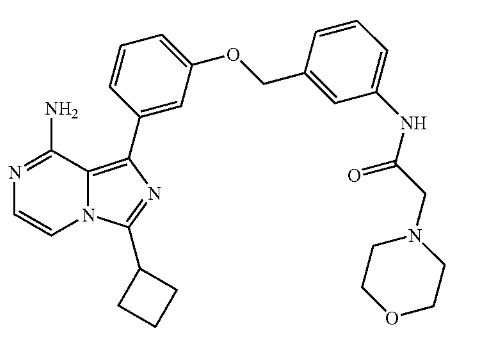 | N-{3-[3-(8-Amino-3-cyclobutyl-imidazo[1,5-a]pyrazin-1-yl)-phenoxymethyl]-phenyl}-2-morpholin-4-yl-acetamide | 513.3 | 22.8 mg | 2.52 min |

-continued

| Example | Structure | Name | (M+H)+ m/z | Mass | HPLC Rt |
|---|---|---|---|---|---|
| 104 | 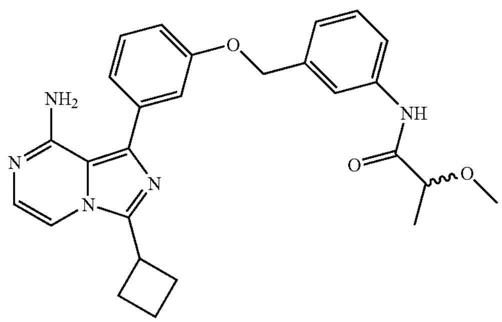 | N-{3-[3-(8-Amino-3-cyclobutyl-imidazo[1,5-a]pyrazin-1-yl)-phenoxymethyl]-phenyl}-2-methoxy-propionamide | 472.2 | 17.1 mg | 2.94 min |
| 105 | 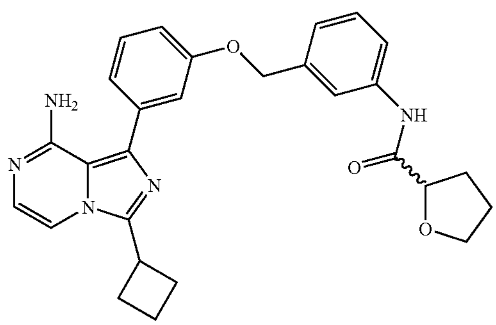 | Tetrahydro-furan-2-carboxylic acid {3-[3-(8-amino-3-cyclobutyl-imidazo[1,5-a]pyrazin-1-yl)-phenoxymethyl]-phenyl}-amide | 484.2 | 22.8 mg | 3.01 min |
| 106 | 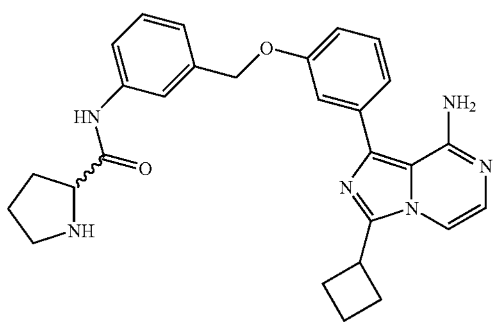 | Pyrrolidine-2-carboxylic acid {3-[3-(8-amino-3-cyclobutyl-imidazo[1,5-a]pyrazin-1-yl)-phhenoxymethyl]-phhenyl}-amide | 483.2 | 8.6 mg | 2.56 min |
| 107 | 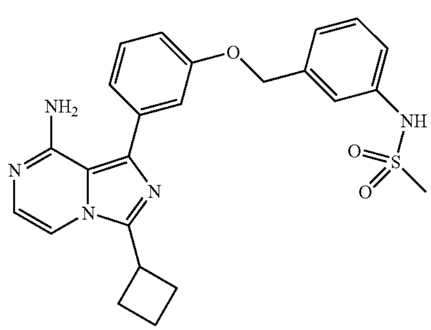 | N-{3-[3-(8-Amino-33-cyclobutyl-imidazo[1,5-a]pyrazin-1-yl)-phenoxymethyl]-phenyl}-methanesulfonamide | 464.1 | 8.1 mg | 2.90 min |

| Example | Structure | Name | (M+H) ⁺m/z | Mass | HPLC Rt |
|---|---|---|---|---|---|
| 108 | 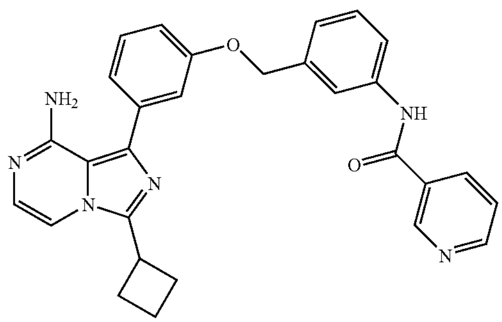 | N-{3-[3-(8-Amino-3-cyclobutyl-imidazo[1,5-a]pyrazin-1-yl)-phenoxymethyl]-phenyl}-nicotinamide | 491.1 | 17.6 mg | 2.79 min |
| 109 | 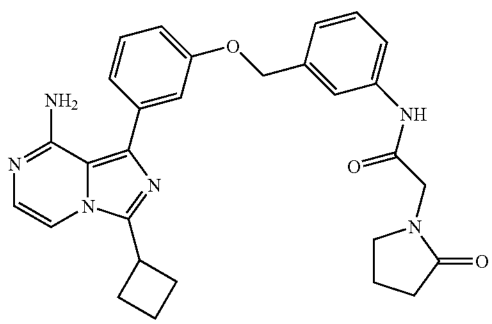 | N-{3-[3-(8-Amino-3-cyclobutyl-imidazo[1,5-a]pyrazin-1-yl)-phenoxymethyl]-phenyl}-2-(2-oxo-pyrrolidin-1-yl)-acetamide | 511.2 | 7.7 mg | 2.84 min |
| 110 | 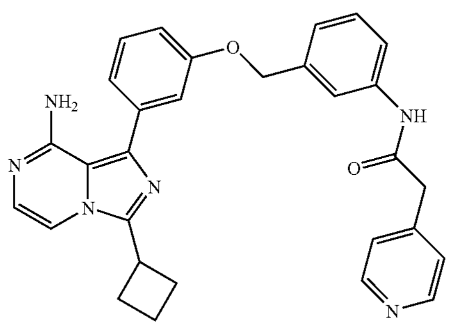 | N-{3-[3-(8-Amino-3-cyclobutyl-imidazo[1,5-a]pyrazin-1-yl)-phenoxymethyl]-phenyl}-2-pyridin-4-yl-acetamide | 505.2 | 6 mg | 2.57 min |
| 111 | 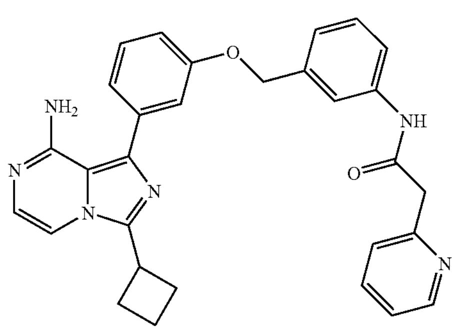 | N-{3-[3-(8-Amino-3-cyclobutyl-imidazo[1,5-a]pyrazin-1-yl)-phenoxymethyl]-phenyl}-2-pyridin-2-yl-acetammide | 505.2 | 10.3 mg | 2.76 min |

-continued

| Example | Structure | Name | (M+H) ⁺m/z | Mass | HPLC Rt |
|---|---|---|---|---|---|
| 112 | 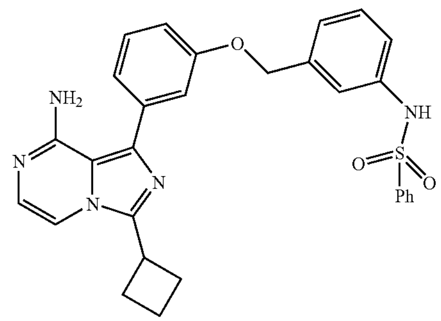 | N-{3-[3-(8-Amino-3-cyclobutyl-imidazo[1,5-a]pyrazin-1-yl)-phenoxymethyl]-phenyl}-benzenesulfonamide | 526.1 | 13.1 mg | 3.20 min |
| 113 | 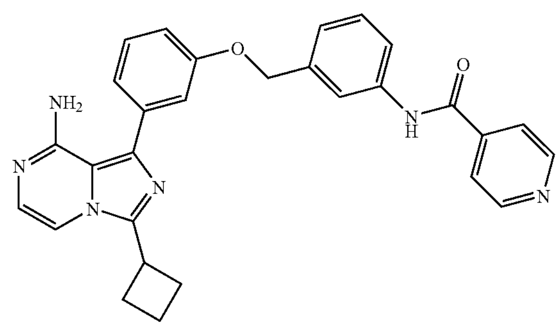 | N-{3-[3-(8-Amino-3-cyclobutyl-imidazo[1,5-a]pyrazin-1-yl)-phenoxymethyl]-phenyl}-isonicotinamide | 491.2 | 10.2 mg | 2.93 mg |
| 114 | 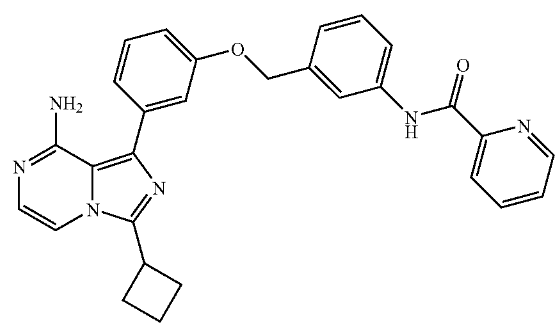 | Pyridine-2-carboxylic acid {3-[3-(8-amino-3-cyclobutyl-imidazo[1,5-a]-pyrazin-1-yl)-phenoxymethyl]-phenyl}-amide | 491.2 | 15.7 mg | 3.26 min |
| 115 | 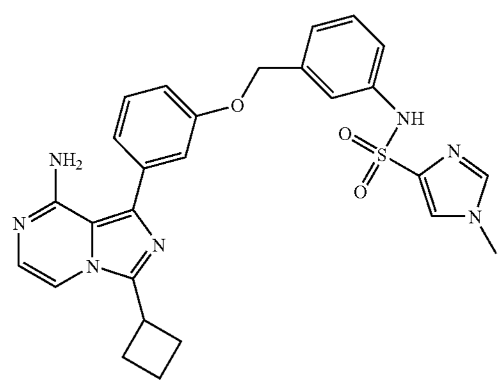 | 1-Methyl-1H-imidazole-4-sulfonic acid {3-[3-(8-amino-3-cyclobutyl-imidazo[1,5-a]pyrazin-1-yl)-phenoxymethyl]-phenyl}-amide | 530.1 | 2.1 mg | 2.87 min |

The following compounds were synthesized in the same manner using the isomeric 1-[3-(2-bromobenzyloxy)-phenyl]-3-cyclobutyl-imidazo[1,5-a]pyrazin-8-ylamine as starting material.

| Example | Structure | Name | (M+H) ⁺m/z | Mass | HPLC Rt |
|---|---|---|---|---|---|
| 116 | 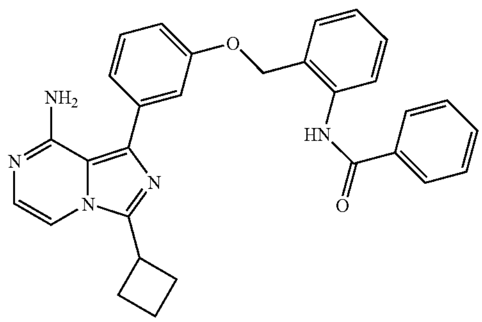 | N-{2-[3-(8-Amino-3-cyclobutyl-imidazo[1,5-a]pyrazin-1-yl)-phenoxymethyl]-phenyl}-benzamide | 490.2 | 14 mg | 3.01 min |
| 117 | 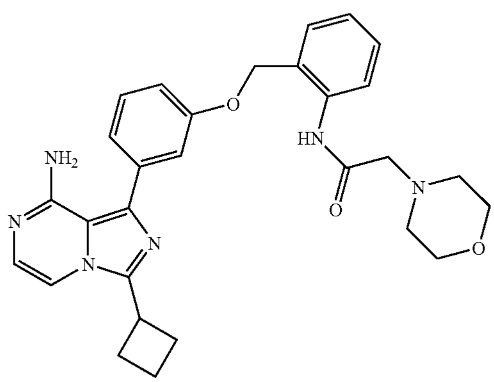 | N-{2-[3-(8-Amino-3-cyclobutyl-imidazo[1,5-a]pyrazin-1-yl)-phenoxymethyl]-pheenyl}-2-morpholin-4-yl-acetammide | 513.2 | 14 mg | 2.57 min |
| 118 | 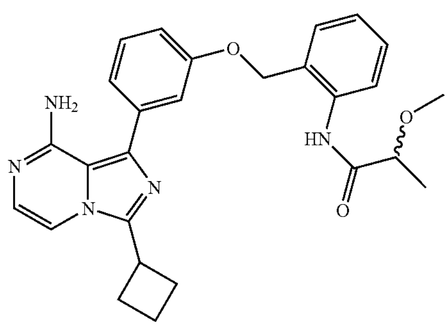 | N-{2-[3-(8-Amino-3-cyclobutyl-imidazo[1,5-a]pyrazin-1-yl)-phenoxymethyl]-phenyl}-2-methoxy-propionamide | 472.2 | 14.9 mg | 2.87 min |
| 119 | 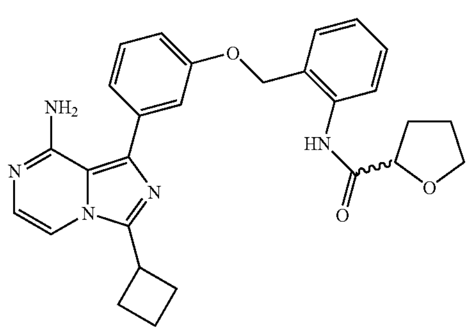 | Tetrahydro-furan-2-carboxylicc acid {2-[3-(8-amino-3-cyclobutyl-imidazo[1,5-a]pyrazin-1-yl)-phenoxymethyl]-phenyl}-amide | 484.2 | 13.7 mg | 2.94 min |

| | | | | | |
|---|---|---|---|---|---|
| 120 | 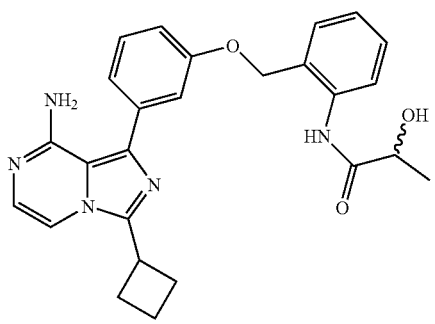 | N-{2-[3-(8-Amino-3-cyclobutyl-imidazo[1,5-a]pyrazin-1-yl)-phenoxymethyl]-phenyl}-2-hydroxy-propionamide | 458.2 | 10 mg | 2.77 mg |
| 121 | 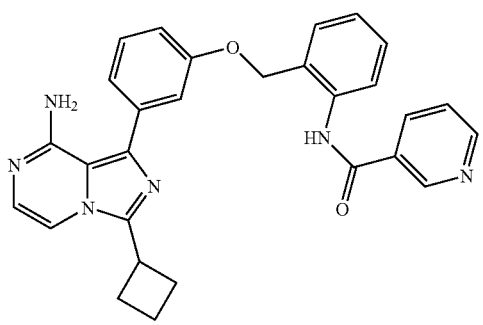 | N-{2-[3-(8-Amino-3-cyclobutyl-imidazo[1,5-a]pyrazin-1-yl)-phenoxymethyl]-phenyl}-nicotinamide | 491.2 | 3.8 mg | 2.79 min |
| 122 | 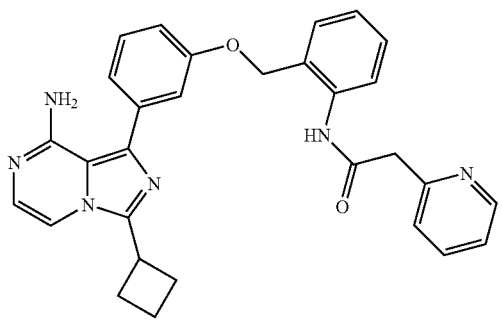 | N-{2-[3-(8-Amino-3-cyclobutyl-imidazo[1,5-a]pyrazin-1-yl)-phenoxymethyl]-phenyl}-2-pyridin-2-yl-acetamide | 505.2 | 7.5 mg | 2.67 min |
| 123 | 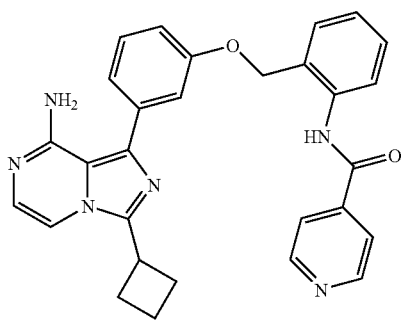 | N-{2-[3-(8-Amino-3-cyclobutyl-imidazo[1,5-a]pyrazin-1-yl)-phenoxymethyl]-phenyl}-isonicotinamide | 491.2 | 11.4 mg | 2.72 min |

General procedure for Alkylation Reactions of toluene-4-sulfonic acid 4-[8-amino-1-(3-benzyloxy-phenyl)-imidazo[1,5-a]pyrazin-3-yl]-cyclohexylmethyl ester and toluene-4-sulfonic acid 4-[8-amino-1-(3-benzyloxy-phenyl)-imidazo[1,5-a]pyrazin-3-yl]-2-ethyl-butyl ester with amines

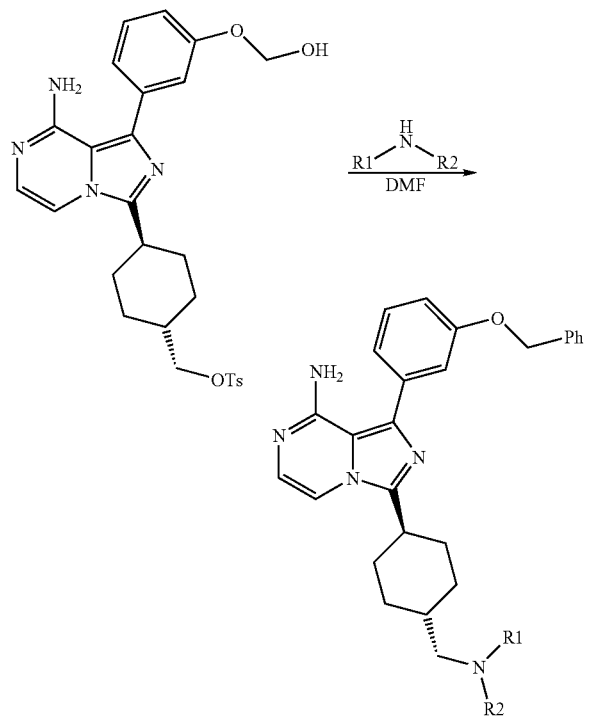

Example 124

1-(3-Benzyloxy-phenyl)-3-(4-phenylaminomethyl-cyclohexyl)-imidazo[1,5-a]pyrazin-8-ylamine To a solution of toluene-4-sulfonic acid 4-[8-amino-1-(3-benzyloxy-phenyl)-imidazo[1,5-a]pyrazin-3-yl]-cyclohexylmethyl ester (29 mg, 0.05 mmol) in DMF (0.5 ml) was added aniline (23 μl, 0.25 mmol). The reaction was irradiated in the microwave (200 W, 150° C., 10 m), then evaporated to dryness. The crude reaction product was dissolved in MeOH (2 ml) and added to a pre-wetted MCX cartridge (6 ml/500 mg). The cartridge was washed with MeOH (10 ml) and the product was then eluted using 1% $NH_3$ in MeOH (15 ml). The product was further purified using mass-directed HPLC, to give 1-(3-benzyloxy-phenyl)-3-(4-phenylaminomethyl-cyclohexyl)-imidazo[1,5-a]pyrazin-8-ylamine formic acid salt (7.8 mg, 31%) as an off-white solid: 1H NMR (400 MHz, $CD_3OD$) δ 8.25 (s, 1H), 7.60 (d, 1H, J=5.5 Hz), 7.48-7.41 (m, 3H), 7.36 (t, 2H, J=7.3 Hz), 7.33-7.27 (m, 1H), 7.25-7.22 (m, 1H), 7.18 (d, 1H, J=7.4 Hz), 7.13 (dd, 1H, J=5.5 Hz, 2.3 Hz), 7.08 (t, 2H, J=7.8 Hz), 6.97 (d, 1H, J=5.5 Hz), 6.63 (d, 2H, J=7.4 Hz), 6.58 (t, 1H, J=7.4 Hz), 5.16 (s, 2H), 3.12 (m, 1H), 3.00 (d, 2H, J=6.7 Hz), 2.06 (br. d, 4H, J=11.7 Hz), 1.88-1.70 (m, 3H), 1.30-1.22 (m, 2H), 3H not observed ($NH_2$ and NH); MS (ES+) m/z 504.24 [MH+] at Rt 3.47 min.

| Example | R1 | Name | MH+ | HPLC Rt |
|---|---|---|---|---|
| | 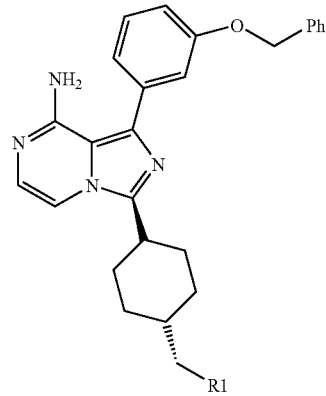 | | | |
| 124 | 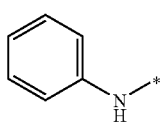 | 1-(3-Benzyloxy-phenyl)-3-(4-phenylaminomethyl-cyclohexyl)-imidazo[1,5-a]pyrazin-8-ylamine | 504.24 | 3.47 mins |

| Example | R1 | Name | MH+ | HPLC Rt |
|---|---|---|---|---|
| 125 | morpholine | 1-(3-Benzyloxy-phenyl)-3-(4-morpholin-4-ylmethyl-cyclohexyl)-imidazo[1,5-a]pyrazin-8-ylamine | 498.24 | 2.69 mins |
| 126 | 4-methylpiperazine | 1-(3-Benzyloxy-phenyl)-3-[4-(4-methyl-piperazin-1-ylmethyl)-cyclohexyl]-imidazo[1,5-a]pyrazin-8-ylammine | 511.37 | 2.47 mins |
| 127 | diethylamine | 1-(3-Benzyloxy-phenyl)-3-(4-diethylaminomethyl-cyclohexyl)-imidazo[1,5-a]pyrazin-8-ylamine | 484.28 | 2.87 mins |
| 128 | 4-hydroxypiperidine | 1-{4-[8-Amino-1-(3-benzyloxy-phenyl)-imidazo[1,5-a]pyrazin-3-yl]-cyclohexylmethyl}-piperidin-4-ol | 512.2 | 2.52 mins |
| 129 | azepane | 3-(4-Azepan-1-ylmethyl-cyclohexyl)-1-(3-benzyloxy-phenyl)-imidazo[1,5-a]pyrazin-8-ylamine | 510.29 | 2.90 mins |
| 130 | ethyl-methyl-amine | 1-(3-Benzyloxy-phenyl)-3-{4-[(ethyl-methyl-amino)-methyl]-cyclohexyl}-imidazo[1,5-a]pyrazin-8-ylamine | 470.18 | 2.59 mins |
| 131 | 3-hydroxypiperidine | 1-{4-[8-Amino-1-(3-benzoyloxy-phenyl)-imidazo[1,5-a]pyrazin-3-yl]-cyclohexylmethyl}-piperidin-3-ol | 512.21 | 2.59 mins |
| 132 | N,N,N'-trimethylethylenediamine | N-{4-[8-Amino-1-(3-benzyloxy-phenyl)-imidazo[1,5-a]pyrazin-3-yl]-cyclohexylmethyl}-N,N',N'-trimethyl-ethasne-1,2-diamine | 513.23 | 2.54 mins |
| 133 | 2-(methylamino)ethanol | 2-({4-[8-Amino-1-(3-benzyloxy-phenyl)-imidazo[1,5-a]pyrazin-3-yl]-cyclohexylmethyl}-methyl-amino)-ethanol | 486.18 | 2.59 mins |
| 134 | piperazin-2-one | 4-{4-[8-Amino-1-(3-benzyloxy-phenyl)-imidazo[1,5-a]pyrazin-3-yl]-cyclohexylmethyl}-piperazin-2-one | 511.17 | 2.49 mins |

-continued

| Example | R1 | Name | MH+ | HPLC Rt |
|---|---|---|---|---|
| 135 | 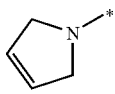 | 1-(3-Benzyloxy-phenyl)-3-[4-(2,5-dihydro-pyrrol-1-ylmethyl)-cyclohexyl]-imidazo[1,5-a]pyrazin-8-ylamine | 480.26 | 2.84 mins |
| 136 | 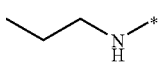 | 1-(3-Benzyloxy-phenyl)-3-(4-propylaminomethyl-cyclohexyl)-imidazo[1,5-a]pyrazin-8-ylamine | 470.26 | 2.69 mins |
| 137 | 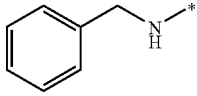 | 3-[4-(Benzylamino-methyl)-cyclohexyl]-1-(3-benzyloxy-phenyl)-imidazo[1,5-a]pyrazin-8-ylamine | 518.25 | 2.74 mins |
| 138 | 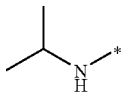 | 1-(3-Benzyloxy-phenyl)-3-[4-(isopropylamino-methyl)-cyclohexyl]-imidazo[1,5-a]pyrazin-8-ylamine | 470.26 | 2.69 mins |
| 139 | 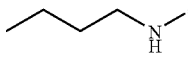 | 1-(3-Benzyloxy-phenyl)-3-(4-butylaminomethyl-cyclohexyl)-imidazo[1,5-a]pyrazin-8-ylamine | 484.27 | 2.69 mins |
| 140 | 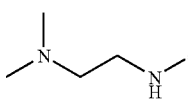 | N-{4-[8-Amino-1-(3-benzyloxy-phenyl)-imidazo[1,5-a]pyrazin-3-yl]-cyclohexylmethyl}-N',N'-dimethyl-ethane-1,2-diamine | 499.23 | 2.32 mins |
| 141 | 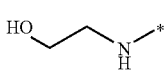 | 2-({4-[8-Amino-1-(3-benzyloxy-phenyl)-imidazo[1,5-a]pyrazin-3-yl]-cyclohexylmethyl}-amino)-ethanol | 472.26 | 2.74 mins |
| 142 | 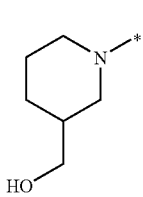 | (1-{4-[8-Amino-1-(3-benzyloxy-phenyl)-imidazo[1,5-a]pyrazin-3-yl]-cyclohexylmethyl}-piperidin-3-yl)-methanol | 526 | 2.95 mins |
| 143 | 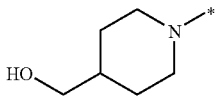 | (1-{4-[8-Amino-1-(3-benzyloxy-phenyl)-imidazo[1,5-a]pyrazin-3-yl]-cyclohexylmethyl}-piperidin-4-yl)-methanol | 526.02 | 2.99 mins |
| 144 | 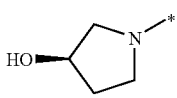 | 1-{4-[8-Amino-1-(3-benzyloxy-phenyl)-imidazo[1,5-a]pyrazin-3-yl]-cyclohexylmethyl}-pyrrolidin-3-ol | 498.02 | 3.24 mins |
| 145 |  | 1-{4-[8-Amino-1-(3-benzyloxy-phenyl)-imidazo[1,5-a]pyrazin-3-yl]-cyclohexylmethyl}-pyrrolidin-3-ol | 497.99 | 2.94 mins |
| 146 | 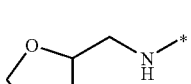 | 1-(3-Benzyloxy-phenyl)-3-(4-{[(tetrahydro-furan-2-ylmethyl)-amino]-methyl}-cyclohexyl)-imidazo[1,5-a]pyrazin-8-ylamine | 511.99 | 2.99 mins |
| 147 | 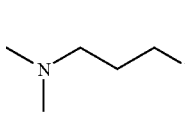 | N-{4-[8-Amino-1-(3-benzyloxy-phenyl)-imidazo[1,5-a]pyrazin-3-yl]-cyclohexylmethyl}-N',N'-dimethyl-propane-1,3-diamine | 513.04 | 2.87 mins |

-continued

| Example | R1 | Name | MH+ | HPLC Rt |
|---|---|---|---|---|
| 148 | (structure: HOCH(CH3)CH2NH-*) | 1-({4-[8-Amino-1-(3-benzyloxy-phenyl)-imidazo[1,5-a]pyrazin-3-yl]-cyclohexylmethyl}-amino)-propan-2-ol | 486.01 | 2.87 mins |
| 149 | HOCH2CH2CH2NH-* | 3-({4-[8-Amino-1-(3-benzyloxy-phenyl)-imidazo[1,5-a]pyrazin-3-yl]-cyclohexylmethyl}-amino)-propan-1-ol | 486 | 2.87 mins |
| 150 | (pyridin-3-ylmethyl-NH-*) | 1-(3-Benzyloxy-phenyl)-3-(4-{[(pyridin-3-ylmethyl)-amino]-methyl}-cyclohexyl)-imidazo[1,5-a]pyrazin-8-ylamine | 518.99 | 2.82 mins |
| 151 | (pyrrolidin-1-yl-CH2CH2-NH-*) | 1-(3-Benzyloxy-phenyl)-3-{4-[2-pyrrolidin-1-yl-ethylamino)-methyl]-cyclohexyl}-imidazo[1,5-a]pyrazin-8-ylamine | 525.05 | 2.99 mins |
| 152 | (Et2N-CH2CH2-NH-*) | N-{4-[8-Ammino-1-(3-benzyloxy-phenyl)-imidazo[1,5-a]pyrazin-3-yl]-cyclohexylmethyl}-N',N'-diethyl-ethane-1,2-diamine | 527.05 | 2.87 mins |
| 153 | (1-methyl-piperidin-4-yl-NH-*) | 1-(3-Benzyloxy-phenyl)-3-{4-[(1-methyl-piperidin-4-ylamino)-methyl]-cyclohexyl}-imidazo[1,5-a]pyrazin-8-ylamine | 524.97 | 2.62 mins |
| 154 | (CH3C(O)NH-CH2CH2-NH-*) | N-[2-({4-[8-Amino-1-(3-benzyloxy-phenyl)-imidazo[1,5-a]pyrazin-3-yl]-cyclohexylmethyl}-amino)-ethyl]-acetamide | 513.02 | 2.72 mins |
| 155 | (piperidin-1-yl-*) | 1-(3-Benzyloxy-phenyl)-3-(4-piperidin-1-ylmethyl-cyclohexyl)-imidazo[1,5-a]pyrazin-8-ylaamine | 496.4 | 2.69 mins |

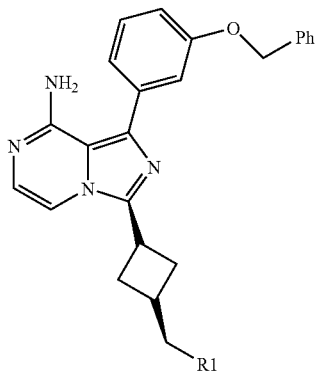

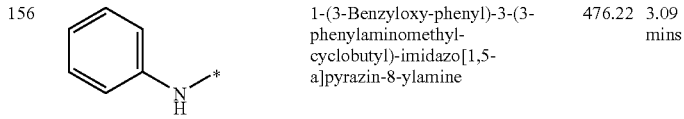

| 156 | (PhNH-*) | 1-(3-Benzyloxy-phenyl)-3-(3-phenylaminomethyl-cyclobutyl)-imidazo[1,5-a]pyrazin-8-ylamine | 476.22 | 3.09 mins |

-continued

| Example | R1 | Name | MH+ | HPLC Rt |
|---|---|---|---|---|
| 157 | ethyl-methyl-amino | 1-(3-Benzyloxy-phenyl)-3-{3-[(ethyl-methyl-amino)-methyl]-cyclobutyl}-imidazo[1,5-a]pyrazin-8-ylamine | 442.18 | 2.59 mins |
| 158 | 2-methyl-pyrrolidinyl | 1-(3-Benzyloxy-phenyl)-3-[3-(2-methyl-pyrrolidin-1-ylmethyl)-cyclobutyl]-imidazo[1,5-a]pyrazin-8-ylammine | 468.26 | 2.64 mins |
| 159 | piperidinyl | 1-(3-Benzyloxy-phenyl)-3-(3-piperidin-1-ylmethyl-cyclobutyl)-imidazo[1,5-a]pyrazin-8-ylamine | 468.26 | 2.81 mins |
| 160 | butylamino | 1-(3-Benzyloxy-phenyl)-3-(3-butylamminomethyl-cyclobutyl)-imidazo[1,5-a]pyrazin-8-ylamine | 456.23 | 2.72 mins |
| 161 | 2,5-dihydro-pyrrolyl | 1-(3-Benzyloxy-phenyl)-3-[3-(2,5-dihydro-pyrrol-1-ylmethyl)-cyclobutyl]-imidazo[1,5-a]pyrazin-8-ylamine | 452.21 | 2.64 mins |
| 162 | azepanyl | 3-(3-Azepan-1-ylmethyl-cyclobutyl)-1-(3-benzyloxy-phenyl)-imidazo[1,5-a]pyrazin-8-ylamine | 482.28 | 2.74 mins |
| 163 | propylamino | 1-(3-Benzyloxy-phenyl)-3-(3-propylaminomethyl-cyclobutyl)-imidazo[1,5-a]pyrazin-8-ylamine | 442.24 | 2.59 mins |
| 164 | piperazin-2-one | 4-{3-[8-Amino-1-(3-benzyloxy-phenyl)-imidazo[1,5-a]pyrazin-3-yl]-cyclobutylmethyl}-piperazin-2-one | 483.18 | 2.49 mins |
| 165 | benzylamino | 3-[3-(Benzylamino-methyl)-cyclobutyl]-1-(3-benzyloxy-phenyl)-imidazo[1,5-a]pyrazin-8-ylamine | 490.224 | 2.99 mins |
| 166 | 4-methyl-piperazinyl | 1-(3-Benzyloxy-phenyl)-3-[3-(4-methyl-piperazin-1-ylmethyl)-cyclobutyl]-imidazo[1,5-a]pyrazin-8-ylamine | 483.19 | 2.37 mins |
| 167 | HO-ethyl-methyl-amino | 2-({3-[8-Amino-1-(3-benzyloxy-phenyl)-imidazo[1,5-a]pyrazin-3-yl]-cyclobutylmethyl}-methyl-amino)-ethanol | 458.24 | 2.57 mins |
| 168 | 4-hydroxy-piperidinyl | 1-{3-[8-Amino-1-(3-benzyloxy-phenyl)-imidazo[1,5-a]pyrazin-3-yl]-cyclobutylmethyl}-piperidin-4-ol | 484.26 | 2.52 mins |
| 169 | isopropylamino | 1-(3-Benzyloxy-phenyl)-3-[3-(isopropylamino-methyl)-cyclobutyl]-imidazo[1,5-a]pyrazin-8-ylamine | 442.25 | 2.82 mins |

-continued

| Example | R1 | Name | MH+ | HPLC Rt |
|---|---|---|---|---|
| 170 | 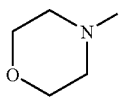 | 1-(3-Benzyloxy-phenyl)-3-(3-morpholin-4-ylmethyl-cyclobutyl)-imidazo[1,5-a]pyrazin-8-ylamine | 470.24 | 2.62 mins |
| 171 | 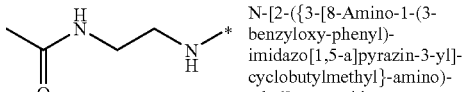 | N-[2-({3-[8-Amino-1-(3-benzyloxy-phenyl)-imidazo[1,5-a]pyrazin-3-yl]-cyclobutylmethyl}-amino)-ethyl]-acetamide | 485.24 | 2.72 mins |
| 172 | 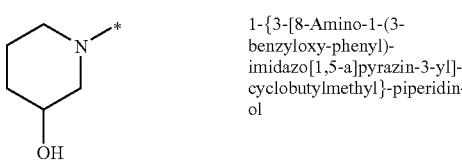 | 1-{3-[8-Amino-1-(3-benzyloxy-phenyl)-imidazo[1,5-a]pyrazin-3-yl]-cyclobutylmethyl}-piperidin-3-ol | 484.24 | 2.49 mins |
| 173 | 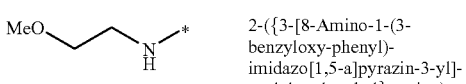 | 2-({3-[8-Amino-1-(3-benzyloxy-phenyl)-imidazo[1,5-a]pyrazin-3-yl]-cyclobutylmethyl}-amino)-ethanol | 458.23 | 2.54 mins |
| 174 | 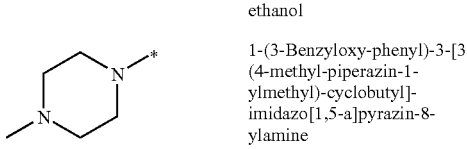 | 1-(3-Benzyloxy-phenyl)-3-[3-(4-methyl-piperazin-1-ylmethyl)-cyclobutyl]-imidazo[1,5-a]pyrazin-8-ylamine | 482.98 | 2.49 mins |

General procedure for amide couplings of 4-[8-amino-1-(3-benzyloxy-phenyl)-imidazo[1,5-a]pyrazin-3-yl]-cyclohexanecarboxylic acid with amines

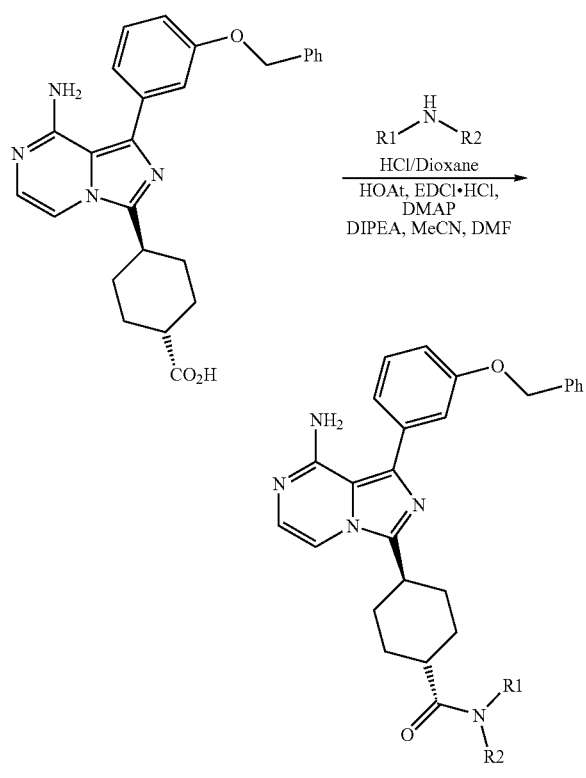

Example 175

4-[8-Amino-1-(3-benzyloxy-phenyl)-imidazo[1,5-a]pyrazin-3-yl]-cyclohexanecarboxylic acid (2-diethylamino-ethyl)-amide To a stirred solution of 2-(dimethylamino)ethylamine (11.6 mg, 0.1 mmol) in MeCN (0.4 ml) was added 4M HCl in 1,4-dioxane (0.1 ml, 0.4 mmol). After stirring for 1 hour at room temperature, a solution of 4-[8-amino-1-(3-benzyloxy-phenyl)-imidazo[1,5-a]pyrazin-3-yl]-cyclohexanecarboxylic acid (22 mg, 0.05 mmol) in DMF (1 ml) was added, followed by a solution of EDCI.HCl (14.3 mg, 0.075 mmol), HOAt (10.2 mg, 0.075 mmol) and a catalytic amount of DMAP in DMF (0.5 ml). DIPEA (0.087 ml, 0.5 mmol) was added, and the reaction was stirred at room temperature overnight. The reaction mixture was poured onto saturated aqueous NaHCO$_3$ solution (10 ml) and extracted with EtOAc (2×10 ml). The combined organics were washed with brine (3×10 ml), dried (MgSO$_4$), filtered and concentrated in vacuo. The crude product was purified using mass-directed HPLC to give 4-[8-Amino-1-(3-benzyloxy-phenyl)-imidazo[1,5-a]pyrazin-3-yl]-cyclohexanecarboxylic acid (2-diethylamino-ethyl)-amide bis-formic acid salt (10.8 mg, 40%) as an off-white solid: 1H NMR (400 MHz, CD$_3$OD) δ 8.38 (s, 2H), 7.60 (d, 1H, J=5.4 Hz), 7.47-7.43 (m, 3H), 7.37 (t, 2H, J=7.4 Hz), 7.33-7.28 (m, 1H), 7.24 (s, 1H), 7.19 (d, 1H, J=7.4 Hz), 7.15-7.13 (dd, 1H, J=5.3 Hz, 2.4 Hz), 6.99 (d, 1H, 5.5 Hz), 5.17 (s, 2H), 3.56 (t, 2H, J=6.1 Hz), 3.32-3.24 (m, 6H), 3.18 (t, 1H, J=10.0 Hz), 2.38 (t, 1H, J=8.4 Hz), 2.10 (dd, 2H, J=7.9 Hz, 2.4 Hz), 2.01 (dd, 2H, J=6.7 Hz, 2.7 Hz), 1.89-1.66 (m, 4H), 1.34 (t, 6H, J=7.4 Hz), 3H not observed (NH$_2$ & NH); LCMS (ES+) m/z 541.01 [MH+] at Rt 2.99 min.

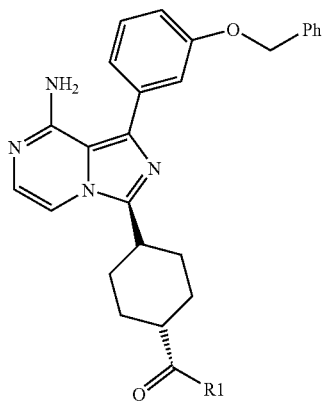

| Example | R1 | Name | MH+ | HPLC Rt |
|---|---|---|---|---|
| 175 | diethylaminoethyl-NH- | 4-[8-Amino-1-(3-benzyloxy-phenyl)-imidazo[1,5-a]pyrazin-3-yl]-cyclohexanecarboxylic acid (2-diethylamino-ethyl)-amide | 541.01 | 2.99 mins |
| 176 | MeO-CH2CH2-NH- | 4-[8-Amino-1-(3-benzyloxy-phenyl)-imidazo[1,5-a]pyrazin-3-yl]-cyclohexanecarboxylic acid (2-methoxy-ethyl)-amide | 500.22 | 2.94 mins |
| 177 | HO-CH2CH2-NH- | 4-[8-Amino-1-(3-benzyloxy-phenyl)-imidazo[1,5-a]pyrazin-3-yl]-cyclohexanecarboxylic acid (2-hydroxy-ethyl)-amidce | 486.25 | 3.02 mins |
| 178 | morpholin-4-yl | {4-[8-Amino-1-(3-benzyloxy-phenyl)-imidazo[1,5-a a]pyrazin-3-yl]-ccyclohexyl}-morpholin-4-yl-methanone | 512.33 | 3.04 mins |
| 179 | benzyl-NH- | 4-[8-Amino-1-(3-benzyloxy-phenyl)-imidazo[1,5-a]pyrazin-3-yl]-cyclohexanecarboxylic acid benzylamide | 532.26 | 3.36 mins |
| 180 | 4-hydroxy-piperidin-1-yl | {4-[8-Amino-1-(3-benzyloxy-phenyl)-imidazo[1,5-a]pyrazin-3-yl-cyclohexyl}-(4-hydroxy-piperidin-1-yl)-methanone | 526.77 | 2.94 mins |
| 181 | HO-CH2CH2-N(Me)- | 4-[8-Amino-1-(3-benzyloxy-phenyl)-imidazo[1,5-a]pyrazin-3-yl]-cyclohexanecarboxylic acid (2-hydroxy-ethyl)-methyl-amide | 500.16 | 2.97 mins |
| 182 | azepan-1-yl | {4-[8-Amino-1-(3-benzyloxy-phenyl)-imidazo[1,5-a]pyrazin-3-yl-cyclohexyl}-azepan-1-yl-methanone | 524.4 | 3.36 mins |
| 183 | piperidin-1-yl | {4-[8-Amino-1-(3-benzyloxy-phenyl)-imidazo[1,5-a]pyrazin-3-yl]-cyclohexyl}-piperidin-1-yl-methanone | 510.19 | 3.27 mins |

-continued

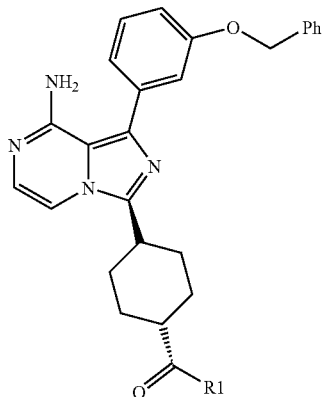

| Example | R1 | Name | MH+ | HPLC Rt |
|---|---|---|---|---|
| 184 | propyl-NH-* | 4-[8-Amino-1-(3-benzyloxy-phenyl)-imidazo[1,5-a]pyrazin-3-yl]-cyclohexanecarboxylic acid butylamide | 498.2 | 3.45 mins |
| 185 | CH3-C(O)-NH-CH2CH2-NH-* | 4-[8-Amino-1-(3-benzyloxy-phenyl)-imidazo[1,5-a]pyrazin-3-yl]-cyclohexanecarboxylic acid (2-acetylamino-ethyl)-amide | 527.21 | 2.94 mins |
| 186 | 3-hydroxy-piperidin-1-yl | {4-[8-Amino-1-(3-benzyloxy-phenyl)-imidazo[1,5-a]pyrazin-3-yl]-cyclohexyl}-(3-hydroxy-piperidin-1-yl)-methanone | 526.2 | 2.97 mins |
| 187 | (CH3)2N-CH2CH2-N(CH3)-* | 4-[8-Amino-1-(3-benzyloxy-phenyl)-imidazo[1,5-a]pyrazin-3-yl]-cyclohexanecarboxylic acid (2-dimethylamino-ethyl)-methyl-amide | 527.26 | 2.87 mins |
| 188 | CH3-N(CH2CH3)-* | 4-[8-Amino-1-(3-benzyloxy-phenyl)-imidazo[1,5-a]pyrazin-3-yl]-cyclohexanecarboxylic acid ethyl-methyl amide | 484.21 | 3.24 mins |
| 189 | pyrrolidin-1-yl | {4-[8-Amino-1-(3-benzyloxy-phenyl)-imidazo[1,5-a]pyrazin-3-yl]-cyclohexyl}-pyrrolidin-1-yl-methanone | 496.22 | 3.09 mins |
| 190 | cyclopropyl-NH-* | 4-[8-Amino-1-(3-benzyloxy-phenyl)-imidazo[1,5-a]pyrazin-3-yl]-cyclohexanecarboxylic acid cycloprropylammide | 482.21 | 3..20 mins |
| 191 | Ph-NH-* | 4-[8-Amino-1-(3-benzyloxy-phenyl)-imidazo[1,5-a]pyrazin-3-yl]-cyclohexanecarboxylic acid phenylamide | 518.21 | 3.34 mins |
| 192 | 4-methyl-piperazin-1-yl | {4-[8-Amino-1-(3-benzyloxy-phenyl)-imidazo[1,5-a]pyrazin-3-yl]-cyclohexyl}-(4-methyl-piperazin-1-yl)-methanone | 525.25 | 2.59 mins |

-continued

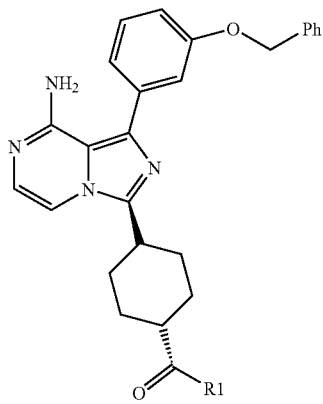

| Example | R1 | Name | MH+ | HPLC Rt |
|---|---|---|---|---|
| 193 | piperazin-2-one (N-linked), with NH and C=O | 44-{4-[8-Amino-1-(3-benzyloxy-phenyl)-imidazo[1,5-a]pyrazin-3-yl]-cyclohexanecarbonyl}-piperazin-2-one | 525.22 | 2.89 mins |
| 194 | 3-(hydroxymethyl)piperidin-1-yl | {4-[8-Amino-1-(3-benzyloxy-phenyl)-imidazo[1,5-a]pyrazin-3-yl]-ccyclohexyl}-(3-hydroxymethyl-piperidin-1-yl)-methanone | 539.94 | 3.45 mins |
| 195 | 4-(hydroxymethyl)piperidin-1-yl | {4-[8-Ammino-1-(3-benzyloxy-phenyl)-imidazo[1,5-a]pyrazin-3-yl]-cyclohexyl}-(4-hydroxymethyl-piperidin-1-yl)-methanone | 539.97 | 3.26 mins |
| 196 | (R)-3-hydroxy-pyrrolidin-1-yl | {4-[8-Amino-1-(3-hydroxy-phenyl)-imidazo[1,5-a]pyrazin-3-yl]-cyclohexyl}-(3-hydroxy-pyrrolidin-1-yl)-methanone | 511.93 | 3.45 mins |
| 197 | (S)-3-hydroxy-pyrrolidin-1-yl | {4-[8-Amino-1-(3-benzyloxy-phenyl)-imidazo[1,5-a]pyrazin-3-yl]-cyclohexyl}-(3-hydroxy-pyrrolidin-1-yl)-methanone | 511.96 | 3.32 mins |
| 198 | pyridin-2-ylmethylamino | 4-[8-Amino-1-(3-benzyloxy-phenyl)-imidazo[1,5-a]pyrazin-3-yl]-cyclohexanecarboxylic acid (pyridin-2-ylmethyl)-amide | 533.03 | 2.74 mins |
| 199 | (tetrahydrofuran-2-yl)methylamino | 4-[8-Amino-1-(3-benzyloxy-phenyl)-imidazo[1,5-a]pyrazin-3-yl]-cyclohexanecarboxylic acid (tetrahydro-furan-2-ylmethyl)-amide | 525.93 | 3.36 mins |
| 200 | 3-(dimethylamino)propylamino | 4-[8-Amino-1-(3-benzyloxy-phenyl)-imidazo[1,5-a]pyrazin-3-yl]-cyclohexanecarboxylic acid (3-dimethylamino-propyl)-amide | 527.02 | 3.20 mins |
| 201 | 2-hydroxypropylamino | 4-[8-Amino-1-(3-benzyloxy-phenyl)-imidazo[1,5-a]pyrazin-3-yl]-cyclohexanecarboxylic acid (2-hydroxy-propyl)-amide | 499.95 | 3.29 mins |

-continued

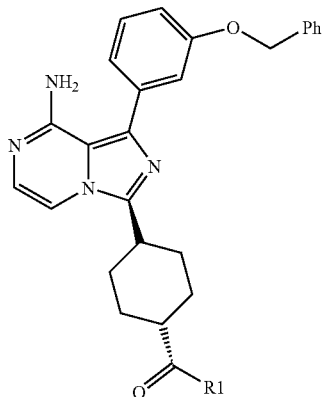

| Example | R1 | Name | MH+ | HPLC Rt |
|---|---|---|---|---|
| 202 | HO~~~N(H)–* | 4-[8-Amino-1-(3-benzyloxy-phenyl)-imidazo[1,5-a]pyrazin-3-yl]-cyclohexanecarboxylic acid (3-hydroxy-propyl)-amide | 499.94 | 3.45 mins |
| 203 | pyridin-3-yl-CH2-N(H)–* | 4-[8-Amino-1-(3-benzyloxy-phenyl)-imidazo[1,5-a]pyrazin-3-yl]-cyclohexanecarboxylic acid (pyridin-3-ylmethyl)-amide | 532.96 | 3.04 mins |
| 204 | pyridin-4-yl-CH2-N(H)–* | 4-[8-Amino-1-(3-benzyloxy-phenyl)-imidazo[1,5-a]pyrazin-3-yl]-cyclohexanecarboxylic acid (pyridin-4-ylmethyl)-amide | 532.96 | 3.06 mins |
| 205 | pyrrolidin-1-yl-CH2CH2-N(H)–* | 4-[8-Amino-1-(3-benzyloxy-phenyl)-imidazo[1,5-a]pyrazin-3-yl]-cyclohexanecarboxylic acid (2-pyrrolidin-1-yl-ethyl)-amide | 539.01 | 2.97 mins |
| 206 | azetidin-1-yl–* | {4-[8-Amino-1-(3-benzyloxy-phenyl)-imidazo[1,5-a]-pyrazin-3-yl]-cyclohexyl}-azetidin-1-yl-methanone | 482.22 | 2.99 mins |
| 207 | 1-methyl-piperidin-4-yl-N(H)–* | 4-[8-Amino-1-(3-benzyloxy-phenyl)-imidazo[1,5-a]pyrazin-3-yl]-cyclohexanecarboxylic acid (1-methyl-piperidin-4-yl)-amide | 539 | 3.17 mins |
| 208 | (1H-imidazol-4-yl)-CH2CH2-N(H)–* | 4-[8-Amino-1-(3-benzyloxy-phenyl)-imidazo[1,5-a]pyrazin-3-yl]-cyclohexanecarboxylic acid [2-(1H-imidazol-4-yl)-ethyl]-amide | 535.98 | 3.09 mins |
| 209 | CH3CH2CH2-N(H)–* | 4-[8-Amino-1-(3-benzyloxy-phenyl)-imidazo[1,5-a]pyrazin-3-yl]-cyclohexanecarboxylic acid propylamide | 484.23 | 3.04 mins |
| 210 | (CH3)2CHCH2-N(H)–* | 4-[8-Amino-1-(3-benzyloxy-phenyl)-imidazo[1,5-a]pyrazin-3-yl]-cyclohexanecarboxylic acid isobutyl-amide | 498.28 | 3.21 mins |

General procedure for phenolic alkylations of 3-(8-Amino-3-cyclobutyl-imidazo[1,5-a]pyrazin-1-yl)-phenol with alkyl halides

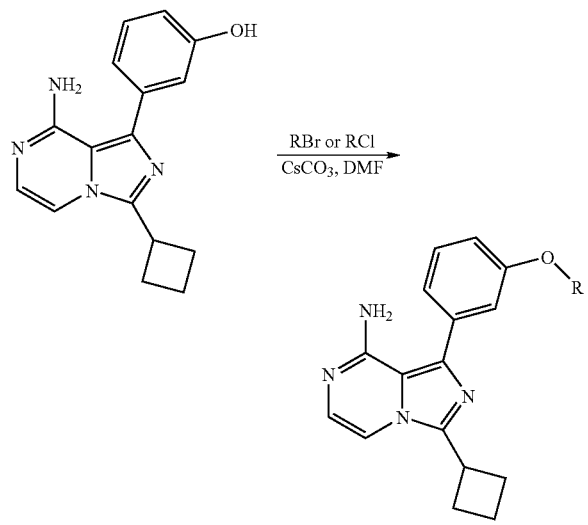

Example 211

2-[3-(8-Amino-3-cyclobutyl-imidazo[1,5-a]pyrazin-1-yl)-phenoxy]-ethanol

To a solution of 3-(8-amino-3-cyclobutyl-imidazo[1,5-a]pyrazin-1-yl)-phenol (28 mg, 0.1 mmol) in anhydrous DMF (1 ml) was added cesium carbonate (49 mg, 0.15 mmol) followed by a solution of 2-bromoethanol (12.5 mg, 0.1 mmol) in DMF (0.5 ml). The reaction was stirred at 60° C. overnight. The reaction was poured onto saturated $NaHCO_3$ (10 ml) and extracted with EtOAc (2×10 ml). The combined organics were washed with water (10 ml) and aqueous brine solution (3×10 ml), dried ($MgSO_4$), filtered and concentrated in vacuo. Purification by mass-directed HPLC gave 2-[3-(8-Amino-3-cyclobutyl-imidazo[1,5-a]pyrazin-1-yl)-phenoxy]-ethanol formic acid salt (4.0 mg, 12%) as an off-white solid: 1H NMR (400 MHz, $CD_3OD$) δ 8.54 (s, 1H), 7.48-7.41 (m, 2H), 7.13-7.09 (m, 2H), 7.01 (d, 1H, J=10.3 Hz), 6.93 (d, 1H, J=5.8 Hz), 4.14 (t, 2H, J=4.9 Hz), 4.03-3.97 (m, 1H), 3.92 (t, 2H, J=4.9 Hz), 2.61-2.51 (m, 4H), 2.15-2.10 (m, 1H), 2.06-2.01 (m, 1H), 3H not observed ($NH_2$ & OH); LCMS (ES+) m/z 325.08 [MH+] at Rt 2.39 min.

| Example | R1 | Name | MH⁺ | HPLC Rt |
|---|---|---|---|---|
| 211 | *~~OH | 2-[3-(8-Amino-3-cyclobutyl-imidazo[1,5-a]pyrazin-1-yl)-phenoxy]-ethanol | 325.08 | 2.39 mins |
| 212 | *~~Ph | 3-Cyclobutyl-1-(3-phenethoxy-phenyl)-imidazo[1,5-a]pyrazin-8-ylamine | 385.37 | 3.32 mins |
| 213 | *~CH(CH3)2 | 3-Cyclobutyl-1-(3-isobutoxy-phenyl)-imidazo[1,5-a]pyrazin-8-ylamine | 337.31 | 3.01 mins |
| 214 | *~~~N(morpholine) | 3-Cyclobutyl-1-[3-(3-morpholin-4-yl-propoxy)-phenyl]-imidazo[1,5-a]pyrazin-8-ylamine | 408.34 | 2.15 mins |

-continued

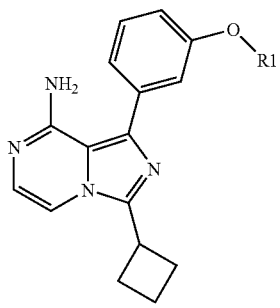

| Example | R1 | Name | MH+ | HPLC Rt |
|---|---|---|---|---|
| 215 | piperidinyl-ethyl | 3-Cyclobutyl-1-[3-(2-piperidin-1-yl-ethoxy)-phenyl]-imidazo[1,5-a]pyrazin-8-ylamine | 392.35 | 2.17 mins |
| 216 | cyclohexylmethyl | 3-Cyclobutyl-1-(3-cyclohexylmethoxy-phenyl)-imidazo[1,5-a]pyrazin-8-ylamine | 377.35 | 3.22 mmins |
| 217 | imidazolyl-ethyl | 3-Cyclobutyl-1-[3-(2-imidazol-1-yl-ethoxy)-phenyl]-imidazo[1,5-a]-pyrazin-8-ylamine | 375.29 | 2.22 mins |
| 218 | CH2C(O)O-tBu | [3-(8-Amino-3-cyclobutyl-imidazo[1,5-a]pyrazin-1-yl)-phenoxy]-acetic acid tert-butyl ester | 395.16 | 2.99 mins |
| 219 | CH2C(O)Et | 1-0[3-(8-Amino-3-cyclobutyl-imidazo[1,5-a]pyrazin-1-yl)-phenoxy]-butan-2-one | 351.15 | 2.69 mins |
| 220 | CH2C(O)OMe | [3-(8-Amino-3-cyclobutyl-imidazo[1,5-a]pyrazin-1-yl)-phenoxy]-acetic acid methyl ester | 353.14 | 2.64 mins |
| 221 | Me | 3-Cyclobutyl-1-(3-methoxy-phenyl)-imidazo[1,5-a]pyrazin-8-ylamine | 295.13 | 2.56 mins |
| 222 | 3-methyl-but-2-enyl | 3-Cyclobutyl-1-[3-(3-methyl-but-2-enyloxy)-phenyl]-imidazo[1,5-a]pyrazin-8-ylamine | 349.17 | 3.06 mins |
| 223 | diethylamino-ethyl | 3-Cyclobutyl-1-[3-(2-diethylamino-ethoxy)-phenyl]-imidazo[1,5-a]pyrazin-8-ylamine | 380.2 | 2.15 mins |
| 224 | CH2CN | [3-(8-Amino-3-cyclobutyl-imidazo[1,5-a]pyrazin-1-yl)-phenoxy]-acetonitrile | 320.15 | 2.64 mins |
| 225 | cyclohexyl | 3-Cyclobutyl-1-(3-cyclohexylmethoxy-phenyl)-imidazo[1,5-a]pyrazin-8-ylamine | 363.17 | 3.24 mins |

-continued

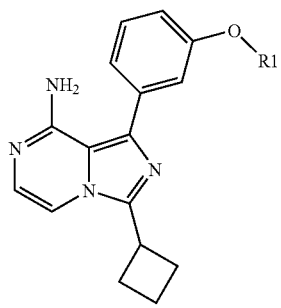

| Example | R1 | Name | MH+ | HPLC Rt |
|---|---|---|---|---|
| 226 | *-CH2-C(=O)-NH2 | 2-[3-(8-Amino-3-cyclobutyl-imidazo[1,5-a]pyrazin-1-yl)-phenoxy]-acetamide | 338.05 | 2.54 mins |
| 227 | *-CH2-cyclopropyl | 3-Cyclobutyl-1-(3-cyclopropylmethoxy-phenyl)-imidazo[1,5-a]pyrazin-8-ylamine | 335.15 | 3.01 mins |
| 228 | *-CH2-cyclopentyl | 3-Cyclobutyl-1-(3-cyclopentylmethoxy-phenyl)-imidazo[1,5-a]pyrazin-8-ylamine | 349.11 | 2.97 mins |
| 229 | *-CH2CH2-OMe | 3-Cyclobutyl-1-[3-(2-methoxy-ethoxy)-phenyl]-imidazo[1,5-a]pyrazin-8-ylamine | 339.11 | 2.79 mins |
| 230 | *-CH2CH2CH(CH3)2 | 3-Cyclobutyl-1-[3-(3-methyl-butoxy)-phenyl]-imidazo[1,5-a]pyrazin-8-ylamine | 351.11 | 3.22 mins |
| 231 | *-CH2CH2-N(pyrrolidine) | 3-Cyclobutyl-1-[3-(2-pyrrolidin-1-yl-ethoxy)-phenyl]-imidazo[1,5-a]pyrazin-8-ylamine | 378.12 | 2.34 mins |
| 232 | *-CH2-C(=O)-N(morpholine) | 2-[3-(8-Amino-3-cyclobutyl-imidazo[1,5-a]pyrazin-1-yl)-phenoxy]-1-morpholin-4-yl-ethanone | 408.15 | 2.65 mins |
| 233 | *-CH2-C(=O)-N(pyrrolidine) | 2-[3-(8-Amino-3-cyclobutyl-imidazo[1,5-a]pyrazin-1-yl)-phenoxy]-1-pyrrolidin-1-yl-ethanone | 392.15 | 2.89 mins |
| 234 | *-CH2-C(=O)-NH-propyl | 2-[3-(8-Amino-3-cyclobutyl-imidazo[1,5-a]pyrazin-1-yl)-phenoxy]-N-propyl-acetamide | 380.15 | 2.72 mins |
| 235 | *-CH2-C(=O)-NH-CH3 | 2-[3-(8-Amino-3-cyclobutyl-imidazo[1,5-a]pyrazin-1-yl)-phenoxy]-N-methyl-acetamide | 352.11 | 2.65 mins |

205

General procedure for phenolic alkylations of 3-(8-Amino-3-cyclobutyl-imidazo[1,5-a]pyrazin-1-yl)-phenol with benzyl halides

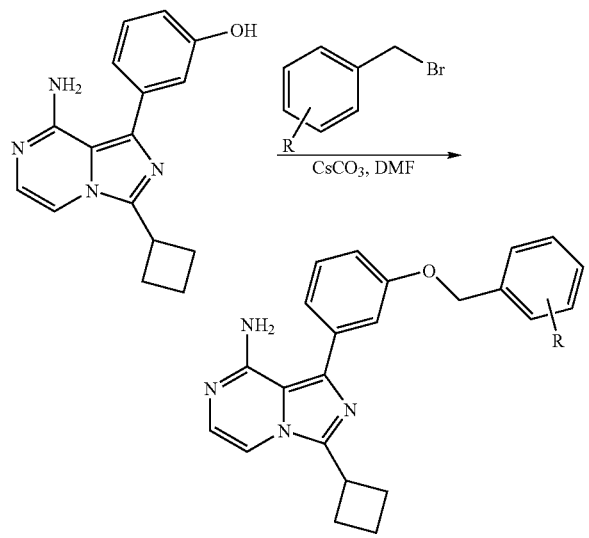

206

Example 236

3-Cyclobutyl-1-[3-(3-methoxy-benzyloxy)-phenyl]-imidazo[1,5-a]pyrazin-8-ylamine

To a solution of 3-(8-amino-3-cyclobutyl-imidazo[1,5-a]pyrazin-1-yl)-phenol (28 mg, 0.1 mmol) in anhydrous DMF (1 ml) was added cesium carbonate (49 mg, 0.15 mmol) followed by a solution of 3-methoxybenzyl bromide (20 mg, 0.1 mmol) in DMF (0.5 ml). The reaction was stirred at room temperature overnight. The reaction was poured onto saturated NaHCO$_3$ (10 ml) and extracted with EtOAc (2×10 ml). The combined organics were washed with water (10 ml) and aqueous brine solution (3×10 ml), dried (MgSO$_4$), filtered and concentrated in vacuo, to give 3-cyclobutyl-1-[3-(3-methoxy-benzyloxy)-phenyl]-imidazo[1,5-a]pyrazin-8-ylamine as a brown solid (24.1 mg, 60%): 1H NMR (400 MHz, CDCl$_3$) δ 7.42 (t, 1H, J=7.8 Hz), 7.35-7.27 (m, 3H), 7.13 (d, 1H, J=5.1 Hz), 7.08-7.03 (m, 4H), 6.90 (d, 1H, J=8.6 Hz), 5.17 (s, 2H), 3.84 (s, 3H), 3.86-3.79 (m, 1H, obscured), 2.72-2.62 (m, 2H), 2.56-2.47 (m, 2H), 2.25-2.14 (m, 1H), 2.11-2.02 (m, 1H), 2H not observed (NH$_2$); LCMS (ES+) m/z 401.34 [MH+] at Rt 3.20 min.

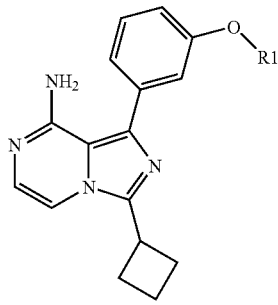

| Example | R1 | Name | MH+ | HPLC Rt |
|---|---|---|---|---|
| 236 | ![3-OMe benzyl] | 3-Cyclobutyl-1-[3-(3-methoxy-benzyloxy)-phenyl]-imidazo[1,5-a]pyrazin-8-ylamine | 4401.34 | 3.20 mins |
| 237 | ![2-Cl benzyl] | 1-[3-(2-Chloro-benzyloxy)-phenyl]-3-cyclobutyl-imidazo[1,5-a]pyrazin-8-ylamine | 405.29 | 3.22 mins |
| 238 | ![3-Cl benzyl] | 1-[3-(3-Chloro-benzyloxy)-phenyl]-3-cyclobutyl-imidazo[1,5-a]pyrazin-8-ylamine | 405.29 | 3.14 mins |

-continued

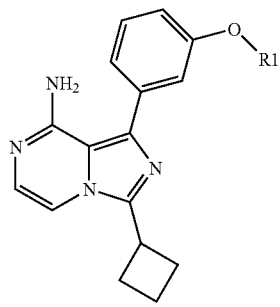

| Example | R1 | Name | MH+ | HPLC Rt |
|---|---|---|---|---|
| 239 | 4-chlorobenzyl | 1-[3-(4-Chloro-benzyloxy)-phenyl]-3-cyclobutyl-imidazo[1,5-a]pyrazin-8-ylamine | 405.29 | 3.14 mins |
| 240 | pyridin-3-ylmethyl | 3-Cyclobutyl-1-[3-(pyridin-3-ylmethoxy)-phenyl]-imidazo[1,5-a]pyrazin-8-ylamine | 372.36 | 2.39 mins |
| 241 | (5-methylisoxazol-3-yl)methyl | 3-Cyclobutyl-1-[3-(5-methyl-isoxazol-3-ylmethoxy)-phenyl]-imidazo[1,5-a]pyrazin-8-ylamine | 376.33 | 2.74 mins |
| 242 | (2,6-dichloropyridin-4-yl)methyl | 3-Cyclobutyl-1-[3-(2,6-dichloro-pyridin-4-ylmethoxy)-phenyl]-imidazo[1,5-a]pyrazin-8-ylamine | 440.27 | 3.12 mins |
| 243 | biphenyl-4-ylmethyl | 1-[3-(Biphenyl-4-ylmethoxy)-phhenyl]-3-cyclobutyl-imidazo[1,5-a]pyrazin-8-ylamine | 447.34 | 3.45 mins |
| 244 | 2-(benzenesulfonyl)benzyl | 1-[3-(2-Benzenesulfonyl-benzyloxy)-phenyl]-3-cyclobutyl-imidazo[1,5-a]pyrazin-8-ylamine | 525.42 | 3.34 mins |
| 245 | naphthalen-2-ylmethyl | 3-Cyclobutyl-1-[3-(naphthalen-2-ylmethoxy)-phenyl]-imidazo[1,5-a]pyrazin-8-ylamine | 421.31 | 3.42 mins |
| 246 | 4-(1,2,4-triazol-1-yl)benzyl | 3-Cyclobutyl-1-[3-(4-[1,2,4]triazol-1-yl-benzyloxy)-phenyl]-imidazo[1,5-a]pyrazin-8-ylammine | 438.35 | 2.87 mins |

-continued

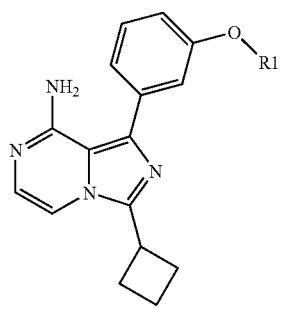

| Example | R1 | Name | MH+ | HPLC Rt |
|---|---|---|---|---|
| 247 | 4-methylbenzyl | 3-Cyclobutyl-1-[3-(4-methyl-benzyloxy)-phenyl]-imidazo[1,5-a]pyrazin-8-ylamine | 385.36 | 2.90 mins |
| 248 | 2,6-dichlorobenzyl | 3-Cyclobutyl-1-[3-(2,6-dichloro-benzyloxy)-phenyl]-imidazo[1,5-a]pyrazin-8-ylamine | 439.27 | 3.39 mins |
| 249 | 3-trifluoromethylbenzyl | 3-Cyclobutyl-1-[3-(3-trifluoromethyl-benzyloxy)-phenyl]-imidazo[1,5-a]pyrazin-8-ylamine | 439.3 | 3.17 mins |
| 250 | 4-tert-butylbenzyl | 1-[3-(4-tert-Butyl-benzyloxy)-phenyl]-3-cyclobutyl-imidazo[1,5-a]pyrazin-8-ylamine | 427.38 | 3.54 mins |
| 251 | 2-phenylbenzyl | 1-[3-(Biphenyl-2-ylmethoxy)-phenyl]-3-cyclobutyl-imidazo[1,5-a]pyrazin-8-ylamine | 447.37 | 3.26 mins |
| 252 | 4-cyanobenzyl | 4-[3-(8-Amino-3-cyclobutyl-imidazo[1,5-a]pyrazin-1-yl)-phenoxymethyl]-benzonitrile | 396.29 | 3.12 mins |
| 253 | 2,3-difluorobenzyl | 3-Cyclobutyl-1-[3-(2,3-difluoro-benzyloxy)-phenyl]-imidazo[1,5-a]pyrazin-8-ylamine | 407.29 | 3.07 mins |
| 254 | 3,5-dimethylbenzyl | 3-Cyclobutyl-1-[3-(3,5-dimethyl-benzyloxy)-phenyl]-imidazo[1,5-a]pyrazin-8-ylamine | 399.34 | 3.36 mins |

-continued

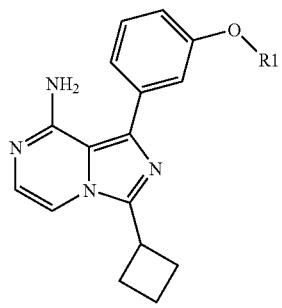

| Example | R1 | Name | MH+ | HPLC Rt |
|---|---|---|---|---|
| 255 | *-CH2-C6H3(OCF3)(CH3) (3,5-substituted) | 3-Cyclobutyl-1-[3-(3-trifluoromethoxy-benzyloxy)-phenyl]-imidazo[1,5-a]pyrazin-8-ylamine | 455.31 | 3.24 mins |
| 256 | *-CH2-C6H4-CN (ortho) | 2-[3-(8-Amino-3-cyclobutyl-imidazo[1,5-a]pyrazin-1-yl)-phenoxymethyl]-benzonitrile | 396.31 | 3.14 mins |
| 257 | *-CH2-C6H4-OCF3 (para) | 3-Cyclobutyl-1-[3-(4-trifluoromethoxy-benzyloxxy)-phenyl]-imidazo[1,5-a]pyrazin-8-ylammine | 455.32 | 3.20 mins |
| 258 | *-CH2-C6H3F2 (3,4-difluoro) | 3-Cyclobutyl-1-[3-(3,4-difluoro-benzyloxy)-phenyl]-imidazo[1,5-a]pyrazin-8-ylammine | 407.31 | 3.24 mins |
| 259 | *-CH2-benzo[1,2,5]oxadiazol-5-yl | 1-[3-(Benzo[1,2,5]oxadiazol-5-ylmethoxy)-phhenyl]-3-cyclobutyl-imidazo[1,5-a]pyrazin-8-ylamine | 413.31 | 3.01 mins |
| 260 | *-CH2-C6H2F3 (2,3,5-trifluoro) | 3-Cyclobutyl-1-[3-(3,4,5-trifluoro-benzyloxy)-phenyl]-imidazo[1,5-a]pyrazin-8-ylamine | 425.3 | 3.37 mins |
| 261 | *-CH2-C6H3(F)(CF3) (2-F,5-CF3) | 3-Cyclobutyl-1-[3-(2-fluoro-5-trifluoromethyl-benzyloxy)-phenyl]-imidazo[1,5-a]pyrazin-8-ylamine | 457.3 | 3.22 mins |
| 262 | *-CH2-C6H4-OCHF2 (para) | 3-Cyclobutyl-1-[3-(4-difluoromethoxy-benzyloxy)-phenyl]-imidazo[1,5-a]pyrazin-8-ylamine | 437.31 | 3.26 mins |

-continued

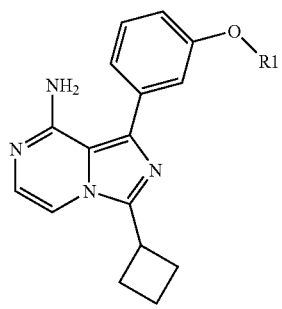

| Example | R1 | Name | MH+ | HPLC Rt |
|---|---|---|---|---|
| 263 | 5-chlorobenzo[b]thiophen-3-ylmethyl | 1-[3-(5-Chloro-benzo[b]thiophen-3-ylmethoxy)-phenyl]-3-ccyclobutyl-imidazo[1,5-a]pyrazin-8-ylamine | 461.29 | 3.37 mins |
| 264 | 4-chloro-2-fluorobenzyl | 1-[3-(4-Chloro-2-fluoro-benzyloxy)-phenyl]-3-ccyclobutyl-imidazo[1,5-a]pyrazin-8-ylamine | 423.27 | 3.36 mins |
| 265 | 3,5-difluorobenzyl | 3-Cyclobutyl-1-[3-(3,5-difluoro-benzyloxy)-phenyl]-imidazo[1,5-a]pyrazin-8-ylamine | 407.27 | 3.09 mins |
| 266 | 2,6-difluorobenzyl | 3-Cyclobutyl-1-[3-(2,6-difluoro-benzyloxy)-phenyl]-imidazo[1,5-a]pyrazin-8-ylamine | 407.25 | 3.09 mins |
| 267 | 3-fluorobenzyl | 3-Cyclobutyl-1-[3-(3-fluoro-benzyloxy)-phenyl]-i imidazo-[1,5-a]pyrazin-8-ylammine | 389.34 | 3.27 mins |
| 268 | naphthalen-1-ylmethyl | 3-Cyclobutyl-1-[3-(naphthalen-1-ylmethoxy)-phenyl]-imidazo[1,5-a]pyrazin-8-ylamine | 421.36 | 3.19 mins |
| 269 | 2,5-difluorobenzyl | 3-Cyclobutyl-1-[3-(2,5-difluoro-benzyloxy)-phenyl]-imidazo[1,5-a]pyrazin-8-ylammine | 407.31 | 3.11 mins |
| 270 | 2-chloro-6-fluorobenzyl | 1-[3-(2-Chloro-6-fluoro-benzyloxy)-phenyl]-3-cyclobutyl-imidazo[1,5-a]pyrazin-8-ylamine | 423.33 | 3.07 mins |

-continued

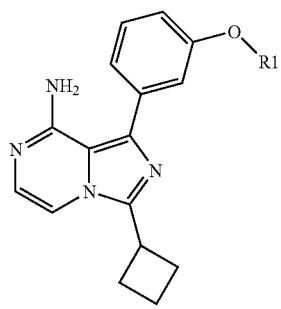

| Example | R1 | Name | MH+ | HPLC Rt |
|---|---|---|---|---|
| 271 | 2,3,6-trifluorobenzyl | 3-Cyclobutyl-1-[3-(2,3,6-trifluoro-benzyloxy)-phenyl]-imidazo[1,5-a]pyrazin-8-ylamine | 425.34 | 3.07 mins |
| 272 | 2,3-difluorobenzyl | 3-Cyclobutyl-1-[3-(2-fluor-benzyloxy)-phenyl]-imidazo[1,5-a]pyrazin-8-ylamine | 389.31 | 2.99 mins |
| 273 | 2-(OCHF2)benzyl | 3-Cyclobutyl-1-[3-(2-difluoromethoxy-benzyloxy)-phenyl]-imidazo[1,5-a]pyrazin-8-ylamine | 437.31 | 3.24 mins |
| 274 | 3-(OCHF2)benzyl | 3-Cyclobutyl-1-[3-(3-difluoromethoxy-benzyloxy)-phenyl]-imidazo[1,5-a]pyrazin-8-ylamine | 437.32 | 3.12 mins |
| 275 | quinolin-8-ylmethyl | 3-Cyclobutyl-1-[3-(quinolin-8-ylmethoxy)-phenyl]-imidazo[1,5-a]pyrazin-8-ylamine | 422.26 | 2.95 mins |
| 276 | 1-phenylethyl | 3-Cyclobutyl-1-[3-(1-phenyl-ethoxy)-phenyl]-imidazo[1,5-a]pyrazin-8-ylammine | 385.33 | 3.04 mins |

-continued

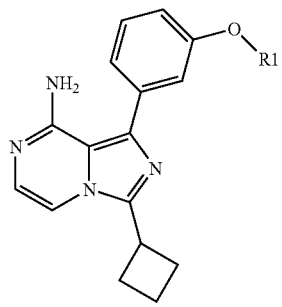

| Example | R1 | Name | MH+ | HPLC Rt |
|---|---|---|---|---|
| 277 | *-CH2-C6H4-CO2H (3-substituted) | 3-[3-(8-Amino-3-cyclobutyl-imidazo[1,5-a]pyrazin-1-yl)-phenoxymethyl]-benzoic acid | 415.34 | 2.90 mins |
| 278 | *-CH2-(pyridin-2-yl) | 3-Cyclobutyl-1-[3-(pyridin-2-ylmethoxy)-phenyl]-imidazo[1,5-a]pyrazin-8-ylamine | 372.18 | 2.49 mins |
| 279 | *-CH2-(3,5-dimethyl-isoxazol-4-yl) | 3-Cyclobutyl-1-[3-(3,5-dimethyl-isoxazol-4-ylmethoxy)-phenyl]-imidazo[1,5-a]pyrazin-8-ylamine | 390.22 | 2.87 mins |
| 280 | *-CH2-(5-methyl-3-phenyl-isoxazol-4-yl) | 3-Cyclobutyl-1-[3-(5-methyl-3-phenyl-isoxazol-4-ylmethoxy)-phenyl]-imidazo[1,5-a]pyrazin-8-ylamine | 452.19 | 3.07 mins |

General procedure for $S_NAr$ reactions of 1-(3-Benzyloxy-phenyl)-8-chloro-3-cyclobutyl-imidazo[1,5-a]pyrazine with amines

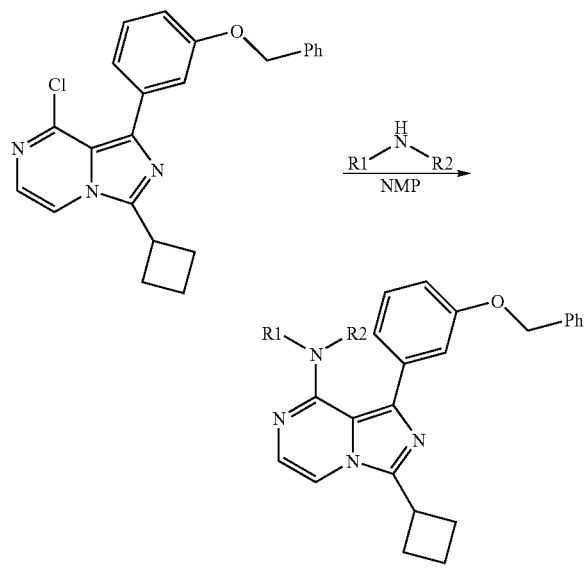

Example 281

[1-(3-Benzyloxy-phenyl)-3-cyclobutyl-imidazo[1,5-a]pyrazin-8-yl]-isopropyl-amine To a solution of 1-(3-benzyloxy-phenyl)-8-chloro-3-cyclobutyl-imidazo[1,5-a]pyrazine (30 mg, 0.075 mmol) in NMP (0.4 ml) was added isopropylamine (44 mg, 0.75 mmol). The reaction was irradiated in the microwave (200 W, 150° C., 5 min.) and then poured onto water (10 ml) and extracted with EtOAc (2×10 ml). The combined organics were washed with brine (3×10 ml), dried (MgSO$_4$), filtered and evaporated to dryness. Purification by mass-directed HPLC gave [1-(3-Benzyloxy-phenyl)-3-cyclobutyl-imidazo[1,5-a]pyrazin-8-yl]-isopropyl-amine formic acid salt (11.0 mg, 36%) as a colorless solid: 1H NMR (400 MHz, CD$_3$OD) δ 8.21 (s, 1H), 7.49 (d, 3H, J=8.2 Hz), 7.44-7.31 (m, 4H), 7.29 (s, 1H), 7.24-7.17 (m, 2H), 7.04 (d, 1H, J=5.1 Hz), 5.21 (s, 2H), 4.24-4.11 (m, 1H), 4.04-3.94 (m, 1H), 2.64-2.47 (m, 4H), 2.28-2.17 (m, 1H), 2.10-2.01 (m, 1H), 1.14 (d, 6H, J=6.7 Hz), 1H not observed (NH); LCMS (ES+) m/z 413.21 [MH+] at Rt 3.40 min.

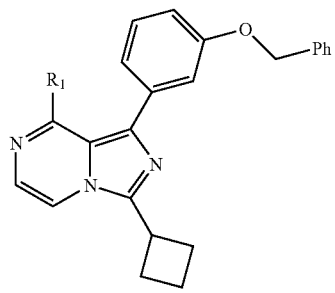

| Example | R1 | Name | MH+ | HPLC Rt |
|---|---|---|---|---|
| 281 | isopropyl | [1-(3-Benzyloxy-phenyl)-3-cyclobutyl-imidazo[1,5-a]pyrazin-8-yl]-isopropyl-amine | 413.21 | 3.40 mins |
| 282 | ethyl | [1-(3-Benzyloxy-phenyl)-3-cyclobutyl-imidazo[1,5-a]pyrazin-8-yl]-ethyl-amine | 399.21 | 3.20 mins |
| 283 | allyl | Allyl-[1-(3-benzyloxy-phenyl)-3-cyclobutyl-imidazo[1,5-a]pyrazin-8-yl]-amine | 411.19 | 3.19 mins |
| 284 | propargyl | [1-(3-Benzyloxy-phenyl)-3-cyclobutyl-imidazo[1,5-a]pyrazin-8-yl]-prop-2-ynyl-amine | 409.22 | 3.47 mins |
| 285 | propyl | [1-(3-Benzyloxy-phenyl)-3-cyclobutyl-imidazo[1,5-a]pyrazin-8-yl]-propyl-amine | 413.21 | 3.40 mins |
| 286 | cyclopropylmethyl | [1-(3-Benzyloxy-phenyl)-3-cyclobutyl-imidazo[1,5-a]pyrazin-8-yl]-cyclopropylmethyl-amine | 411.2 | 3.15 mins |
| 287 | benzyl | Benzyl-[1-(3-benzyloxy-phenyl)-3-cyclobutyl-imidazol[1,5-a]pyrazin-8-yl]-amine | 461.22 | 3.54 mins |
| 288 | phenyl | [1-(3-Benzyloxy-phenyl)-3-cyclobutyl-imidazo[1,5-a]pyrazin-8-yl]-phenyl-amine | 447.21 | 3.94 mins |
| 289 | methyl | [1-(3-Benzyloxy-phenyl)-3-cyclobutyl-imidazo[1,5-a]pyrazin-8-yl]-methyl-amine | 385.35 | 2.99 mins |
| 290 | 2-methoxyethyl | [1-(3-Benzyloxy-phenyl)-3-cyclobutyl-imidazo[1,5-a]pyrazin-8-yl]-(2-methoxy-ethyl)-amine | 429.27 | 3.20 mins |

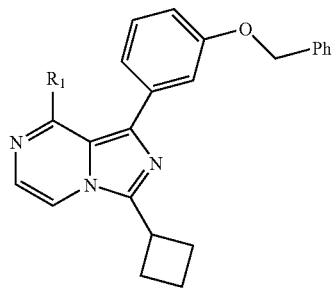

| Example | R1 | Name | MH+ | HPLC Rt |
|---|---|---|---|---|
| 291 | morpholine | 1-(3-Benzyloxy-phenyl)-3-cyclobutyl-8-morpholin-4-yl-imidazo[1,5-a]pyrazine | 441.22 | 3.56 mins |
| 292 | N(Et)2 | [1-(3-Benzyloxy-phenyl)-3-cyclobutyl-imidazo[1,5-a]pyrazin-8-yl]-diethyl-amine | 427.27 | 3.54 mins |
| 293 | HOCH2CH2NH- | [1-(3-Benzyloxy-phenyl)-3-cyclobutyl-imidazo[1,5-a]pyrazin-8-yl]-(2-methoxy-ethyl)-amine | 415.22 | 3.11 mins |

Example 294

8-Amino-1-(3-Benzyloxy-2-fluorophenyl)-3-cyclobutyl-imidazo[1,5-a]pyrazine: 1-(3-Benzyloxy-2-fluoro-phenyl)-8-chloro-3-cyclobutyl-imidazo[1,5-a]pyrazine (500 mg, 1.2 mmole) in methylene chloride was placed in a Parr pressure reactor, cooled in ice salt bath and charged with a saturated solution of NH$_3$ in 2-propanol (10 mL). The pressure reactor was heated at 125° C. overnight. The reaction was cooled to room temperature and the crude reaction mixture was evaporated and triturated with methylene chloride and filtered. The filtrate was evaporated to dryness and purified by silica-gel column chromatography [eluant CH$_2$Cl$_2$:hexane (70:30)] to afford the title compound (350 mg, 75%); FAB-MS: m/z 388.9 (M+H)+.

a) 1-(3-Benzyloxy-2-fluorophenyl)-8-chloro-3-cyclobutylimidazo[1,5-a]pyrazine: Cyclobutanecarboxylic acid [(3-benzyloxy-2-fluoro-phenyl)-(3-chloro-pyrazin-2-yl)-methyl]-amide (0.850 g, 2 mmole) was dissolved in POCl$_3$ (6 mL) and heated at 55° C. overnight. The excess POCl$_3$ was removed in vacuo. The residue was cooled to 0° C. and charged with a saturated solution of NH$_3$ in 2-propanol (6 mL). The mixture was left overnight at room temperature. The separated solid was then filtered and washed with methylene chloride. The filtrate was evaporated to dryness and purified by silica-gel column chromatography using hexane:ethyl acetate (60:40) as the eluant to afford the title compound (615 mg, 75%). FAB-MS: m/z 408.3 (M+H)+.

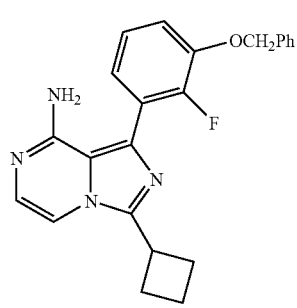

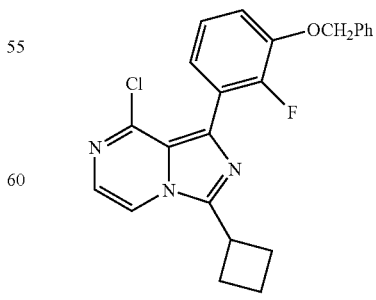

b) N-[(3-benzyloxy-2-fluorophenyl) (3-chloropyrazin-2-yl)methyl]cyclobutylcarboxamide: To a solution of C-(3-benzyloxy-2-fluoro-phenyl)-C-(3-chloro-pyrazin-2-yl)-methylamine (1.1 g, 3.2 mmole) in methylene chloride (10 mL) was added diisopropylethylamine (1.1 mL, 6.4 mmole) under a nitrogen atmosphere. The reaction mixture was cooled in an ice bath and cyclobutanecarboxylic acid chloride (0.55 mL, 4.8 mmole) was added in one portion. The reaction mixture was stirred overnight at room temperature then quenched with water (10 mL). The organic layer separated and washed with 10% aqueous NaHCO$_3$, dried over anhydrous Na$_2$SO$_4$, filtered and concentrated. The crude product was purified by silica gel column chromatography using hexane:ethyl acetate (60:40) as an eluant to give the title compound (911 mg, 67%). FAB-MS: m/z 426.3 (M+H)$^+$.

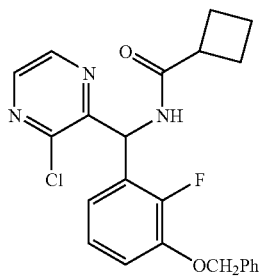

c) (3-Benzyloxy-2-fluorophenyl) (3-chloropyrazin-2-yl) aminomethane: A mixture of 2-[(3-benzyloxy-2-fluoro-phenyl)-(3-chloro-pyrazin-2-yl)-methyl]-isoindole-1,3-dione (1.63 g, 3.45 mmole) and hydrazine (0.270 mL, 8.6 mmole) in ethanol (30 mL) and methylene chloride (10 mL) was stirred at room temperature under nitrogen. After 65 h, separated phthalazine-1,4-dione solid was filtered, and the solid cake was washed with methylene chloride. The filtrate was concentrated in vacuo to obtain red oil comprising the desired title compound, which solidified on standing (1.0 g, 85%).

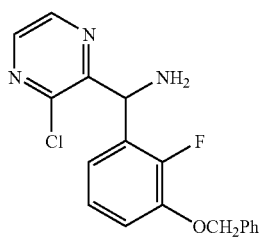

d) 2-[(3-Benzyloxy-2-fluoro-phenyl)-(3-chloro-pyrazin-2-yl)-methyl]-isoindole-1,3-dione: In a 250 mL three-necked flask, equipped with a N$_2$-inlet and a thermometer was placed triphenylphosphine (3.28 g, 12.5 mmole) in THF (30 mL). The mixture was cooled to 0 to 5° C. and DEAD (1.97 mL, 12.5 mmole) was added slowly in 15 minutes while maintaining the temperature at 0-3° C. Stirring was continued for a further 30 minutes at the same temperature. To the cold solution was then added a solution of (3-benzyloxy-2-fluorophenyl) (3-chloropyrazin-2-yl) carbinol (1.96 g, 5.685 mmole) and phthalimide (8, 1.0 g, 6.8 mmole) in THF (30 mL) at 0-5° C. over 10 min. The temperature was slowly allowed to rise to room temperature and then left stirring overnight. The reaction mixture was concentrated in vacuo and purified by column chromatography using hexane:ethyl acetate (70:30) as the eluant. The pure desired product was obtained.

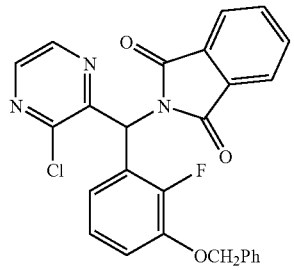

e) (3-Benzyloxy-2-fluorophenyl) (3-chloropyrazin-2-yl) carbinol: In a 100 mL three-necked round-bottom flask equipped with a N$_2$-inlet and a thermometer was placed THF (28 mL). This was cooled to −40° C. and there was added 2.5 M solution of n-BuLi in hexane (11.52 mL, 28.8 mmole) followed by 2,2,6,6-tetramethylpiperidine (4.84 mL, 28.8 mmole). The temperature of the mixture was allowed to rise to 0° C. and stirring was continued at −5 to 0° C. for 30 minutes. The mixture was then cooled to −70° C., and the chloropyrazine (1.28 mL, 14.4 mmole) was added slowly over 15 minutes and the stirring was continued for 30 minutes. A solution of 3-benzyloxy-2-fluorobenzaldehyde (3.04 g. 13.2 mmole) in THF (7 mL) was then added at −70° C. and stirring was continued at −70 to −60° C. for 2 h. There after the temperature was allowed to rise to room temperature over 1 h. The reaction mixture was quenched with 2 N HCl (6 mL) and stirred overnight at room temperature. The mixture was then evaporated on a rotary evaporator to remove most of the THF. Ethyl acetate (20 mL) was added to the residue. The organic layer was separated, washed with water (10 mL), finally with brine (10 mL), dried over Na$_2$SO$_4$, filtered and concentrated. The crude residue obtained was 4.4 g. The above reaction was repeated four times and the products were combined. This was purified by silica-gel column chromatography using as the eluent ethyl acetate:hexane (30:70) and the title compound (3.8 g, 21%) was obtained.

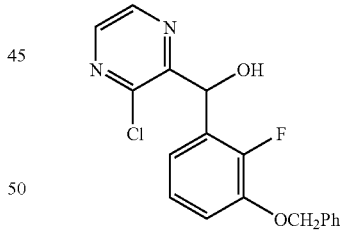

f) 3-Benzyloxy-2-fluorobenzaldehyde: 3-Hydroxy-2-fluorobenzaldehyde {reported by Kirk et. al., *J. Med. Chem.* 1986, 29, 1982} (15 g, 107 mmole) was added to an aqueous NaOH solution {(5.14 g, 128 mmole in water (50 mL)} and the mixture was stirred for 5 min to effect complete dissolution. To this was added a solution of benzyl bromide (16.46 g, 96.3 mmole) in methylene chloride (75 mL) followed by tetrabutylammonium iodide (0.5 g, 1.35 mmole) and vigorous stirring was continued overnight. The organic layer was separated and the aqueous layer was extracted with methylene chloride (100 mL). The combined organic layers were washed with 5% aqueous NaOH solution (2×25 mL) followed by water (50 mL) and finally with brine (20 mL). This solution was dried over anhydrous Na$_2$SO$_4$, filtered and evaporated to dryness. The resulting crude light yellow solid was crystallized from cyclohexane (150 mL) to afford the title compound (16.5 g, 75%); mp 88-89° C.

What is claimed is:

1. A compound represented by Formula I:

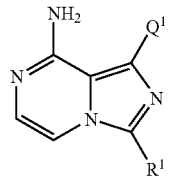

I or a pharmaceutically acceptable salt thereof, wherein:

Q$^1$ is aryl$^1$, heteroaryl$^1$, cycloalkyl, heterocyclyl, cycloalkenyl, or heterocycloalkenyl, any of which is optionally substituted by one to five independent G$^1$ substituents;

R$^1$ is alkyl, cycloalkyl, bicycloalkyl, aryl, heteroaryl, aralkyl, heteroaralkyl, heterocyclyl, or heterobicycloalkyl, any of which is optionally substituted by one or more independent G$^{11}$ substituents;

G$^1$ and G$^{41}$ are each independently halo, oxo, —CF$_3$, —OCF$_3$, —OR$^2$, —NR$^2$R$^3$(R$^{3a}$)$_{j1}$, —C(O)R$^2$, —CO$_2$R$^2$, —CONR$^2$R$^3$, —NO$_2$, —CN, —S(O)$_{j1}$R$^2$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —(C=S)OR$^2$, —(C=O)SR$^2$, —NR$^2$(C=NR$^3$)NR$^{2a}$R$^{3a}$, —NR$^2$(C=NR$^3$)OR$^{2a}$, —NR$^2$(C=NR$^3$)SR$^{3a}$, —O(C=O)OR$^2$, —O(C=O)NR$^2$R$^3$, —O(C=O)SR$^2$, —S(C=O)OR$^2$, —S(C=O)NR$^2$R$^3$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{222}$, —NR$^{222}$R$^{333}$(R$^{333a}$)$_{j1a}$, —C(O)R$^{222}$, —CO$_2$R$^{222}$, —CONR$^{222}$R$^{333}$, —NO$_2$, —CN, —S(O)$_{j1a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or —(X$^1$)$_n$—(Y$^1$)$_m$—R$^4$; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j2a}$, —C(O)R$^{222}$, —CO$_2$R$^{222}$, —CONR$^{222}$R$^{333}$, —NO$_2$, —CN, —S(O)$_{j2a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j2a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$, —C(O)R$^{222}$, —CO$_2$R$^{222}$, —CONR$^{222}$R$^{333}$, —NO$_2$, —CN, —S(O)$_{j3a}$R$^{222}$, —SO$_2$NR$^{222}$R$^{333}$, NR$^{222}$(C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —(C=S)OR$^{222}$, —(C=O)SR$^{222}$, —NR$^{222}$(C=NR$^{333}$)NR$^{222a}$R$^{333a}$, —NR$^{222}$(C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents;

G$^{11}$ is halo, oxo, —CF$_3$, —OCF$_3$, —OR$^{21}$, —NR$^{21}$R$^{31}$(R$^{3a1}$)$_{j4}$, —C(O)R$^{21}$, —CO$_2$R$^{21}$, —CONR$^{21}$R$^{31}$, —NO$_2$, —CN, —S(O)$_{j4}$R$^{21}$, —SO$_2$NR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —(C=S)OR$^{21}$, —(C=O)SR$^{21}$, —NR$^{21}$(C=NR$^{31}$)NR$^{2a1}$R$^{3a1}$, —NR$^{21}$(C=NR$^{31}$)OR$^{2a1}$, —NR$^{21}$(C=NR$^{31}$)SR$^{3a1}$, —O(C=O)OR$^{21}$, —O(C=O)NR$^{21}$R$^{31}$, —O(C=O)SR$^{21}$, —S(C=O)OR$^{21}$, —S(C=O)NR$^{21}$R$^{31}$, —P(O)OR$^{21}$OR$^{31}$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{333a1}$)$_{j4a}$, —C(O)R$^{2221}$, —CO$_2$R$^{2221}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j4a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j5a}$, —C(O)R$^{2221}$, —CO$_2$R$^{2221}$, —CONR$^{2221}$R$^{3331}$, —NO$_2$, —CN, —S(O)$_{j5a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j5a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$R$^{3331}$, or —S(C=O)NR$^{2221}$R$^{3331}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j6a}$, —C(O)R$^{2221}$, —CO$_2$R$^{2221}$, —CONR$^{2221}$R$^{3331}$, —NO$_2$, —CN, —S(O)$_{j6a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$(C=O)NR$^{2221}$R$^{3331}$, NR$^{2221}$S(O)$_{j6a}$R$^{3331}$, —(C=S)OR$^{2221}$, —(C=O)SR$^{2221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$R$^{3331}$ substituents; or G$^{11}$ is taken together with the carbon to which it is attached to form a double bond which is substituted with R$^5$ and G$^{111}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{333a1}$ are each independently equal to C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted by one or more G$^{111}$ substituents; or aryl-C$_{0-10}$alkyl, aryl-C$_{2-10}$alkenyl, or aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more G$^{111}$ substituents; or in the case of —NR$^2$R$^3$ (R$^{3a}$)$_{j1}$ or —NR$^{222}$R$^{333}$(R$^{333a}$)$_{j1a}$ or —NR$_{222}$R$^{333}$(R$^{333a}$)$_{j2a}$ or —NR$^{2221}$R$^{3331}$(R$^{333a1}$)$_{j3a}$ or —NR$^{2221}$R$^{3331}$(R$^{333a1}$)$_{j4a}$ or —NR$_{2221}$R$^{3331}$(R$^{333a1}$)$_{j5a}$ or —NR$^{2221}$R$^{3331}$(R$^{333a1}$)$_{j6a}$, R$^2$ and R$^3$ or R$^{222}$ and R$^{3333}$ or R$^{2221}$ and R$^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more G$^{111}$ substituents;

X$^1$ and Y$^1$ are each independently —O—, —NR$^7$—, —S(O)$_{j7}$—, —CR$^5$R$^6$—, —N(C(O)OR$^7$)—, —N(C(O)R$^7$)—, —N(SO$_2$R$^7$)—, —CH$_2$O—, —CH$_2$S—, —CH$_2$N(R$^7$)—, —CH(NR$^7$)—, —CH$_2$N(C(O)R$^7$)—, —CH$_2$N(C(O)OR$^7$)—, —CH$_2$N(SO$_2$R$^7$)—, —CH(NHR$^7$)—, —CH(NHC(O)R$^7$)—, —CH(NHSO$_2$R$^7$)—, —CH(NHC(O)OR$^7$)—, —CH(OC(O)R$^7$)—, —CH(OC(O)NHR$^7$)—, —CH=CH—, —C≡C—, —C(=NOR$^7$)—, —C(O)—, —CH(OR$^7$)—, —C(O)N(R$^7$)—, —N(R$^7$)C(O)—, —N(R$^7$)S(O)—, —N(R$^7$)S(O)$_2$—, —OC(O)N(R$^7$)—, —N(R$^7$)C(O)N(R$^7$)—, —NR$^7$C(O)O—, —S(O)N(R$^7$)—, —S(O)$_2$N(R$^7$)—, —N(C(O)R$^7$)S(O)—, —N(C(O)R$^7$)S(O)$_2$—, —N(R$^7$)S(O)N(R$^7$)—, —N(R$^7$)S(O)$_2$N(R$^7$)—, —C(O)N(R$^7$)C(O)—, —S(O)N(R$^7$)C(O)—, —S(O)$_2$N(R$^7$)C(O)—, —OS(O)N(R$^7$)—, —OS(O)$_2$N(R$^7$)—, —N(R$^7$)S(O)O—, —N(R$^7$)S(O)$_2$O—, —N(R$^7$)S(O)C(O)—, —N(R$^7$)S(O)$_2$C(O)—, —SON(C(O)R$^7$)—, —SO$_2$N(C(O)R$^7$)—, —N(R$^7$)SON(R$^7$)—, —N(R$^7$)SO$_2$N(R$^7$)—, —C(O)O—, —N(R$^7$)P(OR$^8$)O—, —N(R$^7$)P(OR$^8$)—, —N(R$^7$)P(O)(OR$^8$)O—, —N(R$^7$)P(O)(OR$^8$)—, —N(C(O)R$^7$)P(OR$^8$)O—, —N(C(O)R$^7$)P(OR$^8$)—, —N(C(O)R$^7$)P(O)(OR$^8$)O—, —N(C(O)R$^7$)P(OR$^8$)—, —CH(R$^7$)S(O)—, —CH(R$^7$)S(O)$_2$—, —CH(R$^7$)N(C(O)OR$^7$)—, —CH(R$^7$)N(C(O)R$^7$)—, —CH(R$^7$)N(SO$_2$R$^7$)—, —CH(R$^7$)O—, —CH(R$^7$)S—, —CH(R$^7$)N(R$^7$)—, —CH(R$^7$)N(C(O)R$^7$)—, —CH(R$^7$)N(C(O)OR$^7$)—, —CH(R$^7$)N(SO$_2$R$^7$)—, —CH(R$^7$)C(=NOR$^7$)—, —CH(R$^7$)C(O)—, —CH(R$^7$)CH(OR$^7$)—, —CH(R$^7$)C(O)N(R$^7$)—, —CH(R$^7$)N(R$^7$)C(O)—, —CH(R$^7$)N(R$^7$)S(O)—, —CH(R$^7$)N(R$^7$)S(O)$_2$—, —CH(R$^7$)OC(O)N(R$^7$)—, —CH(R$^7$)N(R$^7$)C(O)N(R$^7$)—, —CH(R$^7$)NR$^7$C(O)O—, —CH(R$^7$)S(O)N(R$^7$)—, —CH(R$^7$)S(O)$_2$N(R$^7$)—, —CH(R$^7$)N(C(O)R$^7$)S(O)—, —CH(R$^7$)N(C(O)R$^7$)S(O)$_2$—, —CH(R$^7$)N(R$^7$)S(O)N(R$^7$)—, —CH(R$^7$)N(R$^7$)S(O)$_2$N(R$^7$)—, —CH(R$^7$)C(O)N(R$^7$)C(O)—, —CH(R$^7$)S(O)N(R$^7$)C(O)—, —CH(R$^7$)S(O)$_2$N(R$^7$)C(O)—, —CH(R$^7$)OS(O)N(R$^7$)—, —CH(R$^7$)OS(O)$_2$N(R$^7$)—, —CH(R$^7$)N(R$^7$)S(O)O—, —CH(R$^7$)N(R$^7$)S(O)$_2$O—, —CH(R$^7$)N(R$^7$)S(O)C(O)—, —CH(R$^7$)N(R$^7$)S(O)$_2$C(O)—, —CH(R$^7$)SON(C(O)R$^7$)—, —CH(R$^7$)SO$_2$N(C(O)R$^7$)—, —CH(R$^7$)N(R$^7$)SON(R$^7$)—, —CH(R$^7$)N(R$^7$)SO$_2$N(R$^7$)—, —CH(R$^7$)C(O)O—, —CH(R$^7$)N(R$^7$)P(OR$^8$)O—, —CH(R$^7$)N(R$^7$)P(OR$^8$)—, —CH(R$^7$)N(R$^7$)P(O)(OR$^8$)O—, —CH(R$^7$)N(R$^7$)P(O)(OR$^8$)—, —CH(R$^7$)N(C(O)R$^7$)P(OR$^8$)O—, —CH(R$^7$)N(C(O)R$^7$)P(OR$^8$)—, —CH(R$^7$)N(C(O)R$^7$)P(O)(OR$^8$)O—, or —CH(R$^7$)N(C(O)R$^7$)P(OR$^8$)—;

or X$^1$ and Y$^1$ are each independently represented by one of the following structural formulas:

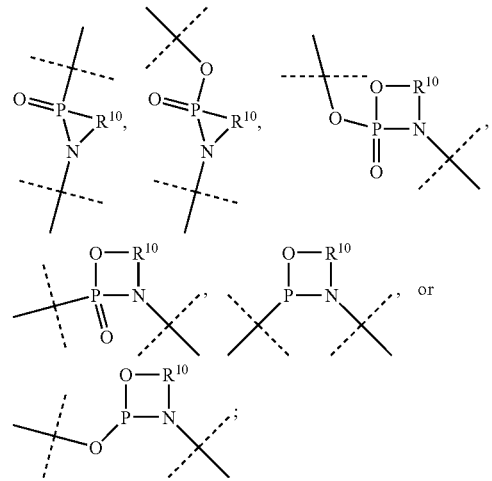

R$^{10}$, taken together with the phosphinamide or phosphonamide, is a 5-, 6-, or 7-membered aryl, heteroaryl or heterocyclyl ring system;

R$^5$, R$^6$, and G$^{111}$ are each independently a C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, NR$^{77}$(C=O)R$^{87}$, NR$^{77}$(C=O)OR$^{87}$, NR$^{77}$(C=O)NR$^{78}$R$^{87}$, NR$^{77}$S(O)$_{j5a}$R$^{87}$, —(C=S)OR$^{77}$, —(C=O)SR$^{77}$, —NR$^{77}$(C=NR$^{87}$)NR$^{78}$R$^{88}$, —NR$^{77}$(C=NR$^{87}$)OR$^{78}$, —NR$^{77}$(C=NR$^{87}$)SR$^{78}$, —O(C=O)OR$^{77}$, —O(C=O)NR$^{77}$R$^{87}$, —O(C=O)SR$^{77}$, —S(C=O)OR$^{77}$, —P(O)OR$^{77}$OR$^{87}$, or —S(C=O)NR$^{77}$R$^{87}$ substituents; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, NR$^{77}$(C=O)R$^{87}$, NR$^{77}$(C=O)OR$^{87}$, $NR^{77}(C=O)NR^{78}R^{87}$, $NR^{77}S(O)_{j5a}R^{87}$, —(C=S)$OR^{77}$, —(C=O)$SR^{77}$, —$NR^{77}(C=NR^{87})NR^{78}R^{88}$, —$NR^{77}(C=NR^{87})OR^{78}$, —$NR^{77}(C=NR^{87})SR^{78}$, —O(C=O)$OR^{77}$, —O(C=O)$NR^{77}R^{87}$, —O(C=O)$SR^{77}$, —S(C=O)$OR^{77}$, —P(O)$OR^{77}R^{87}$, or —S(C=O)$NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{77}$, —$NR^{77}R^{87}$, —C(O)$R^{77}$, —$CO_2R^{77}$, —$CONR^{77}R^{87}$, —$NO_2$, —CN, —S(O)$_{j5a}R^{77}$, —$SO_2NR^{77}R^{87}$, $NR^{77}$(C=O)$R^{87}$, $NR^{77}$(C=O)$OR^{87}$, $NR^{77}$(C=O)$NR^{78}R^{87}$, $NR^{77}S(O)_{j5a}R^{87}$, —(C=S)$OR^{77}$, —(C=O)$SR^{77}$, —$NR^{77}$(C=$NR^{87}$)$NR^{78}R^{88}$, —$NR^{77}$(C=$NR^{87}$)$OR^{78}$, —$NR^{77}$(C=$NR^{87}$)$SR^{78}$, —O(C=O)$OR^{77}$, —O(C=O)$NR^{77}R^{87}$, —O(C=O)$SR^{77}$, —S(C=O)$OR^{77}$, —P(O)$OR^{77}OR^{87}$, or —S(C=O)$NR^{77}R^{87}$ substituents; or $R^5$ with $R^6$ taken together with the respective carbon atom to which they are attached, form a 3-10 membered saturated or unsaturated ring, wherein said ring is optionally substituted with $R^{69}$; or $R^5$ with $R^6$ taken together with the respective carbon atom to which they are attached, form a 3-10 membered saturated or unsaturated heterocyclic ring, wherein said ring is optionally substituted with $R^{69}$;

$R^7$ and $R^8$ are each independently H, acyl, alkyl, alkenyl, aryl, heteroaryl, heterocyclyl or cycloalkyl, any of which is optionally substituted by one or more $G^{111}$ substituents;

$R^4$ is H, alkyl, alkenyl, alkynyl, aryl, heteroaryl, cycloalkyl, heterocyclyl, cycloalkenyl, or heterocycloalkenyl, any of which is optionally substituted by one or more $G^{41}$ substituents;

$R^{69}$ is equal to halo, —$OR^{78}$, —SH, —$NR^{78}R^{88}$, —$CO_2R^{78}$, —$CONR^{78}R^{88}$, —$NO_2$, —CN, —S(O)$_{j8}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{778}$, —$SO_2NR^{778}R^{888}$, or —$NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —$CONR^{778}R^{888}$, —$SO_2NR^{778}R^{888}$, or —$NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$, or —$NR^{778}R^{888}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbo-nyl, —$CONR^{778}R^{888}$ $SO_2NR^{778}R^{888}$, or —$NR^{778}R^{888}$ substituents; or in the case of —$NR^{78}R^{88}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{778}R^{888}$, or —$NR^{778}R^{888}$ substituents;

$R^{77}$, $R^{78}$, $R^{87}$, $R^{88}$, $R^{778}$, and $R^{888}$ are each independently $C_{0-10}$alkyl, $C_{2-10}$alkenyl, $C_{2-10}$alkynyl, $C_{1-10}$alkoxy $C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbo-nyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl)($C_{0-4}$alkyl), or —$N(C_{0-4}$alkyl)($C_{0-4}$alkyl) substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-10}$alkyl), —$SO_2N(C_{0-4}$alkyl)($C_{0-4}$alkyl), or —$N(C_{0-4}$alkyl)($C_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —CON($C_{0-4}$alkyl)($C_{0-4}$alkyl), —$SO_2N(C_{0-4}$alkyl)($C_{0-4}$alkyl), or —$N(C_{0-4}$alkyl)($C_{0-4}$alkyl) substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-4}$alkyl), —$SO_2N(C_{0-4}$alkyl)($C_{0-4}$alkyl), or —$N(C_{0-4}$alkyl)($C_{0-4}$alkyl) substituents; and n, m, j1, j1a, j2a, j3a, j4, j4a, j5a, j6a, j7, and j8 are each independently equal to 0, 1, or 2.

2. The compound or salt of claim 1, wherein $Q^1$ is aryl$^1$ or heteroaryl$^1$, any of which is optionally substituted by one or more independent $G^1$ substituents.

3. The compound or salt of claim 2, wherein $Q^1$ is heteroaryl$^1$, any of which is optionally substituted by one or more independent $G^1$ substituents.

4. The compound or salt of claim 3, wherein $Q^1$ is aryl$^1$, any of which is optionally substituted by one or more independent $G^1$ substituents.

5. The compound or salt of claim 1, wherein $G^1$ is halo, —$CF_3$, —$OCF_3$, —$OR^2$, —$NR^2R^3$, —C(O)$R^2$, —$CO_2R^2$, —$CONR^2R^3$, —S(O)$_{j1}R^2$, —$SO_2NR^2R^3$, $NR^2$(C=O)$R^3$, $NR^2$(C=O)$OR^3$, $NR^2$(C=O)$NR^2R^3$, $NR^2S(O)_{j1}R^3$, —O(C=O)OR², —O(C=O)NR²R³, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, oxo, —CF₃, —OCF₃, —OR²²², —NR²²²R³³³(R³³³ᵃ)$_{j1a}$, —C(O)R²²², —CO₂R²²², —CONR²²²R³³³, —NO₂, —CN, —S(O)$_{j1a}$R²²², —SO₂NR²²²R³³³, NR²²²(C=O)R³³³, NR²²²(C=O)OR³³³, NR²²²(C=O)NR²²²R³³³, NR²²²S(O)$_{j1a}$R³³³, —(C=S)OR²²², —(C=O)SR²²², —NR²²²(C=NR³³³)NR²²²ᵃR³³³ᵃ, —NR²²²(C=NR³³³)OR²²²ᵃ, —NR²²²(C=NR³³³)SR³³³ᵃ, —O(C=O)OR²²², —O(C=O)NR²²²R³³³, —O(C=O)SR²²², —S(C=O)OR²²², or —S(C=O)NR²²²R³³³ substituents; or —(X¹)$_n$—(Y¹)$_m$—R⁴; or aryl-$C_{0-10}$alkyl, aryl-$C_{2-10}$alkenyl, or aryl-$C_{2-10}$alkynyl, any of which is optionally substituted with one or more independent halo, —CF₃, —OCF₃, —OR²²², —NR²²²R³³³(R³³³ᵃ)$_{j2a}$, —C(O)R²²², —CO₂R²²², —CONR²²²R³³³, —NO₂, —CN, —S(O)$_{j2a}$R²²², —SO₂NR²²²R³³³, NR²²²(C=O)R³³³, NR²²²(C=O)OR³³³, NR²²²(C=O)NR²²²R³³³, NR²²²S(O)$_{j2a}$R³³³, —(C=S)OR²²², —(C=O)SR²²², —NR²²²(C=NR³³³)NR²²²ᵃR³³³ᵃ, —NR²²²(C=NR³³³)OR²²²ᵃ, —NR²²²(C=NR³³³)SR³³³ᵃ, —O(C=O)OR²²², —O(C=O)NR²²²R³³³, —O(C=O)SR²²², —S(C=O)OR²²², or —S(C=O)NR²²²R³³³ substituents; or hetaryl-$C_{0-10}$alkyl, hetaryl-$C_{2-10}$alkenyl, or hetaryl-$C_{2-10}$alkynyl, any of which is optionally substituted with one or more independent halo, —CF₃, —OCF₃, —OR²²², —NR²²²R³³³(R³³³ᵃ)$_{j3a}$, —C(O)R²²², —CO₂R²²², —CONR²²²R³³³, —NO₂, —CN, —S(O)$_{j3a}$R²²², —SO₂NR²²²R³³³, NR²²²(C=O)R³³³, NR²²² (C=O)OR³³³, NR²²²(C=O)NR²²²R³³³, NR²²²S(O)$_{j3a}$R³³³, —(C=S)OR²²², —(C=O)SR²²², —NR²²²(C=NR³³³)NR²²²ᵃR³³³ᵃ, —NR²²²(C=NR³³³)OR²²²ᵃ, —NR²²²(C=NR³³³)SR³³³ᵃ, —O(C=O)OR²²², —O(C=O)NR²²²R³³³, —O(C=O)SR²²², —S(C=O)OR²²², or —S(C=O)NR²²²R³³³ substituents.

6. The compound or salt of claim 1, wherein $G^1$ is halo, —OR², —NR²R³, —C(O)R², —CO₂R², —CONR²R³, —SO₂NR²R³, NR²(C=O)R³, NR²(C=O)OR³, NR²(C=O)NR²R³, NR²S(O)$_{j1}$R³, —O(C=O)OR², —O(C=O)NR²R³, $C_{0-10}$alkyl, $C_{2-10}$alkenyl, $C_{1-10}$alkoxy$C_{1-10}$alkyl, $C_{1-10}$alkoxy$C_{2-10}$alkenyl, $C_{1-10}$alkylthio$C_{1-10}$alkyl, $C_{1-10}$alkylthio$C_{2-10}$alkenyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, or heterocyclyl-$C_{0-10}$alkyl, or heterocyclyl-$C_{2-10}$alkenyl, any of which is optionally substituted with one or more independent oxo, —CF₃, —OCF₃, —OR²²², —NR²²²R³³³, —C(O)R²²², —CO₂R²²², —CONR²²²R³³³, —SO₂NR²²²R³³³, NR²²²(C=O)R³³³, NR²²²(C=O)OR³³³, NR²²²(C=O)NR²²²R³³³, NR²²S(O)$_{j1a}$R³³³, —NR²²²(C=NR³³³) NR²²²ᵃR³³³ᵃ, or —O(C=O)NR²²²R³³³ substituents; or —(X¹)$_n$—(Y¹)$_m$—R⁴; or aryl-$C_{0-10}$alkyl optionally substituted with one or more independent halo, —CF₃, —OCF₃, —OR²²², —NR²²²R³³³, —C(O)R²²², —CO₂R²²², —CONR²²²R³³³, —SO₂NR²²²R³³³, NR²²²(C=O)R³³³, NR²²²(C=O)OR³³³, NR²²²(C=O)NR²²²R³³³, NR²²² S(O)$_{j2a}$R³³³, —NR²²²(C=NR³³³)NR²²²ᵃR³³³ᵃ, or —O(C=O)NR²²²R³³³ substituents; or hetaryl-$C_{0-10}$alkyl, optionally substituted with one or more independent halo, —CF₃, —OCF₃, —OR²²², —NR²²²R³³³, —C(O)R²²², —CO₂R²²², —CONR²²²R³³³, —SO₂NR²²²R³³³, NR²²² (C=O)R³³³, NR²²²(C=O)OR³³³, NR²²²(C=O) NR²²²R³³³, NR²²²S(O)$_{j3a}$R³³³, —NR²²²(C=NR³³³)NR²²²ᵃR³³³ᵃ, or —O(C=O)NR²²²R³³³ substituents.

7. The compound or salt of claim 1, wherein $G^1$ is halo, —OR², —NR²R³, —C(O)R², —CO₂R², —CONR²R³, —SO₂NR²R³, NR²(C=O)R³, NR²(C=O)OR³, NR²(C=O)NR²R³, NR²S(O)$_{j1}$R³, —O(C=O)OR², —O(C=O)NR²R³, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, or heterocyclyl-$C_{0-10}$alkyl, or heterocyclyl-$C_{2-10}$alkenyl, any of which is optionally substituted with one or more independent oxo, —CF₃, —OCF₃, —OR²²², —NR²²²R³³³, —C(O)R²²², —CO₂R²²², —CONR²²²R³³³, —SO₂NR²²²R³³³, NR²²²(C=O)R³³³, NR²²²(C=O)OR³³³, NR²²²(C=O)NR²²²R³³³, NR²²²S(O)$_{j1a}$R³³³, —NR²²²(C=NR³³³)NR²²²ᵃR³³³ᵃ, or —O(C=O)NR²²²R³³³ substituents; or —(X¹)$_n$—(Y¹)$_m$—R⁴; or aryl-$C_{0-10}$alkyl, optionally substituted with one or more independent halo, —CF₃, —OCF₃, —OR²²², —NR²²²R³³³, —C(O)R²²², —CO₂R²²², —CONR²²²R³³³, —SO₂NR²²²R³³³, NR²²²(C=O)R³³³, NR²²²(C=O)OR³³³, NR²²²(C=O)NR²²²R³³³, NR²²² S(O)$_{j2a}$R³³³, —NR²²²(C=NR³³³)NR²²²ᵃR$_{333a}$, or —O(C=O)NR²²²R³³³ substituents; or hetaryl-$C_{0-10}$alkyl, optionally substituted with one or more independent halo, —CF₃, —OCF₃, —OR²²², —NR²²²R³³³, —C(O)R²²², —CO₂R²²², —CONR²²²R³³³, —SO₂NR²²²R³³³, NR²²² (C=O)R³³³, NR²²²(C=O)OR³³³, NR²²²(C=O) NR²²²R³³³, NR²²²S(O)$_{j3a}$R³³³, —NR²²²(C=NR³³³) NR²²²ᵃR³³³ᵃ, or —O(C=O)NR²²²R³³³ substituents.

8. The compound or salt of claim 1, wherein $G^1$ is halo, —OR², —NR²R³, —C(O)R², —CO₂R², —CONR²R³, —SO₂NR²R³, NR²(C=O)R³, NR²(C=O)OR³, NR²(C=O)NR²R³, NR²S(O)$_{j1}$R³, —O(C=O)OR², —O(C=O)NR²R³, $C_{0-10}$alkyl, $C_{2-10}$alkenyl, $C_{1-10}$alkoxy$C_{1-10}$alkyl, $C_{1-10}$alkylthio$C_{1-10}$alkyl, cyclo$C_{3-8}$alkyl, cyclo$C_{3-8}$alkenyl, or heterocyclyl-$C_{0-10}$alkyl, or heterocyclyl-$C_{2-10}$alkenyl, any of which is optionally substituted with one or more independent oxo, —CF₃, —OCF₃, —OR²²², —NR²²²R³³³, —C(O)R²²², —CO₂R²²², —CONR²²²R³³³, —SO₂ NR²²²R³³³, NR²²²(C=O)R³³³, NR²²²(C=O)OR³³³, NR²²²(C=O)NR²²²R³³³, NR²²²S(O)$_{j1a}$R³³³, —NR²²²(C=NR³³³) NR²²²ᵃR³³³ᵃ, or —O(C=O)NR²²²R³³³ substituents; or —(X¹)$_n$—(Y¹)$_m$—R⁴.

9. The compound or salt of claim 1, wherein $X^1$ and $Y^1$ are each independently —O—, —NR⁷—, —S(O)$_{j7}$—, —CR⁵R⁶—, —N(C(O)OR⁷)—, —N(C(O)R⁷)—, —N(SO₂R⁷)—, —CH₂O—, —CH₂S—, —CH₂N(R⁷)—, —CH(NR⁷)—, —CH₂N(C(O)R⁷)—, —CH₂N(C(O)OR⁷)—, —CH₂N(SO₂R⁷)—, —CH(NHR⁷)—, —CH(NHC(O)R⁷)—, —CH(NHSO₂R⁷)—, —CH(NHC(O)OR⁷)—, —CH(OC(O)R⁷)—, —CH(OC(O)NHR⁷)—, —C(O)—, —CH(OR⁷)—, —C(O)N(R⁷)—, —N(R⁷)C(O)—, —N(R⁷)S(O)—, —N(R⁷)S(O)₂—, —OC(O)N(R⁷)—, —N(R⁷)C(O)N(R⁷)—, —NR⁷C(O)O—, —S(O)N(R⁷)—, —S(O)₂N(R⁷)—, —N(C(O)R⁷)S(O)—, —N(C(O)R⁷)S(O)₂—, —N(R⁷)S(O)N(R⁷)—, —N(R⁷)S(O)₂N(R⁷)—, —C(O)N(R⁷)C(O)—, —S(O)N(R⁷)C(O)—, —S(O)₂N(R⁷)C(O)—, —OS(O)N(R⁷)—, —OS(O)₂N(R⁷)—, —N(R⁷)S(O)O—, —N(R⁷)S(O)₂O—, —N(R⁷)S(O)C(O)—, —N(R⁷)S(O)₂C(O)—, —SON(C(O)R⁷)—, —SO₂N(C(O)R⁷)—, —N(R⁷)SON(R⁷)—, —N(R⁷)SO₂N(R⁷)—, —C(O)O—, —CH(R⁷)S(O)—, —CH(R⁷)S(O)₂—, —CH(R⁷)N(C(O)OR⁷)—, —CH(R⁷)N(C(O)R⁷)—, —CH(R⁷)N(SO₂R⁷)—, —CH(R⁷)O—, —CH(R⁷)S—, —CH(R⁷)N(R⁷)—, —CH(R⁷)N(C(O)R⁷)—, —CH(R⁷)N(C(O)OR⁷)—, —CH(R⁷)N(SO₂R⁷)—, —CH $(R^7)C(=NOR^7)$—, —$CH(R^7)C(O)$—, —$CH(R^7)CH(OR^7)$—, —$CH(R^7)C(O)N(R^7)$—, —$CH(R^7)N(R^7)C(O)$—, —$CH(R^7)N(R^7)S(O)$—, —$CH(R^7)N(R^7)S(O)_2$—, —$CH(R^7)OC(O)N(R^7)$—, —$CH(R^7)N(R^7)C(O)N(R^7)$—, —$CH(R^7)NR^7C(O)O$—, —$CH(R^7)S(O)N(R^7)$—, —$CH(R^7)S(O)_2N(R^7)$—, —$CH(R^7)N(C(O)R^7)S(O)$—, —$CH(R^7)N(C(O)R^7)S(O)$—, —$CH(R^7)N(R^7)S(O)N(R^7)$—, —$CH(R^7)N(R^7)S(O)_2N(R^7)$—, —$CH(R^7)C(O)N(R^7)C(O)$—, —$CH(R^7)S(O)N(R^7)C(O)$—, —$CH(R^7)S(O)_2N(R^7)C(O)$—, —$CH(R^7)OS(O)N(R^7)$—, —$CH(R^7)OS(O)_2N(R^7)$—, —$CH(R^7)N(R^7)S(O)O$—, —$CH(R^7)N(R^7)S(O)_2O$—, —$CH(R^7)N(R^7)S(O)C(O)$—, —$CH(R^7)N(R^7)S(O)_2C(O)$—, —$CH(R^7)SON(C(O)R^7)$—, —$CH(R^7)SO_2N(C(O)R^7)$—, —$CH(R^7)N(R^7)SON(R^7)$—, —$CH(R^7)N(R^7)SO_2N(R^7)$—, or —$CH(R^7)C(O)O$—.

10. The compound or salt of claim 1 wherein $Q^1$ is substituted by said one to five independent $G^1$ substituents wherein at least one of said $G^1$ substituents is —$(X^1)_n$—$(Y^1)_m$—$R^4$, and wherein $X^1$ and $Y^1$ are each independently equal to —O—, —$NR^7$—, —$CR^5R^6$—, —$S(O)_{j7}$—, or —C(O)—, and wherein n and m are both equal to 1 and j7 is equal to 1 or 2.

11. The compound or salt of claim 1 wherein $Q^1$ is substituted by said one to five independent $G^1$ substituents wherein at least one of said $G^1$ substituents is —$(X^1)_n$—$(Y^1)_m$—$R^4$, and wherein $X^1$ and $Y^1$ are each independently —O— or —$CR^5R^6$—, and wherein n and m are equal to 1.

12. The compound or salt of claim 1 wherein $R^1$ is cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents.

13. The compound or salt of claim 1 wherein $R^1$ is cycloalkyl, aryl, heteroaryl, aralkyl, heteroaralkyl, or heterocyclyl, any of which is optionally substituted by one or more independent $G^{11}$ substituents.

14. The compound or salt of claim 1 wherein $R^1$ is cycloalkyl or heterocyclyl, any of which is optionally substituted by one or more independent $G^{11}$ substituents.

15. The compound or salt of claim 1 wherein $R^1$ is cycloalkyl optionally substituted by one or more independent $G^{11}$ substituents.

16. The compound or salt of claim 1 wherein $R^1$ is heterocyclyl optionally substituted by one or more independent $G^{11}$ substituents.

17. The compound or salt of claim 1 wherein $R^1$ is aryl, heteroaryl, aralkyl, or heteroaralkyl, any of which is optionally substituted by one or more independent $G^{11}$ substituents.

18. The compound or salt of claim 1 wherein $R^1$ is aryl or heteroaryl, any of which is optionally substituted by one or more independent $G^{11}$ substituents.

19. The compound or salt of claim 1 wherein $G^{11}$ is —$OR^{21}$, —$NR^{21}R^{31}(R^{31a})_{j4}$, —$C(O)R^{21}$, —$CO_2R^{21}$, —$CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, —$O(C=O)OR^{21}$, —$O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{333a})_{j4a}$, —$C(O)R^{2221}$, —$CO_2R^{2221}$, —$CONR^{2221}R^{3331}$, —$NO_2$, —CN, —$S(O)_{j4a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$ substituents; or aryl-$C_{0-10}$alkyl, aryl-$C_{2-10}$alkenyl, or aryl-$C_{2-10}$alkynyl, any of which is optionally substituted with one or more independent halo, —$CF_3$, —$OCF_3$, —$OR^{2221}$, —$NR^{2221}R^{3331}(R^{333a1})_{j5a}$, —$C(O)R^{2221}$, —$CO_2R^{2221}$, —$CONR^{2221}R^{3331}$, —$NO_2$, —CN, —$S(O)_{j5a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j5a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{2221}$, —$NR^{2221}R^{3331}(R^{333a1})_{j6a}$, —$C(O)R^{2221}$, —$CO_2R^{2221}$, —$CONR^{2221}R^{3331}$, —$NO_2$, —CN, —$S(O)_{j6a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j6a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$ substituents.

20. The compound or salt of claim 1 wherein $G^{11}$ is —$OR^{21}$, —$NR^{21}R^{31}$, —$CO_2R^{21}$, —$C(O)R^{21}$, —$CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, —$O(C=O)OR^{21}$, —$O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, —$CF_3$, —$OCF_3$, —$OR^{2221}$, —$NR^{2221}R^{3331}(R^{333a1})_{j4a}$, —$C(O)R^{2221}$, —$CO_2R^{2221}$, —$CONR^{2221}R^{3331}$, —$NO_2$, —CN, —$S(O)_{j4a}R^{2221}$, —$SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, —$(C=S)OR^{2221}$, —$(C=O)SR^{2221}$, —$NR^{2221}(C=NR^{3331})NR^{222a1}R^{333a1}$, —$NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$ substituents.

21. The compound or salt of claim 1 wherein $R^4$ is H, alkyl, aryl, heteroaryl, cycloalkyl, heterocyclyl, cycloalkenyl, or heterocycloalkenyl, any of which is optionally substituted by one or more independent $G^{41}$ substituents.

22. The compound or salt of claim 10 wherein $R^4$ is alkyl, aryl, heteroaryl, cycloalkyl, heterocyclyl, cycloalkenyl, or heterocycloalkenyl, any of which is optionally substituted by one or more independent $G^{41}$ substituents.

23. The compound or salt of claim 11 wherein $R^4$ is alkyl, aryl, heteroaryl, cycloalkyl, heterocyclyl, cycloalkenyl, or heterocycloalkenyl, any of which is optionally substituted by one or more independent $G^{41}$ substituents.

24. The compound or salt of claim 1 wherein $Q^1$ is phenyl substituted by said one to five independent $G^1$ substituents wherein at least one of said $G^1$ substituents is —$(X^1)_n$—$(Y^1)_m$—$R^4$, and wherein n=1 and $X^1$ is 3-(—O—), m=1 and $Y^1$ is —(—$CH_2$—), and $R^4$ is aryl optionally substituted by one or more independent $G^{41}$ substituents.

25. The compound or salt of claim 24 wherein $R^1$ is aryl, heteroaryl, cycloalkyl or heterocyclyl, optionally substituted by one or more independent $G^{11}$ substituents.

26. The compound or salt of claim 25 wherein $R^1$ is cycloalkyl or heterocyclyl, optionally substituted by one or more independent $G^{11}$ substituents.

27. The compound or salt of claim 26 wherein $R^1$ is cycloalkyl, optionally substituted by one or more independent $G^{11}$ substituents.

28. The compound or salt of claim 27 wherein $R^1$ is cyclobutyl, cyclopentyl or cyclohexyl, optionally substituted by one or more independent $G^{11}$ substituents.

29. The compound or salt of claim 27 wherein $G^{11}$ is $-OR^{21}$, $-NR^{21}R^{31}$, $-CO_2R^{21}$, $-C(O)R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{333a1})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents.

30. The compound or salt of claim 1 wherein $Q^1$ is phenyl substituted by said one to five independent $G^1$ substituents wherein at least one of said $G^1$ substituents is $-(X^1)_n-(Y^1)_m-R^4$, and wherein n=1 and $X^1$ is 4-($-O-$), m=1 and $Y^1$ is $-(-CH_2-)$, and $R^4$ is aryl optionally substituted by one or more independent $G^{41}$ substituents.

31. The compound or salt of claim 30 wherein $R^1$ is aryl, heteroaryl, cycloalkyl or heterocyclyl, optionally substituted by one or more independent $G^{11}$ substituents.

32. The compound or salt of claim 31 wherein $R^1$ is cycloalkyl or heterocyclyl, optionally substituted by one or more independent $G^{11}$ substituents.

33. The compound or salt of claim 32 wherein $R^1$ is cycloalkyl, optionally substituted by one or more independent $G^{11}$ substituents.

34. The compound or salt of claim 33 wherein $R^1$ is cyclobutyl, cyclopentyl or cyclohexyl, optionally substituted by one or more independent $G^{11}$ substituents.

35. The compound or salt of claim 33 wherein $G^{11}$ is $-OR^{21}$, $-NR^{21}R^{31}$, $-CO_2R^{21}$, $-C(O)R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{333a1})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents.

36. The compound or salt of claim 1 wherein $Q^1$ is phenyl substituted by said one to five independent $G^1$ substituents wherein at least one of said $G^1$ substituents is $-(X^1)_n-(Y^1)_m-R^4$, and wherein n=1 and $X^1$ is 3-($-O-$), m=0, and $R^4$ is $(C_0-C_8)$alkyl or cycloalkyl optionally substituted by one or more independent $G^{41}$ substituents.

37. The compound or salt of claim 36 wherein $R^1$ is aryl, heteroaryl, cycloalkyl or heterocyclyl, optionally substituted by one or more independent $G^{11}$ substituents.

38. The compound or salt of claim 37 wherein $R^1$ is cycloalkyl or heterocyclyl, optionally substituted by one or more independent $G^{11}$ substituents.

39. The compound or salt of claim 38 wherein $R^1$ is cycloalkyl, optionally substituted by one or more independent $G^{11}$ substituents.

40. The compound or salt of claim 39 wherein $R^1$ is cyclobutyl, cyclopentyl or cyclohexyl, optionally substituted by one or more independent $G^{11}$ substituents.

41. The compound or salt of claim 39 wherein $G^{11}$ is $-OR^{21}$, $-NR^{21}R^{31}$, $-CO_2R^{21}$, $-C(O)R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{333a1})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents.

42. The compound or salt of claim 36 wherein $R^4$ is $(C_0-C_6)$alkyl.

43. The compound or salt of claim 41 wherein $R^4$ is $(C_0-C_6)$alkyl.

44. The compounds or salts of claim 36 wherein $R^4$ is H or methyl.

45. The compound or salt of claim 43 wherein $R^4$ is H or methyl.

46. The compound or salt of claim 1 wherein $Q^1$ is phenyl substituted by said one to five independent $G^1$ substituents wherein at least one of said $G^1$ substituents is $-(X^1)_n-(Y^1)_m-R^4$, and wherein n=1 and $X^1$ is 3-($-O-$), m=0, and $R^4$ is aryl optionally substituted by one or more independent $G^{41}$ substituents.

47. The compound or salt of claim 46 wherein $R^1$ is aryl, heteroaryl, cycloalkyl or heterocyclyl, optionally substituted by one or more independent $G^{11}$ substituents.

48. The compound or salt of claim 46 wherein $R^1$ is cycloalkyl or heterocyclyl, optionally substituted by one or more independent $G^{11}$ substituents.

49. The compound or salt of claim 48 wherein $R^1$ is cyclobutyl, cyclopentyl or cyclohexyl, optionally substituted by one or more independent $G^{11}$ substituents.

50. The compound or salt of claim 48 wherein $G^{11}$ is $-OR^{21}$, $-NR^{21}R^{31}$, $-CO_2R^{21}$, $-C(O)R^{21}$, $-CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, $-O(C=O)OR^{21}$, $-O(C=O)NR^{21}R^{31}$, $C_{0-10}$alkyl, cyclo$C_{3-8}$alkyl, cyclo$C_{3-8}$alkenyl, heterocyclyl-$C_{0-10}$alkyl, or heterocyclyl-$C_{2-10}$alkenyl, any of which is optionally substituted with one or more independent halo, oxo, $-CF_3$, $-OCF_3$, $-OR^{2221}$, $-NR^{2221}R^{3331}(R^{333a1})_{j4a}$, $-C(O)R^{2221}$, $-CO_2R^{2221}$, $-CONR^{2221}R^{3331}$, $-NO_2$, $-CN$, $-S(O)_{j4a}R^{2221}$, $-SO_2NR^{2221}R^{3331}$, $NR^{2221}(C=O)R^{3331}$, $NR^{2221}(C=O)OR^{3331}$, $NR^{2221}(C=O)NR^{2221}R^{3331}$, $NR^{2221}S(O)_{j4a}R^{3331}$, $-(C=S)OR^{2221}$, $-(C=O)SR^{2221}$, $-NR^{2221}(C=NR^{3331})NR^{222a1}R^{333a1}$, $-NR^{2221}(C=NR^{3331})OR^{222a1}$, $-NR^{2221}(C=NR^{3331})SR^{333a1}$, $-O(C=O)OR^{2221}$, $-O(C=O)NR^{2221}R^{3331}$, $-O(C=O)SR^{2221}$, $-S(C=O)OR^{2221}$, or $-S(C=O)NR^{2221}R^{3331}$ substituents.

51. The compound or salt of claim 46 wherein $R^4$ is phenyl optionally substituted with $G^{41}$.

52. The compound or salt of claim 1 wherein $Q^1$ is phenyl substituted by said one to five independent $G^1$ substituents wherein at least one of said $G^1$ substituents is —$(X^1)_n$—$(Y^1)_m$—$R^4$, and wherein n=1 and $X^1$ is 3- or 4-(—NH—), m=1 and $Y^1$ is —(—SO$_2$—), and $R^4$ is aryl optionally substituted by one or more independent $G^{41}$ substituents.

53. The compound or salt of claim 52 wherein $R^1$ is aryl, heteroaryl, cycloalkyl or heterocyclyl, optionally substituted by one or more independent $G^{11}$ substituents.

54. The compound or salt of claim 53 wherein $R^1$ is cycloalkyl or heterocyclyl, optionally substituted by one or more independent $G^{11}$ substituents.

55. The compound or salt of claim 54 wherein $R^1$ is cyclobutyl, cyclopentyl or cyclohexyl, optionally substituted by one or more independent $G^{11}$ substituents.

56. The compound or salt of claim 54 wherein $G^{11}$ is —$OR^{21}$, —$NR^{21}R^{31}$, —$CO_2R^{21}$, —$C(O)R^{21}$, —$CONR^{21}R^{31}$, $NR^{21}(C=O)R^{31}$, $NR^{21}(C=O)OR^{31}$, $NR^{21}(C=O)NR^{21}R^{31}$, $NR^{21}S(O)_{j4}R^{31}$, —$O(C=O)OR^{21}$, —$O(C=O)NR^{21}R^{31}$, $C_{0-10}$alkyl, cycloC$_{3-8}$alkyl, cycloC$_{3-8}$alkenyl, heterocyclyl-C$_{0-10}$alkyl, or heterocyclyl-C$_{2-10}$alkenyl, any of which is optionally substituted with one or more independent halo, oxo, —$CF_3$, —$OCF_3$, —$OR^{2221}$, —$NR^{2221}R^{3331}(R^{333a1})_{j4a}$, —$C(O)R^{2221}$, —$CO_2R^{2221}$, —$CONR^{2221}R^{3331}$, —$NO_2$, —$CN$, —$S(O)_{j4a}R^{2221}$, —$SO_2NR^{2221}R^{3331}$, $NR^{2221}(C=O)R^{3331}$, $NR^{2221}(C=O)R^{3331}$, $NR^{2221}(C=O)NR^{2221}R^{3331}$, $NR^{2221}S(O)_{j4a}R^{3331}$, —$(C=S)OR^{2221}$, —$(C=O)SR^{2221}$, $NR^{2221}(C=NR^{3331})OR^{222a1}$, —$NR^{2221}(C=NR^{3331})SR^{333a1}$, —$O(C=O)OR^{2221}$, —$O(C=O)NR^{2221}R^{3331}$, —$O(C=O)SR^{2221}$, —$S(C=O)OR^{2221}$, or —$S(C=O)NR^{2221}R^{3331}$ substituents.

57. The compound or salt of claim 56 wherein $R^1$ is cis- or trans-cyclobutyl substituted at the 3-position by $G^{11}$ wherein $G^{11}$ is —OH, —NH$_2$, —N(CH$_3$)$_2$, —NHAc, —NH(CO)NHCH$_3$, —NH(CO)OCH$_3$, —CH$_2$OH, —CH$_2$NH$_2$, —CH$_2$NHAc, CO$_2$H, CONH$_2$, —CH$_2$N(CH$_3$)$_2$, —CH$_2$NH(CO)NHMe, —CH$_2$NH(CO)OCH$_3$, CO$_2$CH$_3$, CONHCH$_3$,

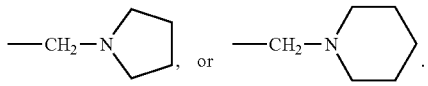

58. The compound or salt of claim 56 wherein $R^1$ is cis- or trans-cyclohexyl substituted at the 4-position by $G^{11}$ wherein $G^{11}$ is —OH, —NH$_2$, —N(CH$_3$)$_2$, —NHAc, —NH(CO)NHCH$_3$, —NH(CO)OCH$_3$, —CH$_2$OH, —CH$_2$NH$_2$, —CH$_2$NHAc, CO$_2$H, CONH$_2$, —CH$_2$N(CH$_3$)$_2$, —CH$_2$NH(CO)NHMe, —CH$_2$NH(CO)OCH$_3$, CO$_2$CH$_3$, CONHCH$_3$,

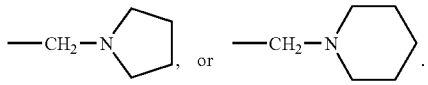

59. A compound selected from the group consisting of:
[1-(3-Benzyloxy-phenyl)-3-cyclobutyl-imidazo[1,5-a]pyrazin-8-ylamine],
1-(3-Benzyloxyphenyl)-3-phenyl-imidazo[1,5-a]pyrazin-8-ylamine,
3-Benzyl-1-(3-benzyloxyphenyl)-imidazo[1,5-a]pyrazin-8-ylamine,
1-(3-Benzyloxyphenyl)-3-naphthalen-1-yl-imidazo[1,5-a]pyrazin-8-ylamine,
1-(3-Benzyloxyphenyl)-3-naphthalen-2-yl-imidazo[1,5-a]pyrazin-8-ylamine,
1-(3-Benzyloxy-phenyl)-3-cyclopentyl-imidazo[1,5-a]pyrazin-8-ylamine,
1-(3-Benzyloxy-phenyl)-3-cyclohexyl-imidazo[1,5-a]pyrazin-8-ylamine,
1-(3-Benzyloxy-phenyl)-3-cycloheptyl-imidazo[1,5-a]pyrazin-8-ylamine,
1-(3-Benzyloxy-phenyl)-3-(tetrahydro-furan-3-yl)-imidazo[1,5-a]pyrazin-8-ylamine,
trans-3-[8-Amino-1-(3-benzyloxy-phenyl)-imidazo[1,5-a]pyrazin-3-yl]-cyclobutanol,
1-(3-Benzyloxy-phenyl)-3-(1-methyl-piperidin-4-yl)-imidazo[1,5-a]pyrazin-8-ylamine,
cis-4-[8-Amino-1-(3-benzyloxy-phenyl)-imidazo[1,5-a]pyrazin-3-yl]-cyclohexanecarboxylic acid amide,
trans-4-[8-Amino-1-(3-benzyloxy-phenyl)-imidazo[1,5-a]pyrazin-3-yl]-cyclohexanecarboxylic acid amide,
cis-{4-[8-Amino-1-(3-benzyloxy-phenyl)-imidazo[1,5-a]pyrazin-3-yl]-cyclohexyl}-methanol,
trans-{4-[8-Amino-1-(3-benzyloxy-phenyl)-imidazo[1,5-a]pyrazin-3-yl]-cyclohexyl}-methanol,
cis-2-{4-[8-Amino-1-(3-benzyloxy-phenyl)-imidazo[1,5-a]pyrazin-3-yl]-cyclohexylmethyl}-isoindole-1,3-dione,
trans-2-{4-[8-Amino-1-(3-benzyloxy-phenyl)-imidazo[1,5-a]pyrazin-3-yl]-cyclohexylmethyl}-isoindole-1,3-dione,
cis-3-(4-Aminomethyl-cyclohexyl)-1-(3-benzyloxy-phenyl)-imidazo[1,5-a]pyrazin-8-ylamine,
trans-3-(4-Aminomethyl-cyclohexyl)-1-(3-benzyloxy-phenyl)-imidazo[1,5-a]pyrazin-8-ylamine,
cis-N-{4-[8-Amino-1-(3-benzyloxy-phenyl)-imidazo[1,5-a]pyrazin-3-yl]-cyclohexylmethyl}-acetamide, or
trans-N-{4-[8-Amino-1-(3-benzyloxy-phenyl)-imidazo[1,5-a]pyrazin-3-yl]-cyclohexylmethyl}-acetamide.
or pharmaceutically acceptable salts thereof.

60. A compound selected from the group consisting of:
trans-N-{4-[8-Amino-1-(3-benzyloxy-phenyl)-imidazo[1,5-a]pyrazin-3-yl]-cyclohexylmethyl}-acetamide,
1-Biphenyl-3-yl-3-cyclobutylimidazo[1,5-a]pyrazin-8-ylamine,
1-(3-Bromo-phenyl)-3-cyclobutylimidazo[1,5-a]pyrazin-8-ylamine,
1-(4'-t-Butylbiphenyl-3-yl)-3-cyclobutylimidazo[1,5-a]pyrazin-8-ylamine,
3-Cyclobutyl-1-(4'-methylbiphenyl-3-yl)-imidazo[1,5-a]pyrazin-8-ylamine,
3-Cyclobutyl-1-(4'-methoxybiphenyl-3-yl)-imidazo[1,5-a]pyrazin-8-ylamine,
1-(3-Benzyloxyphenyl)-3-cyclopentylmethylimidazo[1,5-a]pyrazin-8-ylamine,
1-(3-Benzyloxyphenyl)-3-cyclohexylmethylimidazo[1,5-a]pyrazin-8-ylamine,
1-(3-Benzyloxyphenyl)-imidazo[1,5-a]pyrazin-8-ylamine,
1-(3-Benzyloxyphenyl)-3-trifluoromethylimidazo[1,5-a]pyrazin-8-ylamine,
4-[8-Amino-1-(3-benzyloxyphenyl)-imidazo[1,5-a]pyrazin-3-yl]-benzamide,
3-Cyclobutyl-1-phenylimidazo[1,5-a]pyrazin-8-ylamine,
(trans-3-(4-Azetidin-1-ylmethyl-cyclohexyl)-1-(3-benzyloxy-phenyl)-imidazo[1,5-a]pyrazin-8-ylamine,
trans-1-(3-Benzyloxy-phenyl)-3-(4-pyrrolidin-1-ylmethyl-cyclohexyl)-imidazo[1,5-a]pyrazin-8-ylamine), trans-4-[8-Amino-1-(3-benzyloxy-phenyl)-imidazo[1,5-a]pyrazin-3-yl]-cyclohexanecarboxylic acid methyl ester,
(trans-4-[8-Amino-1-(3-benzyloxy-phenyl)-imidazo[1,5-a]pyrazin-3-yl]-cyclohexanecarboxylic acid,
(trans-4-[8-Amino-1-(3-benzyloxy-phenyl)-imidazo[1,5-a]pyrazin-3-yl]-cyclohexanecarboxylic acid methylamide,
4-[8-Amino-1-(3-benzyloxy-phenyl)-imidazo[1,5-a]pyrazin-3-yl]-cyclohexanecarboxylic acid ethylamide,
trans-1-(3-Benzyloxy-phenyl)-3-(3-pyrrolidin-1-ylmethyl-cyclobutyl)-imidazo[1,5-a]pyrazin-8-ylamine,
cis-1-(3-Benzyloxy-phenyl)-3-(3-pyrrolidin-1-ylmethyl-cyclobutyl)-imidazo[1,5-a]pyrazin-8-ylamine,
trans-3-(3-Azetidin-1-ylmethylcyclobutyl)-1-(3-benzyloxyphenyl)-imidazo[1,5-a]pyrazin-8-ylamine,
cis-3-(3-Azetidin-1-ylmethylcyclobutyl)-1-(3-benzyloxyphenyl)-imidazo[1,5-a]pyrazin-8-ylamine,
toluene-4-sulfonic acid 3-[8-amino-1-(3-benzyloxyphenyl)-imidazo[1,5-a]pyrazin-3-yl]cyclobutylmethyl ester,
{3-[8-Amino-1-(3-benzyloxyphenyl)-imidazo[1,5-a]pyrazin-3-yl]cyclobutyl}methanol,
3-[8-Amino-1-(3-benzyloxy-phenyl)-imidazo[1,5-a]pyrazin-3-yl]-1-methyl-cyclobutanol,
3-[8-Amino-1-(3-benzyloxy-phenyl)-imidazo[1,5-a]pyrazin-3-yl]-1-ethyl-cyclobutanol,
1-Allyl-3-[8-amino-1-(3-benzyloxy-phenyl)-imidazo[1,5-a]pyrazin-3-yl]-cyclobutanol,
1-(3-Benzyloxyphenyl)-3-tert-butylimidazo[1,5-a]pyrazin-8-ylamine,
cis-1-[3-(Benzyloxy)phenyl]-3-[3-(dimethylamino)cyclobutyl]imidazo[1,5-a]pyrazin-8-amine,
3-(8-Amino-3-cyclobutyl-imidazo[1,5-a]pyrazin-1-yl)-phenol,
3-Cyclobutyl-1-[3-(4-fluoro-benzyloxy)-phenyl]-imidazo[1,5-a]pyrazin-8-ylamine,
trans-4-[8-Amino-1-(3-hydroxy-phenyl)-imidazo[1,5-a]pyrazin-3-yl]cyclohexanecarboxylic acid methyl ester,
3-[8-Amino-1-(3-benzyloxyphenyl)-imidazo[1,5-a]pyrazin-3-yl]-benzamide,
{3-[8-Amino-1-(3-benzyloxyphenyl)-imidazo[1,5-a]pyrazin-3-yl]-phenyl}-methanol,
3-(3-Aminomethylphenyl)-1-(3-benzyloxyphenyl)-imidazo[1,5-a]pyrazin-8-ylamine,
2-{3-[8-Amino-1-(3-benzyloxyphenyl)-imidazo[1,5-a]pyrazin-3-yl]-benzyl}-isoindole-1,3-dione,
4-{8-Amino-1-[3-(2,6-difluoro-benzyloxy)-phenyl]-imidazo[1,5-a]pyrazin-3-yl}-cyclohexanecarboxylic acid,
cis-3-(3-Dimethylaminomethyl-cyclobutyl)-1-(3-benzyloxyphenyl)-imidazo[1,5-a]pyrazin-8-ylamine,
cis-3-(3-Azetidin-1-ylmethylcyclobutyl)-1-(3-benzyloxyphenyl)-imidazo[1,5-a]pyrazin-8-ylamine,
cis-3-(3-Pyrrolidin-1-ylmethylcyclobutyl)-1-(3-benzyloxyphenyl)-imidazo[1,5-a]pyrazin-8-ylamine,
cis-3-(3-Azidomethyl-cyclobutyl)-1-(3-benzyloxyphenyl)-imidazo[1,5-a]pyrazin-8-ylamine,
cis-3-(3-aminomethyl-cyclobutyl)-1-(3-benzyloxyphenyl)-imidazo[1,5-a]pyrazin-8-ylamine,
cis-3-[8-Amino-1-(3-benzyloxy-phenyl)-imidazo[1,5-a]pyrazin-3-yl]-cyclobutane-carboxylic acid amide,
trans-3-[8-Amino-1-(3-benzyloxy-phenyl)-imidazo[1,5-a]pyrazin-3-yl]-cyclobutane-carboxylic acid amide,
3-[8-Amino-1-(3-benzyloxy-phenyl)-imidazo[1,5-a]pyrazin-3-yl]-1-hydroxymethyl-cyclobutanol,
cis-Toluene-4-sulfonic acid 3-[8-amino-1-(3-benzyloxy-phenyl)-imidazo[1,5-a]pyrazin-3-yl]-1-hydroxy-cyclobutylmethyl ester,
trans-Toluene-4-sulfonic acid 3-[8-amino-1-(3-benzyloxy-phenyl)-imidazo[1,5-a]pyrazin-3-yl]-1-hydroxy-cyclobutylmethyl ester,
trans-3-[8-Amino-1-(3-benzyloxy-phenyl)-imidazo[1,5-a]pyrazin-3-yl]-1-azetidin-1-ylmethyl-cyclobutanol,
cis-3-[8-Amino-1-(3-benzyloxy-phenyl)-imidazo[1,5-a]pyrazin-3-yl]-1-azetidin-1-ylmethyl-cyclobutanol,
1-[3-(4-tert-Butoxy-benzyloxy)-phenyl]-3-cyclobutyl-imidazo[1,5-a]pyrazin-8-ylamine,
2-[3-(8-Amino-3-cyclobutyl-imidazo[1,5-a]pyrazin-1-yl)-phenoxymethyl]-benzonitrile,
3-Cyclobutyl-1-[3-(2-nitro-benzyloxy)-phenyl]-imidazo[1,5-a]pyrazin-8-ylamine,
1-[3-(2-Bromo-benzyloxy)-phenyl]-3-cyclobutyl-imidazo[1,5-a]pyrazin-8-ylamine,
1-[3-(3-Aminomethyl-benzyloxy)-phenyl]-3-cyclobutyl-imidazo[1,5-a]pyrazin-8-ylamine,
3-[3-(8-Amino-3-cyclobutyl-imidazo[1,5-a]pyrazin-1-yl)-phenoxymethyl]-benzoic acid methyl ester,
3-[3-(8-Amino-3-cyclobutyl-imidazo[1,5-a]pyrazin-1-yl)-phenoxymethyl]-benzamide,
{3-[3-(8-Amino-3-cyclobutyl-imidazo[1,5-a]pyrazin-1-yl)-phenoxymethyl]-phenyl}-methanol,
2-{3-[3-(8-Amino-3-cyclobutyl-imidazo[1,5-a]pyrazin-1-yl)-phenoxymethyl]-benzyl}-isoindole-1,3-dione,
3-[3-(8-Amino-3-cyclobutyl-imidazo[1,5-a]pyrazin-1-yl)-phenoxymethyl]-benzoic acid,
3-[3-(8-Amino-3-cyclobutyl-imidazo[1,5-a]pyrazin-1-yl)-phenoxymethyl]-N-methyl-benzamide,
1-(3-Benzyloxy-phenyl)-3-(3-methoxymethylene-cyclobutyl)-imidazo[1,5-a]pyrazin-8-ylamine,
3-[8-Amino-1-(3-benzyloxy-phenyl)-imidazo[1,5-a]pyrazin-3-yl]cyclobutanecarbaldehyde,
cis-1-(3-Benzyloxy-phenyl)-3-(4-methoxy-cyclohexyl)-imidazo[1,5-a]pyrazin-8-ylamine,
trans-1-(3-Benzyloxy-phenyl)-3-(4-methoxy-cyclohexyl)-imidazo[1,5-a]pyrazin-8-ylamine,
cis-tert-Butyl ({3-[8-amino-1-(3-benzyloxyphenyl)-imidazo[1,5-a]pyrazin-3-yl]-cyclobutyl}oxy)acetate,
cis-2-{3-[8-Amino-1-(3-benzyloxyphenyl)imidazo[1,5-a]pyrazin-3-yl]cyclobutoxy}ethanol,
cis-Toluene-4-sulfonic acid 2-{3-[8-amino-1-(3-benzyloxyphenyl)imidazo[1,5-a]pyrazin-3-yl]cyclobutoxy}ethyl ester,
cis-1-(3-Benzyloxyphenyl)-3-[3-(2-dimethylaminoethoxy)-cyclobutyl]imidazo[1,5-a]pyrazin-8-yl amine,
cis-{3-[8-Amino-1-(3-benzyloxyphenyl)imidazo[1,5-a]pyrazin-3-yl]-cyclobutoxy}acetic acid,
cis-2-{3-[8-Amino-1-(3-benzyloxyphenyl)imidazo[1,5-a]pyrazin-3-yl]cyclobutoxy}-N-methylacetamide,
cis-2-{3-[8-Amino-1-(3-benzyloxy-phenyl)imidazo[1,5-a]pyrazin-3-yl]cyclobutoxy}acetamide,
1-(3-benzyloxy-4-methoxyphenyl)-3-cyclobutyl-imidazo[1,5-a]pyrazin-8-ylamine,
1-(3-Benzyloxy-4-fluorophenyl)-3-cyclobutyl-imidazo[1,5-a]pyrazin-8-ylamine,
1-(3-Benzyloxy-4-isopropoxyphenyl)-3-cyclobutylimidazo[1,5-a]pyrazin-8-ylamine, 1-(3-Benzyloxy-4-ethoxyphenyl)-3-cyclobutylimidazo[1,5-a]pyrazin-8-ylamine, 4-(8-Amino-3-cyclobutylimidazo[1,5-a]pyrazin-1-yl)-2-benzyloxyphenol, 4-{8-Amino-1-[3-(2,6-difluoro-benzyloxy)-phenyl]-imidazo[1,5-a]pyrazin-3-yl}-cyclohexanecarboxylic acid amide, 4-{8-Amino-1-[3-(2,6-difluoro-benzyloxy)-phenyl]-imidazo[1,5-a]pyrazin-3-yl}-cyclohexanecarboxylic acid methylamide, N-{3-[3-(8-Amino-3-cyclobutyl-imidazo[1,5-a]pyrazin-1-yl)-phenoxymethyl]-phenyl}-acetamide, or pharmaceutically acceptable salts thereof.

61. A compound selected from the group consisting of:

| Structure | Name |
|---|---|
| 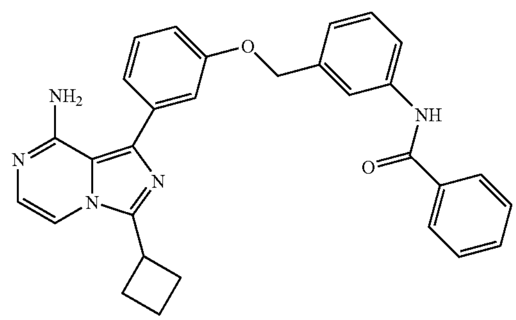 | N-{3-[3-(8-Amino-3-cyclobutyl-imidazo[1,5-a]pyrazin-1-yl)-phenoxymethyl]-phenyl}-benzamide |
| 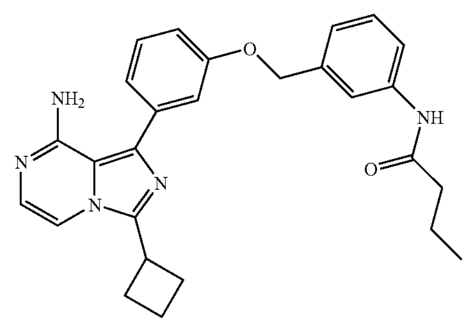 | N-{3-[3-(8-Amino-3-cyclobutyl-imidazo[1,5-a]pyrazin-1-yl)-phenoxymethyl]-phenyl}-butyramide |
| 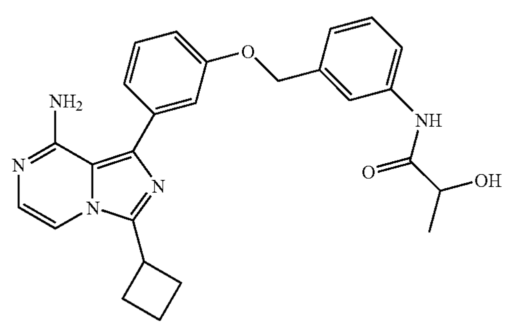 | N-{3-[3-(8-Amino-3-cyclobutyl-imidazo[1,5-a]pyrazin-1-yl)-phenoxymethyl]-phenyl}-2-hydroxy-propionamide |
| 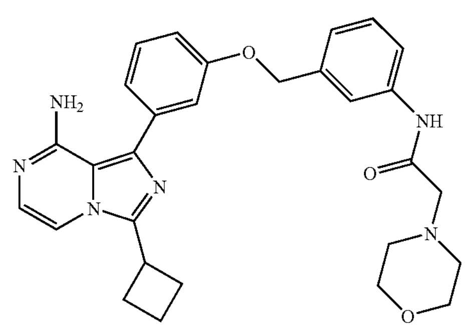 | N-{3-[3-(8-Amino-3-cyclobutyl-imidazo[1,5-a]pyrazin-1-yl)-phenoxymethyl]-phenyl}-2-morpholin-4-yl-acetamide |

| Structure | Name |
|---|---|
| 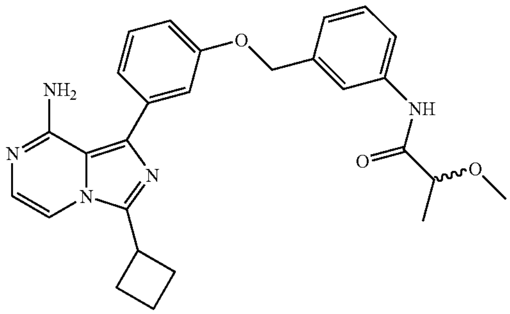 | N-{3-[3-(8-Amino-3-cyclobutyl-imidazo[1,5-a]pyrazin-1-yl)-phenoxymethyl]-phenyl}-2-methoxy-propionamide |
| 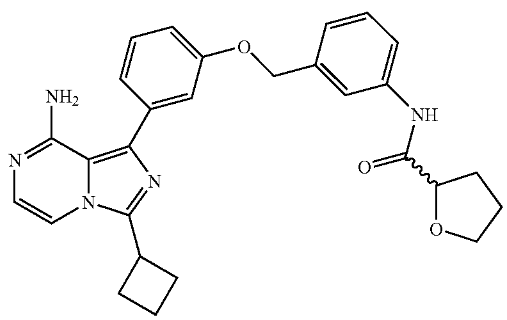 | Tetrahydro-furan-2-carboxylic acid {3-[3-(8-amino-3-cyclobutyl-imidazo[1,5-a]pyrazin-1-yl)-phenoxymethyl]-phenyl}-amide |
| 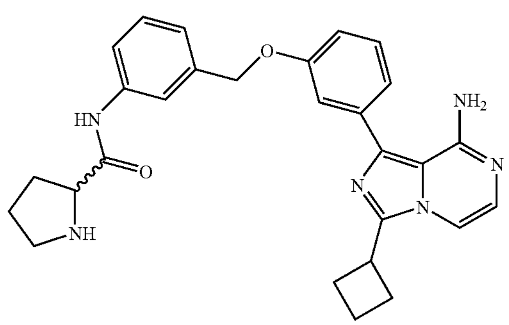 | Pyrrolidine-2-carboxylic acid {3-[3-(8-amino-3-cyclobutyl-imidazo[1,5-a]pyrazin-1-yl)-phenoxymethyl]-phenyl}-amide |
| | N-{3-[3-(8-Amino-3-cyclobutyl-imidazo[1,5-a]pyrazin-1-yl)-phenoxymethyl]-phenyl}-methanesulfonamide |

| Structure | Name |
|---|---|
| 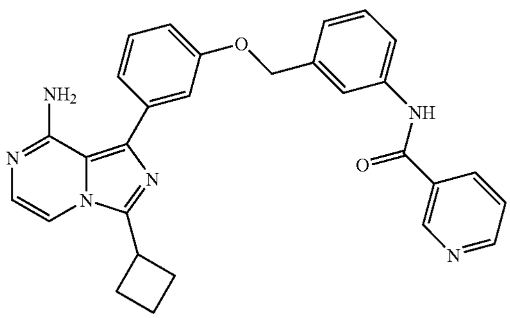 | N-{3-[3-(8-Amino-3-cyclobutyl-imidazo[1,5-a]pyrazin-1-yl)-phenoxymethyl]-phenyl}-nicotinamide |
| 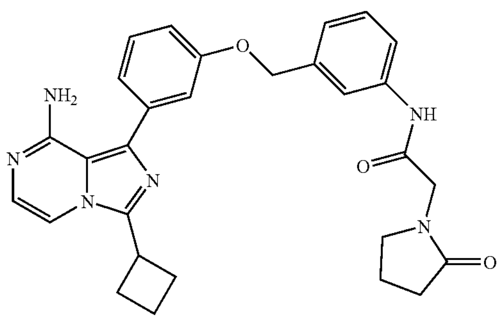 | N-{3-[3-(8-Amino-3-cyclobutyl-imidazo[1,5-a]pyrazin-1-yl)-phenoxymethyl]-phenyl}-2-(2-oxo-pyrrolidin-1-yl)-acetamide |
| 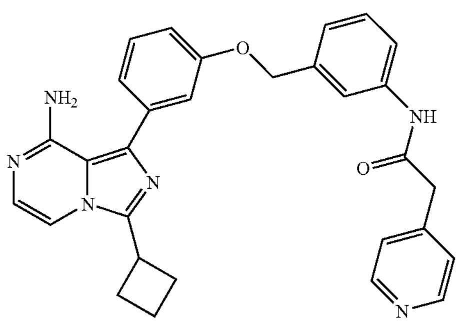 | N-{3-[3-(8-Amino-3-cyclobutyl-imidazo[1,5-a]pyrazin-1-yl)-phenoxymethyl]-phenyl}-2-pyridin-4-yl-acetamide |
| 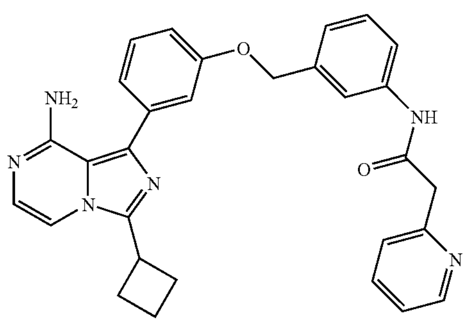 | N-{3-[3-(8-Amino-3-cyclobutyl-imidazo[1,5-a]pyrazin-1-yl)-phenoxymethyl]-phenyl}-2-pyridin-2-yl-acetamide |
| 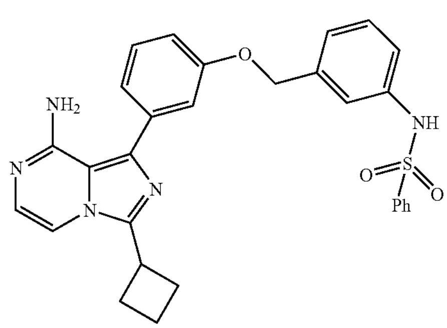 | N-{3-[3-(8-Amino-3-cyclobutyl-imidazo[1,5-a]pyrazin-1-yl)-phenoxymethyl]-phenyl}-benzenesulfonamide |

-continued

| Structure | Name |
|---|---|
| 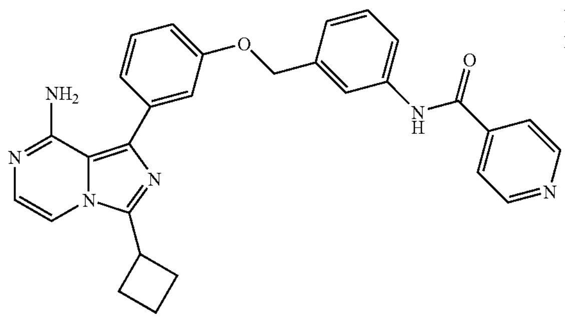 | N-{3-[3-(8-Amino-3-cyclobutyl-imidazo[1,5-a]pyrazin-1-yl)-phenoxymethyl]-phenyl}-isonicotinamide |
| 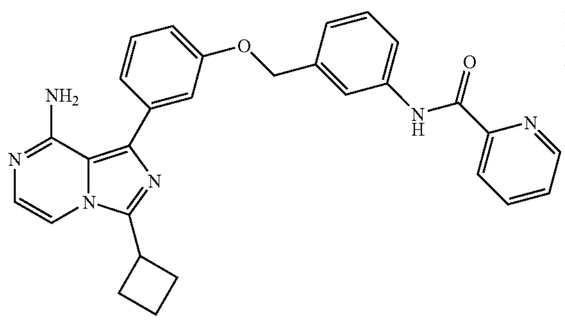 | Pyridine-2-carboxylic acid {3-[3-(8-amino-3-cyclobutyl-imidazo[1,5-a]pyrazin-1-yl)-phenoxymethyl]-phenyl}-amide |
| | 1-Methyl-1H-imidazole-4-sulfonic acid {3-[3-(8-amino-3-cyclobutyl-imidazo[1,5-a]pyrazin-1-yl)-phenoxymethyl]-phenyl}-amide | or a pharmaceutically acceptable salt thereof.

62. A compound selected from the group consisting of:

| Structure | Name |
|---|---|
| 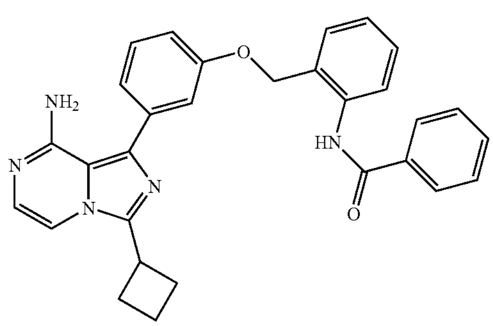 | N-{2-[3-(8-Amino-3-cyclobutyl-imidazol[1,5-a]pyrazin-1-yl)-phenoxymethyl]-phenyl}-benzamide |

| Structure | Name |
|---|---|
| 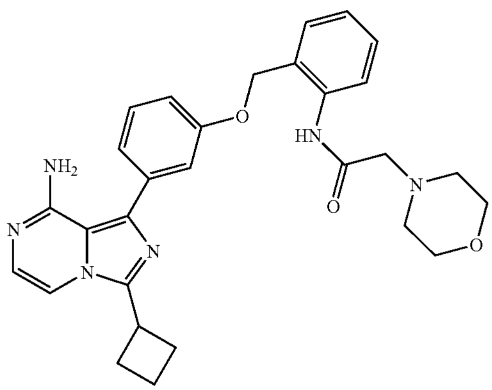 | N-{2-[3-(8-Amino-3-cyclobutyl-imidazo[1,5-a]pyrazin-1-yl)-phenoxymethyl]-phenyl}-2-morpholin-4-yl-acetamide |
| 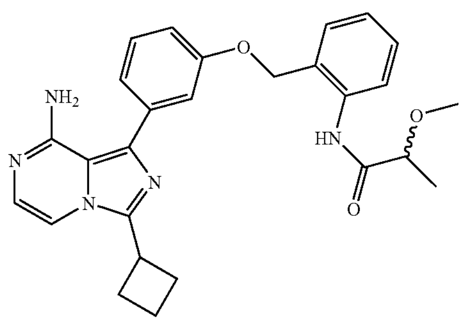 | N-{2-[3-(8-Amino-3-cyclobutyl-imidazo[1,5-a]pyrazin-1-yl)-phenoxymethyl]-phenyl}-2-methoxy-propionamide |
| 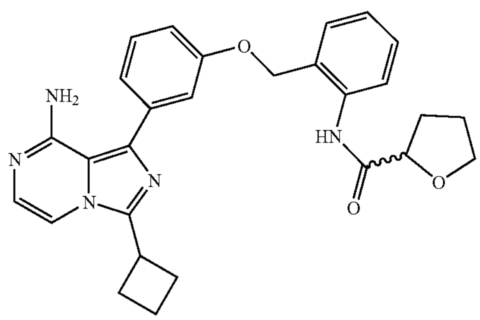 | Tetrahydro-furan-2-carboxylic acid {2-[3-(8-amino-3-cyclobutyl-imidazo[1,5-a]pyrazin-1-yl)-phenoxymethyl]-phenyl}-amide |
| 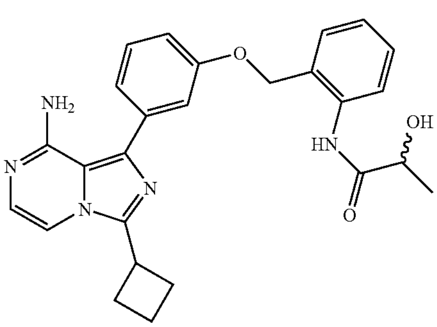 | N-{2-[3-(8-Amino-3-cyclobutyl-imidazo[1,5-a]pyrazin-1-yl)-phenoxymethyl]-phenyl}-2-hydroxy-propionamide |

| Structure | Name |
|---|---|
| 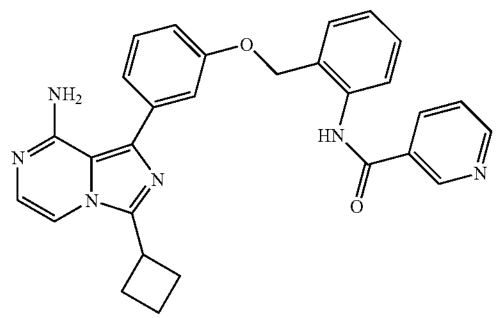 | N-{2-[3-(8-Amino-3-cyclobutyl-imidazo[1,5-a]pyrazin-1-yl)-phenoxymethyl]-phenyl}-nicotinamide |
| 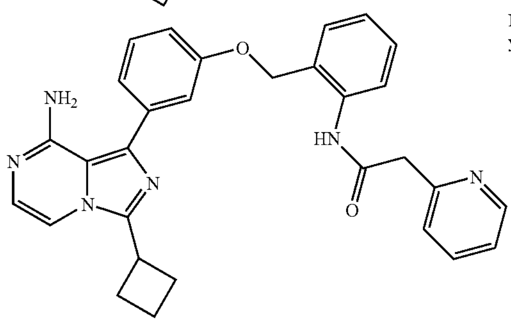 | N-{2-[3-(8-Amino-3-cyclobutyl-imidazo[1,5-a]pyrazin-1-yl)-phenoxymethyl]-phenyl}-2-pyridin-2-yl-acetamide |
| | N-{2-[3-(8-Amino-3-cyclobutyl-imidazo[1,5-a]pyrazin-1-yl)-phenoxymethyl]-phenyl}-isonicotmamide | or a pharmaceutically acceptable salt thereof.

63. A compound selected from the group consisting of:

| R1 | Name |
|---|---|
| | 1-(3-Benzyloxy-phenyl)-3-(4-phenylaminomethyl-cyclohexyl)-imidazo[1,5-a]pyrazin-8-ylamine |

-continued

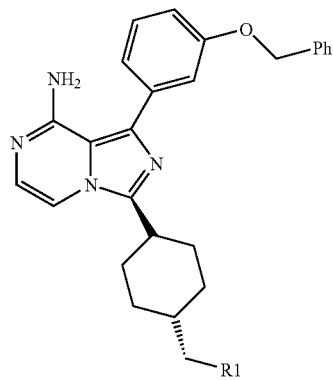

| R1 | Name |
|---|---|
| *-N(morpholine) | 1-(3-Benzyloxy-phenyl)-3-(4-morpholin-4-ylmethyl-cyclohexyl)-imidazo[1,5-a]pyrazin-8-ylamine |
| *-N(N-methylpiperazine) | 1-(3-Benzyloxy-phenyl)-3-[4-(4-methyl-piperazin-1-ylmethyl)-cyclohexyl]-imidazo[1,5-a]pyrazin-8-ylamine |
| *-N(Et)₂ | 1-(3-Benzyloxy-phenyl)-3-(4-diethylaminomethyl-cyclohexyl)-imidazo[1,5-a]pyrazin-8-ylamine |
| 4-hydroxypiperidin-1-yl* | 1-{4-[8-Amino-1-(3-benzyloxy-phenyl)-imidazo[1,5-a]pyrazin-3-yl]-cyclohexylmethyl}-piperidin-4-ol |
| azepan-1-yl* | 3-(4-Azepan-1-ylmethyl-cyclohexyl)-1-(3-benzyloxy-phenyl)-imidazo[1,5-a]pyrazin-8-ylamine |
| *-N(Me)(Et) | 1-(3-Benzyloxy-phenyl)-3-{4-[(ethyl-methyl-amino)-methyl]-cyclohexyl}-imidazo[1,5-a]pyrazin-8-ylamine |
| 3-hydroxypiperidin-1-yl* | 1-{4-[8-Amino-1-(3-benzyloxy-phenyl)-imidazo[1,5-a]pyrazin-3-yl]-cyclohexylmethyl}-piperidin-3-ol |
| Me₂N-CH₂CH₂-N(Me)-* | N-{4-[8-Amino-1-(3-benzyloxy-phenyl)-imidazo[1,5-a]pyrazin-3-yl]-cyclohexylmethyl}-N,N',N'-trimethyl-ethane-1,2-diamine |

-continued

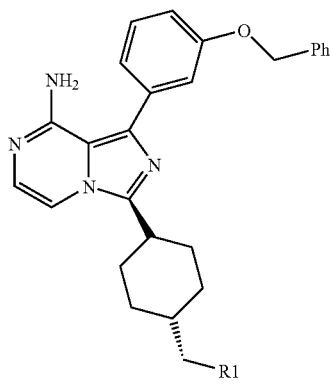

| R1 | Name |
|---|---|
| 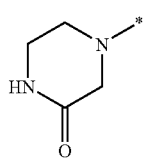 | 2-({4-[8-Amino-1-(3-benzyloxy-phenyl)-imidazo[1,5-a]pyrazin-3-yl]-cyclohexylmethyl}-methyl-amino)-ethanol |
| 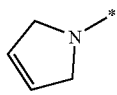 | 4-{4-[8-Amino-1-(3-benzyloxy-phenyl)-imidazo[1,5-a]pyrazin-3-yl]-cyclohexylmethyl}-piperazin-2-one |
| 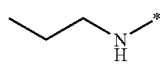 | 1-(3-Benzyloxy-phenyl)-3-[4-(2,5-dihydro-pyrrol-1-ylmethyl)-cyclohexyl]-imidazo[1,5-a]pyrazin-8-ylamine |
| 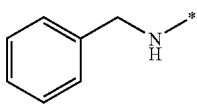 | 1-(3-Benzyloxy-phenyl)-3-(4-propylaminomethyl-cyclohexyl)-imidazo[1,5-a]pyrazin-8-ylamine |
| 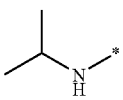 | 3-[4-(Benzylamino-methyl)-cyclohexyl]-1-(3-benzyloxy-phenyl)-imidazo[1,5-a]pyrazin-8-ylamine |
| 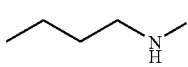 | 1-(3-Benzyloxy-phenyl)-3-[4-(isopropylamino-methyl)-cyclohexyl]-imidazo[1,5-a]pyrazin-8-ylamine |
| 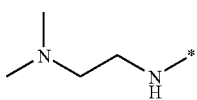 | 1-(3-Benzyloxy-phenyl)-3-(4-butylaminomethyl-cyclohexyl)-imidazo[1,5-a]pyrazin-8-ylamine |
| 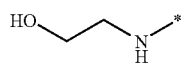 | N-{4-[8-Amino-1-(3-benzyloxy-phenyl)-imidazo[1,5-a]pyrazin-3-yl]-cyclohexylmethyl}-N',N'-dimethyl-ethane-1,2-diamine |
| 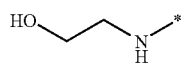 | 2-({4-[8-Amino-1-(3-benzyloxy-phenyl)-imidazo[1,5-a]pyrazin-3-yl]-cyclohexylmethyl}-amino)-ethanol |
| 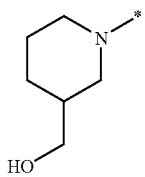 | (1-{4-[8-Amino-1-(3-benzyloxy-phenyl)-imidazo[1,5-a]pyrazin-3-yl]-cyclohexylmethyl}-piperidin-3-yl)-methanol |

-continued

| R1 | Name |
|---|---|
| HO-CH2-piperidin-N-methyl | (1-{4-[8-Amino-1-(3-benzyloxy-phenyl)-imidazo[1,5-a]pyrazin-3-yl]-cyclohexylmethyl}-piperidin-4-yl)-methanol |
| HO-(S)-pyrrolidin-N- | 1-{4-[8-Amino-1-(3-benzyloxy-phenyl)-imidazo[1,5-a]pyrazin-3-yl]-cyclohexylmethyl}-pyrrolidin-3-ol |
| HO-(R)-pyrrolidin-N- | 1-{4-[8-Amino-1-(3-benzyloxy-phenyl)-imidazo[1,5-a]pyrazin-3-yl]-cyclohexylmethyl}-pyrrolidin-3-ol |
| tetrahydrofuran-2-yl-CH2-NH- | 1-(3-Benzyloxy-phenyl)-3-(4-{[(tetrahydro-furan-2-ylmethyl)-amino]-methyl}-cyclohexyl)-imidazo[1,5-a]pyrazin-8-ylamine |
| (CH3)2N-CH2CH2CH2-NH- | N-{4-[8-Amino-1-(3-benzyloxy-phenyl)-imidazo[1,5-a]pyrazin-3-yl]-cyclohexylmethyl}-N',N'-dimethyl-propane-1,3-diamine |
| CH3-CH(OH)-CH2-NH- | 1-({4-[8-Amino-1-(3-benzyloxy-phenyl)-imidazo[1,5-a]pyrazin-3-yl]-cyclohexylmethyl}-amino)-propan-2-ol |
| HO-CH2CH2CH2-NH- | 3-({4-[8-Amino-1-(3-benzyloxy-phenyl)-imidazo[1,5-a]pyrazin-3-yl]-cyclohexylmethyl}-amino)-propan-1-ol |
| pyridin-3-yl-CH2-NH- | 1-(3-Benzyloxy-phenyl)-3-(4-{[(pyridin-3-ylmethyl)-amino]-methyl}-cyclohexyl)-imidazo[1,5-a]pyrazin-8-ylamine |
| pyrrolidin-N-CH2CH2-NH- | 1-(3-Benzyloxy-phenyl)-3-{4-[(2-pyrrolidin-1-yl-ethylamino)-methyl]-cyclohexyl}-imidazo[1,5-a]pyrazin-8-ylamine |
| (Et)2N-CH2CH2-NH- | N-{4-[8-Amino-1-(3-benzyloxy-phenyl)-imidazo[1,5-a]pyrazin-3-yl]-cyclohexylmethyl}-N',N'-diethyl-ethane-1,2-diamine |
| 1-methyl-piperidin-4-yl-NH- | 1-(3-Benzyloxy-phenyl)-3-{4-[(1-methyl-piperidin-4-ylamino)-methyl]-cyclohexyl}-imidazo[1,5-a]pyrazin-8-ylamine |

-continued

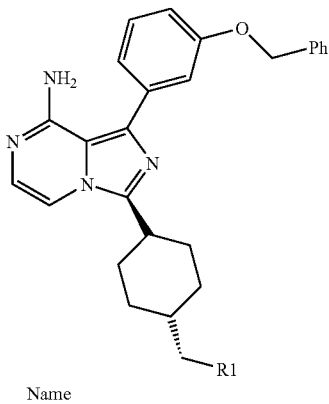

| R1 | Name |
|---|---|
| 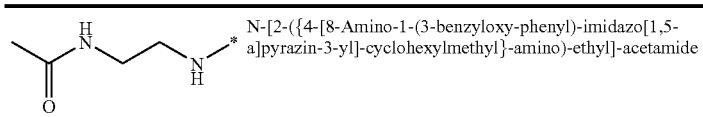 | N-[2-({4-[8-Amino-1-(3-benzyloxy-phenyl)-imidazo[1,5-a]pyrazin-3-yl]-cyclohexylmethyl}-amino)-ethyl]-acetamide |
| 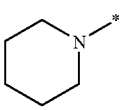 | 1-(3-Benzyloxy-phenyl)-3-(4-piperidin-1-ylmethyl-cyclohexyl)-imidazo[I,5-a]pyrazin-8-ylamine | or a pharmaceutically acceptable salt thereof, wherein * is the point of attachment.

64. A compound selected from the group consisting of:

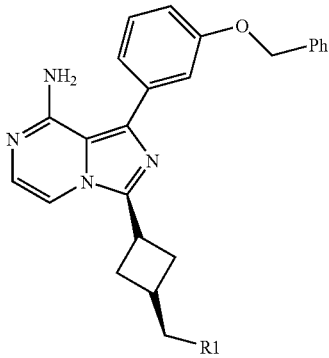

| R1 | Name |
|---|---|
| 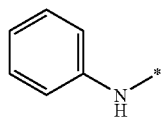 | 1-(3-Benzyloxy-phenyl)-3-(3-phenylaminomethyl-cyclobutyl)-imidazo[1,5-a]pyrazin-8-ylamine |
| 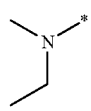 | 1-(3-Benzyloxy-phenyl)-3-{3-[(ethyl-methyl-amino)-methyl]-cyclobutyl}-imidazo[1,5-a]pyrazin-8-ylamine |
| 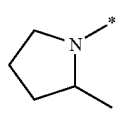 | 1-(3-Benzyloxy-phenyl)-3-[3-(2-methyl-pyrrolidin-1-ylmethyl)-cyclobutyl]-imidazo[1,5-a]pyrazin-8-ylamine |

-continued

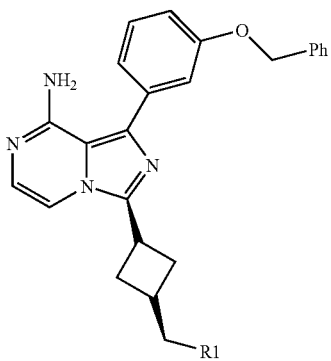

| R1 | Name |
|---|---|
| 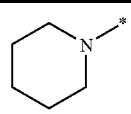 | 1-(3-Benzyloxy-phenyl)-3-(3-piperidin-1-ylmethyl-cyclobutyl)-imidazo[1,5-a]pyrazin-8-ylamine |
| 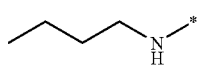 | 1-(3-Benzyloxy-phenyl)-3-(3-butylaminomethyl-cyclobutyl)-imidazo[1,5-a]pyrazin-8-ylamine |
| 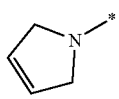 | 1-(3-Benzyloxy-phenyl)-3-[3-(2,5-dihydro-pyrrol-1-ylmethyl)-cyclobutyl]-imidazo[1,5-a]pyrazin-8-ylamine |
| 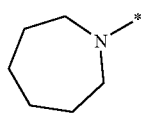 | 3-(3-Azepan-1-ylmethyl-cyclobutyl)-1-(3-benzyloxy-phenyl)-imidazo[1,5-a]pyrazin-8-ylamine |
| 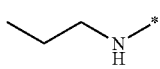 | 1-(3-Benzyloxy-phenyl)-3-(3-propylaminomethyl-cyclobutyl)-imidazo[1,5-a]pyrazin-8-ylamine |
| 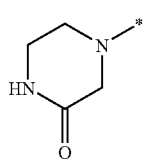 | 4-{3-[8-Amino-1-(3-benzyloxy-phenyl)-imidazo[1,5-a]pyrazin-3-yl]-cyclobutylmethyl}-piperazin-2-one |
| 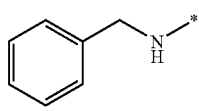 | 3-[3-(Benzylamino-methyl)-cyclobutyl]-1-(3-benzyloxy-phenyl)-imidazol[1,5-a]pyrazin-8-ylamine |
| 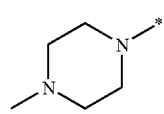 | 1-(3-Benzyloxy-phenyl)-3-[3-(4-methyl-piperazin-1-ylmethyl)-cyclobutyl]-imidazo[1,5-a]pyrazin-8-ylamine |

-continued

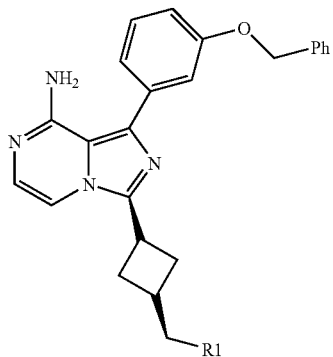

| R1 | Name |
|---|---|
| HO―\―N(CH₃)―* | 2-({3-[8-Amino-1-(3-benzyloxy-phenyl)-imidazo[1,5-a]pyrazin-3-yl]-cyclobutylmethyl}-methyl-amino)-ethanol |
| HO-piperidin-N-* | 1-{3-[8-Amino-1-(3-benzyloxy-phenyl)-imidazo[1,5-a]pyrazin-3-yl]-cyclobutylmethyl}-piperidin-4-ol |
| iPr-NH-* | 1-(3-Benzyloxy-phenyl)-3-[3-(isopropylamino-methyl)-cyclobutyl]-imidazo[1,5-a]pyrazin-8-ylamine |
| morpholin-N-* | 1-(3-Benzyloxy-phenyl)-3-(3-morpholin-4-ylmethyl-cyclobutyl)-imidazo[1,5-a]pyrazin-8-ylamine |
| AcNH-CH₂CH₂-NH-* | N-[2-({3-[8-Amino-1-(3-benzyloxy-phenyl)-imidazo[1,5-a]pyrazin-3-yl]-cyclobutylmethyl}-amino)-ethyl]-acetamide |
| 3-hydroxypiperidin-N-* | 1-{3-[8-Amino-1-(3-benzyloxy-phenyl)-imidazo[1,5-a]pyrazin-3-yl]-cyclobutylmethyl}-piperidin-3-ol |
| MeO-CH₂CH₂-NH-* | 2-({3-[8-Amino-1-(3-benzyloxy-phenyl)-imidazo[1,5-a]pyrazin-3-yl]-cyclobutylmethyl}-amino)-ethanol |
| 4-methylpiperazin-N-* | 1-(3-Benzyloxy-phenyl)-3-[3-(4-methyl-piperazin-1-ylmethyl)-cyclobutyl]-imidazo[1,5-a]pyrazin-8-ylamine | or a pharmaceutically acceptable salt thereof, wherein * is the point of attachment.

65. A compound selected from the group consisting of:

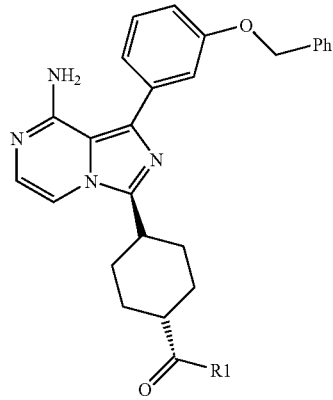

| R1 | Name |
|---|---|
| Et₂N-CH₂CH₂-NH-* | 4-[8-Amino-1-(3-benzyloxy-phenyl)-imidazo[1,5-a]pyrazin-3-yl]-cyclohexanecarboxylic acid (2-diethylamino-ethyl)-amide |
| MeO-CH₂CH₂-NH-* | 4-[8-Amino-1-(3-benzyloxy-phenyl)-imidazo[1,5-a]pyrazin-3-yl]-cyclohexanecarboxylic acid (2-methoxy-ethyl)-amide |
| HO-CH₂CH₂-NH-* | 4-[8-Amino-1-(3-benzyloxy-phenyl)-imidazo[1,5-a]pyrazin-3-yl]-cyclohexanecarboxylic acid (2-hydroxy-ethyl)-amide |
| morpholin-4-yl-* | {4-[8-Amino-(3-benzyloxy-phenyl)-imidazo[1,5-a]pyrazin-3-yl]-cyclohexyl}-morpholin-4-yl-methanone |
| PhCH₂-NH-* | 4-[8-Amino-1-(3-benzyloxy-phenyl)-imidazo[1,5-a]pyrazin-3-yl]-cyclohexanecarboxylic acid benzylamide |
| 4-hydroxy-piperidin-1-yl-* | {4-[8-Amino-1-(3-benzyloxy-phenyl)-imidazo[1,5-a]pyrazin-3-yl]-cyclohexyl}-(4-hydroxy-piperidin-1-yl)-methanone |
| HO-CH₂CH₂-N(Me)-* | 4-[8-Amino-1-(3-benzyloxy-phenyl)-imidazo[1,5-a]pyrazin-3-yl]-cyclohexanecarboxylic acid (2-hydroxy-ethyl)-methyl-amide |
| azepan-1-yl-* | {4-[8-Amino-1-(3-benzyloxy-phenyl)-imidazo[1,5-a]pyrazin-3-yl]-cyclohexyl}-azepan-1-yl-methanone |
| piperidin-1-yl-* | {4-[8-Amino-1-(3-benzyloxy-phenyl)-imidazo[1,5-a]pyrazin-3-yl]-cyclohexyl}-piperidin-1-yl-methanone |
| n-Bu-NH-* | 4-[8-Amino-1-(3-benzyloxy-phenyl)-imidazo[1,5-a]pyrazin-3-yl]-cyclohexanecarboxylic acid butylamide |

-continued

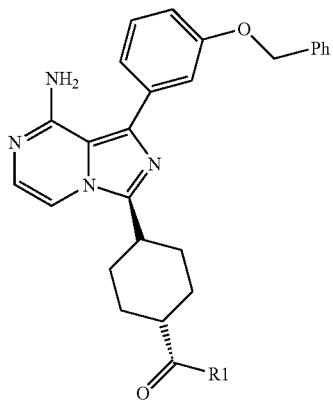

| R1 | Name |
|---|---|
| 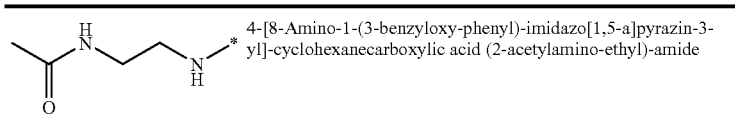 | |

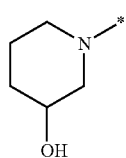

4-[8-Amino-1-(3-benzyloxy-phenyl)-imidazo[1,5-a]pyrazin-3-yl]-cyclohexanecarboxylic acid (2-acetylamino-ethyl)-amide

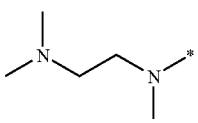

{4-[8-Amino-1-(3-benzyloxy-phenyl)-imidazo[1,5-a]pyrazin-3-yl]-cyclohexyl}-(3-hydroxy-piperidin-1-yl)-methanone

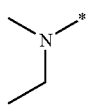

4-[8-Amino-1-(3-benzyloxy-phenyl)-imidazo[1,5-a]pyrazin-3-yl]-cyclohexanecarboxylic acid (2-dimethylamino-ethyl)-methyl-amide

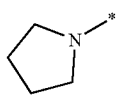

4-[8-Amino-1-(3-benzyloxy-phenyl)-imidazo[1,5-a]pyrazin-3-yl]-cyclohexanecarboxylic acid ethyl-methyl-amide

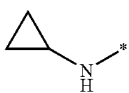

{4-[8-Amino-1-(3-benzyloxy-phenyl)-imidazo[1,5-a]pyrazin-3-yl]-cyclohexyl}-pyrrolidin-1-yl-methanone

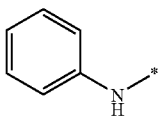

4-[8-Amino-1-(3-benzyloxy-phenyl)-imidazo[1,5-a]pyrazin-3-yl]-cyclohexanecarboxylic acid cyclopropylamide

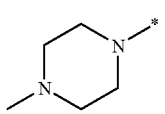

4-[8-Amino-1-(3-benzyloxy-phenyl)-imidazo[1,5-a]pyrazin-3-yl]-cyclohexanecarboxylic acid phenylamide {4-[8-Amino-1-(3-benzyloxy-phenyl)-imidazo[1,5-a]pyrazin-3-yl]-cyclohexyl}-(4-methyl-piperazin-1-yl)-methanone

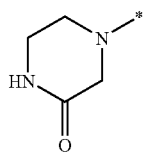

4-{4-[8-Amino-1-(3-benzyloxy-phenyl)-imidazo[1,5-a]pyrazin-3-yl]-cyclohexanecarbonyl}-piperazin-2-one -continued

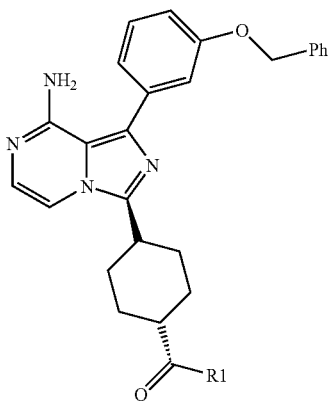

| R1 | Name |
|---|---|
| HO—[3-hydroxymethyl-piperidin-1-yl]—* | {4-[8-Amino-1-(3-benzyloxy-phenyl)-imidazo[1,5-a]pyrazin-3-yl]-cyclohexyl}-(3-hydroxymethyl-piperidin-1-yl)-methanone |
| HO—[4-hydroxymethyl-piperidin-1-yl]—* | {4-[8-Amino-1-(3-benzyloxy-phenyl)-imidazo[1,5-a]pyrazin-3-yl]-cyclohexyl}-(4-hydroxymethyl-piperidin-1-yl)-methanone |
| HO—[(3R)-3-hydroxy-pyrrolidin-1-yl]—* | {4-[8-Amino-1-(3-benzyloxy-phenyl)-imidazo[1,5-a]pyrazin-3-yl]-cyclohexyl}-(3-hydroxy-pyrrolidin-1-yl)-methanone |
| HO—[(3S)-3-hydroxy-pyrrolidin-1-yl]—* | {4-[8-Amino-1-(3-benzyloxy-phenyl)-imidazo[1,5-a]pyrazin-3-yl]-cyclohexyl}-(3-hydroxy-pyrrolidin-1-yl)-methanone |
| pyridin-2-ylmethyl-NH—* | 4-[8-Amino-1-(3-benzyloxy-phenyl)-imidazo[1,5-a]pyrazin-3-yl]-cyclohexanecarboxylic acid (pyridin-2-ylmethyl)-amide |
| tetrahydro-furan-2-ylmethyl-NH—* | 4-[8-Amino-1-(3-benzyloxy-phenyl)-imidazo[1,5-a]pyrazin-3-yl]-cyclohexanecarboxylic acid (tetrahydro-furan-2-ylmethyl)-amide |
| (CH₃)₂N-CH₂CH₂CH₂-NH—* | 4-[8-Amino-1-(3-benzyloxy-phenyl)-imidazo[1,5-a]pyrazin-3-yl]-cyclohexanecarboxylic acid (3-dimethylamino-propyl)-amide |
| CH₃-CH(OH)-CH₂-NH—* | 4-[8-Amino-1-(3-benzyloxy-phenyl)-imidazo[1,5-a]pyrazin-3-yl]-cyclohexanecarboxylic acid (2-hydroxy-propyl)-amide |
| HO-CH₂CH₂CH₂-NH—* | 4-[8-Amino-1-(3-benzyloxy-phenyl)-imidazol[1,5-a]pyrazin-3-yl]-cyclohexanecarboxylic acid (3-hydroxy-propyl)-amide |
| pyridin-3-ylmethyl-NH—* | 4-[8-Amino-1-(3-benzyloxy-phenyl)-imidazo[1,5-a]pyrazin-3-yl]-cyclohexanecarboxylic acid (pyridin-3-ylmethyl)-amide |
| pyridin-4-ylmethyl-NH—* | 4-[8-Amino-1-(3-benzyloxy-phenyl)-imidazo[1,5-a]pyrazin-3-yl]-cyclohexanecarboxylic acid (pyridin-4-ylmethyl)-amide |

-continued

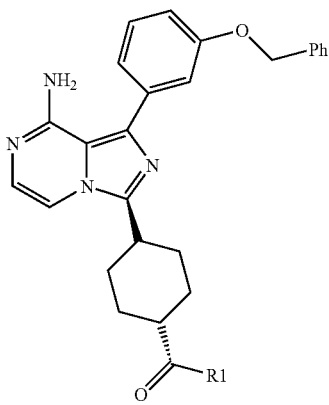

| R1 | Name |
|---|---|
| pyrrolidin-1-yl-ethyl (NH) | 4-[8-Amino-1-(3-benzyloxy-phenyl)-imidazo[1,5-a]pyrazin-3-yl]-cyclohexanecarboxylic acid (2-pyrrolidin-1-yl-ethyl)-amide |
| azetidin-1-yl | {4-[8-Amino-1-(3-benzyloxy-phenyl)-imidazo[1,5-a]pyrazin-3-yl]-cyclohexyl}-azetidin-1-yl-methanone |
| 1-methyl-piperidin-4-yl-NH | 4-[8-Amino-1-(3-benzyloxy-phenyl)-imidazol[1,5-a]pyrazin-3-yl]-cyclohexanecarboxylic acid (1-methyl-piperidin-4-yl)-amide |
| 2-(1H-imidazol-4-yl)-ethyl-NH | 4-[8-Amino-1-(3-benzyloxy-phenyl)-imidazo[1,5-a]pyrazin-3-yl]-cyclohexanecarboxylic acid [2-(1H-imidazol-4-yl)-ethyl]-amide |
| propyl-NH | 4-[8-Amino-1-(3-benzyloxy-phenyl)-imidazo[1,5-a]pyrazin-3-yl]-cyclohexanecarboxylic acid propylamide |
| isobutyl-NH | 4-[8-Amino-1-(3-benzyloxy-phenyl)-imidazo[1,5-a]pyrazin-3-yl]-cyclohexanecarboxylic acid isobutyl-amide | or a pharmaceutically acceptable salt thereof, wherein * is the point of attachment.

66. A compound selected from the group consisting of:

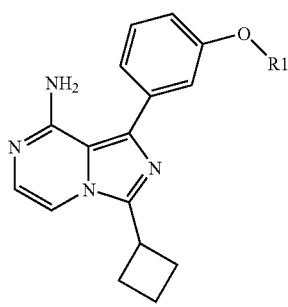

| R1 | Name |
|---|---|
| *–CH₂CH₂OH | 2-[3-(8-Amino-3-cyclobutyl-imidazo[1,5-a]pyrazin-1-yl)-phenoxy]-ethanol |

-continued

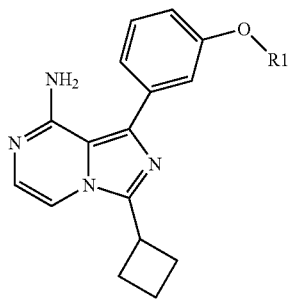

| R1 | Name |
|---|---|
| phenethyl (*-CH2CH2-C6H5) | 3-Cyclobutyl-1-(3-phenethyloxy-phenyl)-imidazo[1,5-a]pyrazin-8-ylamine |
| isobutyl | 3-Cyclobutyl-1-(3-isobutoxy-phenyl)-imidazo[1,5-a]pyrazin-8-ylamine |
| 3-morpholin-4-yl-propyl | 3-Cyclobutyl-1-[3-(3-morpholin-4-yl-propoxy)-phenyl]-imidazo[1,5-a]pyrazin-8-ylamine |
| 2-piperidin-1-yl-ethyl | 3-Cyclobutyl-1-[3-(2-piperidin-1-yl-ethoxy)-phenyl]-imidazo[1,5-a]pyrazin-8-ylamine |
| cyclohexylmethyl | 3-Cyclobutyl-1-(3-cyclohexylmethoxy-phenyl)-imidazo[1,5-a]pyrazin-8-ylamine |
| 2-imidazol-1-yl-ethyl | 3-Cyclobutyl-1-[3-(2-imidazol-1-yl-ethoxy)-phenyl]-imidazo[1,5-a]pyrazin-8-ylamine |
| CH2C(O)O-tBu | [3-(8-Amino-3-cyclobutyl-imidazo[1,5-a]pyrazin-1-yl)-phenoxy]-acetic acid tert-butyl ester |
| CH2C(O)CH2CH3 | 1-[3-(8-Amino-3-cyclobutyl-imidazo[1,5-a]pyrazin-1-yl)-phenoxy]-butan-2-one |
| CH2C(O)OMe | [3-(8-Amino-3-cyclobutyl-imidazo[1,5-a]pyrazin-1-yl)-phenoxy]-acetic acid methyl ester |
| Me | 3-Cyclobutyl-1-(3-methoxy-phenyl)-imidazo[1,5-a]pyrazin-8-ylamine |
| 3-methyl-but-2-enyl | 3-Cyclobutyl-1-[3-(3-methyl-but-2-enyloxy)-phenyl]-imidazo[1,5-a]pyrazin-8-ylamine |
| 2-diethylamino-ethyl | 3-Cyclobutyl-1-[3-(2-diethylamino-ethoxy)-phenyl]-imidazo[1,5-a]pyrazin-8-ylamine |

-continued

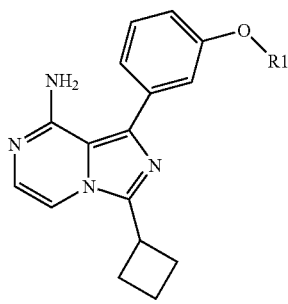

| R1 | Name |
|---|---|
| *⁀CN | [3-(8-Amino-3-cyclobutyl-imidazo[1,5-a]pyrazin-1-yl)-phenoxy]-acetonitrile |
| *-cyclohexyl | 3-Cyclobutyl-1-(3-cyclohexylmethoxy-phenyl)-imidazol[1,5-a]pyrazin-8-ylamine |
| *-CH2C(O)NH2 | 2-[3-(8-Amino-3-cyclobutyl-imidazo[1,5-a]pyrazin-1-yl)-phenoxy]-acetamide |
| *-CH2-cyclopropyl | 3-Cyclobutyl-1-(3-cyclopropylmethoxy-phenyl)-imidazo[1,5-a]pyrazin-8-ylamine |
| *-CH2-cyclopentyl | 3-Cyclobutyl-1-(3-cyclopentylmethoxy-phenyl)-imidazo[1,5-a]pyrazin-8-ylamine |
| *-CH2CH2OMe | 3-Cyclobutyl-1-[3-(2-methoxy-ethoxy)-phenyl]-imidazo[1,5-a]pyrazin-8-ylamine |
| *-CH2CH2CH(CH3)2 | 3-Cyclobutyl-1-[3-(3-methyl-butoxy)-phenyl]-imidazo[1,5-a]pyrazin-8-ylamine |
| *-CH2CH2-pyrrolidinyl | 3-Cyclobutyl-1-[3-(2-pyrrolidin-1-yl-ethoxy)-phenyl]-imidazo[1,5-a]pyrazin-8-ylamine |
| *-CH2C(O)-morpholinyl | 2-[3-(8-Amino-3-cyclobutyl-imidazo[1,5-a]pyrazin-1-yl)-phenoxy]-1-morpholin-4-yl-ethanone |
| *-CH2C(O)-pyrrolidinyl | 2-[3-(8-Amino-3-cyclobutyl-imidazo[1,5-a]pyrazin-1-yl)-phenoxy]-1-pyrrolidin-1-yl-ethanone |
| *-CH2C(O)NHPr | 2-[3-(8-Amino-3-cyclobutyl-imidazo[1,5-a]pyrazin-1-yl)-phenoxy]-N-propyl-acetamide |
| *-CH2C(O)NHMe | 2-[3-(8-Amino-3-cyclobutyl-imidazo[1,5-a]pyrazin-1-yl)-phenoxy]-N-methyl-acetamide | or a pharmaceutically acceptable salt thereof, wherein * is the point of attachment.

67. A compound selected from the group consisting of:

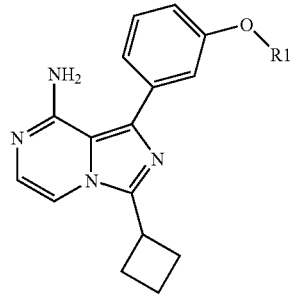

| R1 | Name |
|---|---|
| *-CH2-C6H4-OMe (3-methoxybenzyl) | 3-Cyclobutyl-1-[3-(3-methoxy-benzyloxy)-phenyl]-imidazo[1,5-a]pyrazin-8-ylamine |
| *-CH2-C6H4-Cl (2-chlorobenzyl) | 1-[3-(2-Chloro-benzyloxy)-phenyl]-3-cyclobutyl-imidazo[1,5-a]pyrazin-8-ylamine |
| *-CH2-C6H4-Cl (3-chlorobenzyl) | 1-[3-(3-Chloro-benzyloxy)-phenyl]-3-cyclobutyl-imidazo[1,5-a]pyrazin-8-ylamine |
| *-CH2-C6H4-Cl (4-chlorobenzyl) | 1-[3-(4-Chloro-benzyloxy)-phenyl]-3-cyclobutyl-imidazo[1,5-a]pyrazin-8-ylamine |
| *-CH2-(pyridin-3-yl) | 3-Cyclobutyl-1-[3-(pyridin-3-ylmethoxy)-phenyl]-imidazol[1,5-a]pyrazin-8-ylamine |
| *-CH2-(5-methyl-isoxazol-3-yl) | 3-Cyclobutyl-1-[3-(5-methyl-isoxazol-3-ylmethoxy)-phenyl]-imidazo[1,5-a]pyrazin-8-ylamine |
| *-CH2-(2,6-dichloropyridin-4-yl) | 3-Cyclobutyl-1-[3-(2,6-dichloro-pyridin-4-ylmethoxy)-phenyl]-imidazol[1,5-a]pyrazin-8-ylamine |
| *-CH2-(biphenyl-4-yl) | 1-[3-(Biphenyl-4-ylmethoxy)-phenyl]-3-cyclobutyl-imidazo[1,5-a]pyrazin-8-ylamine |
| *-CH2-C6H4-SO2Ph (2-benzenesulfonylbenzyl) | 1-[3-(2-Benzenesulfonyl-benzyloxy)-phenyl]-3-cyclobutyl-imidazo[1,5-a]pyrazin-8-ylamine |

-continued

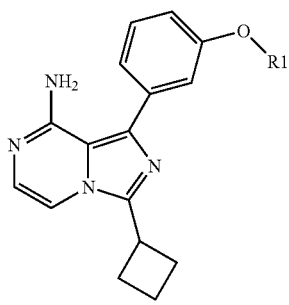

| R1 | Name |
|---|---|
| *-CH2-naphthalen-2-yl | 3-Cyclobutyl-1-[3-(naphthalen-2-ylmethoxy)-phenyl]-imidazo[1,5-a]pyrazin-8-ylamine |
| *-CH2-(4-[1,2,4]triazol-1-yl-phenyl) | 3-Cyclobutyl-1-[3-(4-[1,2,4]triazol-1-yl-benzyloxy)-phenyl]-imidazo[1,5-a]pyrazin-8-ylamine |
| *-CH2-(4-methylphenyl) | 3-Cyclobutyl-1-[3-(4-methyl-benzyloxy)-phenyl]-imidazo[1,5-a]pyrazin-8-ylamine |
| *-CH2-(2,6-dichlorophenyl) | 3-Cyclobutyl-1-[3-(2,6-dichloro-benzyloxy)-phenyl]-imidazo[1,5-a]pyrazin-8-ylamine |
| *-CH2-(3-CF3-phenyl) | 3-Cyclobutyl-1-[3-(3-trifluoromethyl-benzyloxy)-phenyl]-imidazo[1,5-a]pyrazin-8-ylamine |
| *-CH2-(4-tert-butylphenyl) | 1-[3-(4-tert-Butyl-benzyloxy)-phenyl]-3-cyclobutyl-imidazo[1,5-a]pyrazin-8-ylamine |
| *-CH2-(2-Ph-phenyl) | 1-[3-(Biphenyl-2-ylmethoxy)-phenyl]-3-cyclobutyl-imidazo[1,5-a]pyrazin-8-ylamine |
| *-CH2-(4-CN-phenyl) | 4-[3-(8-Amino-3-cyclobutyl-imidazo[1,5-a]pyrazin-1-yl)-phenoxymethyl]-benzonitrile |
| *-CH2-(2,3-difluorophenyl) | 3-Cyclobutyl-1-[3-(2,3-difluoro-benzyloxy)-phenyl]-imidazo[1,5-a]pyrazin-8-ylamine |

-continued

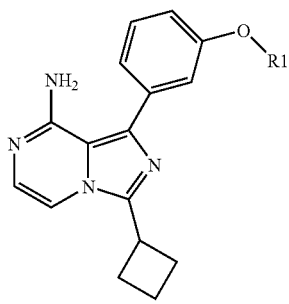

| R1 | Name |
|---|---|
| *-CH2-(3,5-dimethylphenyl) | 3-Cyclobutyl-1-[3-(3,5-dimethyl-benzyloxy)-phenyl]-imidazo[1,5-a]pyrazin-8-ylamine |
| *-CH2-(3-OCF3-phenyl) | 3-Cyclobutyl-1-[3-(3-trifluoromethoxy-benzyloxy)-phenyl]-imidazo[1,5-a]pyrazin-8-ylamine |
| *-CH2-(2-CN-phenyl) | 2-[3-(8-Amino-3-cyclobutyl-imidazo[1,5-a]pyrazin-1-yl)-phenoxymethyl]-benzonitrile |
| *-CH2-(4-OCF3-phenyl) | 3-Cyclobutyl-1-[3-(4-trifluoromethoxy-benzyloxy)-phenyl]-imidazo[1,5-a]pyrazin-8-ylamine |
| *-CH2-(3,4-difluorophenyl) | 3-Cyclobutyl-1-[3-(3,4-difluoro-benzyloxy)-phenyl]-imidazo[1,5-a]pyrazin-8-ylamine |
| *-CH2-(benzo[1,2,5]oxadiazol-5-yl) | 1-[3-(Benzo[1,2,5]oxadiazol-5-ylmethoxy)-phenyl]-3-cyclobutyl-imidazo[1,5-a]pyrazin-8-ylamine |
| *-CH2-(3,4,5-trifluorophenyl) | 3-Cyclobutyl-1-[3-(3,4,5-trifluoro-benzyloxy)-phenyl]-imidazo[1,5-a]pyrazin-8-ylamine |
| *-CH2-(2-fluoro-5-CF3-phenyl) | 3-Cyclobutyl-1-[3-(2-fluoro-5-trifluoromethyl-benzyloxy)-phenyl]-imidazo[1,5-a]pyrazin-8-ylamine |
| *-CH2-(4-OCHF2-phenyl) | 3-Cyclobutyl-1-[3-(4-difluoromethoxy-benzyloxy)-phenyl]-imidazo[1,5-a]pyrazin-8-ylamine |

-continued

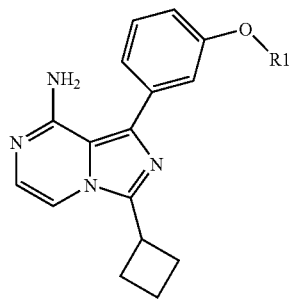

| R1 | Name |
|---|---|
| [5-chloro-benzo[b]thiophen-3-ylmethyl] | 1-[3-(5-Chloro-benzo[b]thiophen-3-ylmethoxy)-phenyl]-3-cyclobutyl-imidazo[1,5-a]pyrazin-8-ylamine |
| [4-chloro-2-fluoro-benzyl] | 1-[3-(4-Chloro-2-fluoro-benzyloxy)-phenyl]-3-cyclobutyl-imidazo[1,5-a]pyrazin-8-ylamine |
| [3,5-difluoro-benzyl] | 3-Cyclobutyl-1-[3-(3,5-difluoro-benzyloxy)-phenyl]-imidazol[1,5-a]pyrazin-8-ylamine |
| [2,6-difluoro-benzyl] | 3-Cyclobutyl-1-[3-(2,6-difluoro-benzyloxy)-phenyl]-imidazo[1,5-a]pyrazin-8-ylamine |
| [3-fluoro-benzyl] | 3-Cyclobutyl-1-[3-(3-fluoro-benzyloxy)-phenyl]-imidazol[1,5-a]pyrazin-8-ylamine |
| [naphthalen-1-ylmethyl] | 3-Cyclobutyl-1-[3-(naphthalen-1-ylmethoxy)-phenyl]-imidazo[1,5-a]pyrazin-8-ylamine |
| [2,5-difluoro-benzyl] | 3-Cyclobutyl-1-[3-(2,5-difluoro-benzyloxy)-phenyl]-imidazo[1,5-a]pyrazin-8-ylamine |
| [2-chloro-6-fluoro-benzyl] | 1-[3-(2-Chloro-6-fluoro-benzyloxy)-phenyl]-3-cyclobutyl-imidazo[1,5-a]pyrazin-8-ylamine |

-continued

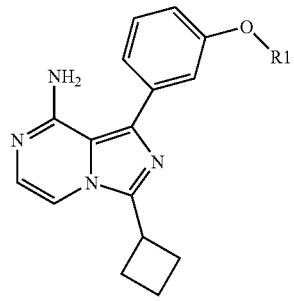

| R1 | Name |
|---|---|
| ![*-CH2-(2,3,6-trifluorophenyl)] | 3-Cyclobutyl-1-[3-(2,3,6-trifluoro-benzyloxy)-phenyl]-imidazo[1,5-a]pyrazin-8-ylamine |
| ![*-CH2-(2-fluorophenyl)] | 3-Cyclobutyl-1-[3-(2-fluoro-benzyloxy)-phenyl]-imidazo[1,5-a]pyrazin-8-ylamine |
| ![*-CH2-(2-OCHF2-phenyl)] | 3-Cyclobutyl-1-[3-(2-difluoromethoxy-benzyloxy)-phenyl]-imidazo[1,5-a]pyrazin-8-ylamine |
| ![*-CH2-(3-OCHF2-phenyl)] | 3-Cyclobutyl-1-[3-(3-difluoromethoxy-benzyloxy)-phenyl]-imidazo[1,5-a]pyrazin-8-ylamine |
| ![*-CH2-quinolin-8-yl] | 3-Cyclobutyl-1-[3-(quinolin-8-ylmethoxy)-phenyl]-imidazo[1,5-a]pyrazin-8-ylamine |
| ![*-CH(CH3)-phenyl] | 3-Cyclobutyl-1-[3-(1-phenyl-ethoxy)-phenyl]-imidazo[1,5-a]pyrazin-8-ylamine |
| ![*-CH2-(3-CO2H-phenyl)] | 3-[3-(8-Amino-3-cyclobutyl-imidazo[1,5-a]pyrazin-1-yl)-phenoxymethyl]-benzoic acid |
| ![*-CH2-pyridin-2-yl] | 3-Cyclobutyl-1-[3-(pyridin-2-ylmethoxy)-phenyl]-imidazo[1,5-a]pyrazin-8-ylamine |

-continued

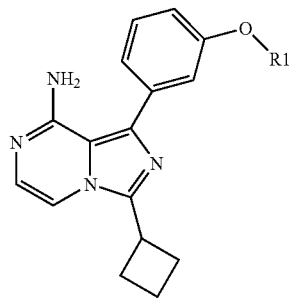

| R1 | Name |
|---|---|
| *—CH2— (3,5-dimethylisoxazol-4-yl) | 3-Cyclobutyl-1-[3-(3,5-dimethyl-isoxazol-4-ylmethoxy)-phenyl]-imidazo[1,5-a]pyrazin-8-ylamine |
| *—CH2— (5-methyl-3-phenyl-isoxazol-4-yl) | 3-Cyclobutyl-1-[3-(5-methyl-3-phenyl-isoxazol-4-ylmethoxy)-phenyl]-imidazo[1,5-a]pyrazin-8-ylamine | or a pharmaceutically acceptable salt thereof, wherein * is the point of attachment.

68. A compound selected from the group consisting of:

| R1 | Name |
|---|---|
| isopropyl | [1-(3-Benzyloxy-phenyl)-3-cyclobutyl-imidazo[1,5-a]pyrazin-8-yl]-isopropyl-amine |
| ethyl | [1-(3-Benzyloxy-phenyl)-3-cyclobutyl-imidazo[1,5-a]pyrazin-8-yl]-ethyl-amine |
| allyl | Allyl-[1-(3-benzyloxy-phenyl)-3-cyclobutyl-imidazo[1,5-a]pyrazin-8-yl]-amine |
| propargyl | [1-(3-Benzyloxy-phenyl)-3-cyclobutyl-imidazo[1,5-a]pyrazin-8-yl]-prop-2-ynyl-amine |
| propyl | [1-(3-Benzyloxy-phenyl)-3-cyclobutyl-imidazo[1,5-a]pyrazin-8-yl]-propyl-amine |
| cyclopropylmethyl | [1-(3-Benzyloxy-phenyl)-3-cyclobutyl-imidazo[1,5-a]pyrazin-8-yl]-cyclopropylmethyl-amine |
| benzyl | Benzyl-[1-(3-benzyloxy-phenyl)-3-cyclobutyl-imidazo[1,5-a]pyrazin-8-yl]-amine |
| phenyl | [1-(3-Benzyloxy-phenyl)-3-cyclobutyl-imidazo[1,5-a]pyrazin-8-yl]-phenyl-amine |

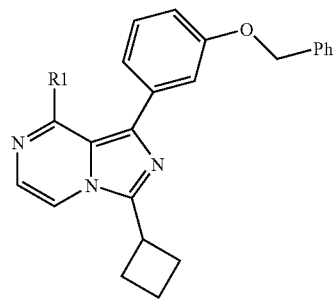

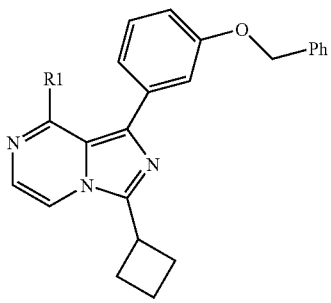

| R1 | Name |
|---|---|
| —NH—* (methyl) | [1-(3-Benzyloxy-phenyl)-3-cyclobutyl-imidazo[1,5-a]pyrazin-8-yl]-methyl-amine |
| MeO\~\~NH—* | [1-(3-Benzyloxy-phenyl)-3-cyclobutyl-imidazo[1,5-a]pyrazin-8-yl]-(2-methoxy-ethyl)-amine |
| morpholin-4-yl —N(*)—(CH2CH2)2O | 1-(3-Benzyloxy-phenyl)-3-cyclobutyl-8-morpholin-4-yl-imidazo[1,5-a]pyrazine |
| Et2N—* | [1-(3-Benzyloxy-phenyl)-3-cyclobutyl-imidazo[1,5-a]pyrazin-8-yl]-diethyl-amine |
| HO\~\~NH—* | [1-(3-Benzyloxy-phenyl)-3-cyclobutyl-imidazo[1,5-a]pyrazin-8-yl]-(2-methoxy-ethyl)-amine | or a pharmaceutically acceptable salt thereof, wherein * is the point of attachment.

* * * * *

UNITED STATES PATENT AND TRADEMARK OFFICE
CERTIFICATE OF CORRECTION

| | | |
|---|---|---|
| PATENT NO. | : 7,459,554 B2 | Page 1 of 1 |
| APPLICATION NO. | : 10/965182 | |
| DATED | : December 2, 2008 | |
| INVENTOR(S) | : Han-Qing Dong et al. | |

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 365 days.

Delete the phrase "by 365 days" and insert -- by 771 days --

Signed and Sealed this

Sixth Day of July, 2010

David J. Kappos
*Director of the United States Patent and Trademark Office*